US007892183B2

(12) United States Patent
Boecker et al.

(10) Patent No.: US 7,892,183 B2
(45) Date of Patent: Feb. 22, 2011

(54) METHOD AND APPARATUS FOR BODY FLUID SAMPLING AND ANALYTE SENSING

(75) Inventors: Dirk Boecker, Palo Alto, CA (US); Dominique M. Freeman, La Honda, CA (US); Don Alden, Sunnyvale, CA (US)

(73) Assignee: Pelikan Technologies, Inc., Palo Alto, CA (US)

( * ) Notice: Subject to any disclaimer, the term of this patent is extended or adjusted under 35 U.S.C. 154(b) by 1789 days.

(21) Appl. No.: 10/613,517

(22) Filed: Jul. 3, 2003

(65) Prior Publication Data

US 2004/0098009 A1 May 20, 2004

Related U.S. Application Data

(63) Continuation-in-part of application No. 10/452,815, filed on May 30, 2003, and a continuation-in-part of application No. 10/323,622, filed on Dec. 18, 2002, now Pat. No. 7,708,701, which is a continuation-in-part of application No. 10/127,395, filed on Apr. 19, 2002, now Pat. No. 7,025,774, application No. 10/613,517, which is a continuation-in-part of application No. 10/237,261, filed on Sep. 5, 2002, now Pat. No. 7,344,507, and a continuation-in-part of application No. 10/420,535, filed on Apr. 21, 2003, now Pat. No. 7,258,693, and a continuation-in-part of application No. 10/335,142, filed on Dec. 31, 2002, now Pat. No. 7,374,544, and a continuation-in-part of application No. 10/423,851, filed on Apr. 24, 2003, now Pat. No. 7,141,058.

(60) Provisional application No. 60/422,988, filed on Nov. 1, 2002, provisional application No. 60/424,429, filed on Nov. 6, 2002.

(51) Int. Cl.
*A61B 5/00* (2006.01)
*A61B 17/14* (2006.01)
*A61B 17/32* (2006.01)
*B65D 81/00* (2006.01)

(52) U.S. Cl. ...................... 600/583; 600/573; 600/575; 600/576; 600/579; 606/181

(58) Field of Classification Search ................ 600/583, 600/564, 568, 573, 575, 576, 577, 579, 584; 604/318, 322, 326; 606/181
See application file for complete search history.

(56) References Cited

U.S. PATENT DOCUMENTS 2,061 A 4/1841 Osdel ........................ 606/182

(Continued)

FOREIGN PATENT DOCUMENTS

DE 4420232 12/1995

(Continued)

OTHER PUBLICATIONS

Tietz Textbook of Clinical Chemistry, 3d Ed., Sec. V, pp. 776-778 (Burtis & Ashwood, Eds., W.B. Saunders Company, Philadelphia, 1999).

*Primary Examiner*—Jeffrey G Hoekstra
(74) *Attorney, Agent, or Firm*—Paul Davis; Goodwin Procter LLP

(57) ABSTRACT

A body fluid sampling system is provided for use on a tissue site. In one embodiment, the system comprises a cartridge; a penetrating member driver; a plurality of penetrating members arranged in a radial configuration on the cartridge wherein sharpened distal tips of the penetrating members point radially outward; wherein an active one of the penetrating members may be operatively coupled to the penetrating member driver, the penetrating member driver moving the active one along a path out of a housing having a penetrating member exit, into the tissue site, stopping in the tissue site, and withdrawing out of the tissue site; and a plurality of analyte detecting members, wherein at least one of the analyte detecting members is positioned to receive fluid from a wound created by the active one of the penetrating members, wherein the detecting members are not pierced by the active one of the penetrating members.

11 Claims, 74 Drawing Sheets

246
248
250
244
262
264
256
252
253
253
260
254

U.S. PATENT DOCUMENTS

| Patent No. | Kind | Date | Inventor | Class |
|---|---|---|---|---|
| 55,620 | A | 6/1866 | Capewell | 606/181 |
| 1,135,465 | A | 4/1915 | Pollock | 606/181 |
| 1,733,847 | A | 10/1929 | Wilmot | |
| 2,258,857 | A | 10/1941 | McCann | 601/81 |
| 2,628,319 | A | 2/1953 | Vang | 310/15 |
| 2,714,890 | A | 8/1955 | Alfred | 606/169 |
| 2,763,935 | A | 9/1956 | Whaley | 33/511 |
| 2,801,633 | A | 8/1957 | Mauze et al. | |
| 3,046,987 | A | 7/1962 | Ehrlich | 128/314 |
| 3,030,959 | A | 9/1962 | Cirunert | 128/329 |
| 3,086,288 | A | 4/1963 | Balamuth | 30/277.4 |
| 3,208,452 | A | 9/1965 | Stern | 606/182 |
| 3,358,689 | A | 12/1967 | Higgins | 128/329 |
| 3,412,729 | A | 11/1968 | Smith, Jr | 128/2.05 |
| 3,448,307 | A | 6/1969 | Rudolph | 310/23 |
| 3,494,358 | A | 2/1970 | Grossenbacher | 128/218 |
| 3,620,209 | A | 11/1971 | Kravitz | 601/79 |
| 3,626,929 | A | 12/1971 | Sanz | 128/2 R |
| 3,628,026 | A | 12/1971 | Cronin | 250/214.1 |
| 3,665,672 | A | 5/1972 | Speelman | 53/435 |
| 3,673,475 | A | 6/1972 | Britton | 318/122 |
| 3,712,292 | A | 1/1973 | Mielke, Jr. | 128/2 G |
| 3,712,293 | A | 1/1973 | Mielke, Jr. | 128/2 |
| 3,734,812 | A | 5/1973 | Yazawa | 428/107 |
| 3,742,954 | A | 7/1973 | Strickland | 128/302 |
| 3,780,960 | A | 12/1973 | Tokuno | 242/555.2 |
| 3,832,776 | A | 9/1974 | Sawyer | 30/272 |
| 3,836,148 | A | 9/1974 | Manning | 273/368 |
| 3,851,543 | A | 12/1974 | Krom | 74/493 |
| 3,853,010 | A | 12/1974 | Christen | 73/864.24 |
| 3,924,818 | A | 12/1975 | Pfeifle | 242/364.7 |
| 3,938,526 | A | 2/1976 | Anderson | 128/303.1 |
| 3,953,172 | A | 4/1976 | Shapiro | 23/230 |
| 3,971,365 | A | 7/1976 | Smith | 128/2.17 |
| 4,057,394 | A | 11/1977 | Genshaw | 23/230 |
| 4,077,406 | A | 3/1978 | Sandhage | 604/61 |
| 4,109,655 | A | 8/1978 | Chaconac | 128/253 |
| 4,139,011 | A | 2/1979 | Benoit | 606/182 |
| 4,154,228 | A | 5/1979 | Feldstein et al. | 128/329 |
| 4,168,130 | A | 9/1979 | Barth | 404/99 |
| 4,184,486 | A | 1/1980 | Papa | 600/373 |
| 4,190,420 | A | 2/1980 | Covington | 422/63 |
| 4,191,193 | A | 3/1980 | Seo | 600/488 |
| 4,193,690 | A | 3/1980 | Levenson | 356/301 |
| 4,203,446 | A | 5/1980 | Hofert | 606/182 |
| 4,207,870 | A | 6/1980 | Eldridge | 128/766 |
| 4,223,674 | A | 9/1980 | Fluent | 604/504 |
| 4,224,125 | A | 9/1980 | Nakamura | 204/195 B |
| 4,224,949 | A | 9/1980 | Scott | 128/734 |
| 4,230,118 | A | 10/1980 | Holman et al. | 128/314 |
| 4,240,439 | A | 12/1980 | Abe | 600/412 |
| 4,254,083 | A | 3/1981 | Columbus | 422/55 |
| 4,258,001 | A | 3/1981 | Pierce | 422/56 |
| 4,259,653 | A | 3/1981 | McGonigal | 310/15 |
| 4,299,230 | A | 11/1981 | Kubota | 600/300 |
| 4,301,412 | A | 11/1981 | Hill | 324/442 |
| 4,321,397 | A | 3/1982 | Nix | 548/366 |
| 4,338,174 | A | 7/1982 | Tamura | 204/195 |
| 4,340,669 | A | 7/1982 | Bauer | 435/14 |
| 4,350,762 | A | 9/1982 | De Luca | 435/10 |
| 4,353,984 | A | 10/1982 | Yamada | 435/14 |
| 4,356,826 | A | 11/1982 | Kubota | 600/300 |
| 4,360,016 | A | 11/1982 | Sarrine | 128/763 |
| 4,388,922 | A | 6/1983 | Telang | 604/319 |
| 4,391,905 | A | 7/1983 | Bauer | 435/14 |
| 4,391,906 | A | 7/1983 | Bauer | 435/14 |
| 4,392,933 | A | 7/1983 | Nakamura et al. | 204/403 |
| 4,394,512 | A | 7/1983 | Batz | 548/365 |
| 4,397,556 | A | 8/1983 | Muller | 356/301 |
| 4,407,008 | A | 9/1983 | Schmidt | 356/301 |
| 4,411,266 | A | 10/1983 | Cosman | 128/303.18 |
| 4,414,975 | A | 11/1983 | Ryder | 128/314 |
| 4,418,037 | A | 11/1983 | Katsuyama | 422/56 |
| 4,420,564 | A | 12/1983 | Tsuji | 435/288 |
| 4,425,039 | A | 1/1984 | Grant | 356/35.5 |
| 4,426,451 | A | 1/1984 | Columbus | 436/518 |
| 4,426,884 | A | 1/1984 | Polchaninoff | 73/172 |
| 4,440,301 | A | 4/1984 | Intengan | 206/456 |
| 4,442,836 | A | 4/1984 | Meinecke | 128/314 |
| 4,442,972 | A | 4/1984 | Sahay | 236/1 EA |
| 4,449,529 | A | 5/1984 | Burns | 606/182 |
| 4,462,405 | A | 7/1984 | Ehrlich | 606/182 |
| 4,469,110 | A | 9/1984 | Slama | 128/770 |
| 4,517,978 | A | 5/1985 | Levin | 128/314 |
| 4,518,384 | A | 5/1985 | Tarello | 604/61 |
| 4,523,994 | A | 6/1985 | Shono | 549/352 |
| 4,535,769 | A | 8/1985 | Burns | 128/314 |
| 4,535,773 | A | 8/1985 | Yoon | 606/185 |
| 4,537,197 | A | 8/1985 | Hulka | 128/633 |
| 4,539,988 | A | 9/1985 | Shirley | 128/314 |
| 4,545,382 | A | 10/1985 | Higgins | 128/635 |
| 4,553,541 | A | 11/1985 | Burns | 128/314 |
| 4,561,445 | A | 12/1985 | Berke | 128/642 |
| 4,577,630 | A | 3/1986 | Nitzsche | 128/314 |
| 4,580,564 | A | 4/1986 | Anderson | 502/8 |
| 4,580,565 | A | 4/1986 | Cornell | 128/314 |
| 4,586,819 | A | 5/1986 | Tochigi | 356/301 |
| 4,590,411 | A | 5/1986 | Kelly | 318/687 |
| 4,595,479 | A | 6/1986 | Kimura | 204/294 |
| 4,600,014 | A | 7/1986 | Beraha | 128/754 |
| 4,603,209 | A | 7/1986 | Tsien | 549/352 |
| 4,608,997 | A | 9/1986 | Conway | 128/763 |
| 4,615,340 | A | 10/1986 | Cronenberg | 128/635 |
| 4,616,649 | A | 10/1986 | Burns | 128/314 |
| 4,619,754 | A | 10/1986 | Niki | 204/290 |
| 4,622,974 | A | 11/1986 | Coleman | 128/634 |
| 4,624,253 | A | 11/1986 | Burns | 128/314 |
| 4,627,445 | A | 12/1986 | Garcia | 600/583 |
| 4,637,393 | A | 1/1987 | Ray | 128/305 |
| 4,637,403 | A | 1/1987 | Garcia | 600/583 |
| 4,643,189 | A | 2/1987 | Mintz | 128/314 |
| 4,648,408 | A | 3/1987 | Hutcheson | 128/770 |
| 4,648,714 | A | 3/1987 | Benner | 356/301 |
| 4,653,511 | A | 3/1987 | Goch | 128/763 |
| 4,653,513 | A | 3/1987 | Dombrowski | 600/578 |
| 4,655,225 | A | 4/1987 | Dahne | 600/316 |
| 4,661,768 | A | 4/1987 | Carusillo | |
| 4,666,438 | A | 5/1987 | Raulerson | 604/272 |
| 4,676,244 | A | 6/1987 | Enstrom | 128/314 |
| 4,677,979 | A | 7/1987 | Burns | 128/314 |
| 4,678,277 | A | 7/1987 | Delhaye | 356/301 |
| 4,682,892 | A | 7/1987 | Chawla | 356/353 |
| 4,702,594 | A | 10/1987 | Grant | 356/35.5 |
| 4,711,245 | A | 12/1987 | Higgins | 128/635 |
| 4,712,460 | A | 12/1987 | Allen | 83/208 |
| 4,712,548 | A | 12/1987 | Enstrom | 128/314 |
| 4,714,462 | A | 12/1987 | DiDomenico | 604/67 |
| 4,715,374 | A | 12/1987 | Maggio | 128/314 |
| 4,731,330 | A | 3/1988 | Hill | 436/16 |
| 4,731,726 | A | 3/1988 | Allen, III | 600/300 |
| 4,734,360 | A | 3/1988 | Phillips | 435/25 |
| 4,735,203 | A | 4/1988 | Ryder | 128/314 |
| 4,737,458 | A | 4/1988 | Batz | 435/28 |
| 4,750,489 | A | 6/1988 | Berkman | 606/166 |
| 4,753,776 | A | 6/1988 | Hillman | 422/101 |
| 4,756,884 | A | 7/1988 | Hillman | 422/73 |
| 4,757,022 | A | 7/1988 | Shults | 204/403.05 |
| 4,758,323 | A | 7/1988 | Davis | 204/403 |
| 4,774,192 | A | 9/1988 | Terminiello | 436/530 |
| 4,784,486 | A | 11/1988 | Van Wagenen | 356/301 |
| 4,787,398 | A | 11/1988 | Garcia | 600/583 |
| 4,790,979 | A | 12/1988 | Terminiello | 422/56 |
| 4,794,926 | A | 1/1989 | Munsch | 606/183 |
| 4,797,283 | A | 1/1989 | Allen | 424/443 |

4,814,142 A 3/1989 Gleisner ..................... 422/56
4,814,661 A 3/1989 Ratzlaff ..................... 310/328
4,817,603 A 4/1989 Turner ..................... 606/182
4,818,493 A 4/1989 Coville ..................... 422/102
4,820,010 A 4/1989 Scifres ..................... 385/43
4,820,399 A 4/1989 Senda ..................... 204/403
4,823,806 A 4/1989 Bajada ..................... 600/557
4,824,639 A 4/1989 Hildenbrand ..................... 422/56
RE32,922 E 5/1989 Levin ..................... 128/314
4,825,711 A 5/1989 Jensen ..................... 73/865.8
4,827,763 A 5/1989 Bourland ..................... 73/172
4,829,011 A 5/1989 Gibbons ..................... 436/512
4,830,959 A 5/1989 McNeil ..................... 435/53
4,836,904 A 6/1989 Armstrong ..................... 204/294
4,840,893 A 6/1989 Hill ..................... 435/6
4,844,095 A 7/1989 Chiodo ..................... 128/314
4,845,392 A 7/1989 Mumbower ..................... 310/14
4,850,973 A 7/1989 Jordan ..................... 604/157
4,857,274 A 8/1989 Simon ..................... 422/72
4,868,129 A 9/1989 Gibbons ..................... 436/179
4,869,249 A 9/1989 Crossman ..................... 128/314
4,869,265 A 9/1989 McEwen ..................... 128/774
4,873,993 A 10/1989 Meserol ..................... 128/780
4,877,026 A 10/1989 de Laforcade ..................... 128/305
4,882,013 A 11/1989 Turner ..................... 204/1
4,883,055 A 11/1989 Merrick ..................... 128/633
4,883,068 A 11/1989 Dechow ..................... 128/760
4,886,499 A 12/1989 Cirelli ..................... 604/131
4,889,529 A 12/1989 Haindl ..................... 604/274
4,892,097 A 1/1990 Ranalletta ..................... 606/182
4,895,147 A 1/1990 Bodicky ..................... 606/182
4,895,156 A 1/1990 Schulze ..................... 600/342
4,897,173 A 1/1990 Nankai ..................... 204/403
4,900,424 A 2/1990 Birch ..................... 204/409
4,900,666 A 2/1990 Phillips ..................... 435/25
4,911,794 A 3/1990 Parce ..................... 204/1 T
4,920,977 A 5/1990 Haynes ..................... 128/770
4,924,879 A 5/1990 O'Brien
4,935,346 A 6/1990 Phillips ..................... 435/14
4,938,218 A 7/1990 Goodman ..................... 128/633
4,940,468 A 7/1990 Petillo ..................... 606/170
4,944,304 A 7/1990 Nishina ..................... 128/667
4,945,045 A 7/1990 Forrest ..................... 435/25
4,946,795 A 8/1990 Gibbons ..................... 436/179
4,948,727 A 8/1990 Cass ..................... 435/18
4,948,961 A 8/1990 Hillman ..................... 250/252.1
4,952,373 A 8/1990 Sugarman ..................... 422/99
4,952,515 A 8/1990 Gleisner ..................... 436/169
4,953,552 A 9/1990 DeMarzo ..................... 128/635
4,953,976 A 9/1990 Adler-Golden ..................... 356/301
4,963,498 A 10/1990 Hillman ..................... 436/69
4,966,581 A 10/1990 Landau ..................... 604/72
4,966,646 A 10/1990 Zdeblick ..................... 156/633
4,966,671 A 10/1990 Nylander ..................... 204/153.14
4,975,581 A 12/1990 Robinson ..................... 250/339
4,976,724 A 12/1990 Nieto ..................... 606/182
4,977,910 A 12/1990 Miyahara ..................... 134/7
4,983,178 A 1/1991 Schnell ..................... 606/181
4,984,085 A 1/1991 Landowski ..................... 358/213
4,990,154 A 2/1991 Brown ..................... 606/182
4,995,402 A 2/1991 Smith ..................... 600/584
4,999,582 A 3/1991 Parks ..................... 324/438
5,001,054 A 3/1991 Wagner ..................... 435/14
5,001,873 A 3/1991 Rufin ..................... 451/39
5,004,923 A 4/1991 Hillman ..................... 250/341
5,010,772 A 4/1991 Bourland ..................... 73/862.04
5,010,774 A 4/1991 Kikuo ..................... 73/862.04
5,014,718 A 5/1991 Mitchen ..................... 128/771
5,019,974 A 5/1991 Beckers ..................... 364/413.02
5,026,388 A 6/1991 Ingalz ..................... 606/182
D318,331 S 7/1991 Phillips ..................... D24/169
5,028,142 A 7/1991 Ostoich et al. ..................... 366/273
5,029,583 A 7/1991 Meserol et al. ..................... 128/633
5,035,704 A 7/1991 Lambert et al. ..................... 606/182
5,039,617 A 8/1991 McDonald ..................... 436/69
5,043,143 A 8/1991 Shaw ..................... 422/65
5,046,496 A 9/1991 Betts ..................... 600/352
5,047,044 A 9/1991 Smith ..................... 606/182
5,049,487 A 9/1991 Phillips ..................... 435/4
5,049,673 A 9/1991 Tsien et al. ..................... 549/352
5,054,487 A 10/1991 Clarke ..................... 128/633
5,054,499 A 10/1991 Swierczek ..................... 128/770
5,057,082 A 10/1991 Burchette, Jr. ..................... 604/164
5,057,277 A 10/1991 Mauze ..................... 422/56
5,059,394 A 10/1991 Phillips et al. ..................... 422/68.1
5,059,789 A 10/1991 Salcudean ..................... 250/206.1
5,060,174 A 10/1991 Gross ..................... 702/139
5,062,898 A 11/1991 McDermott ..................... 134/7
5,070,874 A 12/1991 Barnes ..................... 128/633
5,070,886 A 12/1991 Mitchen ..................... 128/771
5,074,872 A 12/1991 Brown ..................... 606/182
5,077,017 A 12/1991 Gorin ..................... 422/100
5,077,199 A 12/1991 Basagni ..................... 435/14
5,080,865 A 1/1992 Leiner ..................... 422/68.1
5,086,229 A 2/1992 Rosenthal ..................... 250/341
5,089,112 A 2/1992 Skotheim ..................... 204/403
5,092,842 A 3/1992 Bechtold ..................... 604/135
5,094,943 A 3/1992 Siedel ..................... 435/25
5,096,669 A 3/1992 Lauks ..................... 204/403.02
5,097,810 A 3/1992 Fishman ..................... 600/556
5,100,427 A 3/1992 Crossman ..................... 606/182
5,100,428 A 3/1992 Mumford ..................... 606/182
5,104,380 A 4/1992 Holman ..................... 604/117
5,104,619 A 4/1992 Castro ..................... 422/56
5,104,813 A 4/1992 Besemer ..................... 436/179
5,107,764 A 4/1992 Gasparrini ..................... 101/425
5,108,564 A 4/1992 Szuminsky ..................... 204/153.12
5,108,889 A 4/1992 Smith ..................... 435/4
5,116,759 A 5/1992 Klainer ..................... 435/288
5,120,420 A 6/1992 Nankai ..................... 204/403
5,122,244 A 6/1992 Hoenes ..................... 204/153
5,126,034 A 6/1992 Carter ..................... 204/403
5,128,015 A 7/1992 Szuminsky ..................... 204/403
5,128,171 A 7/1992 Gleisner ..................... 427/2
5,132,801 A 7/1992 Yamano ..................... 358/213
5,133,730 A 7/1992 Biro ..................... 606/182
5,135,719 A 8/1992 Hillman ..................... 422/101
5,139,685 A 8/1992 Castro ..................... 210/767
5,140,161 A 8/1992 Hillman ..................... 250/341
5,141,868 A 8/1992 Shanks ..................... 435/288
5,144,139 A 9/1992 Hillman ..................... 250/341
5,145,565 A 9/1992 Kater ..................... 600/341
5,146,091 A 9/1992 Knudson ..................... 250/341.6
5,152,296 A 10/1992 Simons ..................... 128/670
5,152,775 A 10/1992 Ruppert ..................... 606/182
5,153,671 A 10/1992 Miles ..................... 356/301
5,156,611 A 10/1992 Haynes ..................... 606/181
5,162,525 A 11/1992 Masilamani ..................... 549/352
5,163,442 A 11/1992 Ono ..................... 128/760
5,164,598 A 11/1992 Hillman ..................... 250/341
5,167,619 A 12/1992 Wuchinich ..................... 604/22
5,170,364 A 12/1992 Gross ..................... 702/139
5,174,726 A 12/1992 Findlay ..................... 417/205
D332,490 S 1/1993 Brown ..................... D24/146
5,178,142 A 1/1993 Harjunmaa ..................... 128/633
5,179,005 A 1/1993 Phillips ..................... 435/14
5,181,910 A 1/1993 Scanlon ..................... 604/67
5,181,914 A 1/1993 Zook ..................... 604/307
5,183,042 A 2/1993 Harjunmaa ..................... 128/633
5,185,256 A 2/1993 Nankai ..................... 435/174
5,187,100 A 2/1993 Matzinger ..................... 436/16
5,188,118 A 2/1993 Terwilliger ..................... 600/566
5,189,751 A 3/1993 Giuliani ..................... 15/22.1
5,192,415 A 3/1993 Yoshioka ..................... 204/403
5,194,391 A 3/1993 Mauze ..................... 436/166
5,196,025 A 3/1993 Ranalletta ..................... 606/182

| | | | | |
|---|---|---|---|---|
| 5,201,324 | A | 4/1993 | Swierczek | 128/770 |
| 5,205,920 | A | 4/1993 | Oyama | 204/403 |
| 5,209,028 | A | 5/1993 | McDermott | 51/426 |
| 5,211,652 | A | 5/1993 | Derbyshire | 606/182 |
| 5,212,879 | A | 5/1993 | Biro | 29/437 |
| 5,215,587 | A | 6/1993 | McConnellogue | 118/699 |
| 5,216,597 | A | 6/1993 | Beckers | 364/413.02 |
| 5,217,480 | A | 6/1993 | Haber | 606/182 |
| 5,218,966 | A | 6/1993 | Yamasawa | 600/499 |
| 5,222,504 | A | 6/1993 | Solomon | 600/557 |
| 5,228,972 | A | 7/1993 | Osaka | 204/415 |
| 5,229,282 | A | 7/1993 | Yoshioka | 435/177 |
| 5,230,866 | A | 7/1993 | Shartle | 422/103 |
| 5,231,993 | A | 8/1993 | Haber et al. | 128/770 |
| 5,241,969 | A | 9/1993 | Carson | 600/566 |
| 5,247,932 | A | 9/1993 | Chung | 128/633 |
| 5,249,583 | A | 10/1993 | Mallaby | 600/567 |
| 5,250,066 | A | 10/1993 | Lambert | 606/181 |
| 5,251,126 | A | 10/1993 | Kahn | 364/413.11 |
| 5,253,656 | A | 10/1993 | Rincoe | 128/782 |
| 5,256,998 | A | 10/1993 | Becker | 335/229 |
| 5,264,103 | A | 11/1993 | Yoshioka | 204/403 |
| 5,264,105 | A | 11/1993 | Gregg | 204/403 |
| 5,264,106 | A | 11/1993 | McAleer | 204/403 |
| 5,266,179 | A | 11/1993 | Nankai | 204/401 |
| 5,266,359 | A | 11/1993 | Spielvogel | 427/388.4 |
| D342,573 | S | 12/1993 | Cerola | D24/147 |
| 5,272,087 | A | 12/1993 | El Murr | 435/291 |
| 5,277,181 | A | 1/1994 | Mendelson | 128/633 |
| 5,279,294 | A | 1/1994 | Anderson | 600/322 |
| 5,279,791 | A | 1/1994 | Aldrich | 422/58 |
| 5,282,822 | A | 2/1994 | Macors | 606/182 |
| 5,286,362 | A | 2/1994 | Hoenes | 204/403 |
| 5,286,364 | A | 2/1994 | Yacynych | 204/418 |
| 5,288,636 | A | 2/1994 | Pollmann | 435/288 |
| 5,294,261 | A | 3/1994 | McDermott | 134/7 |
| 5,296,378 | A | 3/1994 | Sakata | 436/63 |
| 5,300,779 | A | 4/1994 | Hillman | 250/341 |
| 5,304,192 | A | 4/1994 | Crouse | 606/181 |
| 5,304,193 | A | 4/1994 | Zhadanov | 606/182 |
| 5,304,347 | A | 4/1994 | Mann | 422/67 |
| 5,304,468 | A | 4/1994 | Phillips | 435/14 |
| 5,306,623 | A | 4/1994 | Kiser | 435/14 |
| 5,307,263 | A | 4/1994 | Brown | 600/301 |
| 5,312,590 | A | 5/1994 | Gunasingham | 422/56 |
| 5,314,441 | A | 5/1994 | Cusack | 606/182 |
| 5,314,442 | A | 5/1994 | Morita | 606/182 |
| 5,315,793 | A | 5/1994 | Peterson | 451/2 |
| 5,316,012 | A | 5/1994 | Siegal | 128/744 |
| 5,318,583 | A | 6/1994 | Rabenau | 606/182 |
| 5,318,584 | A | 6/1994 | Lange et al. | 606/182 |
| 5,320,607 | A | 6/1994 | Ishibashi | 604/115 |
| 5,320,808 | A | 6/1994 | Holen | 422/64 |
| 5,324,302 | A | 6/1994 | Crouse | 606/181 |
| 5,324,303 | A | 6/1994 | Strong | 606/181 |
| 5,330,634 | A | 7/1994 | Wong | 205/777.5 |
| 5,332,479 | A | 7/1994 | Uenoyama | 204/153.12 |
| 5,341,206 | A | 8/1994 | Pittaro | 356/301 |
| 5,342,382 | A | 8/1994 | Brinkerhoff | 606/184 |
| 5,344,703 | A | 9/1994 | Kovar | 428/312.6 |
| 5,350,392 | A | 9/1994 | Purcell | 606/182 |
| 5,352,351 | A | 10/1994 | White | 204/406 |
| 5,354,287 | A | 10/1994 | Wacks | 604/232 |
| 5,354,447 | A | 10/1994 | Uenoyama | 204/403 |
| 5,356,420 | A | 10/1994 | Czernecki | 606/182 |
| 5,360,410 | A | 11/1994 | Wacks | 604/232 |
| 5,365,699 | A | 11/1994 | Armstrong | 451/7 |
| 5,366,469 | A | 11/1994 | Steg | 606/182 |
| 5,366,470 | A | 11/1994 | Ramel | 606/183 |
| 5,366,609 | A | 11/1994 | White | 204/403 |
| 5,368,047 | A | 11/1994 | Suzuki | 600/578 |
| 5,370,509 | A | 12/1994 | Golding | 417/423.1 |
| 5,371,687 | A | 12/1994 | Holmes | 364/514 |
| 5,372,135 | A | 12/1994 | Mendelson | 600/322 |
| 5,375,397 | A | 12/1994 | Ferrand | 54/66 |
| 5,378,628 | A | 1/1995 | Gratzel | 435/288 |
| 5,382,346 | A | 1/1995 | Uenoyama | 204/403 |
| 5,383,885 | A | 1/1995 | Bland | 606/182 |
| 5,389,534 | A | 2/1995 | Gentzkow | 435/180 |
| 5,390,450 | A | 2/1995 | Goenka | 451/39 |
| 5,393,903 | A | 2/1995 | Gratzel | 556/137 |
| 5,395,339 | A | 3/1995 | Talonn | 604/111 |
| 5,395,387 | A | 3/1995 | Burns | 606/181 |
| 5,397,334 | A | 3/1995 | Schenk | 606/182 |
| 5,401,376 | A | 3/1995 | Foos | 204/415 |
| 5,402,798 | A | 4/1995 | Swierczek | 128/770 |
| 5,405,283 | A | 4/1995 | Goenka | 451/39 |
| 5,405,510 | A | 4/1995 | Betts | 205/782 |
| 5,405,511 | A | 4/1995 | White | 204/153.1 |
| 5,407,545 | A | 4/1995 | Hirose | 204/153.12 |
| 5,407,554 | A | 4/1995 | Saurer | 204/403 |
| 5,407,818 | A | 4/1995 | Gentzkow | 435/180 |
| 5,409,583 | A | 4/1995 | Yoshioka | 204/153.12 |
| 5,409,664 | A | 4/1995 | Allen | 422/56 |
| 5,410,059 | A | 4/1995 | Fraser | 546/10 |
| 5,415,169 | A | 5/1995 | Siczek | 600/427 |
| 5,418,142 | A | 5/1995 | Kiser | 435/14 |
| 5,423,847 | A | 6/1995 | Strong et al. | 606/182 |
| 5,424,545 | A | 6/1995 | Block | 350/343 |
| 5,426,032 | A | 6/1995 | Phillips | 435/14 |
| 5,436,161 | A | 7/1995 | Bergstrom | 435/291 |
| 5,437,999 | A | 8/1995 | Diebold | 435/288 |
| 5,438,271 | A | 8/1995 | White | 324/444 |
| 5,443,701 | A | 8/1995 | Willner | 204/153 |
| 5,445,920 | A | 8/1995 | Saito | 430/311 |
| D362,719 | S | 9/1995 | Kaplan | D24/147 |
| 5,453,360 | A | 9/1995 | Yu | 435/28 |
| 5,454,828 | A | 10/1995 | Schraga | 606/181 |
| 5,456,875 | A | 10/1995 | Lambert | 264/328.1 |
| 5,459,325 | A | 10/1995 | Hueton | 250/458.1 |
| 5,460,182 | A | 10/1995 | Goodman | 600/342 |
| 5,462,533 | A | 10/1995 | Daugherty | 604/164 |
| 5,464,418 | A | 11/1995 | Schraga | 606/182 |
| 5,465,722 | A | 11/1995 | Fort | 600/447 |
| 5,471,102 | A | 11/1995 | Becker | 310/50 |
| 5,472,427 | A | 12/1995 | Rammler | 604/164.01 |
| 5,474,084 | A | 12/1995 | Cunniff | 600/557 |
| 5,476,474 | A | 12/1995 | Davis | 606/182 |
| 5,480,387 | A | 1/1996 | Gabriel | 604/134 |
| 5,487,748 | A | 1/1996 | Marshall | 606/182 |
| D367,109 | S | 2/1996 | Ryner | D24/224 |
| 5,490,505 | A | 2/1996 | Diab | 600/323 |
| 5,496,274 | A | 3/1996 | Graves | 604/86 |
| 5,496,453 | A | 3/1996 | Uenoyama | 205/777.5 |
| 5,498,542 | A | 3/1996 | Corey | 435/283.1 |
| 5,501,836 | A | 3/1996 | Myerson | 42/57 |
| 5,501,893 | A | 3/1996 | Laermer | 428/161 |
| 5,507,288 | A | 4/1996 | Bocker | 128/633 |
| 5,507,629 | A | 4/1996 | Jarvik | 417/423.3 |
| 5,508,171 | A | 4/1996 | Walling | 205/777.5 |
| 5,509,410 | A | 4/1996 | Hill | 128/637 |
| 5,510,266 | A | 4/1996 | Bonner et al. | 436/43 |
| 5,512,159 | A | 4/1996 | Yoshioka et al. | 204/403 |
| 5,514,152 | A | 5/1996 | Smith | 606/182 |
| 5,515,170 | A | 5/1996 | Matzinger | 356/423 |
| 5,518,006 | A | 5/1996 | Mawhirt | 128/770 |
| D371,198 | S | 6/1996 | Savage | D24/169 |
| 5,524,636 | A | 6/1996 | Sarvazyan | 128/774 |
| 5,525,511 | A | 6/1996 | D'Costa | 435/287.9 |
| 5,525,518 | A | 6/1996 | Lundsgaard | 436/68 |
| 5,526,120 | A | 6/1996 | Jina | 356/446 |
| 5,527,333 | A | 6/1996 | Nikkels | 606/182 |
| 5,527,334 | A | 6/1996 | Kanner | 606/182 |
| 5,529,074 | A | 6/1996 | Greenfield | 600/557 |
| 5,540,676 | A | 7/1996 | Freiberg | |
| 5,540,709 | A | 7/1996 | Ramel | 606/183 |

| | | | | |
|---|---|---|---|---|
| 5,543,326 | A | 8/1996 | Heller et al. | 435/287.9 |
| 5,545,174 | A | 8/1996 | Schenk | 606/182 |
| 5,545,291 | A | 8/1996 | Smith | 438/107 |
| 5,547,702 | A | 8/1996 | Gleisner | 427/2.13 |
| D373,419 | S | 9/1996 | Muramatsu | D24/165 |
| 5,554,153 | A | 9/1996 | Costello | 606/9 |
| 5,554,166 | A | 9/1996 | Lange | 606/182 |
| 5,558,834 | A | 9/1996 | Chu | 422/55 |
| 5,562,384 | A | 10/1996 | Alvite | 414/226.01 |
| 5,562,696 | A | 10/1996 | Nobles | 606/185 |
| 5,563,031 | A | 10/1996 | Yu | 435/4 |
| 5,563,042 | A | 10/1996 | Phillips | 435/14 |
| 5,569,286 | A | 10/1996 | Peckham | 606/181 |
| 5,569,287 | A | 10/1996 | Tezuka | 606/182 |
| 5,571,132 | A | 11/1996 | Mawhirt | 606/182 |
| 5,575,284 | A | 11/1996 | Athan | 600/323 |
| 5,575,403 | A | 11/1996 | Charlton | 221/31 |
| 5,575,895 | A | 11/1996 | Ikeda | 204/403 |
| 5,582,697 | A | 12/1996 | Ikeda | 204/403 |
| 5,584,846 | A | 12/1996 | Mawhirt | 606/181 |
| 5,591,139 | A | 1/1997 | Lin | 604/264 |
| 5,593,852 | A | 1/1997 | Heller | 435/14 |
| 5,599,501 | A | 2/1997 | Carey | 422/64 |
| 5,605,837 | A | 2/1997 | Karimi | 436/14 |
| D378,612 | S | 3/1997 | Clark | D24/169 |
| 5,608,006 | A | 3/1997 | Myerson | 525/54.1 |
| 5,609,749 | A | 3/1997 | Yamauchi | 205/777.5 |
| 5,611,809 | A | 3/1997 | Marshall | 606/181 |
| 5,611,810 | A | 3/1997 | Arnold | 606/185 |
| 5,613,978 | A | 3/1997 | Harding | 606/181 |
| 5,616,135 | A | 4/1997 | Thorne | 604/192 |
| 5,617,851 | A | 4/1997 | Lipkovker | 600/573 |
| 5,618,297 | A | 4/1997 | Hart | 606/185 |
| 5,620,579 | A | 4/1997 | Genshaw et al. | 204/402 |
| 5,620,863 | A | 4/1997 | Tomasco | 435/14 |
| 5,624,458 | A | 4/1997 | Lipscher | 606/181 |
| 5,624,459 | A | 4/1997 | Kortenbach | 606/185 |
| 5,624,537 | A | 4/1997 | Turner | 204/403 |
| D379,516 | S | 5/1997 | Rutter | D24/146 |
| 5,628,764 | A | 5/1997 | Schraga | 606/182 |
| 5,628,765 | A | 5/1997 | Morita | 606/182 |
| 5,628,890 | A | 5/1997 | Carter | 204/403 |
| 5,628,961 | A | 5/1997 | Davis | 422/63 |
| 5,630,828 | A | 5/1997 | Mawhirt | 606/187 |
| 5,630,986 | A | 5/1997 | Charlton et al. | 422/64 |
| 5,632,410 | A | 5/1997 | Moulton | 221/79 |
| 5,640,954 | A | 6/1997 | Pfeiffer | 128/635 |
| D381,591 | S | 7/1997 | Rice | D10/81 |
| 5,643,306 | A | 7/1997 | Schraga | 606/182 |
| 5,643,308 | A | 7/1997 | Markman | 606/187 |
| 5,645,555 | A | 7/1997 | Davis | 606/182 |
| 5,647,851 | A | 7/1997 | Pokras | 604/131 |
| 5,650,062 | A | 7/1997 | Ikeda | 205/778 |
| 5,653,863 | A | 8/1997 | Genshaw | 205/777.5 |
| 5,657,760 | A | 8/1997 | Ying et al. | 128/660.03 |
| 5,658,444 | A | 8/1997 | Black | 204/415 |
| 5,660,791 | A | 8/1997 | Brenneman | 422/58 |
| D383,550 | S | 9/1997 | Larson | D24/225 |
| 5,662,127 | A | 9/1997 | De Vaughn | 128/765 |
| 5,662,672 | A | 9/1997 | Pambianchi | 606/181 |
| 5,666,966 | A | 9/1997 | Horie | 128/760 |
| 5,676,143 | A | 10/1997 | Simonsen | 128/633 |
| 5,678,306 | A | 10/1997 | Bozeman | 29/888.025 |
| 5,680,858 | A | 10/1997 | Hansen et al. | 128/635 |
| 5,680,872 | A | 10/1997 | Sesekura | 128/760 |
| 5,682,233 | A | 10/1997 | Brinda | 356/246 |
| 5,682,884 | A | 11/1997 | Hill | 128/637 |
| 5,683,562 | A | 11/1997 | Schaffar | 204/403 |
| 5,691,898 | A | 11/1997 | Rosenberg | 700/85 |
| 5,692,514 | A | 12/1997 | Bowman | 600/504 |
| 5,695,947 | A | 12/1997 | Guo | 435/11 |
| 5,700,695 | A | 12/1997 | Yassinzadeh | 436/180 |
| 5,705,045 | A | 1/1998 | Park | 204/403 |
| 5,707,384 | A | 1/1998 | Kim | 606/181 |
| 5,708,247 | A | 1/1998 | McAleer | 204/403 |
| 5,709,668 | A | 1/1998 | Wacks | 604/232 |
| 5,709,699 | A | 1/1998 | Warner | 606/181 |
| 5,710,011 | A | 1/1998 | Forrow | 435/25 |
| 5,714,123 | A | 2/1998 | Sohrab | 422/99 |
| 5,714,390 | A | 2/1998 | Hallowitz | 436/526 |
| 5,719,034 | A | 2/1998 | Kiser | 435/14 |
| 5,720,862 | A | 2/1998 | Hamamoto | 204/403 |
| 5,720,924 | A | 2/1998 | Eikmeier | 422/102 |
| D392,391 | S | 3/1998 | Douglas | D24/225 |
| D392,740 | S | 3/1998 | Yung | D24/169 |
| 5,723,284 | A | 3/1998 | Ye | 435/4 |
| 5,727,548 | A | 3/1998 | Hill | 128/637 |
| 5,729,905 | A | 3/1998 | Mathiasmeier | 33/3 R |
| 5,730,753 | A | 3/1998 | Morita | 606/181 |
| 5,733,085 | A | 3/1998 | Shida | 411/442 |
| 5,733,300 | A | 3/1998 | Pambianchi | 606/181 |
| D393,716 | S | 4/1998 | Brenneman | D24/147 |
| D393,717 | S | 4/1998 | Brenneman | D24/147 |
| 5,735,868 | A | 4/1998 | Lee | 606/189 |
| 5,736,103 | A | 4/1998 | Pugh | 422/68.1 |
| 5,738,244 | A | 4/1998 | Charlton | 221/26 |
| 5,741,228 | A | 4/1998 | Lambrecht | 604/93 |
| 5,741,634 | A | 4/1998 | Nozoe | 435/4 |
| RE35,803 | E | 5/1998 | Lange | 606/182 |
| 5,746,217 | A | 5/1998 | Erickson | 128/760 |
| 5,746,761 | A | 5/1998 | Turchin | 606/181 |
| 5,746,898 | A | 5/1998 | Preidel | 204/403 |
| 5,753,429 | A | 5/1998 | Pugh | 435/4 |
| 5,753,452 | A | 5/1998 | Smith | 435/14 |
| 5,755,228 | A | 5/1998 | Wilson | 600/459 |
| 5,755,733 | A | 5/1998 | Morita | 606/182 |
| 5,758,643 | A | 6/1998 | Wong | 600/309 |
| 5,759,364 | A | 6/1998 | Charlton | 204/403 |
| 5,762,770 | A | 6/1998 | Pritchard | 204/403 |
| 5,770,086 | A | 6/1998 | Indriksons | 210/643 |
| 5,770,369 | A | 6/1998 | Meade | 435/6 |
| 5,772,586 | A | 6/1998 | Heinonen | 600/300 |
| 5,772,677 | A | 6/1998 | Mawhirt | 606/181 |
| 5,773,270 | A | 6/1998 | D'Orazio | 435/177 |
| 5,776,157 | A | 7/1998 | Thorne | 606/182 |
| 5,776,719 | A | 7/1998 | Douglas | 435/28 |
| 5,779,365 | A | 7/1998 | Takaki | 374/161 |
| 5,780,304 | A | 7/1998 | Matzinger | 436/169 |
| 5,782,770 | A | 7/1998 | Mooradian | 600/476 |
| 5,782,852 | A | 7/1998 | Foggia | 606/182 |
| 5,788,651 | A | 8/1998 | Weilandt | 600/567 |
| 5,788,652 | A | 8/1998 | Rahn | 600/577 |
| 5,789,255 | A | 8/1998 | Yu | 536/95 |
| 5,794,219 | A | 8/1998 | Brown | 705/37 |
| 5,795,725 | A | 8/1998 | Buechler | 435/7.1 |
| 5,795,774 | A | 8/1998 | Matsumoto | 435/287.9 |
| 5,797,940 | A | 8/1998 | Mawhirt | 606/167 |
| 5,797,942 | A | 8/1998 | Schraga | 606/182 |
| 5,798,030 | A | 8/1998 | Raguse | 204/403 |
| 5,798,031 | A | 8/1998 | Charlton | 204/403 |
| 5,800,781 | A | 9/1998 | Gavin | 422/73 |
| 5,801,057 | A | 9/1998 | Smart | 436/68 |
| 5,807,375 | A | 9/1998 | Gross | 604/890.1 |
| 5,810,199 | A | 9/1998 | Charlton | 221/31 |
| D399,566 | S | 10/1998 | Sohrab | D24/169 |
| 5,820,551 | A | 10/1998 | Hill | 600/347 |
| 5,822,715 | A | 10/1998 | Worthington | 702/19 |
| 5,823,973 | A | 10/1998 | Racchini | 600/573 |
| 5,824,491 | A | 10/1998 | Priest | 435/28 |
| 5,827,181 | A | 10/1998 | Dias | 600/322 |
| 5,828,943 | A | 10/1998 | Brown | 434/258 |
| 5,829,589 | A | 11/1998 | Nguyen | 206/366 |
| 5,830,219 | A | 11/1998 | Bird et al. | 606/130 |
| 5,832,448 | A | 11/1998 | Brown | 705/2 |
| 5,840,020 | A | 11/1998 | Heinonen | 600/309 |
| 5,840,171 | A | 11/1998 | Birch | 205/335 |

5,843,691 A 12/1998 Douglas ........................ 435/14
5,843,692 A 12/1998 Phillips ........................ 435/14
5,846,216 A 12/1998 Gonzales ........................ 604/2
5,846,486 A 12/1998 Pugh ........................ 422/56
5,846,490 A 12/1998 Yokota ........................ 422/66
5,849,174 A 12/1998 Sanghera ........................ 205/775
5,853,373 A 12/1998 Griffith ........................ 600/554
5,854,074 A 12/1998 Charlton et al. ........................ 436/46
D403,975 S 1/1999 Douglas ........................ D10/81
5,855,377 A 1/1999 Murphy ........................ 279/50
5,855,801 A 1/1999 Lin et al. ........................ 216/2
5,856,174 A 1/1999 Lipshutz ........................ 435/286.5
5,856,195 A 1/1999 Charlton ........................ 436/50
5,857,967 A 1/1999 Frid ........................ 600/301
5,857,983 A 1/1999 Douglas ........................ 600/538
5,858,804 A 1/1999 Zanzucchi ........................ 506/9
5,860,922 A 1/1999 Gordon et al. ........................ 600/431
5,863,800 A 1/1999 Eikmeier ........................ 436/48
5,866,353 A 2/1999 Berneth ........................ 435/26
5,868,135 A 2/1999 Kaufman ........................ 128/630
5,868,772 A 2/1999 LeVaughn ........................ 606/181
5,869,972 A 2/1999 Birch ........................ 324/439
5,871,494 A 2/1999 Simons et al.
5,872,713 A 2/1999 Douglas ........................ 702/85
5,873,887 A 2/1999 King ........................ 606/182
5,876,351 A 3/1999 Rohde ........................ 600/523
5,876,957 A 3/1999 Douglas ........................ 435/28
5,879,163 A 3/1999 Brown ........................ 434/236
5,879,310 A 3/1999 Sopp ........................ 600/578
5,879,311 A 3/1999 Duchon ........................ 600/583
5,879,373 A 3/1999 Roper ........................ 606/344
5,880,829 A 3/1999 Kauhaniemi ........................ 356/246
5,882,494 A 3/1999 van Antwerp ........................ 204/403
5,885,211 A 3/1999 Eppstein ........................ 600/309
5,886,056 A 3/1999 Hershkowitz ........................ 518/703
5,887,133 A 3/1999 Brown ........................ 395/200.3
5,890,128 A 3/1999 Diaz ........................ 705/2
RE36,191 E 4/1999 Solomon ........................ 395/308
5,891,053 A 4/1999 Sesekura ........................ 600/583
5,893,848 A 4/1999 Negus ........................ 606/41
5,893,870 A 4/1999 Talen ........................ 606/201
5,897,493 A 4/1999 Brown ........................ 600/300
5,897,569 A 4/1999 Kellogg ........................ 606/169
5,899,855 A 5/1999 Brown ........................ 600/301
5,899,915 A 5/1999 Saadat ........................ 606/170
5,900,130 A 5/1999 Benvegnu ........................ 204/453
5,902,731 A 5/1999 Ouyang ........................ 435/26
5,906,921 A 5/1999 Ikeda ........................ 435/25
D411,619 S 6/1999 Duchon ........................ D24/146
5,908,416 A 6/1999 Costello ........................ 606/9
5,911,937 A 6/1999 Hekal ........................ 264/255
5,912,134 A 6/1999 Shartle ........................ 435/7.24
5,913,310 A 6/1999 Brown ........................ 128/897
5,916,156 A 6/1999 Hildenbrand ........................ 600/347
5,916,229 A 6/1999 Evans ........................ 606/171
5,916,230 A 6/1999 Brenneman ........................ 606/172
5,918,603 A 7/1999 Brown ........................ 128/897
5,919,711 A 7/1999 Boyd ........................ 436/178
5,921,963 A 7/1999 Erez ........................ 604/192
5,922,188 A 7/1999 Ikeda ........................ 204/777.5
5,922,530 A 7/1999 Yu ........................ 435/4
5,922,591 A 7/1999 Anderson ........................ 435/287.2
RE36,268 E 8/1999 Szuminsky ........................ 205/777.5
5,931,794 A 8/1999 Pitesky ........................ 600/556
5,933,136 A 8/1999 Brown ........................ 345/327
5,935,075 A 8/1999 Casscells et al. ........................ 600/474
5,938,679 A 8/1999 Freeman ........................ 606/181
5,940,153 A 8/1999 Castaneda
5,942,102 A 8/1999 Hodges ........................ 205/775
5,942,189 A 8/1999 Wolfbeis ........................ 422/82.08
5,947,957 A 9/1999 Morris ........................ 606/13
5,951,300 A 9/1999 Brown ........................ 434/236
5,951,492 A 9/1999 Douglas ........................ 600/583
5,951,493 A 9/1999 Douglas et al. ........................ 600/583
5,951,582 A 9/1999 Thorne ........................ 606/182
5,951,836 A 9/1999 McAleer ........................ 204/403
5,954,738 A 9/1999 LeVaughn ........................ 606/181
5,956,501 A 9/1999 Brown ........................ 395/500.32
5,957,846 A 9/1999 Chiang ........................ 600/447
5,958,199 A 9/1999 Miyamoto ........................ 204/403
5,959,098 A 9/1999 Goldberg ........................ 536/25.3
5,960,403 A 9/1999 Brown ........................ 705/2
5,961,451 A 10/1999 Reber ........................ 600/322
5,964,718 A 10/1999 Duchon ........................ 600/583
5,965,380 A 10/1999 Heller ........................ 435/14
5,968,063 A 10/1999 Chu ........................ 606/185
5,968,760 A 10/1999 Phillips ........................ 436/14
5,968,836 A 10/1999 Matzinger ........................ 436/169
5,971,941 A 10/1999 Simons et al. ........................ 600/573
5,972,199 A 10/1999 Heller ........................ 205/777.5
5,972,294 A 10/1999 Smith ........................ 422/58
5,972,715 A 10/1999 Celentano ........................ 436/164
5,974,124 A 10/1999 Schlueter ........................ 379/106.02
5,976,085 A 11/1999 Kimball ........................ 600/309
5,983,193 A 11/1999 Heinonen ........................ 705/2
5,985,116 A 11/1999 Ikeda ........................ 204/403
5,985,559 A 11/1999 Brown ........................ 435/6
5,986,754 A 11/1999 Harding ........................ 356/246
5,993,400 A 11/1999 Rincoe ........................ 600/595
5,993,434 A 11/1999 Dev ........................ 604/501
D417,504 S 12/1999 Love ........................ D24/169
5,997,476 A 12/1999 Brown ........................ 600/300
5,997,561 A 12/1999 Boecker ........................ 606/182
5,997,817 A 12/1999 Crismore et al. ........................ 422/58
5,997,818 A 12/1999 Hackner ........................ 422/681
6,001,067 A 12/1999 Shults ........................ 600/584
6,007,497 A 12/1999 Huitema ........................ 600/567
D418,602 S 1/2000 Prokop ........................ D24/169
6,014,577 A 1/2000 Henning ........................ 600/345
6,015,392 A 1/2000 Douglas ........................ 600/583
6,018,289 A 1/2000 Sekura ........................ 340/309.4
6,020,110 A 2/2000 Williams ........................ 430/315
6,022,324 A 2/2000 Skinner ........................ 600/566
6,022,366 A 2/2000 Schraga ........................ 606/181
6,022,748 A 2/2000 Charych ........................ 436/527
6,023,629 A 2/2000 Tamada ........................ 600/347
6,023,686 A 2/2000 Brown ........................ 705/37
6,027,459 A 2/2000 Shain et al. ........................ 600/573
6,030,399 A 2/2000 Ignotz ........................ 606/167
6,030,827 A 2/2000 Davis ........................ 435/287
6,030,967 A 2/2000 Marui ........................ 514/215
6,032,059 A 2/2000 Henning ........................ 600/345
6,032,119 A 2/2000 Brown ........................ 705/2
6,033,421 A 3/2000 Theiss ........................ 606/186
6,033,866 A 3/2000 Guo ........................ 435/14
6,036,924 A 3/2000 Simons et al. ........................ 422/100
6,037,178 A 3/2000 Leiner ........................ 436/50
6,041,253 A 3/2000 Kost ........................ 604/20
6,045,567 A 4/2000 Taylor ........................ 606/181
6,046,055 A 4/2000 Wolfbeis ........................ 436/172
6,048,352 A 4/2000 Douglas ........................ 606/181
D424,696 S 5/2000 Ray ........................ D24/169
6,056,701 A 5/2000 Duchon ........................ 600/583
6,059,815 A 5/2000 Lee ........................ 606/209
6,060,327 A 5/2000 Keen ........................ 436/518
6,061,128 A 5/2000 Zweig ........................ 356/243.4
6,063,039 A 5/2000 Cunningham ........................ 600/573
6,066,103 A 5/2000 Duchon ........................ 600/583
6,066,243 A 5/2000 Anderson ........................ 422/82.01
6,066,296 A 5/2000 Brady ........................ 422/63
6,067,463 A 5/2000 Jeng ........................ 600/336
6,068,615 A 5/2000 Brown ........................ 604/207
D426,638 S 6/2000 Ray ........................ D24/169
6,070,761 A 6/2000 Bloom ........................ 222/81
6,071,249 A 6/2000 Cunningham ........................ 600/578
6,071,250 A 6/2000 Douglas ........................ 600/583

| | | | |
|---|---|---|---|
| 6,071,251 A | 6/2000 | Cunningham | 600/584 |
| 6,071,294 A | 6/2000 | Simons et al. | 606/181 |
| 6,071,391 A | 6/2000 | Gotoh | 204/403 |
| 6,074,360 A | 6/2000 | Haar et al. | 604/57 |
| 6,077,408 A | 6/2000 | Miyamoto | 204/403 |
| 6,080,106 A | 6/2000 | Lloyd | 600/300 |
| 6,080,172 A | 6/2000 | Fujiwara | 606/166 |
| D428,150 S | 7/2000 | Ruf | D24/146 |
| 6,083,196 A | 7/2000 | Trautman | 604/46 |
| 6,083,710 A | 7/2000 | Heller | 435/14 |
| 6,084,660 A | 7/2000 | Shartle | 356/39 |
| 6,085,576 A | 7/2000 | Sunshine | 73/29.01 |
| 6,086,544 A | 7/2000 | Hibner | 600/568 |
| 6,086,545 A | 7/2000 | Roe | 600/570 |
| 6,086,562 A | 7/2000 | Jacobsen | 604/156 |
| 6,090,078 A | 7/2000 | Erskine | 604/198 |
| 6,091,975 A | 7/2000 | Daddona | 600/345 |
| 6,093,146 A | 7/2000 | Filangeri | 600/300 |
| 6,093,156 A | 7/2000 | Cunningham | |
| D428,993 S | 8/2000 | Lubs | D24/165 |
| 6,099,484 A | 8/2000 | Douglas | 600/583 |
| 6,099,802 A | 8/2000 | Pugh | 422/58 |
| 6,100,107 A | 8/2000 | Lei | 438/50 |
| 6,101,478 A | 8/2000 | Brown | 705/2 |
| 6,102,933 A | 8/2000 | Lee | 606/209 |
| 6,103,033 A | 8/2000 | Say | 156/73.1 |
| 6,103,509 A | 8/2000 | Sode | 435/190 |
| 6,104,940 A | 8/2000 | Watanabe | 600/345 |
| 6,106,751 A | 8/2000 | Talbot | 264/81 |
| 6,107,083 A | 8/2000 | Collins | 435/288 |
| 6,113,578 A | 9/2000 | Brown | 604/207 |
| 6,117,630 A | 9/2000 | Reber | 435/4 |
| 6,118,126 A | 9/2000 | Zanzucchi | 250/458.1 |
| 6,119,033 A | 9/2000 | Spigelman | 600/426 |
| 6,120,462 A | 9/2000 | Hibner | 600/566 |
| 6,120,676 A | 9/2000 | Heller | 205/777.5 |
| 6,121,009 A | 9/2000 | Heller | 435/14 |
| 6,122,536 A | 9/2000 | Sun | 600/341 |
| 6,126,804 A | 10/2000 | Andresen | 204/601 |
| 6,126,899 A | 10/2000 | Woudenberg | 422/50 |
| 6,129,823 A | 10/2000 | Hughes | 204/403.01 |
| 6,132,449 A | 10/2000 | Lum et al. | 606/181 |
| 6,133,837 A | 10/2000 | Riley | 340/573.1 |
| 6,134,461 A | 10/2000 | Say | 600/345 |
| 6,136,013 A | 10/2000 | Marshall | 606/167 |
| 6,139,562 A | 10/2000 | Mauze | 606/171 |
| 6,143,164 A | 11/2000 | Heller | 600/583 |
| 6,144,837 A | 11/2000 | Quy | 434/307 R |
| 6,149,203 A | 11/2000 | Hanlon | 283/72 |
| 6,151,586 A | 11/2000 | Brown | 705/14 |
| 6,152,875 A | 11/2000 | Hakamata | 600/319 |
| 6,152,942 A | 11/2000 | Brenneman | 606/181 |
| 6,153,069 A | 11/2000 | Pottgen | 204/403 |
| RE36,991 E | 12/2000 | Yamamoto et al. | 204/403 |
| 6,155,267 A | 12/2000 | Nelson | 128/899 |
| 6,155,992 A | 12/2000 | Henning et al. | 600/583 |
| 6,156,051 A | 12/2000 | Schraga | 600/181 |
| 6,157,442 A | 12/2000 | Raskas | 356/39 |
| 6,159,147 A | 12/2000 | Lichter | 600/300 |
| 6,159,424 A | 12/2000 | Kauhaniemi | 422/63 |
| 6,161,095 A | 12/2000 | Brown | 705/2 |
| 6,162,397 A | 12/2000 | Jurik | 422/56 |
| 6,162,611 A | 12/2000 | Heller | 435/14 |
| 6,167,362 A | 12/2000 | Brown | 703/11 |
| 6,167,386 A | 12/2000 | Brown | 705/37 |
| 6,168,563 B1 | 1/2001 | Brown | 600/301 |
| 6,168,957 B1 | 1/2001 | Matzinger | 436/518 |
| 6,171,325 B1 | 1/2001 | Mauze et al. | 606/171 |
| 6,175,752 B1 | 1/2001 | Say | 600/345 |
| 6,176,847 B1 | 1/2001 | Humphreys | 604/246 |
| 6,176,865 B1 | 1/2001 | Mauze et al. | 606/171 |
| 6,177,000 B1 | 1/2001 | Peterson | 205/777.5 |
| 6,177,931 B1 | 1/2001 | Alexander et al. | |
| 6,183,489 B1 | 2/2001 | Douglas | 606/181 |
| 6,186,145 B1 | 2/2001 | Brown | 128/897 |
| 6,190,612 B1 | 2/2001 | Berger | 422/82.07 |
| 6,191,852 B1 | 2/2001 | Paffhausen | 356/244 |
| 6,192,891 B1 | 2/2001 | Gravel | 128/920 |
| 6,193,673 B1 | 2/2001 | Viola | 600/568 |
| 6,193,873 B1 | 2/2001 | Ohara et al. | 205/792 |
| 6,194,900 B1 | 2/2001 | Freeman | 324/321 |
| 6,197,040 B1 | 3/2001 | LeVaughn | 205/792 |
| 6,197,257 B1 | 3/2001 | Raskas | 422/82.05 |
| 6,200,773 B1 | 3/2001 | Ouyang | 435/26 |
| 6,203,504 B1 | 3/2001 | Latterell | 600/576 |
| 6,206,841 B1 | 3/2001 | Cunningham et al. | 600/584 |
| 6,210,133 B1 | 4/2001 | Aboul-Hosn | 417/423.1 |
| 6,210,272 B1 | 4/2001 | Brown | 463/1 |
| 6,210,369 B1 | 4/2001 | Wilmot | 604/157 |
| 6,210,420 B1 | 4/2001 | Mauze | 606/182 |
| 6,210,421 B1 | 4/2001 | Bocker | 606/182 |
| 6,212,417 B1 | 4/2001 | Ikeda | 204/403.14 |
| 6,214,626 B1 | 4/2001 | Meller | 436/165 |
| 6,214,804 B1 | 4/2001 | Felgner | 514/44 |
| 6,218,571 B1 | 4/2001 | Zheng | 562/61 |
| 6,219,574 B1 | 4/2001 | Cormier | 604/20 |
| 6,221,023 B1 | 4/2001 | Matsuba | 600/486 |
| 6,221,238 B1 | 4/2001 | Grundig | 205/777.5 |
| 6,225,078 B1 | 5/2001 | Ikeda | 435/25 |
| 6,228,100 B1 | 5/2001 | Schraga | |
| 6,230,051 B1 | 5/2001 | Cormier | 604/20 |
| 6,230,501 B1 | 5/2001 | Bailey | 62/51.1 |
| 6,231,531 B1 | 5/2001 | Lum | 601/46 |
| 6,233,471 B1 | 5/2001 | Berner | 600/345 |
| 6,233,539 B1 | 5/2001 | Brown | 703/11 |
| 6,234,772 B1 | 5/2001 | Wampler | 417/423.12 |
| 6,240,393 B1 | 5/2001 | Brown | 705/1 |
| D444,235 S | 6/2001 | Roberts | D24/169 |
| 6,241,862 B1 | 6/2001 | McAleer | 204/403 |
| 6,242,207 B1 | 6/2001 | Douglas | 435/25 |
| 6,245,060 B1 | 6/2001 | Loomis | 606/9 |
| 6,245,215 B1 | 6/2001 | Douglas | 205/775 |
| 6,246,992 B1 | 6/2001 | Brown | 705/2 |
| 6,248,065 B1 | 6/2001 | Brown | 600/300 |
| 6,251,083 B1 | 6/2001 | Yum | 600/584 |
| 6,251,121 B1 | 6/2001 | Saadat | 606/180 |
| 6,251,260 B1 | 6/2001 | Heller | 205/777.5 |
| 6,251,344 B1 | 6/2001 | Goldstein | 422/123 |
| D444,557 S | 7/2001 | Levaughn | D24/146 |
| 6,254,831 B1 | 7/2001 | Barnard | 422/82.08 |
| 6,256,533 B1 | 7/2001 | Yuzhakov | 604/21 |
| 6,258,111 B1 | 7/2001 | Ross | 606/171 |
| 6,258,229 B1 | 7/2001 | Winarta | 204/403 |
| 6,258,254 B1 | 7/2001 | Miyamoto | 205/777.5 |
| 6,261,241 B1 | 7/2001 | Burbank | 600/564 |
| 6,261,245 B1 | 7/2001 | Kawai | 600/576 |
| 6,261,519 B1 | 7/2001 | Harding | |
| 6,264,635 B1 | 7/2001 | Wampler | 604/151 |
| 6,268,161 B1 | 7/2001 | Han | 435/14 |
| 6,268,162 B1 | 7/2001 | Phillips | 435/14 |
| 6,269,314 B1 | 7/2001 | Iitawaki | 702/23 |
| 6,270,455 B1 | 8/2001 | Brown | 600/300 |
| 6,270,637 B1 | 8/2001 | Crismore | 204/403 |
| 6,272,359 B1 | 8/2001 | Kivela | 455/567 |
| 6,272,364 B1 | 8/2001 | Kurnik | 600/345 |
| 6,275,717 B1 | 8/2001 | Gross | 600/345 |
| 6,280,254 B1 | 8/2001 | Wu | 439/630 |
| 6,281,006 B1 | 8/2001 | Heller | 435/287.9 |
| 6,283,926 B1 | 9/2001 | Cunningham | 600/573 |
| 6,283,982 B1 | 9/2001 | Levaughn | 606/172 |
| 6,284,478 B1 | 9/2001 | Heller | 435/14 |
| 6,285,448 B1 | 9/2001 | Kuenstner | 356/39 |
| 6,285,454 B1 | 9/2001 | Douglas | 356/446 |
| 6,289,254 B1 | 9/2001 | Shimizu | 700/96 |
| 6,290,683 B1 | 9/2001 | Erez | 604/273 |
| 6,294,897 B1 | 9/2001 | Champlin | 320/153 |

| Patent No. | Kind | Date | Inventor | Class |
|---|---|---|---|---|
| 6,295,506 | B1 | 9/2001 | Heinonen | 702/104 |
| 6,299,578 | B1 | 10/2001 | Kurnik | 600/309 |
| 6,299,596 | B1 | 10/2001 | Ding | 604/96.01 |
| 6,299,757 | B1 | 10/2001 | Feldman | 205/775 |
| 6,302,844 | B1 | 10/2001 | Walker | 600/300 |
| 6,302,855 | B1 | 10/2001 | Lav | 600/584 |
| 6,305,804 | B1 | 10/2001 | Rice | 351/221 |
| 6,306,104 | B1 | 10/2001 | Cunningham | 600/573 |
| 6,306,152 | B1 | 10/2001 | Verdonk | 606/182 |
| 6,306,347 | B1 | 10/2001 | Mason | 422/58 |
| 6,309,351 | B1 | 10/2001 | Kurnik | 600/309 |
| 6,309,535 | B1 | 10/2001 | Williams | 205/777.5 |
| 6,312,612 | B1 | 11/2001 | Sherman | 216/2 |
| 6,315,738 | B1 | 11/2001 | Nishikawa et al. | 600/583 |
| 6,318,970 | B1 | 11/2001 | Backhouse | 417/92 |
| 6,319,210 | B1 | 11/2001 | Douglas | 600/583 |
| 6,322,574 | B1 | 11/2001 | Lloyd | 606/181 |
| 6,322,808 | B1 | 11/2001 | Trautman | 424/448 |
| 6,322,963 | B1 | 11/2001 | Bauer | 435/4 |
| 6,329,161 | B1 | 12/2001 | Heller | 435/14 |
| 6,330,426 | B2 | 12/2001 | Brown | 434/307 R |
| 6,331,163 | B1 | 12/2001 | Kaplan | 600/486 |
| 6,332,871 | B1 | 12/2001 | Douglas | 600/583 |
| 6,334,363 | B1 | 1/2002 | Testud | 73/862 |
| 6,334,778 | B1 | 1/2002 | Brown | 434/258 |
| 6,334,856 | B1 | 1/2002 | Allen | 604/191 |
| 6,335,203 | B1 | 1/2002 | Patel | 436/169 |
| 6,336,900 | B1 | 1/2002 | Alleckson | 600/485 |
| 6,338,790 | B1 | 1/2002 | Feldman | 205/777.5 |
| 6,346,120 | B1 | 2/2002 | Yamazaki | 623/3.13 |
| 6,349,229 | B1 | 2/2002 | Watanabe | 600/345 |
| 6,350,273 | B1 | 2/2002 | Minagawa | 606/186 |
| 6,350,451 | B1 | 2/2002 | Horn | 424/184.1 |
| 6,352,514 | B1 | 3/2002 | Douglas | 600/583 |
| 6,352,523 | B1 | 3/2002 | Brown | 604/207 |
| 6,353,753 | B1 | 3/2002 | Flock | 600/473 |
| 6,364,889 | B1 | 4/2002 | Kheiri | 606/181 |
| 6,364,890 | B1 | 4/2002 | Lum | 606/181 |
| 6,368,273 | B1 | 4/2002 | Brown | 600/300 |
| 6,375,469 | B1 | 4/2002 | Brown | 434/236 |
| 6,375,627 | B1 | 4/2002 | Mauze | 600/584 |
| 6,379,301 | B1 | 4/2002 | Worthington | 600/309 |
| 6,379,317 | B1 | 4/2002 | Kintzig | 600/573 |
| 6,379,324 | B1 | 4/2002 | Gartstein | 604/22 |
| 6,379,969 | B1 | 4/2002 | Mauze et al. | |
| 6,381,577 | B1 | 4/2002 | Brown | 705/2 |
| D456,910 | S | 5/2002 | Clark | D24/225 |
| 6,387,709 | B1 | 5/2002 | Mason | 436/164 |
| 6,391,005 | B1 | 5/2002 | Lum | 604/117 |
| 6,395,227 | B1 | 5/2002 | Kiser | 422/56 |
| 6,398,522 | B2 | 6/2002 | Skill | 417/410.3 |
| 6,398,562 | B1 | 6/2002 | Butler | 439/91 |
| 6,399,394 | B1 | 6/2002 | Dahm | 436/180 |
| 6,402,701 | B1 | 6/2002 | Kaplan | 600/567 |
| 6,402,704 | B1 | 6/2002 | McMorrow | 600/576 |
| 6,409,740 | B1 | 6/2002 | Kuhr | 606/182 |
| 6,413,410 | B1 | 7/2002 | Hodges | 205/775 |
| 6,413,411 | B1 | 7/2002 | Pottgen | 205/777.5 |
| 6,415,821 | B2 | 7/2002 | Kamholz | 137/827 |
| 6,420,128 | B1 | 7/2002 | Ouyang | 435/14 |
| 6,421,633 | B1 | 7/2002 | Heinonen | 703/11 |
| 6,423,014 | B1 | 7/2002 | Churchill | 600/587 |
| 6,428,664 | B1 | 8/2002 | Bhullar | 204/403.03 |
| 6,436,055 | B1 | 8/2002 | Roe | 600/584 |
| 6,436,256 | B1 | 8/2002 | Williams | 204/403.06 |
| 6,436,721 | B1 | 8/2002 | Kuo | 436/514 |
| 6,440,645 | B1 | 8/2002 | Yon-Hin | 430/322 |
| 6,444,115 | B1 | 9/2002 | Hodges | 205/792 |
| 6,447,265 | B1 | 9/2002 | Antaki | 417/354 |
| 6,451,040 | B1 | 9/2002 | Purcell | 606/181 |
| 6,453,810 | B1 | 9/2002 | Rossmeisl | 101/123 |
| 6,458,258 | B2 | 10/2002 | Taniike | 204/403 |
| 6,461,496 | B1 | 10/2002 | Feldman et al. | 205/777.5 |
| 6,462,162 | B2 | 10/2002 | van Antwerp | 528/77 |
| 6,464,649 | B1 | 10/2002 | Duchon | 600/583 |
| 6,471,903 | B2 | 10/2002 | Sherman | 264/328.1 |
| 6,472,220 | B1 | 10/2002 | Simons | 436/63 |
| 6,475,360 | B1 | 11/2002 | Hodges | 204/403.14 |
| 6,475,372 | B1 | 11/2002 | Ohara | 205/777.5 |
| 6,475,436 | B1 | 11/2002 | Schabbach | 422/64 |
| 6,475,750 | B1 | 11/2002 | Han | 435/14 |
| 6,477,394 | B2 | 11/2002 | Rice | 600/318 |
| 6,477,424 | B1 | 11/2002 | Thompson | 607/60 |
| 6,484,046 | B1 | 11/2002 | Say | 600/345 |
| 6,485,439 | B1 | 11/2002 | Roe | 600/578 |
| 6,485,461 | B1 | 11/2002 | Mason | 604/132 |
| 6,485,923 | B1 | 11/2002 | Yani | 435/14 |
| 6,488,827 | B1 | 12/2002 | Shartle | 204/403 |
| 6,488,891 | B2 | 12/2002 | Mason | 422/58 |
| 6,489,133 | B2 | 12/2002 | Phillips | 435/14 |
| 6,491,709 | B2 | 12/2002 | Sharma | 606/181 |
| 6,491,870 | B2 | 12/2002 | Patel | 422/58 |
| 6,494,830 | B1 | 12/2002 | Wessel | 600/300 |
| 6,497,845 | B1 | 12/2002 | Sacherer | 422/104 |
| 6,501,404 | B2 | 12/2002 | Walker | 341/143 |
| 6,501,976 | B1 | 12/2002 | Sohrab | 600/347 |
| 6,503,209 | B2 | 1/2003 | Hakky et al. | |
| 6,503,210 | B1 | 1/2003 | Hirao | 600/576 |
| 6,503,231 | B1 | 1/2003 | Praunsnitz | 604/272 |
| 6,503,381 | B1 | 1/2003 | Gotoh | 204/403.14 |
| 6,506,165 | B1 | 1/2003 | Sweeney | 600/562 |
| 6,506,168 | B1 | 1/2003 | Fathallah | 600/578 |
| 6,506,575 | B1 | 1/2003 | Knappe | 435/25 |
| 6,508,785 | B1 | 1/2003 | Eppstein | 604/113 |
| 6,512,986 | B1 | 1/2003 | Harmon | 702/84 |
| 6,514,270 | B1 | 2/2003 | Schraga | 606/182 |
| 6,514,460 | B1 | 2/2003 | Fendrock | 422/55 |
| 6,519,241 | B1 | 2/2003 | Theimer | 370/338 |
| 6,520,326 | B2 | 2/2003 | McIvor | 206/305 |
| 6,521,110 | B1 | 2/2003 | Hodges | 204/403.14 |
| 6,521,182 | B1 | 2/2003 | Shartle | 422/58 |
| 6,527,521 | B2 | 3/2003 | Noda | 417/355 |
| 6,527,716 | B1 | 3/2003 | Eppstein | 600/309 |
| 6,527,778 | B2 | 3/2003 | Athanasiou | 606/80 |
| 6,529,377 | B1 | 3/2003 | Nelson et al. | 361/699 |
| 6,530,892 | B1 | 3/2003 | Kelly | 600/583 |
| 6,530,937 | B1 | 3/2003 | Schraga | 606/182 |
| 6,531,322 | B1 | 3/2003 | Jurik | 436/95 |
| 6,533,949 | B1 | 3/2003 | Yeshurun | 216/11 |
| 6,537,207 | B1 | 3/2003 | Rice | 600/121 |
| 6,537,242 | B1 | 3/2003 | Palmer | 604/22 |
| 6,537,292 | B1 | 3/2003 | Lee | 606/182 |
| 6,540,672 | B1 | 4/2003 | Simonsen | 600/300 |
| 6,540,675 | B2 | 4/2003 | Aceti | 600/309 |
| 6,540,762 | B1 | 4/2003 | Bertling | 606/182 |
| 6,540,891 | B1 | 4/2003 | Stewart | 204/403.14 |
| 6,541,266 | B2 | 4/2003 | Modzelewski | 436/95 |
| 6,547,954 | B2 | 4/2003 | Ikeda | 205/777.5 |
| 6,549,796 | B2 | 4/2003 | Sohrab | 600/345 |
| 6,551,494 | B1 | 4/2003 | Heller et al. | 205/777.5 |
| 6,553,244 | B2 | 4/2003 | Lesho | 600/347 |
| 6,554,381 | B2 | 4/2003 | Locher | 347/7 |
| 6,555,061 | B1 | 4/2003 | Leong et al. | 422/58 |
| D475,136 | S | 5/2003 | Taniguchi | D24/165 |
| 6,558,320 | B1 | 5/2003 | Causey | 600/300 |
| 6,558,361 | B1 | 5/2003 | Yeshurun | 604/272 |
| 6,558,402 | B1 | 5/2003 | Chelak | 606/182 |
| 6,558,528 | B1 | 5/2003 | Matzinger | 205/777.5 |
| 6,560,471 | B1 | 5/2003 | Heller | 600/347 |
| 6,561,978 | B1 | 5/2003 | Conn | 600/309 |
| 6,561,989 | B2 | 5/2003 | Whitson | 600/573 |
| 6,562,210 | B1 | 5/2003 | Bhullar | 204/403.3 |
| 6,565,509 | B1 | 5/2003 | Plante | 600/365 |
| 6,565,808 | B2 | 5/2003 | Hudak | 422/58 |
| 6,569,157 | B1 | 5/2003 | Shain | 606/12 |
| 6,571,651 | B1 | 6/2003 | Hodges | 73/864.72 |

| | | | | |
|---|---|---|---|---|
| 6,572,566 | B2 | 6/2003 | Effenhauser | 600/584 |
| 6,572,822 | B2 | 6/2003 | Jurik | 422/56 |
| 6,574,490 | B2 | 6/2003 | Abbink | 600/316 |
| 6,575,905 | B2 | 6/2003 | Knobbe | 600/365 |
| 6,576,101 | B1 | 6/2003 | Heller | 204/403.14 |
| 6,576,117 | B1 | 6/2003 | Iketaki | 205/777.5 |
| 6,576,416 | B2 | 6/2003 | Haviland | 435/4 |
| 6,579,690 | B1 | 6/2003 | Bonnecaze | 435/14 |
| 6,582,573 | B2 | 6/2003 | Douglas | 204/403.1 |
| 6,584,338 | B1 | 6/2003 | Van Muiswinkel | 435/419 |
| D477,670 | S | 7/2003 | Jurik | D24/225 |
| 6,586,199 | B2 | 7/2003 | Ouyang | 435/26 |
| 6,587,705 | B1 | 7/2003 | Berner et al. | 600/347 |
| 6,589,260 | B1 | 7/2003 | Schmelzeisen-Redeker | 606/181 |
| 6,589,261 | B1 | 7/2003 | Abulhaj | 606/181 |
| 6,591,124 | B2 | 7/2003 | Sherman | 600/345 |
| 6,591,125 | B1 | 7/2003 | Buse | 600/347 |
| 6,592,744 | B1 | 7/2003 | Hodges | 205/775 |
| 6,592,745 | B1 | 7/2003 | Feldman | 205/777.5 |
| 6,595,919 | B2 | 7/2003 | Berner | 600/365 |
| 6,599,407 | B2 | 7/2003 | Taniike | 204/403.1 |
| 6,599,693 | B1 | 7/2003 | Webb | 435/4 |
| 6,599,769 | B2 | 7/2003 | Kondo | 438/28 |
| 6,601,534 | B2 | 8/2003 | Hebrank | 119/6.8 |
| 6,602,205 | B1 | 8/2003 | Erickson | 600/573 |
| 6,602,268 | B2 | 8/2003 | Kuhr | 606/181 |
| 6,602,678 | B2 | 8/2003 | Kwon | 435/14 |
| 6,604,050 | B2 | 8/2003 | Trippel | 702/19 |
| 6,607,362 | B2 | 8/2003 | Lum | 417/53 |
| 6,607,494 | B1 | 8/2003 | Fowler | 600/570 |
| 6,607,658 | B1 | 8/2003 | Heller | 205/777.5 |
| 6,612,111 | B1 | 9/2003 | Hodges | 60/593 |
| 6,616,616 | B2 | 9/2003 | Fritz | 600/583 |
| 6,616,819 | B1 | 9/2003 | Liamos | 204/403.02 |
| 6,618,934 | B1 | 9/2003 | Feldman | 29/830 |
| 6,620,112 | B2 | 9/2003 | Klitmose | 600/583 |
| 6,620,310 | B1 | 9/2003 | Ohara | 205/792 |
| 6,623,501 | B2 | 9/2003 | Heller | 606/181 |
| 6,626,851 | B2 | 9/2003 | Hirao | 600/576 |
| 6,632,349 | B1 | 10/2003 | Hodges | 205/792 |
| 6,635,222 | B2 | 10/2003 | Kent | 422/22 |
| 6,638,415 | B1 | 10/2003 | Hodges | 205/775 |
| 6,638,772 | B1 | 10/2003 | Douglas | 436/518 |
| 6,641,533 | B2 | 11/2003 | Causey | 600/300 |
| 6,645,142 | B2 | 11/2003 | Braig | 600/300 |
| 6,645,219 | B2 | 11/2003 | Roe | 606/182 |
| 6,645,368 | B1 | 11/2003 | Beaty | 205/792 |
| 6,649,416 | B1 | 11/2003 | Kauer | 436/164 |
| 6,650,915 | B2 | 11/2003 | Routt | 600/319 |
| 6,652,720 | B1 | 11/2003 | Mansouri | 204/403.11 |
| 6,652,734 | B1 | 11/2003 | Hodges | 205/777.5 |
| 6,652,814 | B1 | 11/2003 | House | 422/104 |
| D484,600 | S | 12/2003 | Kaar | D24/169 |
| 6,656,697 | B1 | 12/2003 | Ouyang | 435/7.9 |
| 6,656,702 | B1 | 12/2003 | Yugawa | 435/26 |
| 6,659,966 | B2 | 12/2003 | Essenpreis | 600/583 |
| 6,660,018 | B2 | 12/2003 | Lum | 606/181 |
| 6,662,439 | B1 | 12/2003 | Bhullar | 29/825 |
| 6,669,669 | B2 | 12/2003 | Flaherty | 604/132 |
| 6,671,527 | B2 | 12/2003 | Petersson | 600/316 |
| D484,980 | S | 1/2004 | Hartwein | D24/165 |
| 6,673,617 | B2 | 1/2004 | Patel | 436/8 |
| 6,676,995 | B2 | 1/2004 | Dick | 427/286 |
| 6,679,841 | B2 | 1/2004 | Bojan | 600/309 |
| 6,679,852 | B1 | 1/2004 | Schmelzeisen-Redeker | 600/583 |
| 6,682,933 | B2 | 1/2004 | Patel | 436/8 |
| 6,689,411 | B2 | 2/2004 | Dick | 427/2.13 |
| 6,706,000 | B2 | 3/2004 | Perez | 600/583 |
| 6,706,049 | B2 | 3/2004 | Moerman | 606/181 |
| 6,706,159 | B2 | 3/2004 | Moerman | 204/403.03 |
| 6,706,232 | B2 | 3/2004 | Hasegawa et al. | 264/403.09 |
| 6,709,692 | B2 | 3/2004 | Sudor | 427/2.1 |
| 6,713,660 | B1 | 3/2004 | Roe | 604/361 |
| 6,716,577 | B1 | 4/2004 | Yu | 435/6 |
| 6,719,887 | B2 | 4/2004 | Hasegawa | 204/403.09 |
| 6,719,923 | B2 | 4/2004 | Stiene | 252/511 |
| 6,721,586 | B2 | 4/2004 | Kiser | 600/345 |
| 6,723,046 | B2 | 4/2004 | Lichtenstein | 600/300 |
| 6,723,111 | B2 | 4/2004 | Abulhaj | 606/181 |
| 6,723,371 | B2 | 4/2004 | Chih-hui | 472/2.13 |
| 6,723,500 | B2 | 4/2004 | Yu | 435/4 |
| 6,726,818 | B2 | 4/2004 | Cui et al. | 204/403.01 |
| 6,730,494 | B1 | 5/2004 | Toranto | 435/28 |
| 6,731,966 | B1 | 5/2004 | Spigelman | 600/407 |
| 6,733,493 | B2 | 5/2004 | Gruzdev | 606/9 |
| 6,736,777 | B2 | 5/2004 | Kim | 600/365 |
| 6,738,654 | B2 | 5/2004 | Sohrab | 600/345 |
| 6,740,215 | B1 | 5/2004 | Nakaminami et al. | 204/403.14 |
| 6,743,211 | B1 | 6/2004 | Prausnitz | 604/239 |
| 6,743,597 | B1 | 6/2004 | Guo | 435/14 |
| 6,743,635 | B2 | 6/2004 | Neel | 436/95 |
| 6,746,872 | B2 | 6/2004 | Zheng | 436/16 |
| 6,749,618 | B2 | 6/2004 | Levaughn | 606/182 |
| 6,749,740 | B2 | 6/2004 | Liamos et al. | 205/792 |
| 6,749,792 | B2 | 6/2004 | Olson | 264/328.1 |
| 6,749,887 | B1 | 6/2004 | Dick | 427/2.13 |
| 6,751,491 | B2 | 6/2004 | Lew | 600/345 |
| 6,752,817 | B2 | 6/2004 | Flora | 606/181 |
| 6,753,187 | B2 | 6/2004 | Cizdziel | 436/169 |
| 6,759,190 | B2 | 7/2004 | Lin | 435/4 |
| 6,764,496 | B2 | 7/2004 | Schraga | 606/182 |
| 6,764,581 | B1 | 7/2004 | Forrow | 204/403 |
| 6,767,441 | B1 | 7/2004 | Cai | 204/403.03 |
| 6,773,671 | B1 | 8/2004 | Lewis | 422/58 |
| 6,776,888 | B2 | 8/2004 | Yamamoto | 204/403.06 |
| 6,780,645 | B2 | 8/2004 | Hayter | 436/8 |
| 6,780,647 | B2 | 8/2004 | Fujiwara | 436/169 |
| 6,783,502 | B2 | 8/2004 | Orloff | 600/583 |
| 6,783,537 | B1 | 8/2004 | Kuhr | 606/182 |
| 6,784,274 | B2 | 8/2004 | van Antwerp | 528/77 |
| 6,786,874 | B2 | 9/2004 | Grace | 600/573 |
| 6,787,013 | B2 | 9/2004 | Chang | 204/412 |
| 6,787,109 | B2 | 9/2004 | Haar | 422/82.05 |
| 6,790,327 | B2 | 9/2004 | Nankai et al. | 204/403.1 |
| 6,790,599 | B1 | 9/2004 | Madou | 430/320 |
| 6,792,791 | B2 | 9/2004 | Sato | 73/1.02 |
| 6,793,632 | B2 | 9/2004 | Sohrab | 600/573 |
| 6,793,633 | B2 | 9/2004 | Douglas | 600/583 |
| 6,793,802 | B2 | 9/2004 | Lee | 205/777.5 |
| 6,797,150 | B2 | 9/2004 | Kermani | 205/777.5 |
| 6,800,488 | B2 | 10/2004 | Khan | 436/166 |
| 6,801,041 | B2 | 10/2004 | Karinka | 324/444 |
| 6,801,804 | B2 | 10/2004 | Miller | 604/20 |
| 6,802,199 | B2 | 10/2004 | Hilgers | 72/370.1 |
| 6,802,811 | B1 | 10/2004 | Slepian | 600/309 |
| 6,802,957 | B2 | 10/2004 | Jung | 205/777.5 |
| 6,805,780 | B1 | 10/2004 | Ryu | 204/403.01 |
| 6,808,499 | B1 | 10/2004 | Churchill | 600/587 |
| 6,808,908 | B2 | 10/2004 | Yao | 435/181 |
| 6,808,937 | B2 | 10/2004 | Ligler | 436/518 |
| 6,809,807 | B1 | 10/2004 | Erickson | 356/213 |
| 6,811,406 | B2 | 11/2004 | Grube | 439/66 |
| 6,811,557 | B2 | 11/2004 | Schraga | 606/182 |
| 6,811,659 | B2 | 11/2004 | Vachon | 204/224 |
| 6,811,753 | B2 | 11/2004 | Hirao | 422/101 |
| 6,811,792 | B2 | 11/2004 | Roser | 424/423 |
| 6,812,031 | B1 | 11/2004 | Carlsson | 436/52 |
| 6,814,843 | B1 | 11/2004 | Bhullar | 204/403.01 |
| 6,814,844 | B2 | 11/2004 | Bhullar | 204/403.1 |
| 6,814,845 | B2 | 11/2004 | Wilson | 204/486 |
| 6,815,186 | B2 | 11/2004 | Clark | 435/183 |
| 6,816,742 | B2 | 11/2004 | Kim | 600/345 |
| 6,818,180 | B2 | 11/2004 | Douglas | 422/58 |
| 6,821,483 | B2 | 11/2004 | Phillips | 422/58 |
| 6,823,750 | B2 | 11/2004 | Hodges | 73/864.72 |
| 6,825,047 | B1 | 11/2004 | Woudenberg | 436/518 |

| | | | |
|---|---|---|---|
| 6,827,250 B2 | 12/2004 | Uhland | 228/110.1 |
| 6,827,829 B2 | 12/2004 | Kawanaka | 204/403.02 |
| 6,829,507 B1 | 12/2004 | Lidman | 607/19 |
| 6,830,551 B1 | 12/2004 | Uchigaki | 600/584 |
| 6,830,668 B2 | 12/2004 | Musho | 204/400 |
| 6,830,669 B2 | 12/2004 | Miyazaki | 204/409 |
| 6,830,934 B1 | 12/2004 | Harding | 436/166 |
| 6,833,540 B2 | 12/2004 | MacKenzie | 250/214 |
| 6,835,184 B1 | 12/2004 | Sage | 604/46 |
| 6,835,553 B2 | 12/2004 | Han | 435/14 |
| 6,835,570 B2 | 12/2004 | Patel | 436/8 |
| 6,837,858 B2 | 1/2005 | Cunningham | 600/573 |
| 6,837,976 B2 | 1/2005 | Cai | 204/403.14 |
| 6,837,988 B2 | 1/2005 | Leong | 205/792 |
| 6,840,912 B2 | 1/2005 | Kloepfer | 600/583 |
| 6,841,052 B2 | 1/2005 | Musho | 204/401 |
| 6,843,254 B2 | 1/2005 | Tapper | 128/898 |
| 6,843,902 B1 | 1/2005 | Penner | 205/76 |
| 6,847,451 B2 | 1/2005 | Pugh | 356/436 |
| 6,849,052 B2 | 2/2005 | Uchigaki | 600/584 |
| 6,849,168 B2 | 2/2005 | Madou | 204/416 |
| 6,849,216 B2 | 2/2005 | Rappin | 264/134 |
| 6,849,456 B2 | 2/2005 | Patel | 436/8 |
| 6,850,790 B2 | 2/2005 | Berner | 600/347 |
| 6,852,119 B1 | 2/2005 | Abulhaj | 606/182 |
| 6,852,212 B2 | 2/2005 | Maxwell | 205/775 |
| 6,852,500 B1 | 2/2005 | Hoss | 435/14 |
| 6,853,854 B1 | 2/2005 | Proniewicz | 600/319 |
| 6,855,243 B2 | 2/2005 | Khan | 205/777.5 |
| 6,856,125 B2 | 2/2005 | Kermani | 324/71.1 |
| 6,856,928 B2 | 2/2005 | Harmon | 702/84 |
| 6,858,015 B2 | 2/2005 | List | 600/583 |
| 6,858,401 B2 | 2/2005 | Phillips | 435/14 |
| 6,859,738 B2 | 2/2005 | Bush | 702/25 |
| 6,862,466 B2 | 3/2005 | Ackerman | 600/347 |
| 6,862,534 B2 | 3/2005 | Sterling | 702/23 |
| 6,863,800 B2 | 3/2005 | Karinka | 205/777.5 |
| 6,863,801 B2 | 3/2005 | Hodges | 205/792 |
| 6,865,408 B1 | 3/2005 | Abbink | 600/310 |
| 6,866,641 B2 | 3/2005 | Marshall | 600/583 |
| 6,866,675 B2 | 3/2005 | Perez | 606/181 |
| 6,866,758 B2 | 3/2005 | Bhullar | 204/403.2 |
| 6,866,822 B1 | 3/2005 | House | 422/82.05 |
| 6,869,418 B2 | 3/2005 | Marano-Ford | 604/192 |
| 6,872,200 B2 | 3/2005 | Mann | 604/890.1 |
| 6,872,297 B2 | 3/2005 | Mansouri | 205/775 |
| 6,872,298 B2 | 3/2005 | Kermani | 205/777.5 |
| 6,872,299 B2 | 3/2005 | Kermani | 205/777.5 |
| 6,872,358 B2 | 3/2005 | Hagen | 422/61 |
| 6,875,208 B2 | 4/2005 | Santini | 604/890.1 |
| 6,875,327 B1 | 4/2005 | Miyazaki | 204/403.14 |
| 6,875,613 B2 | 4/2005 | Shartle | 436/63 |
| 6,878,120 B2 | 4/2005 | Roe | 600/583 |
| 6,878,251 B2 | 4/2005 | Hodges | 204/403.14 |
| 6,878,255 B1 | 4/2005 | Wang | 204/452 |
| 6,878,262 B2 | 4/2005 | Taniike | 205/777.5 |
| 6,880,968 B1 | 4/2005 | Haar | 374/131 |
| 6,881,203 B2 | 4/2005 | Delmore | 604/272 |
| 6,881,322 B2 | 4/2005 | Tokunaga | 205/775 |
| 6,881,378 B1 | 4/2005 | Zimmer | 422/58 |
| 6,881,541 B2 | 4/2005 | Petersen | 435/6 |
| 6,881,550 B2 | 4/2005 | Phillips | 435/14 |
| 6,881,551 B2 | 4/2005 | Heller | 435/14 |
| 6,881,578 B2 | 4/2005 | Otake | 436/44 |
| 6,882,940 B2 | 4/2005 | Potts | 702/23 |
| 6,884,592 B2 | 4/2005 | Matzinger | 435/7.1 |
| 6,885,196 B2 | 4/2005 | Taniike | 324/444 |
| 6,885,883 B2 | 4/2005 | Parris | 600/347 |
| 8,752,233 | 4/2005 | Argauer | 606/181 |
| 6,887,202 B2 | 5/2005 | Currie | 600/309 |
| 6,887,239 B2 | 5/2005 | Elstrom | 606/41 |
| 6,887,253 B2 | 5/2005 | Schraga | 606/181 |
| 6,887,254 B1 | 5/2005 | Curie | 606/181 |
| 6,887,426 B2 | 5/2005 | Phillips et al. | 422/56 |
| 6,887,709 B2 | 5/2005 | Leong | 436/8 |
| 6,889,069 B2 | 5/2005 | Routt | 600/319 |
| 6,890,319 B1 | 5/2005 | Crocker | 604/131 |
| 6,890,421 B2 | 5/2005 | Ohara | 205/777.5 |
| 6,890,484 B2 | 5/2005 | Bautista | 422/58 |
| 6,891,936 B2 | 5/2005 | Kai | 379/106.02 |
| 6,892,085 B2 | 5/2005 | McIvor | 600/347 |
| 6,893,396 B2 | 5/2005 | Schulze | 600/300 |
| 6,893,545 B2 | 5/2005 | Gotoh | 204/403.5 |
| 6,893,552 B1 | 5/2005 | Wang | 205/777.5 |
| 6,895,263 B2 | 5/2005 | Shin | 600/316 |
| 6,895,264 B2 | 5/2005 | Rice | 600/319 |
| 6,895,265 B2 | 5/2005 | Silver | 600/345 |
| 6,896,793 B2 | 5/2005 | Erdosy | 205/775 |
| 6,897,788 B2 | 5/2005 | Khair | 340/870.16 |
| 6,902,905 B2 | 6/2005 | Burson | 435/14 |
| 6,904,301 B2 | 6/2005 | Raskas | 600/310 |
| 6,905,733 B2 | 6/2005 | Russell | 427/393.5 |
| 6,908,008 B2 | 6/2005 | Pugh | 221/135 |
| 6,908,535 B2 | 6/2005 | Rankin | 204/406 |
| 6,908,591 B2 | 6/2005 | MacPhee | 422/22 |
| 6,908,593 B1 | 6/2005 | Shartle | 422/58 |
| 6,911,130 B2 | 6/2005 | Brenneman | 204/400 |
| 6,911,131 B2 | 6/2005 | Miyazaki | 204/403.14 |
| 6,911,621 B2 | 6/2005 | Bhullar | 219/121.69 |
| 6,911,937 B1 | 6/2005 | Sparrow | 342/188 |
| 6,913,210 B2 | 7/2005 | Baasch | 239/407 |
| 6,913,668 B2 | 7/2005 | Matzinger | 156/256 |
| 6,916,410 B2 | 7/2005 | Katsuki | 204/403 |
| 6,918,874 B1 | 7/2005 | Hatch | 600/365 |
| 6,918,901 B1 | 7/2005 | Theeuwes | 604/500 |
| 6,918,918 B1 | 7/2005 | Schraga | 606/182 |
| 6,922,576 B2 | 7/2005 | Raskas | 600/316 |
| 6,922,578 B2 | 7/2005 | Eppstein | 600/347 |
| 6,923,764 B2 | 8/2005 | Aceti | 600/309 |
| 6,923,894 B2 | 8/2005 | Huang | 204/403.06 |
| 6,923,936 B2 | 8/2005 | Swanson | 422/22 |
| 6,924,093 B2 | 8/2005 | Haviland | 435/4 |
| 6,925,317 B1 | 8/2005 | Samuels | 600/344 |
| 6,925,393 B1 | 8/2005 | Kalatz | 702/27 |
| 6,929,631 B1 | 8/2005 | Brugger | 604/502 |
| 6,929,649 B2 | 8/2005 | Pugh | 606/182 |
| 6,929,650 B2 | 8/2005 | Fukuzawa | 606/182 |
| 6,931,327 B2 | 8/2005 | Goode | 702/22 |
| 6,931,328 B2 | 8/2005 | Braig | 702/23 |
| 6,939,310 B2 | 9/2005 | Matzinger | 600/573 |
| 6,939,312 B2 | 9/2005 | Hodges | 600/583 |
| 6,939,450 B2 | 9/2005 | Karinka | 204/409 |
| 6,939,685 B2 | 9/2005 | Ouyang | 435/26 |
| 6,940,591 B2 | 9/2005 | Sopp | 356/244 |
| 6,942,518 B2 | 9/2005 | Liamos | 439/495 |
| 6,942,769 B2 | 9/2005 | Cheng | 204/400 |
| 6,942,770 B2 | 9/2005 | Cai | 204/403.04 |
| 6,944,486 B2 | 9/2005 | Braig | 600/310 |
| 6,945,943 B2 | 9/2005 | Pugh | 600/584 |
| 6,946,067 B2 | 9/2005 | Hodges | 205/792 |
| 6,946,098 B2 | 9/2005 | Miekka | 422/22 |
| 6,946,299 B2 | 9/2005 | Neel | 436/95 |
| 6,949,111 B2 | 9/2005 | Schraga | 606/182 |
| 6,949,221 B2 | 9/2005 | Kiser | 422/56 |
| 6,951,631 B1 | 10/2005 | Catt | 422/56 |
| 6,951,728 B2 | 10/2005 | Qian | 435/14 |
| 6,952,603 B2 | 10/2005 | Gerber | 600/310 |
| 6,952,604 B2 | 10/2005 | DeNuzzio | 600/345 |
| 6,953,693 B2 | 10/2005 | Neel | 436/149 |
| 6,954,662 B2 | 10/2005 | Freger | 600/316 |
| 6,958,072 B2 | 10/2005 | Schraga | 606/182 |
| 6,958,129 B2 | 10/2005 | Galen | 422/57 |
| 6,958,809 B2 | 10/2005 | Sterling | 356/39 |
| 6,959,211 B2 | 10/2005 | Rule | 600/310 |
| 6,959,247 B2 | 10/2005 | Neel | 702/19 |
| 6,960,287 B2 | 11/2005 | Charlton | 205/775 |

6,960,289 B2 11/2005 Hodges ........................ 205/778
6,960,323 B2 11/2005 Guo ............................ 422/60
6,964,871 B2 11/2005 Bell ............................ 436/95
6,965,791 B1 11/2005 Hitchcock .................. 600/345
6,966,880 B2 11/2005 Boecker ..................... 600/583
6,966,977 B2 11/2005 Hasegawa ............. 204/403.07
6,967,105 B2 11/2005 Nomura ...................... 436/169
6,968,375 B1 11/2005 Brown ........................ 709/224
6,969,359 B2 11/2005 Duchon ...................... 600/583
6,969,450 B2 11/2005 Taniike ................. 204/403.01
6,969,451 B2 11/2005 Shin ........................... 204/412
6,973,706 B2 12/2005 Say ............................. 29/595
6,975,893 B2 12/2005 Say ............................ 600/347
6,977,032 B2 12/2005 Hasegawa ............. 204/403.05
6,979,544 B2 12/2005 Keen ............................. 435/6
6,979,571 B2 12/2005 Modzelewski ............. 436/164
6,982,027 B2 1/2006 Yagi ..................... 204/403.06
6,982,431 B2 1/2006 Modlin ....................... 250/573
6,983,176 B2 1/2006 Gardner ...................... 600/310
6,983,177 B2 1/2006 Rule .......................... 600/310
6,984,307 B2 1/2006 Zweig .................... 205/777.5
6,986,777 B2 1/2006 Kim ........................... 606/182
6,986,869 B2 1/2006 Tuohy ......................... 422/56
6,988,996 B2 1/2006 Roe ........................... 600/584
6,989,243 B2 1/2006 Yani ............................ 435/14
6,989,891 B2 1/2006 Braig .......................... 356/39
6,990,365 B1 1/2006 Parker ........................ 600/328
6,990,366 B2 1/2006 Say ............................ 600/345
6,990,367 B2 1/2006 Kiser ......................... 600/345
6,990,849 B2 1/2006 Bohm ...................... 73/53.01
6,991,918 B2 1/2006 Keith .......................... 435/31
6,991,940 B2 1/2006 Carroll ....................... 436/514
6,994,825 B2 2/2006 Haviland ..................... 422/58
6,997,317 B2 2/2006 Catelli ....................... 206/438
6,997,343 B2 2/2006 May ........................... 221/232
6,997,344 B2 2/2006 Brown ........................ 221/258
6,997,936 B2 2/2006 Marshall ..................... 606/181
6,998,247 B2 2/2006 Monfre ........................ 435/14
6,998,248 B2 2/2006 Yani ............................ 435/14
6,999,810 B2 2/2006 Berner ....................... 600/345
7,001,343 B2 2/2006 Erickson ..................... 600/573
7,001,344 B2 2/2006 Freeman ..................... 600/583
7,003,337 B2 2/2006 Harjunmaa ................. 600/316
7,003,340 B2 2/2006 Say ............................ 600/345
7,003,341 B2 2/2006 Say ............................ 600/345
7,004,928 B2 2/2006 Aceti ......................... 604/191
7,005,048 B1 2/2006 Watanabe ............. 204/403.04
7,005,273 B2 2/2006 Heller ......................... 435/25
7,005,459 B2 2/2006 Hekal ......................... 523/102
7,005,857 B2 2/2006 Stiene ........................ 324/449
7,006,857 B2 2/2006 Braig ......................... 600/310
7,006,858 B2 2/2006 Silver ........................ 600/345
7,008,384 B2 3/2006 Tapper ....................... 600/573
7,010,432 B2 3/2006 Kermani ...................... 702/19
7,011,630 B2 3/2006 Desai ......................... 600/309
7,011,954 B2 3/2006 Ouyang ...................... 435/7.9
7,014,615 B2 3/2006 Erickson ..................... 600/573
7,015,262 B2 3/2006 Leong ........................ 523/205
7,016,713 B2 3/2006 Gardner ...................... 600/310
7,018,568 B2 3/2006 Tierney ...................... 252/511
7,018,848 B2 3/2006 Douglas ..................... 436/524
7,022,217 B2 4/2006 Hodges ................... 205/777.5
7,022,218 B2 4/2006 Taniike .................... 205/777.5
7,022,286 B2 4/2006 Lemke ........................ 422/67
7,024,236 B2 4/2006 Ford ........................... 600/345
7,024,248 B2 4/2006 Penner ........................ 607/60
7,024,399 B2 4/2006 Sumner ....................... 706/45
7,025,425 B2 4/2006 Kovatchev .................. 300/365
7,025,774 B2 4/2006 Freeman ..................... 606/181
7,027,848 B2 4/2006 Robinson .................... 600/310
7,029,444 B2 4/2006 Shin ........................... 600/365
7,033,322 B2 4/2006 Silver ........................ 600/486
7,033,371 B2 4/2006 Alden ........................ 606/181
7,039,560 B2 5/2006 Kawatahara ................ 702/187
7,041,057 B1 5/2006 Faupel ........................ 600/365
7,041,063 B2 5/2006 Abreu ........................ 600/549
7,041,068 B2 5/2006 Freeman ..................... 600/583
7,041,210 B2 5/2006 Hodges ...................... 205/792
7,041,254 B2 5/2006 Haviland ..................... 422/58
7,041,468 B2 5/2006 Drucker ....................... 435/14
7,043,287 B1 5/2006 Khalil ........................ 600/310
7,043,821 B2 5/2006 Hodges ...................... 205/792
7,044,911 B2 5/2006 Drinan ....................... 600/300
7,045,046 B2 5/2006 Chambers ................... 204/400
7,045,054 B1 5/2006 Buck .......................... 205/778
7,045,097 B2 5/2006 Kovacs .................... 422/82.08
7,045,310 B2 5/2006 Buck ......................... 435/7.93
7,045,361 B2 5/2006 Heiss ......................... 436/172
7,047,070 B2 5/2006 Wilkinson ................... 604/20
7,047,795 B2 5/2006 Sato ......................... 73/64.56
7,049,087 B2 5/2006 Jenny .......................... 435/13
7,049,130 B2 5/2006 Carroll .................... 435/287.2
7,050,843 B2 5/2006 Shartle ....................... 600/345
7,051,495 B2 5/2006 Lang ........................... 53/475
7,052,268 B2 5/2006 Powell ....................... 425/542
7,052,591 B2 5/2006 Gao ........................... 204/490
7,052,652 B2 5/2006 Zanzucchi .............. 422/82.05
7,052,864 B2 5/2006 Durkop ........................ 435/25
7,054,682 B2 5/2006 Young ......................... 604/20
7,054,759 B2 5/2006 Fukunaga .................... 702/23
D522,656 S 6/2006 Orr ........................... D24/169
D523,555 S 6/2006 Loerwald .................. D24/146
7,056,425 B2 6/2006 Hasegawa ............. 204/403.04
7,056,495 B2 6/2006 Roser .......................... 424/45
7,058,437 B2 6/2006 Buse .......................... 600/347
7,059,352 B2 6/2006 Bohm ........................ 137/828
7,060,059 B2 6/2006 Keith ......................... 604/504
7,060,168 B2 6/2006 Taniike .................. 204/403.04
7,060,192 B2 6/2006 Yuzhakov .................... 216/11
7,061,593 B2 6/2006 Braig .......................... 356/39
7,063,234 B2 6/2006 Giraud ....................... 221/271
7,063,774 B2 6/2006 Bhullar .................. 204/403.02
7,063,775 B2 6/2006 Yamaoka ............... 204/403.06
7,063,776 B2 6/2006 Huang .................. 204/403.14
7,066,884 B2 6/2006 Custer ........................ 600/309
7,066,885 B2 6/2006 Erickson ..................... 600/309
7,070,564 B2 7/2006 Matzinger ................... 600/300
7,070,680 B2 7/2006 Bae ...................... 204/403.04
7,073,246 B2 7/2006 Bhullar ........................ 29/595
7,074,307 B2 7/2006 Simpson ................ 204/403.04
7,074,308 B2 7/2006 Mao ...................... 204/403.14
7,077,328 B2 7/2006 Krishnaswamy ....... 235/472.01
7,077,828 B2 7/2006 Kuhr .......................... 604/207
7,078,480 B2 7/2006 Nagel ......................... 530/322
7,079,252 B1 7/2006 Debreczeny ................ 356/451
7,081,188 B1 7/2006 Cho ...................... 204/403.04
7,083,712 B2 8/2006 Morita ....................... 205/775
7,086,277 B2 8/2006 Tess ......................... 73/53.01
7,087,149 B1 8/2006 Muguruma ................. 205/778
7,090,764 B2 8/2006 Iyengar ...................... 205/775
7,096,053 B2 8/2006 Loeb .......................... 600/317
7,096,124 B2 8/2006 Sterling ....................... 702/23
7,097,631 B2 8/2006 Trautman ..................... 604/46
7,098,038 B2 8/2006 Fukuoka ..................... 436/164
7,103,578 B2 9/2006 Beck ........................... 705/75
7,105,066 B2 9/2006 Schraga ...................... 606/182
7,107,253 B1 9/2006 Sumner ....................... 706/45
7,108,680 B2 9/2006 Rohr .......................... 604/151
7,108,778 B2 9/2006 Simpson ..................... 205/778
7,109,271 B2 9/2006 Liu ............................ 525/283
7,110,112 B2 9/2006 Uchida ....................... 356/364
7,110,803 B2 9/2006 Shults ........................ 600/347
7,112,265 B1 9/2006 McAleer ................ 204/403.09
7,112,451 B2 9/2006 Takahashi ................... 436/514
7,113,172 B2 9/2006 Hohl .......................... 345/168
7,115,362 B2 10/2006 Douglas ........................ 435/4

| | | | |
|---|---|---|---|
| 7,118,351 B2 | 10/2006 | Effenhauser | 417/208 |
| 7,118,667 B2 | 10/2006 | Lee | 205/777.5 |
| 7,118,668 B1 | 10/2006 | Edelbrock | 205/777.5 |
| 7,118,916 B2 | 10/2006 | Matzinger | 436/34 |
| 7,118,919 B2 | 10/2006 | Yatscoff | 436/56 |
| 7,120,483 B2 | 10/2006 | Russell | 600/345 |
| 7,122,102 B2 | 10/2006 | Wogoman | 204/400 |
| 7,122,110 B2 | 10/2006 | Deng | 205/777.5 |
| 7,122,111 B2 | 10/2006 | Tokunaga | 205/792 |
| 7,125,481 B2 | 10/2006 | Musho | 205/775 |
| 7,129,038 B2 | 10/2006 | Gopalan | 435/4 |
| RE39,390 E | 11/2006 | Hasegawa | 204/403.09 |
| D531,725 S | 11/2006 | Loerwald | D24/146 |
| 7,131,342 B2 | 11/2006 | Hodges | 73/864.72 |
| 7,131,984 B2 | 11/2006 | Sato | 606/182 |
| 7,132,041 B2 | 11/2006 | Deng | 205/777.5 |
| 7,133,710 B2 | 11/2006 | Acosta | 600/316 |
| 7,134,550 B2 | 11/2006 | Groth | 206/366 |
| 7,134,999 B2 | 11/2006 | Brauker | 600/309 |
| 7,135,100 B1 | 11/2006 | Lau | 204/403.14 |
| 7,137,957 B2 | 11/2006 | Erickson | 600/573 |
| 7,138,041 B2 | 11/2006 | Su | 204/403.04 |
| 7,138,089 B2 | 11/2006 | Aitken | 422/82.01 |
| 7,141,034 B2 | 11/2006 | Eppstein | 604/22 |
| 7,141,058 B2 | 11/2006 | Briggs | 606/181 |
| 7,144,404 B2 | 12/2006 | Whitson | 606/181 |
| 7,144,485 B2 | 12/2006 | Hsu | 204/403.02 |
| 7,144,495 B2 | 12/2006 | Teodorczyk | 205/792 |
| 7,144,496 B2 | 12/2006 | Meserol | 205/792 |
| 7,144,709 B2 | 12/2006 | Ouyang | 435/7.9 |
| 7,147,825 B2 | 12/2006 | Matsuda | 422/58 |
| 7,150,755 B2 | 12/2006 | Levaughn | 606/181 |
| 7,150,975 B2 | 12/2006 | Tamada | 435/14 |
| 7,150,995 B2 | 12/2006 | Xie | 436/67 |
| 7,153,696 B2 | 12/2006 | Fukuoka | 436/164 |
| 7,155,371 B2 | 12/2006 | Kawatahara | 702/187 |
| 7,156,117 B2 | 1/2007 | Bohm | 137/14 |
| 7,156,810 B2 | 1/2007 | Cho | 600/365 |
| 7,157,723 B2 | 1/2007 | Colvin | 250/458.1 |
| 7,160,251 B2 | 1/2007 | Neel | 600/365 |
| 7,160,313 B2 | 1/2007 | Galloway | 606/167 |
| 7,160,678 B1 | 1/2007 | Kayyem | 435/6 |
| 7,162,289 B2 | 1/2007 | Shah | 600/345 |
| 7,163,616 B2 | 1/2007 | Vreeke | 205/777.5 |
| 7,166,074 B2 | 1/2007 | Reghabi | 600/365 |
| 7,166,208 B2 | 1/2007 | Zweig | 205/777.5 |
| 7,167,734 B2 | 1/2007 | Khalil | 600/310 |
| 7,167,735 B2 | 1/2007 | Uchida | 600/310 |
| 7,167,818 B2 | 1/2007 | Brown | 703/11 |
| 7,169,116 B2 | 1/2007 | Day | 600/583 |
| 7,169,117 B2 | 1/2007 | Allen | 600/584 |
| 7,169,289 B2 | 1/2007 | Schulein | 205/777.5 |
| 7,169,600 B2 | 1/2007 | Hoss | 435/287.1 |
| 7,172,728 B2 | 2/2007 | Otake | 422/58 |
| 7,174,199 B2 | 2/2007 | Berner et al. | 600/347 |
| 7,175,641 B1 | 2/2007 | Schraga | 606/181 |
| 7,175,642 B2 | 2/2007 | Briggs | 606/181 |
| 7,179,233 B2 | 2/2007 | Chang | 600/584 |
| 7,182,910 B2 | 2/2007 | Allen | 422/50 |
| 7,183,068 B2 | 2/2007 | Burson | 435/14 |
| 7,183,508 B2 | 2/2007 | Kasai | 200/51.09 |
| 7,188,034 B2 | 3/2007 | Staib | 702/22 |
| 7,189,576 B2 | 3/2007 | Fukuoka | 436/170 |
| 7,190,988 B2 | 3/2007 | Say | 600/345 |
| 7,192,405 B2 | 3/2007 | DeNuzzio | 600/583 |
| 7,192,450 B2 | 3/2007 | Brauker | 623/23.76 |
| 7,195,704 B2 | 3/2007 | Kermani | 205/777.5 |
| 7,198,606 B2 | 4/2007 | Boecker | 600/583 |
| 7,199,594 B2 | 4/2007 | Kermani | 324/663 |
| 7,202,854 B2 | 4/2007 | Hohl | 345/168 |
| 7,206,620 B2 | 4/2007 | Erickson | 600/310 |
| 7,206,623 B2 | 4/2007 | Blank | 600/344 |
| D542,681 S | 5/2007 | Young | D10/80 |
| 7,211,052 B2 | 5/2007 | Roe | 600/584 |
| 7,211,096 B2 | 5/2007 | Kuhr | 606/182 |
| 7,212,925 B2 | 5/2007 | Genshaw | 702/23 |
| 7,213,720 B2 | 5/2007 | Giraud | 220/839 |
| 7,215,982 B2 | 5/2007 | Oshima | 600/310 |
| 7,215,983 B2 | 5/2007 | Cho | 600/316 |
| 7,223,248 B2 | 5/2007 | Erickson | 600/584 |
| 7,225,008 B1 | 5/2007 | Ward | 600/345 |
| D543,878 S | 6/2007 | Castillo | D10/81 |
| D545,438 S | 6/2007 | Huang | D24/186 |
| 7,225,535 B2 | 6/2007 | Feldman | 29/831 |
| 7,226,414 B2 | 6/2007 | Ballerstadt | 600/365 |
| 7,226,461 B2 | 6/2007 | Boecker | 606/181 |
| 7,226,978 B2 | 6/2007 | Tapsak | 525/296 |
| 7,227,156 B2 | 6/2007 | Colvin | 250/458.1 |
| 7,228,159 B2 | 6/2007 | Petersson | 600/316 |
| 7,228,162 B2 | 6/2007 | Ward | 600/345 |
| 7,228,163 B2 | 6/2007 | Ackerman | 600/347 |
| 7,229,458 B2 | 6/2007 | Freeman et al. | 606/181 |
| 7,232,451 B2 | 6/2007 | Boecker | 606/181 |
| 7,232,510 B2 | 6/2007 | Miyazaki | 204/403.1 |
| 7,233,816 B2 | 6/2007 | Blank | 600/310 |
| 7,235,056 B2 | 6/2007 | Duchon | 600/583 |
| 7,235,170 B2 | 6/2007 | Watanabe | 205/777.5 |
| 7,235,378 B2 | 6/2007 | Yonehara | 435/14 |
| 7,236,812 B1 | 6/2007 | Ballerstadt | 600/316 |
| 7,236,814 B2 | 6/2007 | Shioi | 600/344 |
| D545,705 S | 7/2007 | Voege | D10/81 |
| D546,216 S | 7/2007 | Bolognesi | D10/81 |
| D546,218 S | 7/2007 | Grasso | D10/81 |
| 7,238,192 B2 | 7/2007 | List | 606/182 |
| 7,238,534 B1 | 7/2007 | Zimmer | 436/169 |
| 7,241,265 B2 | 7/2007 | Cummings | 600/300 |
| 7,244,264 B2 | 7/2007 | Roe | 606/181 |
| 7,244,265 B2 | 7/2007 | Freeman | 606/181 |
| 7,244,266 B2 | 7/2007 | Garthe | 606/181 |
| 7,247,138 B2 | 7/2007 | Reghabi | 600/365 |
| 7,247,144 B2 | 7/2007 | Douglas | 600/583 |
| 7,250,037 B2 | 7/2007 | Shermer | 604/134 |
| 7,250,056 B2 | 7/2007 | Hamamoto | 606/181 |
| 7,250,095 B2 | 7/2007 | Black | 204/403.14 |
| 7,250,105 B1 | 7/2007 | Davies | 205/777.5 |
| 7,251,513 B2 | 7/2007 | Kondoh et al. | 600/310 |
| 7,251,514 B2 | 7/2007 | Cho | 600/316 |
| 7,251,515 B2 | 7/2007 | Cho | 600/316 |
| 7,251,516 B2 | 7/2007 | Walker | 600/316 |
| 7,251,517 B2 | 7/2007 | Cho | 600/316 |
| 7,251,518 B2 | 7/2007 | Herrmann | 600/322 |
| 7,252,804 B2 | 8/2007 | Miyashita | 422/104 |
| 7,254,426 B2 | 8/2007 | Cho | 600/316 |
| 7,254,427 B2 | 8/2007 | Cho | 600/316 |
| 7,254,428 B2 | 8/2007 | Cho | 600/316 |
| 7,254,429 B2 | 8/2007 | Schurman | 600/316 |
| 7,254,430 B2 | 8/2007 | Cho | 600/316 |
| 7,254,432 B2 | 8/2007 | Fine | 600/335 |
| 7,258,673 B2 | 8/2007 | Racchini | 600/583 |
| 7,258,693 B2 | 8/2007 | Freeman | 606/181 |
| 7,262,061 B2 | 8/2007 | Petrich | 436/169 |
| 7,264,139 B2 | 9/2007 | Brickwood | 221/270 |
| 7,264,627 B2 | 9/2007 | Perez | 606/181 |
| 7,266,400 B2 | 9/2007 | Fine | 600/316 |
| 7,267,665 B2 | 9/2007 | Steil | 604/131 |
| 7,267,750 B2 | 9/2007 | Watanabe | 204/403.04 |
| 7,270,247 B2 | 9/2007 | Charlton | 221/59 |
| 7,271,912 B2 | 9/2007 | Sterling | 356/436 |
| 7,273,484 B2 | 9/2007 | Thoes | 606/181 |
| 7,276,027 B2 | 10/2007 | Haar | 600/309 |
| 7,276,029 B2 | 10/2007 | Goode | 600/365 |
| 7,276,146 B2 | 10/2007 | Wilsey | 205/792 |
| 7,276,147 B2 | 10/2007 | Wilsey | 205/792 |
| 7,276,380 B2 | 10/2007 | Fukuyama | 436/164 |
| 7,277,740 B2 | 10/2007 | Rohleder | 600/316 |
| 7,278,983 B2 | 10/2007 | Ireland | 604/66 |

| Patent No. | Kind | Date | Name | Class |
|---|---|---|---|---|
| 7,279,130 | B2 | 10/2007 | Brown | 422/64 |
| 7,282,058 | B2 | 10/2007 | Levin | 606/181 |
| 7,287,318 | B2 | 10/2007 | Bhullar | 29/825 |
| 7,288,073 | B2 | 10/2007 | Effenhauser | 600/584 |
| 7,288,102 | B2 | 10/2007 | Griffin | 606/182 |
| 7,288,174 | B2 | 10/2007 | Cui | 204/403.14 |
| 7,289,836 | B2 | 10/2007 | Colvin | 600/316 |
| 7,291,117 | B2 | 11/2007 | Boecker | 600/583 |
| 7,291,159 | B2 | 11/2007 | Schmelzeisen-Redeker | 606/181 |
| 7,291,256 | B2 | 11/2007 | Teodorczyk | 205/777.5 |
| 7,291,497 | B2 | 11/2007 | Holmes | 435/287.2 |
| 7,294,246 | B2 | 11/2007 | Gundel | 204/403.14 |
| 7,295,867 | B2 | 11/2007 | Berner | 600/345 |
| 7,297,122 | B2 | 11/2007 | Boecker | 600/583 |
| 7,297,151 | B2 | 11/2007 | Boecker | 606/181 |
| 7,297,152 | B2 | 11/2007 | Fukuzawa | 606/181 |
| 7,297,241 | B2 | 11/2007 | Kontschieder | 204/403.01 |
| 7,297,248 | B2 | 11/2007 | Bae | 205/777.5 |
| 7,297,627 | B2 | 11/2007 | Shah | 438/622 |
| 7,299,079 | B2 | 11/2007 | Rebec | 600/316 |
| 7,299,080 | B2 | 11/2007 | Acosta | 600/316 |
| 7,299,081 | B2 | 11/2007 | Mace | 600/345 |
| 7,299,082 | B2 | 11/2007 | Feldman | 600/347 |
| 7,300,402 | B2 | 11/2007 | Iliff | 600/300 |
| 7,301,629 | B2 | 11/2007 | Bambot | 356/337 |
| 7,303,573 | B2 | 12/2007 | D'Agostino | 606/181 |
| 7,303,726 | B2 | 12/2007 | McAllister et al. | 422/68.1 |
| 7,303,922 | B2 | 12/2007 | Jeng | 436/164 |
| 7,305,896 | B2 | 12/2007 | Howell | 73/864.02 |
| 7,306,560 | B2 | 12/2007 | Iliff | 600/300 |
| 7,308,164 | B1 | 12/2007 | Banks | 385/12 |
| 7,308,292 | B2 | 12/2007 | Colvin | 600/310 |
| 7,310,542 | B2 | 12/2007 | Jeon | 600/344 |
| 7,310,543 | B2 | 12/2007 | Smart | 600/345 |
| 7,310,544 | B2 | 12/2007 | Brister | 600/345 |
| 7,311,718 | B2 | 12/2007 | Schraga | 606/181 |
| 7,311,812 | B2 | 12/2007 | Forrow | 204/403.06 |
| 7,312,042 | B1 | 12/2007 | Petyt | 435/7.1 |
| 7,313,425 | B2 | 12/2007 | Finarov | 600/310 |
| 7,314,453 | B2 | 1/2008 | Kuo | 600/584 |
| 7,315,752 | B2 | 1/2008 | Kraemer | 600/316 |
| 7,316,700 | B2 | 1/2008 | Alden | 606/181 |
| 7,316,766 | B2 | 1/2008 | Chen | 204/403.01 |
| 7,316,929 | B2 | 1/2008 | Purcell | 436/8 |
| 7,317,938 | B2 | 1/2008 | Lorenz | 600/316 |
| 7,317,939 | B2 | 1/2008 | Fine | 600/322 |
| 7,322,942 | B2 | 1/2008 | Roe | 600/583 |
| 7,322,996 | B2 | 1/2008 | Taylor | 606/181 |
| 7,322,997 | B2 | 1/2008 | Shi | 606/181 |
| 7,322,998 | B2 | 1/2008 | Kuhr | 606/182 |
| 7,323,098 | B2 | 1/2008 | Miyashita | 205/777.5 |
| 7,323,141 | B2 | 1/2008 | Kirchhevel | 422/68.1 |
| 7,323,315 | B2 | 1/2008 | Marfurt | 435/7.25 |
| 7,324,012 | B2 | 1/2008 | Mann | 340/870.07 |
| 7,328,052 | B2 | 2/2008 | Samsoondar | 600/310 |
| 7,331,931 | B2 | 2/2008 | Freeman | 600/583 |
| 7,335,292 | B2 | 2/2008 | Hodges | 205/775 |
| 7,335,294 | B2 | 2/2008 | Heller | 205/792 |
| 7,337,918 | B2 | 3/2008 | Fowler | 221/65 |
| 7,338,639 | B2 | 3/2008 | Burke | 422/82.1 |
| 7,343,188 | B2 | 3/2008 | Sohrab | 600/345 |
| 7,344,499 | B1 | 3/2008 | Prausnitz | 600/309 |
| 7,344,500 | B2 | 3/2008 | Talbot | 600/365 |
| 7,344,507 | B2 | 3/2008 | Briggs | 600/583 |
| 7,344,626 | B2 | 3/2008 | Harding | 204/403.01 |
| 7,347,925 | B2 | 3/2008 | Hsieh | 205/777.5 |
| 7,347,926 | B2 | 3/2008 | Morita | 205/792 |
| 7,347,973 | B2 | 3/2008 | Douglas | 422/61 |
| RE40,198 | E | 4/2008 | Buck | 205/777.5 |
| 7,351,213 | B2 | 4/2008 | Wong | 600/584 |
| 7,351,323 | B2 | 4/2008 | Iketaki | 205/777.5 |
| 7,351,375 | B2 | 4/2008 | Noda | 422/82.01 |
| 7,351,770 | B2 | 4/2008 | Liu | 525/283 |
| 7,357,808 | B2 | 4/2008 | Kennedy | 606/181 |
| 7,357,851 | B2 | 4/2008 | Reid | 204/403.04 |
| 7,361,182 | B2 | 4/2008 | Fukuda | 606/181 |
| 7,361,307 | B2 | 4/2008 | Shartle | 422/82.01 |
| 7,371,247 | B2 | 5/2008 | Boecker | 606/181 |
| 7,372,277 | B2 | 5/2008 | Diamond | 324/444 |
| 7,374,544 | B2 | 5/2008 | Freeman | 600/583 |
| 7,374,546 | B2 | 5/2008 | Roe | 600/583 |
| 7,378,007 | B2 | 5/2008 | Moerman | 204/403.03 |
| 7,378,720 | B2 | 5/2008 | Fu et al. | 435/287.2 |
| 7,402,616 | B2 | 7/2008 | Rodgers | 523/160 |
| 7,404,815 | B2 | 7/2008 | Kollias | 604/501 |
| 7,410,468 | B2 | 8/2008 | Freeman | 600/583 |
| 7,429,630 | B2 | 9/2008 | Liu | 525/283 |
| 7,431,814 | B2 | 10/2008 | Hodges | 204/403.02 |
| 7,431,820 | B2 | 10/2008 | Hodges | 205/777.5 |
| 7,438,694 | B2 | 10/2008 | Boozer | 600/583 |
| D579,652 | S | 11/2008 | Lim | D3/201 |
| D579,653 | S | 11/2008 | Lim | D3/201 |
| 7,462,265 | B2 | 12/2008 | Leach | 204/403.14 |
| 7,465,380 | B2 | 12/2008 | Rodgers | 204/403.14 |
| 7,468,125 | B2 | 12/2008 | Kraft | 205/792 |
| D585,314 | S | 1/2009 | Schvetz | D10/78 |
| 7,473,264 | B2 | 1/2009 | Allen | 606/181 |
| 7,474,390 | B2 | 1/2009 | Robinson | 356/42 |
| 7,474,391 | B2 | 1/2009 | Baskeyfield | 356/42 |
| 7,481,776 | B2 | 1/2009 | Boecker | 600/583 |
| 7,481,818 | B2 | 1/2009 | Allen | 606/181 |
| D586,465 | S | 2/2009 | Faulkner | D24/146 |
| D586,466 | S | 2/2009 | Smith | D24/186 |
| D586,678 | S | 2/2009 | Schvetz | D10/81 |
| D586,916 | S | 2/2009 | Faulkner | D24/146 |
| 7,485,128 | B2 | 2/2009 | Boecker | 606/181 |
| 7,491,178 | B2 | 2/2009 | Boecker | 600/583 |
| 7,498,132 | B2 | 3/2009 | Yu | 435/6 |
| 7,501,052 | B2 | 3/2009 | Iyengar | 205/777.5 |
| 7,501,093 | B2 | 3/2009 | Demelo | 422/58 |
| 7,521,019 | B2 | 4/2009 | Polak | 600/82.06 |
| 7,524,293 | B2 | 4/2009 | Freeman | 600/583 |
| 7,537,571 | B2 | 5/2009 | Freeman | 600/583 |
| 7,547,287 | B2 | 6/2009 | Boecker | 600/583 |
| 7,548,772 | B2 | 6/2009 | Shartle | 600/345 |
| 7,553,511 | B2 | 6/2009 | Hleong | 427/2.28 |
| 7,563,232 | B2 | 7/2009 | Freeman | 600/583 |
| D598,126 | S | 8/2009 | Alvarez-Icaza | D24/225 |
| 7,572,356 | B2 | 8/2009 | Rodgers | 204/403.05 |
| 7,575,558 | B2 | 8/2009 | Boecker | 600/573 |
| D600,349 | S | 9/2009 | Bell | D24/169 |
| D600,812 | S | 9/2009 | Lei | D24/169 |
| D600,813 | S | 9/2009 | Bell | D24/169 |
| D601,255 | S | 9/2009 | Schvetz | D24/169 |
| D601,258 | S | 9/2009 | Bell | D24/169 |
| 7,582,063 | B2 | 9/2009 | Wurster | 600/584 |
| 7,582,099 | B2 | 9/2009 | Freeman | 606/181 |
| 7,586,590 | B2 | 9/2009 | Baskeyfield | 356/42 |
| 7,588,670 | B2 | 9/2009 | Rodgers | 204/403.14 |
| 7,589,828 | B2 | 9/2009 | Robinson | 356/42 |
| 7,592,151 | B2 | 9/2009 | Liu | 435/14 |
| 7,593,097 | B2 | 9/2009 | Robinson | 356/42 |
| 7,604,592 | B2 | 10/2009 | Freeman | 600/309 |
| 7,604,722 | B2 | 10/2009 | Hodges | 204/403.02 |
| 7,608,175 | B2 | 10/2009 | Hodges | 204/403.02 |
| 7,618,522 | B2 | 11/2009 | Davies | 204/403.14 |
| 7,648,468 | B2 | 1/2010 | Boecker | 600/583 |
| 7,648,469 | B2 | 1/2010 | Boecker | 600/583 |
| 7,653,492 | B2 | 1/2010 | Davies | 702/22 |
| 7,654,127 | B2 | 2/2010 | Krulevitch | 73/1.16 |
| 7,655,119 | B2 | 2/2010 | Davies | 204/403.14 |
| 7,665,303 | B2 | 2/2010 | Bohm | 60/643 |
| 7,666,287 | B2 | 2/2010 | Zhao | 204/600 |
| D611,151 | S | 3/2010 | Lei | D24/169 |
| D611,372 | S | 3/2010 | Salter | D10/81 |
| D611,489 | S | 3/2010 | Bell | D14/486 |

D611,853 S 3/2010 Salter .......... D10/81
D612,274 S 3/2010 Heidemann .......... D10/78
D612,275 S 3/2010 Salter .......... D10/81
D612,279 S 3/2010 Heidemann .......... D10/103
7,674,232 B2 3/2010 Boecker .......... 600/583
7,682,318 B2 3/2010 Alden .......... 600/583
2001/0011157 A1 8/2001 Latterell .......... 600/576
2001/0016682 A1 8/2001 Berner .......... 600/345
2001/0017269 A1 8/2001 Heller .......... 205/777.5
2001/0027328 A1 10/2001 Lum .......... 606/186
2001/0031931 A1 10/2001 Cunningham .......... 600/573
2001/0037355 A1 11/2001 Britt .......... 709/201
2001/0042004 A1 11/2001 Taub .......... 705/11
2001/0045355 A1 11/2001 Gephart .......... 204/400
2001/0054319 A1 12/2001 Heller .......... 73/849
2002/0002326 A1 1/2002 Causey .......... 600/300
2002/0002344 A1 1/2002 Douglas .......... 600/583
2002/0004196 A1 1/2002 Whitson .......... 600/573
2002/0016568 A1 2/2002 Lebel .......... 604/131
2002/0016606 A1 2/2002 Moerman .......... 606/181
2002/0016923 A1 2/2002 Knaus .......... 713/200
2002/0019606 A1 2/2002 Lebel .......... 604/66
2002/0019747 A1 2/2002 Ware .......... 705/2
2002/0019748 A1 2/2002 Brown .......... 705/2
2002/0025469 A1 2/2002 Heller .......... 429/43
2002/0029058 A1 3/2002 Levaughn .......... 606/181
2002/0040208 A1 4/2002 Flaherty .......... 604/288.01
2002/0040230 A1 4/2002 Kuhr .......... 606/181
2002/0042090 A1 4/2002 Heller .......... 435/14
2002/0042594 A1 4/2002 Lum et al.
2002/0044890 A1 4/2002 Black .......... 422/56
2002/0052618 A1 5/2002 Haar .......... 606/181
2002/0053523 A1 5/2002 Liamos .......... 205/787
2002/0057993 A1 5/2002 Maisey .......... 422/82.01
2002/0076349 A1 6/2002 Aitken .......... 422/58
2002/0078091 A1 6/2002 Vu .......... 707/513
2002/0081559 A1 6/2002 Brown .......... 434/307 R
2002/0081588 A1 6/2002 Lumley-woodyear .......... 435/6
2002/0082543 A1 6/2002 Park .......... 604/21
2002/0084196 A1 7/2002 Liamos .......... 205/792
2002/0087056 A1 7/2002 Aceti
2002/0092612 A1 7/2002 Davies .......... 156/292
2002/0099308 A1 7/2002 Bojan et al.
2002/0103499 A1 8/2002 Perez .......... 606/182
2002/0120216 A1 8/2002 Fritz .......... 600/583
2002/0120261 A1 8/2002 Morris .......... 606/41
2002/0123335 A1 9/2002 Luna .......... 455/419
2002/0130042 A1 9/2002 Moerman .......... 204/403.01
2002/0133377 A1 9/2002 Brown .......... 705/3
2002/0136667 A1 9/2002 Subramanian .......... 422/100
2002/0136863 A1 9/2002 Subramanian .......... 428/156
2002/0137998 A1 9/2002 Smart .......... 600/347
2002/0138040 A1 9/2002 Flora .......... 604/116
2002/0148739 A2 10/2002 Liamos .......... 205/787
2002/0160520 A1 10/2002 Orloff .......... 436/72
2002/0161289 A1 10/2002 Hopkins .......... 600/322
2002/0168290 A1 11/2002 Yuzhakov .......... 422/56
2002/0169393 A1 11/2002 Cunningham .......... 600/573
2002/0169394 A1 11/2002 Eppstein .......... 600/573
2002/0176984 A1 11/2002 Smart .......... 428/336
2002/0177761 A1 11/2002 Orloff .......... 600/309
2002/0177763 A1 11/2002 Burns .......... 600/345
2002/0188224 A1 12/2002 Roe .......... 600/584
2003/0014010 A1 1/2003 Carpenter .......... 604/117
2003/0018282 A1 1/2003 Effenhauser .......... 600/583
2003/0018300 A1 1/2003 Duchon .......... 604/164.01
2003/0028125 A1 2/2003 Yuzhakov
2003/0028126 A1 2/2003 List .......... 600/583
2003/0032077 A1 2/2003 Itoh .......... 435/14
2003/0038047 A1 2/2003 Sleva .......... 206/370
2003/0050537 A1 3/2003 Wessel .......... 600/300
2003/0050573 A1 3/2003 Kuhr .......... 600/567
2003/0050656 A1 3/2003 Schraga .......... 606/182
2003/0057391 A1 3/2003 Krulevitch .......... 251/11
2003/0060730 A1 3/2003 Perez .......... 600/576
2003/0069753 A1 4/2003 Brown .......... 705/2
2003/0072647 A1 4/2003 Lum .......... 415/1
2003/0073089 A1 4/2003 Mauze .......... 435/6
2003/0073229 A1 4/2003 Greenstein .......... 435/287.2
2003/0073931 A1 4/2003 Boecker .......... 600/573
2003/0083685 A1 5/2003 Freeman .......... 606/181
2003/0083686 A1 5/2003 Freeman .......... 606/181
2003/0088160 A1 5/2003 Halleck .......... 600/300
2003/0088191 A1 5/2003 Freeman et al. .......... 600/583
2003/0089730 A1 5/2003 May .......... 221/232
2003/0093010 A1 5/2003 Essenpreis .......... 600/583
2003/0100040 A1 5/2003 Bonnecaze .......... 435/14
2003/0106810 A1 6/2003 Douglas .......... 205/777.5
2003/0109777 A1 6/2003 Kloepfer .......... 600/367
2003/0109860 A1 6/2003 Black
2003/0111357 A1 6/2003 Black .......... 205/775
2003/0113827 A1 6/2003 Burkoth .......... 435/14
2003/0116447 A1 6/2003 Surridge .......... 205/777.5
2003/0120297 A1 6/2003 Beyerlein .......... 606/185
2003/0135333 A1 7/2003 Aceti .......... 702/31
2003/0136189 A1 7/2003 Lauman et al.
2003/0139653 A1 7/2003 Manser .......... 600/300
2003/0143113 A2 7/2003 Yuzhakov .......... 422/56
2003/0144608 A1 7/2003 Kojima .......... 600/583
2003/0144609 A1 7/2003 Kennedy .......... 600/583
2003/0146110 A1 8/2003 Karinka .......... 205/777.5
2003/0149348 A1 8/2003 Raskas .......... 600/310
2003/0149377 A1 8/2003 Erickson .......... 600/573
2003/0153900 A1 8/2003 Aceti .......... 604/890.1
2003/0159944 A1 8/2003 Pottgen .......... 205/777.5
2003/0163351 A1 8/2003 Brown .......... 705/2
2003/0178322 A1 9/2003 Iyengar .......... 205/775
2003/0191376 A1 10/2003 Samuels .......... 600/309
2003/0191415 A1 10/2003 Moerman .......... 600/584
2003/0195435 A1 10/2003 Williams .......... 600/583
2003/0195540 A1 10/2003 Moerman .......... 606/181
2003/0199744 A1 10/2003 Buse .......... 600/347
2003/0199789 A1 10/2003 Boecker .......... 600/575
2003/0199790 A1 10/2003 Boecker .......... 600/576
2003/0199791 A1 10/2003 Boecker .......... 600/576
2003/0199891 A1 10/2003 Argauer .......... 606/181
2003/0199893 A1 10/2003 Boecker .......... 606/181
2003/0199894 A1 10/2003 Boecker .......... 606/181
2003/0199895 A1 10/2003 Boecker .......... 606/181
2003/0199896 A1 10/2003 Boecker .......... 606/181
2003/0199897 A1 10/2003 Boecker .......... 606/181
2003/0199898 A1 10/2003 Boecker .......... 606/181
2003/0199899 A1 10/2003 Boecker .......... 606/181
2003/0199900 A1 10/2003 Boecker .......... 606/181
2003/0199901 A1 10/2003 Boecker .......... 606/181
2003/0199902 A1 10/2003 Boecker .......... 606/181
2003/0199903 A1 10/2003 Boecker .......... 606/181
2003/0199904 A1 10/2003 Boecker .......... 606/181
2003/0199905 A1 10/2003 Boecker .......... 606/181
2003/0199906 A1 10/2003 Boecker .......... 606/181
2003/0199907 A1 10/2003 Boecker .......... 606/181
2003/0199908 A1 10/2003 Boecker .......... 606/181
2003/0199909 A1 10/2003 Boecker .......... 606/181
2003/0199910 A1 10/2003 Boecker .......... 606/181
2003/0199911 A1 10/2003 Boecker .......... 606/181
2003/0199912 A1 10/2003 Pugh .......... 606/182
2003/0201194 A1 10/2003 Heller .......... 205/777.5
2003/0203352 A1 10/2003 Haviland .......... 435/4
2003/0206828 A1 11/2003 Bell .......... 422/44
2003/0208140 A1 11/2003 Pugh .......... 600/584
2003/0210811 A1 11/2003 Dubowsky .......... 382/128
2003/0212344 A1 11/2003 Yuzhakov .......... 600/583
2003/0212345 A1 11/2003 McAllister .......... 600/584
2003/0212346 A1 11/2003 McAllister et al. .......... 600/584
2003/0212347 A1 11/2003 Sohrab .......... 600/584
2003/0212379 A1 11/2003 Bylund .......... 604/504

| Publication No. | Kind | Date | Name | Class |
|---|---|---|---|---|
| 2003/0212423 | A1 | 11/2003 | Pugh | 606/181 |
| 2003/0212424 | A1 | 11/2003 | Briggs | 606/181 |
| 2003/0212579 | A1 | 11/2003 | Brown | 705/2 |
| 2003/0216767 | A1 | 11/2003 | List | 606/181 |
| 2003/0217918 | A1 | 11/2003 | Davies | 204/403.14 |
| 2003/0220552 | A1 | 11/2003 | Reghabi | 600/365 |
| 2003/0220663 | A1 | 11/2003 | Fletcher | 606/182 |
| 2003/0223906 | A1 | 12/2003 | McAllister | 422/58 |
| 2003/0225317 | A1 | 12/2003 | Schell | 600/300 |
| 2003/0225429 | A1 | 12/2003 | Garthe | 606/182 |
| 2003/0225430 | A1 | 12/2003 | Schraga | 606/182 |
| 2003/0228637 | A1 | 12/2003 | Wang | 435/7.9 |
| 2003/0229514 | A2 | 12/2003 | Brown | 705/2 |
| 2003/0232370 | A1 | 12/2003 | Trifiro | 435/6 |
| 2003/0233055 | A1 | 12/2003 | Erickson | 600/573 |
| 2003/0233112 | A1 | 12/2003 | Alden et al. | 606/181 |
| 2003/0233113 | A1 | 12/2003 | Alden et al. | 606/182 |
| 2004/0006285 | A1 | 1/2004 | Douglas | 600/583 |
| 2004/0007585 | A1 | 1/2004 | Griffith | 221/232 |
| 2004/0009100 | A1 | 1/2004 | Simons | 422/102 |
| 2004/0010279 | A1 | 1/2004 | Freeman | 606/182 |
| 2004/0015064 | A1 | 1/2004 | Parsons | 600/347 |
| 2004/0019250 | A1 | 1/2004 | Catelli | 600/1 |
| 2004/0019259 | A1 | 1/2004 | Brown | 600/300 |
| 2004/0026243 | A1 | 2/2004 | Davies | 204/403.14 |
| 2004/0026244 | A1 | 2/2004 | Hodges | 204/409 |
| 2004/0030353 | A1 | 2/2004 | Schmelzeisen-Redeker et al. | 606/201 |
| 2004/0031682 | A1 | 2/2004 | Wilsey | 204/403.1 |
| 2004/0034318 | A1 | 2/2004 | Fritz | 604/19 |
| 2004/0038045 | A1 | 2/2004 | Smart | 428/446 |
| 2004/0039303 | A1 | 2/2004 | Wurster | 600/584 |
| 2004/0039342 | A1 | 2/2004 | Eppstein | 604/200 |
| 2004/0039407 | A1 | 2/2004 | Schraga | 606/181 |
| 2004/0039408 | A1 | 2/2004 | Abulhaj | 606/181 |
| 2004/0049219 | A1 | 3/2004 | Briggs | 606/181 |
| 2004/0049220 | A1 | 3/2004 | Boecker | 606/181 |
| 2004/0050694 | A1 | 3/2004 | Yang | 204/403.02 |
| 2004/0054267 | A1 | 3/2004 | Feldman | 600/316 |
| 2004/0055898 | A1 | 3/2004 | Heller et al. | 205/777.5 |
| 2004/0059256 | A1 | 3/2004 | Perez | 600/583 |
| 2004/0060818 | A1 | 4/2004 | Feldman | 204/403.01 |
| 2004/0061841 | A1 | 4/2004 | Black | 355/30 |
| 2004/0064068 | A1 | 4/2004 | DeNuzzio | 600/583 |
| 2004/0069657 | A1 | 4/2004 | Hodges | 205/787 |
| 2004/0087990 | A1 | 5/2004 | Boecker | 606/181 |
| 2004/0092842 | A1 | 5/2004 | Boecker | 600/575 |
| 2004/0092994 | A1 | 5/2004 | Briggs | 606/181 |
| 2004/0092995 | A1 | 5/2004 | Boecker | 606/181 |
| 2004/0096991 | A1 | 5/2004 | Zhang | 436/518 |
| 2004/0098009 | A1 | 5/2004 | Boecker | 606/181 |
| 2004/0098010 | A1 | 5/2004 | Davison | 606/181 |
| 2004/0102803 | A1 | 5/2004 | Boecker | 606/183 |
| 2004/0106855 | A1 | 6/2004 | Brown | 600/301 |
| 2004/0106858 | A1 | 6/2004 | Say | 600/345 |
| 2004/0106859 | A1 | 6/2004 | Say | 600/345 |
| 2004/0106860 | A1 | 6/2004 | Say | 600/345 |
| 2004/0106904 | A1 | 6/2004 | Gonnelli | 604/173 |
| 2004/0106941 | A1 | 6/2004 | Roe | 606/181 |
| 2004/0107116 | A1 | 6/2004 | Brown | 705/2 |
| 2004/0115754 | A1 | 6/2004 | Chang | 435/14 |
| 2004/0115831 | A1 | 6/2004 | Meathrel | 436/514 |
| 2004/0116780 | A1 | 6/2004 | Brown | 600/300 |
| 2004/0116829 | A1 | 6/2004 | Raney | 600/573 |
| 2004/0117207 | A1 | 6/2004 | Brown | 705/2 |
| 2004/0117208 | A1 | 6/2004 | Brown | 705/2 |
| 2004/0117209 | A1 | 6/2004 | Brown | 705/2 |
| 2004/0117210 | A1 | 6/2004 | Brown | 705/2 |
| 2004/0122339 | A1 | 6/2004 | Roe | |
| 2004/0127818 | A1 | 7/2004 | Roe | 600/583 |
| 2004/0127819 | A1 | 7/2004 | Roe | 600/583 |
| 2004/0127928 | A1 | 7/2004 | Whitson | 606/181 |
| 2004/0127929 | A1 | 7/2004 | Roe | 606/181 |
| 2004/0132167 | A1 | 7/2004 | Rule | 435/287.1 |
| 2004/0133125 | A1 | 7/2004 | Miyashita | 600/573 |
| 2004/0133127 | A1 | 7/2004 | Roe | 600/583 |
| 2004/0137640 | A1 | 7/2004 | Hirao | 436/514 |
| 2004/0138541 | A1 | 7/2004 | Ward | 600/345 |
| 2004/0138588 | A1 | 7/2004 | Saikley | 600/583 |
| 2004/0138688 | A1 | 7/2004 | Giraud | 606/181 |
| 2004/0146958 | A1 | 7/2004 | Bae | 435/14 |
| 2004/0154932 | A1 | 8/2004 | Deng | 205/777.5 |
| 2004/0157017 | A1 | 8/2004 | Mauze | 428/35.7 |
| 2004/0157149 | A1 | 8/2004 | Hofmann | 430/131 |
| 2004/0157319 | A1 | 8/2004 | Keen | 435/287.2 |
| 2004/0157338 | A1 | 8/2004 | Burke | 436/147 |
| 2004/0157339 | A1 | 8/2004 | Burke | 436/149 |
| 2004/0158137 | A1 | 8/2004 | Eppstein | 600/347 |
| 2004/0158271 | A1 | 8/2004 | Hamamoto | 606/181 |
| 2004/0161737 | A1 | 8/2004 | Yang | 435/5 |
| 2004/0162473 | A1 | 8/2004 | Sohrab | 600/345 |
| 2004/0162474 | A1 | 8/2004 | Kiser | 600/345 |
| 2004/0162506 | A1 | 8/2004 | Duchon | 600/583 |
| 2004/0162573 | A1 | 8/2004 | Kheiri | 606/182 |
| 2004/0167383 | A1 | 8/2004 | Kim | 600/365 |
| 2004/0171057 | A1 | 9/2004 | Yang et al. | 435/6 |
| 2004/0171968 | A1 | 9/2004 | Katsuki | 600/583 |
| 2004/0172000 | A1 | 9/2004 | Roe | 604/361 |
| 2004/0173472 | A1 | 9/2004 | Jung | 205/777.5 |
| 2004/0173488 | A1 | 9/2004 | Griffin | 206/363 |
| 2004/0176705 | A1 | 9/2004 | Stevens | 600/584 |
| 2004/0176732 | A1 | 9/2004 | Frazier | 604/345 |
| 2004/0178066 | A1 | 9/2004 | Miyazaki | 204/403.01 |
| 2004/0178067 | A1 | 9/2004 | Miyazaki | 204/403.1 |
| 2004/0178216 | A1 | 9/2004 | Brickwood | 221/268 |
| 2004/0180379 | A1 | 9/2004 | van Duyne | 435/7.1 |
| 2004/0182703 | A1 | 9/2004 | Bell | 204/403.11 |
| 2004/0185568 | A1 | 9/2004 | Matsumoto | 436/8 |
| 2004/0186359 | A1 | 9/2004 | Beaudoin | 600/310 |
| 2004/0186394 | A1 | 9/2004 | Roe | 600/598 |
| 2004/0186500 | A1 | 9/2004 | Koilke | 606/181 |
| 2004/0193201 | A1 | 9/2004 | Kim | 606/181 |
| 2004/0193377 | A1 | 9/2004 | Brown | 702/19 |
| 2004/0194302 | A1 | 10/2004 | Bhullar | 29/847 |
| 2004/0197231 | A1 | 10/2004 | Katsuki | 422/68.1 |
| 2004/0197821 | A1 | 10/2004 | Bauer | 437/7.1 |
| 2004/0199062 | A1 | 10/2004 | Petersson | 600/316 |
| 2004/0199409 | A1 | 10/2004 | Brown | 705/3 |
| 2004/0200720 | A1 | 10/2004 | Musho | 204/403.01 |
| 2004/0200721 | A1 | 10/2004 | Bhullar | 204/403.01 |
| 2004/0202576 | A1 | 10/2004 | Aceti | 422/82.05 |
| 2004/0204662 | A1 | 10/2004 | Perez | 600/583 |
| 2004/0206625 | A1 | 10/2004 | Bhullar | 204/403.1 |
| 2004/0206636 | A1 | 10/2004 | Hodges | 205/792 |
| 2004/0206658 | A1 | 10/2004 | Hammerstedt | 206/524.1 |
| 2004/0209307 | A1 | 10/2004 | Valkirs | 435/7.1 |
| 2004/0209350 | A1 | 10/2004 | Sakata | 435/287.1 |
| 2004/0209354 | A1 | 10/2004 | Mathies | 435/287.2 |
| 2004/0210279 | A1 | 10/2004 | Gruzdev | 607/89 |
| 2004/0211666 | A1 | 10/2004 | Pamidi | 204/403.01 |
| 2004/0214253 | A1 | 10/2004 | Paek | 435/7.92 |
| 2004/0215224 | A1 | 10/2004 | Sakata | 606/181 |
| 2004/0215225 | A1 | 10/2004 | Nakayama | 606/182 |
| 2004/0216516 | A1 | 11/2004 | Sato | 73/64.56 |
| 2004/0217019 | A1 | 11/2004 | Cai | 205/792 |
| 2004/0219500 | A1 | 11/2004 | Brown | 434/307 R |
| 2004/0219535 | A1 | 11/2004 | Bell | 435/6 |
| 2004/0220456 | A1 | 11/2004 | Eppstein | 600/309 |
| 2004/0220495 | A1 | 11/2004 | Cahir | 600/562 |
| 2004/0220564 | A1 | 11/2004 | Ho | 606/47 |
| 2004/0220603 | A1 | 11/2004 | Rutynowski | 606/181 |
| 2004/0222092 | A1 | 11/2004 | Musho | 204/401 |
| 2004/0224369 | A1 | 11/2004 | Cai | 435/7.7 |
| 2004/0225230 | A1 | 11/2004 | Liamos | 600/583 |
| 2004/0225311 | A1 | 11/2004 | Levaughn | 606/181 |
| 2004/0225312 | A1 | 11/2004 | Orloff | 606/182 |

2004/0230216 A1 11/2004 Levaughn ................... 606/181
2004/0231983 A1 11/2004 Shen ..................... 204/403.01
2004/0231984 A1 11/2004 Lauks ........................ 204/416
2004/0232009 A1 11/2004 Okuda ........................ 205/789
2004/0236250 A1 11/2004 Hodges ...................... 600/583
2004/0236251 A1 11/2004 Roe et al. ................... 600/583
2004/0236268 A1 11/2004 Mitragotri et al. ............. 604/20
2004/0236362 A1 11/2004 Shraga ....................... 606/181
2004/0238357 A1 12/2004 Bhullar ....................... 204/400
2004/0238358 A1 12/2004 Forrow ....................... 204/403
2004/0238359 A1 12/2004 Ikeda ...................... 204/403.1
2004/0241746 A1 12/2004 Adlassnig ................... 435/7.1
2004/0242977 A1 12/2004 Dosmann .................... 600/315
2004/0243164 A1 12/2004 D'Agostino ................ 606/181
2004/0243165 A1 12/2004 Koike ......................... 606/181
2004/0245101 A1 12/2004 Willner ...................... 204/403
2004/0248282 A1 12/2004 Sobha ..................... 435/287.2
2004/0248312 A1 12/2004 Vreeke ........................ 436/95
2004/0249254 A1 12/2004 Racchini ..................... 600/347
2004/0249310 A1 12/2004 Shartle ....................... 600/583
2004/0249311 A1 12/2004 Haar .......................... 600/584
2004/0249405 A1 12/2004 Watanabe ................... 606/181
2004/0249406 A1 12/2004 Griffin ........................ 606/182
2004/0251131 A1 12/2004 Ueno ......................... 204/403
2004/0253634 A1 12/2004 Wang ......................... 435/7.1
2004/0254434 A1 12/2004 Goodnow .................. 600/365
2004/0254599 A1 12/2004 Lipoma ...................... 606/181
2004/0256228 A1 12/2004 Huang ........................ 204/434
2004/0256248 A1 12/2004 Burke ......................... 205/792
2004/0256685 A1 12/2004 Chou ......................... 257/414
2004/0258564 A1 12/2004 Charlton ...................... 422/58
2004/0260204 A1 12/2004 Boecker ..................... 600/584
2004/0260324 A1 12/2004 Fukuzawa ................... 606/181
2004/0260325 A1 12/2004 Kuhr .......................... 606/181
2004/0260326 A1 12/2004 Lipoma ...................... 606/182
2004/0260511 A1 12/2004 Burke ......................... 702/182
2004/0267105 A1 12/2004 Monfre ....................... 600/344
2004/0267160 A9 12/2004 Perez ......................... 600/583
2004/0267229 A1 12/2004 Moerman ................... 604/500
2004/0267299 A1 12/2004 Kuriger ...................... 606/181
2004/0267300 A1 12/2004 Mace ......................... 606/182
2005/0000806 A1 1/2005 Hsieh ...................... 203/403.1
2005/0000807 A1 1/2005 Wang .................... 204/403.81
2005/0000808 A1 1/2005 Cui ....................... 203/403.14
2005/0003470 A1 1/2005 Nelson ........................ 435/14
2005/0004437 A1 1/2005 Kaufmann .................. 600/300
2005/0004494 A1 1/2005 Perez ......................... 600/583
2005/0008537 A1 1/2005 Mosolu ....................... 422/56
2005/0008851 A1 1/2005 Ezoe .......................... 428/336
2005/0009191 A1 1/2005 Swenson ..................... 436/43
2005/0010090 A1 1/2005 Acosta ....................... 600/316
2005/0010093 A1 1/2005 Ford ........................... 600/345
2005/0010134 A1 1/2005 Douglas ..................... 600/573
2005/0010137 A1 1/2005 Hodges ...................... 600/583
2005/0010198 A1 1/2005 Marchitto ...................... 606/9
2005/0011759 A1 1/2005 Moerman ............. 204/403.03
2005/0013731 A1 1/2005 Burke .......................... 422/56
2005/0014997 A1 1/2005 Ruchti ........................ 600/310
2005/0015020 A1 1/2005 LeVaughn ................... 600/583
2005/0016844 A1 1/2005 Burke ...................... 204/403.1
2005/0019212 A1 1/2005 Bhullar ........................ 422/56
2005/0019219 A1 1/2005 Oshiman ................. 422/82.12
2005/0019805 A1 1/2005 Groll ............................ 435/6
2005/0019945 A1 1/2005 Groll .......................... 436/169
2005/0019953 A1 1/2005 Groll .......................... 436/514
2005/0021066 A1 1/2005 Kuhr .......................... 606/181
2005/0027181 A1 2/2005 Goode et al.
2005/0027211 A1 2/2005 Kuhr .......................... 600/583
2005/0027562 A1 2/2005 Brown ........................... 705/2
2005/0033340 A1 2/2005 Lipoma ...................... 606/181
2005/0033341 A1 2/2005 Vreeke ....................... 606/181
2005/0034983 A1 2/2005 Chambers ............. 204/403.01
2005/0036020 A1 2/2005 Li ............................. 347/100
2005/0036146 A1 2/2005 Braig ......................... 356/246
2005/0036906 A1 2/2005 Nakahara et al. .............. 422/58
2005/0036909 A1 2/2005 Erickson ...................... 422/61
2005/0037482 A1 2/2005 Braig ......................... 435/287
2005/0038329 A1 2/2005 Morris ....................... 600/319
2005/0038330 A1 2/2005 Jansen ....................... 600/345
2005/0038463 A1 2/2005 Davar ......................... 606/181
2005/0038464 A1 2/2005 Schraga ..................... 606/182
2005/0038465 A1 2/2005 Schraga ..................... 606/182
2005/0038674 A1 2/2005 Braig ........................... 705/2
2005/0042766 A1 2/2005 Ohman ....................... 436/174
2005/0043894 A1 2/2005 Fernandez ................... 702/19
2005/0043965 A1 2/2005 Heller ........................... 705/2
2005/0045476 A1 3/2005 Neel ....................... 204/403.2
2005/0049472 A1 3/2005 Manda ....................... 600/345
2005/0050859 A1 3/2005 Coppeta ...................... 53/471
2005/0054082 A1 3/2005 Pachl ...................... 435/287.2
2005/0054908 A1 3/2005 Blank ......................... 600/316
2005/0059872 A1 3/2005 Shartle ....................... 600/347
2005/0059895 A1 3/2005 Brown ........................ 600/481
2005/0060194 A1 3/2005 Brown ........................... 705/2
2005/0061668 A1 3/2005 Brenneman ............ 204/403.01
2005/0064528 A1 3/2005 Kwon .......................... 435/14
2005/0067280 A1 3/2005 Reid ..................... 204/403.14
2005/0067737 A1 3/2005 Rappin ................. 264/272.19
2005/0070771 A1 3/2005 Rule .......................... 600/316
2005/0070819 A1 3/2005 Poux .......................... 600/576
2005/0070945 A1 3/2005 Schraga ..................... 606/182
2005/0494473 3/2005 Desai, S ..................... 600/347
2005/0072670 A1 4/2005 Hasegawa ............. 204/403.01
2005/0077176 A1 4/2005 Hodges ................ 204/403.01
2005/0077584 A1 4/2005 Uhland ....................... 257/414
2005/0079542 A1 4/2005 Cullen ........................ 435/7.1
2005/0080652 A1 4/2005 Brown ........................... 705/2
2005/0085839 A1 4/2005 Allen ......................... 606/181
2005/0085840 A1 4/2005 Yi ............................. 606/182
2005/0086083 A1 4/2005 Brown ........................... 705/2
2005/0090754 A1 4/2005 Wolf .......................... 600/509
2005/0090850 A1 4/2005 Toes .......................... 606/182
2005/0096520 A1 5/2005 Maekawa ................... 600/365
2005/0096565 A1 5/2005 Chang ........................ 600/584
2005/0096586 A1 5/2005 Trautman .................... 604/46
2005/0096587 A1 5/2005 Santini ........................ 604/66
2005/0096686 A1 5/2005 Allen ......................... 606/181
2005/0098431 A1 5/2005 Hodges ................ 204/403.01
2005/0098432 A1 5/2005 Gundel .................... 204/403.2
2005/0098433 A1 5/2005 Gundel .................... 204/403.2
2005/0098434 A1 5/2005 Gundel .................. 204/403.02
2005/0100880 A1 5/2005 Chang ........................... 435/4
2005/0101841 A9 5/2005 Kaylor ....................... 600/300
2005/0101979 A1 5/2005 Alden ........................ 606/181
2005/0101980 A1 5/2005 Alden ........................ 606/181
2005/0101981 A1 5/2005 Alden ........................ 606/181
2005/0103624 A1 5/2005 Bhullar .................. 204/403.01
2005/0106713 A1 5/2005 Phan ....................... 435/287.2
2005/0109637 A1 5/2005 Iyengar ...................... 205/775
2005/0112712 A1 5/2005 Ouyang ........................ 435/14
2005/0112782 A1 5/2005 Buechler .................... 436/518
2005/0113658 A1 5/2005 Jacobson .................... 600/342
2005/0113717 A1 5/2005 Matzinger ................... 600/573
2005/0114062 A1 5/2005 Davies ....................... 702/104
2005/0114154 A1 5/2005 Wolkowicz .................... 705/1
2005/0114444 A1 5/2005 Brown ........................ 709/203
2005/0118056 A1 6/2005 Swanson ..................... 423/23
2005/0118062 A1 6/2005 Otake ........................ 422/68.1
2005/0119681 A1 6/2005 Marshall ..................... 606/181
2005/0123443 A1 6/2005 Fujiwara ...................... 422/58
2005/0123680 A1 6/2005 Kang ...................... 427/248.1
2005/0124869 A1 6/2005 Hefti .......................... 600/316
2005/0125017 A1 6/2005 Kudrna ....................... 606/181
2005/0125018 A1 6/2005 Galloway ................... 606/181
2005/0125019 A1 6/2005 Kudrna ....................... 606/182
2005/0126929 A1 6/2005 Mansouri .................... 205/778

2005/0130248 A1 6/2005 Willner ........................ 435/14
2005/0130249 A1 6/2005 Parris .......................... 435/14
2005/0130292 A1 6/2005 Ahn ........................ 435/287.1
2005/0131286 A1 6/2005 Parker ........................ 600/328
2005/0131441 A1 6/2005 Iio ............................ 606/182
2005/0133368 A1 6/2005 Davies ................. 204/403.01
2005/0136471 A1 6/2005 Bhullar .......................... 435/6
2005/0136501 A1 6/2005 Kuriger ....................... 435/14
2005/0136529 A1 6/2005 Yang .......................... 435/287
2005/0136550 A1 6/2005 Yang .......................... 436/514
2005/0137536 A1 6/2005 Gonnelli ..................... 604/264
2005/0140659 A1 6/2005 Hohl .......................... 345/169
2005/0143675 A1 6/2005 Neel .......................... 600/583
2005/0143713 A1 6/2005 Delmore ..................... 604/506
2005/0143771 A1 6/2005 Stout .......................... 606/181
2005/0145490 A1 7/2005 Shinno ....................... 204/403
2005/0145491 A1 7/2005 Amano ....................... 204/403
2005/0145520 A1 7/2005 Ilo ............................ 206/365
2005/0149088 A1 7/2005 Fukuda ....................... 606/181
2005/0149089 A1 7/2005 Trissel ........................ 606/181
2005/0149090 A1 7/2005 Morita ....................... 606/181
2005/0150762 A1 7/2005 Butters ....................... 204/403
2005/0150763 A1 7/2005 Butters ....................... 204/403
2005/0154277 A1 7/2005 Ting ........................... 600/407
2005/0154374 A1 7/2005 Hunter ....................... 604/890
2005/0154410 A1 7/2005 Conway ..................... 606/181
2005/0154616 A1 7/2005 Iliff ............................... 705/3
2005/0158850 A1 7/2005 Kubo ...................... 435/287.2
2005/0159656 A1 7/2005 Hockersmith ............... 600/315
2005/0159768 A1 7/2005 Boehm ....................... 606/182
2005/0164322 A1 7/2005 Heller ......................... 435/14
2005/0164329 A1 7/2005 Wallace-Davis ............. 435/25
2005/0165285 A1 7/2005 Iliff ............................ 600/300
2005/0165393 A1 7/2005 Eppstein ..................... 606/41
2005/0165622 A1 7/2005 Neel ............................ 705/2
2005/0169810 A1 8/2005 Hagen ........................ 422/102
2005/0169961 A1 8/2005 Hunter ....................... 424/423
2005/0170448 A1 8/2005 Burson ........................ 435/14
2005/0171567 A1 8/2005 DeHart ....................... 606/181
2005/0172021 A1 8/2005 Brown ........................ 709/224
2005/0172022 A1 8/2005 Brown ........................ 709/224
2005/0173245 A1 8/2005 Feldman ............... 204/403.01
2005/0173246 A1 8/2005 Hodges ................ 204/403.11
2005/0175509 A1 8/2005 Nakaminami ............ 422/82.03
2005/0176084 A1 8/2005 Burkoth ....................... 435/14
2005/0176133 A1 8/2005 Miyashita ................ 435/287.1
2005/0176153 A1 8/2005 O'hara ........................ 436/70
2005/0177071 A1 8/2005 Nakayama .................. 600/583
2005/0177201 A1 8/2005 Freeman ...................... 607/46
2005/0177398 A1 8/2005 Watanabe ...................... 705/3
2005/0178218 A1 8/2005 Montagu ................. 73/864.34
2005/0181010 A1 8/2005 Hunter ....................... 424/423
2005/0181497 A1 8/2005 Saito ....................... 435/287.1
2005/0182307 A1 8/2005 Currie ........................ 600/300
2005/0187439 A1 8/2005 Blank ......................... 600/310
2005/0187444 A1 8/2005 Hubner ....................... 600/322
2005/0192488 A1 9/2005 Bryenton .................... 600/301
2005/0196821 A1 9/2005 Monfre ........................ 435/14
2005/0197666 A1 9/2005 Raney ........................ 606/181
2005/0201897 A1 9/2005 Zimmer .................. 422/82.05
2005/0202567 A1 9/2005 Zanzucchi ................... 436/95
2005/0203358 A1 9/2005 Monfre ....................... 600/331
2005/0203364 A1 9/2005 Monfre ....................... 600/365
2005/0204939 A1 9/2005 Krejci ........................ 101/129
2005/0205136 A1 9/2005 Freeman ..................... 137/554
2005/0205422 A1 9/2005 Moser ................... 204/403.06
2005/0205816 A1 9/2005 Hayenga .................... 251/61.1
2005/0209515 A1 9/2005 Hockersmith ............... 600/316
2005/0209564 A1 9/2005 Bonner ...................... 604/173
2005/0209625 A1 9/2005 Chan .......................... 606/181
2005/0211571 A1 9/2005 Schulein ................. 205/777.5
2005/0211572 A1 9/2005 Buck .......................... 205/778
2005/0214881 A1 9/2005 Azarnia .................... 435/7.92
2005/0214892 A1 9/2005 Kovatchev ................... 435/25
2005/0215871 A1 9/2005 Feldman ..................... 600/309
2005/0215872 A1 9/2005 Berner ....................... 600/347
2005/0215923 A1 9/2005 Wiegel ....................... 600/573
2005/0215925 A1 9/2005 Chan .......................... 600/583
2005/0216046 A1 9/2005 Yeoh .......................... 606/181
2005/0218024 A1 10/2005 Lang .......................... 206/438
2005/0221276 A1 10/2005 Rozakis ......................... 435/4
2005/0221470 A1 10/2005 Matsumoto ............. 435/287.1
2005/0222599 A1 10/2005 Czernecki .................. 606/182
2005/0227372 A1 10/2005 Khan ......................... 436/514
2005/0228242 A1 10/2005 Kawamura ................. 600/300
2005/0228883 A1 10/2005 Brown ........................ 709/224
2005/0230252 A1 10/2005 Tsai ........................... 204/450
2005/0230253 A1 10/2005 Marquant .................. 204/451
2005/0232813 A1 10/2005 Karmali ....................... 422/58
2005/0232815 A1 10/2005 Ruhl ........................... 422/66
2005/0234368 A1 10/2005 Wong ......................... 600/583
2005/0234486 A1 10/2005 Allen ......................... 606/181
2005/0234487 A1 10/2005 Shi ............................ 600/181
2005/0234488 A1 10/2005 Allen ......................... 606/181
2005/0234489 A1 10/2005 Allen ......................... 606/181
2005/0234490 A1 10/2005 Allen ......................... 606/181
2005/0234491 A1 10/2005 Allen ......................... 606/181
2005/0234492 A1 10/2005 Tsai ........................... 606/181
2005/0234494 A1 10/2005 Conway ..................... 606/181
2005/0234495 A1 10/2005 Schraga ..................... 606/181
2005/0235060 A1 10/2005 Brown ........................ 709/224
2005/0239154 A1 10/2005 Feldman ...................... 435/14
2005/0239156 A1 10/2005 Drucker ....................... 435/14
2005/0239194 A1 10/2005 Takahashi ................ 435/287.2
2005/0240090 A1 10/2005 Ruchti ........................ 600/316
2005/0240119 A1 10/2005 Draudt ....................... 600/583
2005/0240207 A1 10/2005 Marshall .................... 606/181
2005/0240778 A1 10/2005 Saito .......................... 713/186
2005/0245798 A1 11/2005 Yamaguchi ................. 600/345
2005/0245843 A1 11/2005 Day ........................... 600/583
2005/0245844 A1 11/2005 Mace ......................... 600/583
2005/0245845 A1 11/2005 Roe ........................... 600/583
2005/0245954 A1 11/2005 Roe ........................... 606/181
2005/0245955 A1 11/2005 Schraga ..................... 606/181
2005/0256534 A1 11/2005 Alden ........................ 606/182
2005/0258035 A1 11/2005 Harding ................. 204/403.01
2005/0258036 A1 11/2005 Harding ................. 204/403.01
2005/0258050 A1 11/2005 Harding ...................... 205/775
2005/0265094 A1 12/2005 Harding ...................... 365/203
2005/0276133 A1 12/2005 Harding ...................... 365/203
2005/0278945 A1 12/2005 Feldman ...................... 29/830
2005/0279631 A1 12/2005 Celentano .............. 204/403.01
2005/0279647 A1 12/2005 Beaty ......................... 205/792
2005/0283094 A1 12/2005 Thym ......................... 600/583
2005/0284110 A1 12/2005 Lang ........................... 53/473
2005/0284757 A1 12/2005 Allen ......................... 204/400
2005/0287620 A1 12/2005 Heller ......................... 435/14
2005/0288637 A1 12/2005 Kuhr .......................... 604/204
2005/0288698 A1 12/2005 Matsumoto ................. 606/181
2005/0288699 A1 12/2005 Schraga ..................... 606/181
2006/0000549 A1 1/2006 Lang .......................... 156/320
2006/0003398 A1 1/2006 Heller ......................... 435/14
2006/0004270 A1 1/2006 Bedard ....................... 600/316
2006/0004271 A1 1/2006 Peyser ....................... 600/362
2006/0004272 A1 1/2006 Shah .......................... 600/365
2006/0006574 A1 1/2006 Lang .......................... 264/165
2006/0008389 A1 1/2006 Sacherer ..................... 422/102
2006/0015129 A1 1/2006 Shahrokni ................... 606/181
2006/0016698 A1 1/2006 Lee ......................... 205/777.5
2006/0020228 A1 1/2006 Fowler ....................... 600/583
2006/0024774 A1 2/2006 Zocchi ........................ 435/14
2006/0025662 A1 2/2006 Buse .......................... 600/347
2006/0029979 A1 2/2006 Bai ............................ 435/7.1
2006/0029991 A1 2/2006 Hagino ........................ 435/14
2006/0030028 A1 2/2006 Nakaminami ............ 435/287.2
2006/0030050 A1 2/2006 Milne .......................... 436/67

| | | | | |
|---|---|---|---|---|
| 2006/0030761 | A1 | 2/2006 | Raskas | 600/316 |
| 2006/0030788 | A1 | 2/2006 | Wong | 600/583 |
| 2006/0034728 | A1 | 2/2006 | Kloepfer | 422/68.1 |
| 2006/0037859 | A1 | 2/2006 | Hodges | 204/400 |
| 2006/0040333 | A1 | 2/2006 | Zocchi | 435/14 |
| 2006/0047220 | A1 | 3/2006 | Sakata | 600/583 |
| 2006/0047294 | A1 | 3/2006 | Mori | 606/181 |
| 2006/0052723 | A1 | 3/2006 | Roe | 600/583 |
| 2006/0052724 | A1 | 3/2006 | Roe | 600/583 |
| 2006/0052809 | A1 | 3/2006 | Karbowniczek | 606/181 |
| 2006/0052810 | A1 | 3/2006 | Freeman | 606/181 |
| 2006/0058827 | A1 | 3/2006 | Sakata | 606/181 |
| 2006/0058828 | A1 | 3/2006 | Shi | 606/181 |
| 2006/0062852 | A1 | 3/2006 | Holmes | 424/484 |
| 2006/0063988 | A1 | 3/2006 | Schurman | 600/316 |
| 2006/0064035 | A1 | 3/2006 | Wang | 600/583 |
| 2006/0079739 | A1 | 4/2006 | Chen Wang | 600/300 |
| 2006/0079810 | A1 | 4/2006 | Patel | 600/583 |
| 2006/0079811 | A1 | 4/2006 | Roe | 600/583 |
| 2006/0079920 | A1 | 4/2006 | Schraga | 606/181 |
| 2006/0081469 | A1 | 4/2006 | Lee | 204/403.02 |
| 2006/0085020 | A1 | 4/2006 | Freeman | 606/181 |
| 2006/0085137 | A1 | 4/2006 | Bartkowiak | 702/19 |
| 2006/0086624 | A1 | 4/2006 | Tapsak | 205/775 |
| 2006/0088945 | A1 | 4/2006 | Douglas . | 436/518 |
| 2006/0089566 | A1 | 4/2006 | DeHart | 600/573 |
| 2006/0091006 | A1 | 5/2006 | Wang | 204/403.02 |
| 2006/0094944 | A1 | 5/2006 | Chuang | 600/347 |
| 2006/0094947 | A1 | 5/2006 | Kovatchev | 600/365 |
| 2006/0094985 | A1 | 5/2006 | Aceti | 600/575 |
| 2006/0094986 | A1 | 5/2006 | Neel | 600/583 |
| 2006/0095061 | A1 | 5/2006 | Trautman | 606/185 |
| 2006/0096859 | A1 | 5/2006 | Lau | 204/403.14 |
| 2006/0099107 | A1 | 5/2006 | Yamamoto | 422/57 |
| 2006/0099703 | A1 | 5/2006 | Choi | 435/287.1 |
| 2006/0100542 | A9 | 5/2006 | Wong | 600/583 |
| 2006/0100543 | A1 | 5/2006 | Raney | 600/583 |
| 2006/0100654 | A1 | 5/2006 | Fukuda | 606/181 |
| 2006/0100655 | A1 | 5/2006 | Leong | 606/181 |
| 2006/0100656 | A1 | 5/2006 | Olson | 606/181 |
| 2006/0106373 | A1 | 5/2006 | Cahir | 606/9 |
| 2006/0108236 | A1 | 5/2006 | Kasielke | 205/792 |
| 2006/0113187 | A1 | 6/2006 | Deng | 204/403.01 |
| 2006/0115857 | A1 | 6/2006 | Keen | 435/7.1 |
| 2006/0116562 | A1 | 6/2006 | Acosta | 600/316 |
| 2006/0116704 | A1 | 6/2006 | Ashby | 606/167 |
| 2006/0116705 | A1 | 6/2006 | Schraga | 606/181 |
| 2006/0119362 | A1 | 6/2006 | Kermani | 324/324 |
| 2006/0121547 | A1 | 6/2006 | McIntire | 435/14 |
| 2006/0121625 | A1 | 6/2006 | Clemens | 436/514 |
| 2006/0121759 | A1 | 6/2006 | Kasai | 439/188 |
| 2006/0122099 | A1 | 6/2006 | Aoki | 514/3 |
| 2006/0122536 | A1 | 6/2006 | Haar | 600/581 |
| 2006/0129065 | A1 | 6/2006 | Matsumoto | 600/583 |
| 2006/0129172 | A1 | 6/2006 | Crossman | 606/181 |
| 2006/0129173 | A1 | 6/2006 | Wilkinson | 606/181 |
| 2006/0134713 | A1 | 6/2006 | Rylatt | 435/7.92 |
| 2006/0140457 | A1 | 6/2006 | Simshauser | 382/124 |
| 2006/0144704 | A1 | 7/2006 | Ghesquiere | 204/403.01 |
| 2006/0151323 | A1 | 7/2006 | Cho | 204/403.04 |
| 2006/0155215 | A1 | 7/2006 | Cha | 600/583 |
| 2006/0155316 | A1 | 7/2006 | Perez | 606/181 |
| 2006/0155317 | A1 | 7/2006 | List | 606/181 |
| 2006/0156796 | A1 | 7/2006 | Burke | 73/61.44 |
| 2006/0157362 | A1 | 7/2006 | Schraga | 206/363 |
| 2006/0160100 | A1 | 7/2006 | Gao | 435/6 |
| 2006/0161078 | A1 | 7/2006 | Schraga | 600/583 |
| 2006/0161194 | A1 | 7/2006 | Freeman | 606/185 |
| 2006/0163061 | A1 | 7/2006 | Hodges | 204/401 |
| 2006/0166302 | A1 | 7/2006 | Clarke | 435/25 |
| 2006/0167382 | A1 | 7/2006 | Deshmukh | 600/583 |
| 2006/1051342 | | 7/2006 | Yaguchi | 206/306 |
| 2006/0169599 | A1 | 8/2006 | Feldman | 205/792 |
| 2006/0173254 | A1 | 8/2006 | Acosta | 600/316 |
| 2006/0173255 | A1 | 8/2006 | Acosta | 600/316 |
| 2006/0173379 | A1 | 8/2006 | Rasch-Menges | 600/583 |
| 2006/0173380 | A1 | 8/2006 | Hoenes | 600/583 |
| 2006/0173478 | A1 | 8/2006 | Schraga | 606/181 |
| 2006/0175216 | A1 | 8/2006 | Freeman | 206/363 |
| 2006/0178573 | A1 | 8/2006 | Kermani | 600/347 |
| 2006/0178599 | A1 | 8/2006 | Faupel | 600/578 |
| 2006/0178600 | A1 | 8/2006 | Kennedy | 600/584 |
| 2006/0178686 | A1 | 8/2006 | Schraga | 606/181 |
| 2006/0178687 | A1 | 8/2006 | Freeman | 606/181 |
| 2006/0178688 | A1 | 8/2006 | Freeman | 606/181 |
| 2006/0178689 | A1 | 8/2006 | Freeman | 606/181 |
| 2006/0178690 | A1 | 8/2006 | Freeman | 606/181 |
| 2006/0183871 | A1 | 8/2006 | Ward | 525/464 |
| 2006/0183983 | A1 | 8/2006 | Acosta | 600/316 |
| 2006/0184065 | A1 | 8/2006 | Deshmukh | 600/583 |
| 2006/0184101 | A1 | 8/2006 | Srinivasan | 604/68 |
| 2006/0188395 | A1 | 8/2006 | Taniike | 422/57 |
| 2006/0189895 | A1 | 8/2006 | Neel | 600/584 |
| 2006/0191787 | A1 | 8/2006 | Wang | 204/400 |
| 2006/0195023 | A1 | 8/2006 | Acosta | 600/316 |
| 2006/0195047 | A1 | 8/2006 | Freeman | 600/583 |
| 2006/0195128 | A1 | 8/2006 | Alden | 606/181 |
| 2006/0195129 | A1 | 8/2006 | Freeman | 606/181 |
| 2006/0195130 | A1 | 8/2006 | Freeman | 606/181 |
| 2006/0195131 | A1 | 8/2006 | Freeman | 606/181 |
| 2006/0195132 | A1 | 8/2006 | Freeman | 606/181 |
| 2006/0195133 | A1 | 8/2006 | Freeman | 606/181 |
| 2006/0196031 | A1 | 9/2006 | Hoenes | 29/432 |
| 2006/0196795 | A1 | 9/2006 | Windus-Smith | 206/438 |
| 2006/0200044 | A1 | 9/2006 | Freeman | 600/583 |
| 2006/0200045 | A1 | 9/2006 | Roe | 600/583 |
| 2006/0200046 | A1 | 9/2006 | Windus-Smith | 600/583 |
| 2006/0200181 | A1 | 9/2006 | Fukuzawa | 606/181 |
| 2006/0200981 | A1 | 9/2006 | Bhullar | 29/847 |
| 2006/0200982 | A1 | 9/2006 | Bhullar | 29/847 |
| 2006/0201804 | A1 | 9/2006 | Chambers | 204/400 |
| 2006/0204399 | A1 | 9/2006 | Freeman | 422/58 |
| 2006/0205029 | A1 | 9/2006 | Heller | 435/25 |
| 2006/0205060 | A1 | 9/2006 | Kim | 435/287.2 |
| 2006/0206135 | A1 | 9/2006 | Uehata | 606/181 |
| 2006/0211127 | A1 | 9/2006 | Iwaki | 436/169 |
| 2006/0211927 | A1 | 9/2006 | Acosta | 600/316 |
| 2006/0211931 | A1 | 9/2006 | Blank | 600/344 |
| 2006/0219551 | A1 | 10/2006 | Edelbrock | 204/403.14 |
| 2006/0222567 | A1 | 10/2006 | Kloepfer | 422/68.1 |
| 2006/0224171 | A1 | 10/2006 | Sakata | 606/181 |
| 2006/0224172 | A1 | 10/2006 | LeVaughn | 606/181 |
| 2006/0229532 | A1 | 10/2006 | Wong | 600/583 |
| 2006/0229533 | A1 | 10/2006 | Hoenes | 600/584 |
| 2006/0229651 | A1 | 10/2006 | Marshall | 606/181 |
| 2006/0231396 | A1 | 10/2006 | Yamaoka | 204/403.14 |
| 2006/0231418 | A1 | 10/2006 | Harding | 205/775 |
| 2006/0231421 | A1 | 10/2006 | Diamond | 205/777.5 |
| 2006/0231423 | A1 | 10/2006 | Harding | 205/792 |
| 2006/0231425 | A1 | 10/2006 | Harding | 205/792 |
| 2006/0231442 | A1 | 10/2006 | Windus-Smith | 206/438 |
| 2006/0232278 | A1 | 10/2006 | Diamond | 324/444 |
| 2006/0232528 | A1 | 10/2006 | Harding | 345/87 |
| 2006/0233666 | A1 | 10/2006 | Vu | 422/68.1 |
| 2006/0234369 | A1 | 10/2006 | Sih | 435/287.1 |
| 2006/0235284 | A1 | 10/2006 | Lee | 600/345 |
| 2006/0235454 | A1 | 10/2006 | LeVaughn | 606/181 |
| 2006/0241517 | A1 | 10/2006 | Fowler | 600/583 |
| 2006/0241666 | A1 | 10/2006 | Briggs | 606/181 |
| 2006/0241667 | A1 | 10/2006 | Freeman | 606/181 |
| 2006/0241668 | A1 | 10/2006 | Schraga | 606/181 |
| 2006/0241669 | A1 | 10/2006 | Stout | 606/182 |
| 2006/0247154 | A1 | 11/2006 | Palmieri | 514/8 |
| 2006/0247554 | A1 | 11/2006 | Roe | 600/583 |
| 2006/0247555 | A1 | 11/2006 | Harttig | 600/584 |
| 2006/0247670 | A1 | 11/2006 | LeVaughn | 606/181 |

| | | | | |
|---|---|---|---|---|
| 2006/0247671 | A1 | 11/2006 | LeVaughn | 606/182 |
| 2006/0254932 | A1 | 11/2006 | Hodges | 205/775 |
| 2006/0259057 | A1 | 11/2006 | Kim | 606/181 |
| 2006/0259058 | A1 | 11/2006 | Schiff | 606/181 |
| 2006/0259060 | A1 | 11/2006 | Whitson | 606/182 |
| 2006/0264718 | A1 | 11/2006 | Ruchti | 600/310 |
| 2006/0264996 | A1 | 11/2006 | LeVaughn | 606/181 |
| 2006/0264997 | A1 | 11/2006 | Colonna | 606/181 |
| 2006/0266644 | A1 | 11/2006 | Pugh | 204/400 |
| 2006/0266765 | A1 | 11/2006 | Pugh | 222/1 |
| 2006/0271083 | A1 | 11/2006 | Boecker | 606/181 |
| 2006/0271084 | A1 | 11/2006 | Schraga | 606/182 |
| 2006/0276724 | A1 | 12/2006 | Freeman | 600/583 |
| 2006/0277048 | A1 | 12/2006 | Kintzig | 704/275 |
| 2006/0278545 | A1 | 12/2006 | Henning | 206/363 |
| 2006/0279431 | A1 | 12/2006 | Bakarania | 340/870.02 |
| 2006/0281187 | A1 | 12/2006 | Emery | 436/169 |
| 2006/0282109 | A1 | 12/2006 | Jansen | 606/181 |
| 2006/0286620 | A1 | 12/2006 | Werner | 435/14 |
| 2006/0287664 | A1 | 12/2006 | Grage | 606/181 |
| 2006/0293577 | A1 | 12/2006 | Morrison | 600/365 |
| 2007/0004989 | A1 | 1/2007 | Dhillon | 600/583 |
| 2007/0004990 | A1 | 1/2007 | Kistner | 600/583 |
| 2007/0007183 | A1 | 1/2007 | Schulat | 209/573 |
| 2007/0009381 | A1 | 1/2007 | Schulat | 422/58 |
| 2007/0010839 | A1 | 1/2007 | Galloway | 606/167 |
| 2007/0010841 | A1 | 1/2007 | Teo | 606/181 |
| 2007/0015978 | A1 | 1/2007 | Kanayama | 600/310 |
| 2007/0016079 | A1 | 1/2007 | Freeman | 600/476 |
| 2007/0016103 | A1 | 1/2007 | Calasso | 600/583 |
| 2007/0016104 | A1 | 1/2007 | Jansen | 600/583 |
| 2007/0016239 | A1 | 1/2007 | Sato | 606/181 |
| 2007/0017805 | A1 | 1/2007 | Hodges | 204/400 |
| 2007/0027370 | A1 | 2/2007 | Brauker | 600/309 |
| 2007/0027427 | A1 | 2/2007 | Trautman | 604/46 |
| 2007/0032812 | A1 | 2/2007 | Loerwald | 606/181 |
| 2007/0032813 | A1 | 2/2007 | Flynn | 606/181 |
| 2007/0038149 | A1 | 2/2007 | Calasso | 600/583 |
| 2007/0038235 | A1 | 2/2007 | Freeman et al. | |
| 2007/0043305 | A1 | 2/2007 | Boecker | 600/583 |
| 2007/0043386 | A1 | 2/2007 | Freeman | 606/181 |
| 2007/0049901 | A1 | 3/2007 | Wu | 604/506 |
| 2007/0049959 | A1 | 3/2007 | Feaster | 606/181 |
| 2007/0055174 | A1 | 3/2007 | Freeman | 600/583 |
| 2007/0055297 | A1 | 3/2007 | Fukuzawa | 606/181 |
| 2007/0055298 | A1 | 3/2007 | Uehata | 606/181 |
| 2007/0060842 | A1 | 3/2007 | Alvarez-Icaza | 600/583 |
| 2007/0060843 | A1 | 3/2007 | Alvarez-Icaza | 600/583 |
| 2007/0060844 | A1 | 3/2007 | Alvarez-Icaza | 600/583 |
| 2007/0060845 | A1 | 3/2007 | Perez | 600/583 |
| 2007/0061393 | A1 | 3/2007 | Moore | 205/777.5 |
| 2007/0062250 | A1 | 3/2007 | Krulevitch | 73/1.16 |
| 2007/0062251 | A1 | 3/2007 | Anex | 73/1.36 |
| 2007/0062315 | A1 | 3/2007 | Hodges | 73/864.72 |
| 2007/0064516 | A1 | 3/2007 | Briggs | 365/230.05 |
| 2007/0066939 | A1 | 3/2007 | Krulevitch | 604/152 |
| 2007/0066940 | A1 | 3/2007 | Karunaratne | 604/152 |
| 2007/0068807 | A1 | 3/2007 | Feldman | 204/403.01 |
| 2007/0073188 | A1 | 3/2007 | Freeman | 600/583 |
| 2007/0073189 | A1 | 3/2007 | Freeman | 600/583 |
| 2007/0074977 | A1 | 4/2007 | Guo | 205/792 |
| 2007/0078358 | A1 | 4/2007 | Escutia | 600/573 |
| 2007/0078360 | A1 | 4/2007 | Matsumoto | 600/583 |
| 2007/0078474 | A1 | 4/2007 | Kim | 606/181 |
| 2007/0080093 | A1 | 4/2007 | Boozer | 206/569 |
| 2007/0083130 | A1 | 4/2007 | Thomson | 600/583 |
| 2007/0083131 | A1 | 4/2007 | Escutia | 600/583 |
| 2007/0083222 | A1 | 4/2007 | Schraga | 606/181 |
| 2007/0083335 | A1 | 4/2007 | Moerman | 702/19 |
| 2007/0084749 | A1 | 4/2007 | Demelo | 206/569 |
| 2007/0088377 | A1 | 4/2007 | LeVaughn | 606/181 |
| 2007/0092923 | A1 | 4/2007 | Chang | 435/14 |
| 2007/0093728 | A1 | 4/2007 | Douglas | 600/583 |
| 2007/0093752 | A1 | 4/2007 | Zhao | 604/131 |
| 2007/0093753 | A1 | 4/2007 | Krulevitch | 604/131 |
| 2007/0093863 | A1 | 4/2007 | Pugh | 606/181 |
| 2007/0093864 | A1 | 4/2007 | Pugh | 606/181 |
| 2007/0095178 | A1 | 5/2007 | Schraga | 83/13 |
| 2007/0100255 | A1 | 5/2007 | Boecker | 600/583 |
| 2007/0100256 | A1 | 5/2007 | Sansom | 600/583 |
| 2007/0100364 | A1 | 5/2007 | Sansom | 606/181 |
| 2007/0102312 | A1 | 5/2007 | Cha | 206/363 |
| 2007/0106178 | A1 | 5/2007 | Roe | 600/583 |
| 2007/0108048 | A1 | 5/2007 | Wang | 204/403.01 |
| 2007/0112281 | A1 | 5/2007 | Olson | 600/583 |
| 2007/0112367 | A1 | 5/2007 | Olson | 606/181 |
| 2007/0119710 | A1 | 5/2007 | Goldberger | 204/403.01 |
| 2007/0123801 | A1 | 5/2007 | Goldberger | 600/583 |
| 2007/0123802 | A1 | 5/2007 | Freeman | 600/583 |
| 2007/0129618 | A1 | 6/2007 | Goldberger | 600/345 |
| 2007/0129650 | A1 | 6/2007 | Freeman et al. | |
| 2007/0131565 | A1 | 6/2007 | Fujiwara | 205/777.5 |
| 2007/0135828 | A1 | 6/2007 | Rutynowski | 606/181 |
| 2007/0142747 | A1 | 6/2007 | Boecker | 600/583 |
| 2007/0142748 | A1 | 6/2007 | Deshmukh et al. | |
| 2007/0142776 | A9 | 6/2007 | Kovelman | 604/136 |
| 2007/0142854 | A1 | 6/2007 | Schraga | 606/181 |
| 2007/0144235 | A1 | 6/2007 | Werner | 73/1.82 |
| 2007/0149875 | A1 | 6/2007 | Ouyang | 600/347 |
| 2007/0149897 | A1 | 6/2007 | Ghesquiere | 600/583 |
| 2007/0161960 | A1 | 7/2007 | Chen | 604/187 |
| 2007/0162064 | A1 | 7/2007 | Starnes | 606/181 |
| 2007/0162065 | A1 | 7/2007 | Li | 606/182 |
| 2007/0167869 | A1 | 7/2007 | Roe | 600/583 |
| 2007/0167870 | A1 | 7/2007 | Freeman | 600/583 |
| 2007/0167871 | A1 | 7/2007 | Freeman | 600/583 |
| 2007/0167872 | A1 | 7/2007 | Freeman | 600/583 |
| 2007/0167873 | A1 | 7/2007 | Freeman | 600/583 |
| 2007/0167874 | A1 | 7/2007 | Freeman | 600/583 |
| 2007/0167875 | A1 | 7/2007 | Freeman | 600/583 |
| 2007/0173739 | A1 | 7/2007 | Chan | 600/583 |
| 2007/0173740 | A1 | 7/2007 | Chan | 600/583 |
| 2007/0173741 | A1 | 7/2007 | Deshmukh et al. | |
| 2007/0173742 | A1 | 7/2007 | Freeman et al. | 600/583 |
| 2007/0173743 | A1 | 7/2007 | Freeman | 600/583 |
| 2007/0173874 | A1 | 7/2007 | Uschold | 606/181 |
| 2007/0173875 | A1 | 7/2007 | Uschold | 606/181 |
| 2007/0173876 | A1 | 7/2007 | Aylett | 606/181 |
| 2007/0176120 | A1 | 8/2007 | Schwind et al. | 250/492.1 |
| 2007/0179356 | A1 | 8/2007 | Wessel | 600/300 |
| 2007/0179404 | A1 | 8/2007 | Escutia | 600/583 |
| 2007/0179405 | A1 | 8/2007 | Emery | 600/583 |
| 2007/0179406 | A1 | 8/2007 | DeNuzzio | 600/583 |
| 2007/0182051 | A1 | 8/2007 | Harttig | 264/138 |
| 2007/0185412 | A1 | 8/2007 | Boecker | 600/583 |
| 2007/0185515 | A1 | 8/2007 | Stout | 606/181 |
| 2007/0185516 | A1 | 8/2007 | Schosnig | 606/181 |
| 2007/0191702 | A1 | 8/2007 | Yodfat | 600/365 |
| 2007/0191737 | A1 | 8/2007 | Freeman | 600/583 |
| 2007/0191738 | A1 | 8/2007 | Raney | 600/583 |
| 2007/0191739 | A1 | 8/2007 | Roe | 600/583 |
| 2007/0193019 | A1 | 8/2007 | Feldman | 29/592.1 |
| 2007/0193882 | A1 | 8/2007 | Dai | 204/403.02 |
| 2007/0196240 | A1 | 8/2007 | Boozer | 422/102 |
| 2007/0196242 | A1 | 8/2007 | Boozer | 422/102 |
| 2007/0203514 | A1 | 8/2007 | Flaherty | 606/181 |
| 2007/0203903 | A1 | 8/2007 | Attaran Rezaei | 707/5 |
| 2007/0205103 | A1 | 9/2007 | Hodges | 204/403.01 |
| 2007/0207498 | A1 | 9/2007 | Palmieri | 435/7.1 |
| 2007/0213601 | A1 | 9/2007 | Freeman | 600/300 |
| 2007/0213637 | A1 | 9/2007 | Boozer | 600/583 |
| 2007/0213682 | A1 | 9/2007 | Haar | 604/500 |
| 2007/0213756 | A1 | 9/2007 | Freeman | 606/181 |
| 2007/0218543 | A1 | 9/2007 | Flaherty | 435/287.1 |
| 2007/0219346 | A1 | 9/2007 | Trifiro | 530/308 |
| 2007/0219432 | A1 | 9/2007 | Thompson | 600/300 |

2007/0219436 A1 9/2007 Takase ....................... 600/310
2007/0219462 A1 9/2007 Briggs ....................... 600/583
2007/0219463 A1 9/2007 Briggs ....................... 600/583
2007/0219572 A1 9/2007 Deck ....................... 606/181
2007/0219573 A1 9/2007 Freeman ....................... 606/183
2007/0219574 A1 9/2007 Freeman ....................... 606/185
2007/0225741 A1 9/2007 Ikeda ....................... 606/182
2007/0225742 A1 9/2007 Abe ....................... 606/182
2007/0227907 A1 10/2007 Shah ....................... 205/777.5
2007/0227911 A1 10/2007 Wang ....................... 205/792
2007/0227912 A1 10/2007 Chatelier ....................... 205/792
2007/0229085 A1 10/2007 Kawai ....................... 324/450
2007/0232872 A1 10/2007 Prough ....................... 600/316
2007/0232956 A1 10/2007 Harman ....................... 600/573
2007/0233013 A1 10/2007 Schoenberg ....................... 604/192
2007/0233166 A1 10/2007 Stout ....................... 606/182
2007/0233167 A1 10/2007 Weiss ....................... 606/182
2007/0233395 A1 10/2007 Neel ....................... 702/19
2007/0235329 A1 10/2007 Harding ....................... 205/403.01
2007/0235347 A1 10/2007 Chatelier ....................... 205/792
2007/0239068 A1 10/2007 Rasch-Menges ....................... 600/573
2007/0239188 A1 10/2007 Boozer ....................... 606/181
2007/0239189 A1 10/2007 Freeman ....................... 606/181
2007/0239190 A1 10/2007 Alden ....................... 606/181
2007/0240984 A1 10/2007 Popovich ....................... 204/403.01
2007/0240986 A1 10/2007 Reymond ....................... 204/412
2007/0244380 A1 10/2007 Say ....................... 600/347
2007/0244412 A1 10/2007 Lav ....................... 600/584
2007/0244498 A1 10/2007 Steg ....................... 606/181
2007/0244499 A1 10/2007 Briggs ....................... 600/182
2007/0249921 A1 10/2007 Groll ....................... 600/347
2007/0249962 A1 10/2007 Alden ....................... 600/583
2007/0249963 A1 10/2007 Alden ....................... 600/583
2007/0250099 A1 10/2007 Flora ....................... 606/181
2007/0251836 A1 11/2007 Hsu ....................... 205/792
2007/0254359 A1 11/2007 Rezania ....................... 435/325
2007/0255141 A1 11/2007 Esenaliev ....................... 600/475
2007/0255178 A1 11/2007 Alvarez-Icaza ....................... 600/583
2007/0255179 A1 11/2007 Alvarez-Icaza ....................... 600/583
2007/0255180 A1 11/2007 Alvarez-Icaza ....................... 600/583
2007/0255181 A1 11/2007 Alvarez-Icaza ....................... 600/583
2007/0255300 A1 11/2007 Vanhiel ....................... 606/181
2007/0255301 A1 11/2007 Freeman ....................... 606/181
2007/0255302 A1 11/2007 Koeppel ....................... 606/182
2007/0260271 A1 11/2007 Freeman ....................... 606/181
2007/0260272 A1 11/2007 Weiss ....................... 606/181
2007/0264721 A1 11/2007 Buck ....................... 436/150
2007/0265511 A1 11/2007 Renouf ....................... 600/319
2007/0265532 A1 11/2007 Maynard ....................... 600/477
2007/0265654 A1 11/2007 Iio ....................... 606/185
2007/0273901 A1 11/2007 Baskeyfield ....................... 358/1.9
2007/0273903 A1 11/2007 Baskeyfield ....................... 358/1.9
2007/0273904 A1 11/2007 Robinson ....................... 358/1.9
2007/0273928 A1 11/2007 Robinson ....................... 358/1.9
2007/0276197 A1 11/2007 Harmon ....................... 600/300
2007/0276211 A1 11/2007 Mir ....................... 600/345
2007/0276290 A1 11/2007 Boecker ....................... 600/583
2007/0276425 A1 11/2007 Kim ....................... 606/3
2007/0276621 A1 11/2007 Davies ....................... 702/104
2007/0278097 A1 12/2007 Bhullar ....................... 204/403.01
2007/0282186 A1 12/2007 Gilmore ....................... 600/365
2007/0282362 A1 12/2007 Berg ....................... 606/181
2007/0288047 A1 12/2007 Thoes ....................... 606/182
2007/0293743 A1 12/2007 Monfre ....................... 600/316
2007/0293744 A1 12/2007 Monfre ....................... 600/316
2007/0293790 A1 12/2007 Bainczyk ....................... 600/583
2007/0293882 A1 12/2007 Harttig ....................... 606/181
2007/0293883 A1 12/2007 Horie ....................... 606/181
2007/0295616 A1 12/2007 Harding ....................... 205/777.5
2008/0004651 A1 1/2008 Nicholls ....................... 606/182
2008/0007141 A1 1/2008 Deck ....................... 310/328
2008/0009767 A1 1/2008 Effenhauser ....................... 600/583
2008/0009768 A1 1/2008 Sohrab ....................... 600/583
2008/0009892 A1 1/2008 Freeman ....................... 606/181
2008/0009893 A1 1/2008 LeVaughn ....................... 606/181
2008/0015425 A1 1/2008 Douglas ....................... 600/347
2008/0015623 A1 1/2008 Deck ....................... 606/181
2008/0017522 A1 1/2008 Heller ....................... 205/777.5
2008/0019870 A1 1/2008 Newman ....................... 422/68.1
2008/0021291 A1 1/2008 Zocchi ....................... 600/300
2008/0021293 A1 1/2008 Schurman ....................... 600/316
2008/0021295 A1 1/2008 Wang ....................... 600/347
2008/0021296 A1 1/2008 Creaven ....................... 600/365
2008/0021346 A1 1/2008 Haar ....................... 600/583
2008/0021490 A1 1/2008 Briggs ....................... 606/181
2008/0021491 A1 1/2008 Freeman ....................... 606/181
2008/0021492 A1 1/2008 Freeman ....................... 606/181
2008/0021493 A1 1/2008 Levaughn ....................... 606/181
2008/0021494 A1 1/2008 Schmelzeisen-Redeker et al. ....................... 606/181
2008/0027385 A1 1/2008 Freeman ....................... 604/117
2008/0031778 A1 2/2008 Kramer ....................... 422/68.1
2008/0033268 A1 2/2008 Stafford ....................... 600/345
2008/0033318 A1 2/2008 Mace ....................... 600/583
2008/0033319 A1 2/2008 Kloepfer ....................... 600/583
2008/0033468 A1 2/2008 Lathrop ....................... 606/181
2008/0033469 A1 2/2008 Winheim ....................... 606/181
2008/0034834 A1 2/2008 Schell ....................... 73/1.02
2008/0034835 A1 2/2008 Schell ....................... 73/1.02
2008/0039885 A1 2/2008 Purcell ....................... 606/182
2008/0039886 A1 2/2008 Shi ....................... 606/182
2008/0039887 A1 2/2008 Conway ....................... 606/182
2008/0040919 A1 2/2008 Griss ....................... 29/777
2008/0045825 A1 2/2008 Melker ....................... 600/365
2008/0045992 A1 2/2008 Schraga ....................... 606/182
2008/0047764 A1 2/2008 Lee et al.
2008/0053201 A1 3/2008 Roesicke ....................... 73/61.41
2008/0057484 A1 3/2008 Miyata ....................... 434/739
2008/0058624 A1 3/2008 Smart ....................... 600/345
2008/0058626 A1 3/2008 Miyata ....................... 600/365
2008/0058631 A1 3/2008 Draudt ....................... 600/385
2008/0058847 A1 3/2008 Abe ....................... 606/181
2008/0058848 A1 3/2008 Griffin ....................... 606/182
2008/0058849 A1 3/2008 Conway ....................... 606/183
2008/0060424 A1 3/2008 Babic ....................... 73/61.41
2008/0064986 A1 3/2008 Kraemer ....................... 600/583
2008/0064987 A1 3/2008 Escutia ....................... 600/583
2008/0065130 A1 3/2008 Patel ....................... 606/181
2008/0065131 A1 3/2008 List ....................... 606/181
2008/0065132 A1 3/2008 Trissel ....................... 606/209
2008/0065133 A1 3/2008 Kennedy ....................... 606/182
2008/0065134 A1 3/2008 Conway ....................... 606/182
2008/0073224 A1 3/2008 Diamond ....................... 205/775
2008/0077048 A1 3/2008 Escutia ....................... 600/583
2008/0077167 A1 3/2008 Flynn ....................... 606/172
2008/0077168 A1 3/2008 Nicholls ....................... 606/182
2008/0081969 A1 4/2008 Feldman ....................... 600/322
2008/0081976 A1 4/2008 Hodges ....................... 600/345
2008/0082023 A1 4/2008 Deck ....................... 600/583
2008/0082116 A1 4/2008 Lathrop ....................... 606/181
2008/0082117 A1 4/2008 Ruf ....................... 606/182
2008/0086042 A1 4/2008 Brister ....................... 600/347
2008/0086044 A1 4/2008 Brister ....................... 600/365
2008/0086273 A1 4/2008 Shults ....................... 702/19
2008/0093227 A1 4/2008 Diamond ....................... 205/775
2008/0093228 A1 4/2008 Diamond ....................... 205/782
2008/0093230 A1 4/2008 Diamond ....................... 205/792
2008/0094804 A1 4/2008 Reynolds ....................... 361/727
2008/0097171 A1 4/2008 Smart ....................... 600/309
2008/0097241 A1 4/2008 Maltezos ....................... 600/576
2008/0097503 A1 4/2008 Creaven ....................... 606/182
2008/0098802 A1 5/2008 Burke ....................... 73/61.61
2008/0103396 A1 5/2008 Johnson ....................... 600/477
2008/0103415 A1 5/2008 Roe ....................... 600/583
2008/0103517 A1 5/2008 Takemoto ....................... 606/182
2008/0105024 A1 5/2008 Creaven ....................... 73/1.02

| | | | | |
|---|---|---|---|---|
| 2008/0105568 | A1 | 5/2008 | Wu | 205/780.5 |
| 2008/0108130 | A1 | 5/2008 | Nakaminami | 435/287.1 |
| 2008/0108942 | A1 | 5/2008 | Brister | 604/118 |
| 2008/0109024 | A1 | 5/2008 | Berkovitch | 606/181 |
| 2008/0109025 | A1 | 5/2008 | Yang | 606/182 |
| 2008/0109259 | A1 | 5/2008 | Thompson | 705/3 |
| 2008/0114227 | A1 | 5/2008 | Haar | 600/347 |
| 2008/0114228 | A1 | 5/2008 | McCluskey | 600/365 |
| 2008/0118400 | A1 | 5/2008 | Neel | 422/68.1 |
| 2008/0119703 | A1 | 5/2008 | Brister | 600/347 |
| 2008/0119704 | A1 | 5/2008 | Brister | 600/347 |
| 2008/0119706 | A1 | 5/2008 | Brister | 600/365 |
| 2008/0119761 | A1 | 5/2008 | Boecker | 600/583 |
| 2008/0119883 | A1 | 5/2008 | Conway | 606/181 |
| 2008/0119884 | A1 | 5/2008 | Flora | 606/182 |
| 2008/0121533 | A1 | 5/2008 | Hodges | 205/775 |
| 2008/0125800 | A1 | 5/2008 | List | 606/181 |
| 2008/0125801 | A1 | 5/2008 | List | 606/181 |
| 2008/0134806 | A1 | 6/2008 | Capriccio | 73/863.21 |
| 2008/0134810 | A1 | 6/2008 | Neel | 73/866 |
| 2008/0135559 | A1 | 6/2008 | Byrd | 220/506 |
| 2008/0140105 | A1 | 6/2008 | Zhong | 606/182 |
| 2008/0144022 | A1 | 6/2008 | Schulat | 356/213 |
| 2008/0146899 | A1 | 6/2008 | Ruchti | 600/316 |
| 2008/0146966 | A1 | 6/2008 | LeVaughn | 600/583 |
| 2008/0147108 | A1 | 6/2008 | Kennedy | 606/182 |
| 2008/0149268 | A1 | 6/2008 | Zhao | 156/299 |
| 2008/0149599 | A1 | 6/2008 | Bohm | 216/94 |
| 2008/0152507 | A1 | 6/2008 | Bohm | 417/44.1 |
| 2008/0154187 | A1 | 6/2008 | Krulevitch | 604/48 |
| 2008/0154513 | A1 | 6/2008 | Kovatchev | 702/19 |
| 2008/0159913 | A1 | 7/2008 | Jung | 422/57 |
| 2008/0161664 | A1 | 7/2008 | Mastrototaro | 600/583 |
| 2008/0161724 | A1 | 7/2008 | Roe | 600/583 |
| 2008/0161725 | A1 | 7/2008 | Wong | 600/583 |
| 2008/0166269 | A1 | 7/2008 | Jansen | 422/63 |
| 2008/0167578 | A1 | 7/2008 | Bryer | 600/583 |
| 2008/0167673 | A1 | 7/2008 | Zhong | 606/181 |
| 2008/0188771 | A1 | 8/2008 | Boecker | 600/583 |
| 2008/0194987 | A1 | 8/2008 | Boecker | |
| 2008/0194989 | A1 | 8/2008 | Briggs | 600/583 |
| 2008/0208026 | A1 | 8/2008 | Noujaim | 600/365 |
| 2008/0208079 | A1 | 8/2008 | Hein | 600/583 |
| 2008/0210574 | A1 | 9/2008 | Boecker | 205/777.5 |
| 2008/0214909 | A1 | 9/2008 | Fuerst | 600/309 |
| 2008/0214917 | A1 | 9/2008 | Boecker | 606/347 |
| 2008/0214919 | A1 | 9/2008 | Harmon | 600/365 |
| 2008/0214956 | A1 | 9/2008 | Briggs | 600/575 |
| 2008/0228212 | A1 | 9/2008 | List | 606/182 |
| 2008/0249435 | A1 | 10/2008 | Haar | 600/583 |
| 2008/0249554 | A1 | 10/2008 | Freeman | 606/181 |
| 2008/0262387 | A1 | 10/2008 | List | 600/583 |
| 2008/0262388 | A1 | 10/2008 | List | 600/583 |
| 2008/0267822 | A1 | 10/2008 | List | 422/68.1 |
| 2008/0269723 | A1 | 10/2008 | Mastrototaro | 604/890.1 |
| 2008/0269791 | A1 | 10/2008 | Hoenes | 606/181 |
| 2008/0275365 | A1 | 11/2008 | Guthrie | 600/584 |
| 2008/0275384 | A1 | 11/2008 | Mastrototaro | 604/66 |
| 2008/0277291 | A1 | 11/2008 | Heller | 205/777.5 |
| 2008/0277292 | A1 | 11/2008 | Heller | 205/777.5 |
| 2008/0277293 | A1 | 11/2008 | Heller | 205/777.5 |
| 2008/0277294 | A1 | 11/2008 | Heller | 205/777.5 |
| 2008/0286149 | A1 | 11/2008 | Roe | 422/58 |
| 2008/0294068 | A1 | 11/2008 | Briggs | 600/583 |
| 2008/0300614 | A1 | 12/2008 | Freeman | 606/181 |
| 2008/0318193 | A1 | 12/2008 | Alvarez-Icaza | 434/262 |
| 2008/0319284 | A1 | 12/2008 | Alvarez-Icaza | 600/309 |
| 2008/0319291 | A1 | 12/2008 | Freeman | 600/347 |
| 2009/0005664 | A1 | 1/2009 | Freeman | 600/347 |
| 2009/0020438 | A1 | 1/2009 | Hodges | 205/782 |
| 2009/0024009 | A1 | 1/2009 | Freeman | 600/309 |
| 2009/0024059 | A1 | 1/2009 | Hoerauf et al. | 600/583 |
| 2009/0026075 | A1 | 1/2009 | Harding | 204/403.14 |
| 2009/0026091 | A1 | 1/2009 | Harding | 205/777.5 |
| 2009/0027040 | A1 | 1/2009 | Kermani | 324/123 |
| 2009/0029479 | A1 | 1/2009 | Docherty | 436/149 |
| 2009/0043177 | A1 | 2/2009 | Milledge | 600/309 |
| 2009/0043183 | A1 | 2/2009 | Kermani | 600/365 |
| 2009/0048536 | A1 | 2/2009 | Freeman | 600/583 |
| 2009/0054813 | A1 | 2/2009 | Freeman | 600/584 |
| 2009/0057146 | A1 | 3/2009 | Teodorezyk | 204/403.01 |
| 2009/0069716 | A1 | 3/2009 | Freeman | 600/583 |
| 2009/0084687 | A1 | 4/2009 | Chatelier | 205/792 |
| 2009/0105572 | A1 | 4/2009 | Malecha | 600/365 |
| 2009/0105573 | A1 | 4/2009 | Malecha | 600/365 |
| 2009/0112123 | A1 | 4/2009 | Freeman | 600/583 |
| 2009/0112155 | A1 | 4/2009 | Zhao | 604/67 |
| 2009/0112180 | A1 | 4/2009 | Krulevitch | 604/506 |
| 2009/0112185 | A1 | 4/2009 | Krulevitch | 604/523 |
| 2009/0124932 | A1 | 5/2009 | Freeman | 606/181 |
| 2009/0131829 | A1 | 5/2009 | Freeman | 600/583 |
| 2009/0131830 | A1 | 5/2009 | Freeman | 600/583 |
| 2009/0131964 | A1 | 5/2009 | Freeman | 606/181 |
| 2009/0131965 | A1 | 5/2009 | Freeman | 606/181 |
| 2009/0137930 | A1 | 5/2009 | Freeman | 600/583 |
| 2009/0138032 | A1 | 5/2009 | Freeman | 606/181 |
| 2009/0139300 | A1 | 6/2009 | Pugh | 73/1.36 |
| 2009/0184004 | A1 | 7/2009 | Chatelier | 205/777.5 |
| 2009/0187351 | A1 | 7/2009 | Orr | 702/19 |
| 2009/0192410 | A1 | 7/2009 | Freeman | 600/583 |
| 2009/0192411 | A1 | 7/2009 | Freeman | 600/583 |
| 2009/0196580 | A1 | 8/2009 | Freeman | 386/124 |
| 2009/0204025 | A1 | 8/2009 | Marsot | 600/573 |
| 2009/0216100 | A1 | 8/2009 | Ebner | 600/347 |
| 2009/0237262 | A1 | 9/2009 | Smith | 340/634 |
| 2009/0240127 | A1 | 9/2009 | Ray | 600/365 |
| 2009/0247838 | A1 | 10/2009 | Cummings | 600/365 |
| 2009/0247982 | A1 | 10/2009 | Krulevitch | 604/500 |
| 2009/0259146 | A1 | 10/2009 | Freeman | 600/583 |
| 2009/0280551 | A1 | 11/2009 | Cardosi | 435/190 |
| 2009/0281457 | A1 | 11/2009 | Faulkner | 600/583 |
| 2009/0281458 | A1 | 11/2009 | Faulkner | 600/583 |
| 2009/0281459 | A1 | 11/2009 | Faulkner | 600/583 |
| 2009/0301899 | A1 | 12/2009 | Hodges | 205/777.5 |
| 2009/0302872 | A1 | 12/2009 | Haggett | 324/715 |
| 2009/0302873 | A1 | 12/2009 | Haggett | 324/724 |
| 2009/0322630 | A1 | 12/2009 | Friman | 343/720 |
| 2009/0325307 | A1 | 12/2009 | Haggett | 436/150 |
| 2010/0016700 | A1 | 1/2010 | Sieh | 600/365 |
| 2010/0018878 | A1 | 1/2010 | Davies | 606/782 |
| 2010/0030110 | A1 | 2/2010 | Choi | 600/583 |
| 2010/0041084 | A1 | 2/2010 | Stephens | 435/14 |

FOREIGN PATENT DOCUMENTS

| | | | |
|---|---|---|---|
| DE | 29824204 | | 10/2000 |
| DE | 10032042 | | 1/2002 |
| DE | 10057832 | | 2/2002 |
| DE | 10057832 | C1 | 2/2002 |
| DE | 10142232 | | 3/2003 |
| DE | 10208575 | C1 | 8/2003 |
| DE | 10245721 | | 12/2003 |
| DE | 10361560 | A1 | 7/2005 |
| EP | 137975 | A2 | 4/1985 |
| EP | 0160768 | | 11/1985 |
| EP | 0199484 | A2 | 10/1986 |
| EP | 0254246 | | 1/1988 |
| EP | 0289 269 | | 11/1988 |
| EP | 0317847 | A1 | 5/1989 |
| EP | 0320109 | | 6/1989 |
| EP | 0170375 | | 5/1990 |
| EP | 0136362 | | 12/1990 |
| EP | 0449525 | | 10/1991 |

| | | |
|---|---|---|
| EP | 0453283 | 10/1991 |
| EP | 0263948 | 2/1992 |
| EP | 0530994 | 3/1993 |
| EP | 0374355 | 6/1993 |
| EP | 0351891 | 9/1993 |
| EP | 0593096 | 4/1994 |
| EP | 0415388 | 5/1995 |
| EP | 0654659 | 5/1995 |
| EP | 0505494 | 7/1995 |
| EP | 0662367 A1 | 7/1995 |
| EP | 0359831 | 8/1995 |
| EP | 0471986 | 10/1995 |
| EP | 0368474 | 12/1995 |
| EP | 0461601 | 12/1995 |
| EP | 0429076 | 1/1996 |
| EP | 0552223 | 7/1996 |
| EP | 0735363 | 10/1996 |
| EP | 0505504 | 3/1997 |
| EP | 0777123 | 6/1997 |
| EP | 0406304 | 8/1997 |
| EP | 0537761 | 8/1997 |
| EP | 0795601 | 9/1997 |
| EP | 0562370 | 11/1997 |
| EP | 0415393 | 12/1997 |
| EP | 0823239 | 2/1998 |
| EP | 0560336 | 5/1998 |
| EP | 0878 708 | 11/1998 |
| EP | 0505475 | 3/1999 |
| EP | 0901018 | 3/1999 |
| EP | 0470649 | 6/1999 |
| EP | 0847447 | 11/1999 |
| EP | 0964059 | 12/1999 |
| EP | 0964060 | 12/1999 |
| EP | 0969097 | 1/2000 |
| EP | 1021950 | 7/2000 |
| EP | 0894869 | 2/2001 |
| EP | 1074832 | 2/2001 |
| EP | 1093854 | 4/2001 |
| EP | 1 101 443 | 5/2001 |
| EP | 1101443 | 5/2001 |
| EP | 1114995 | 7/2001 |
| EP | 0736607 | 8/2001 |
| EP | 0874984 | 11/2001 |
| EP | 1157660 | 11/2001 |
| EP | 0730037 | 12/2001 |
| EP | 0636879 | 1/2002 |
| EP | 01174083 | 1/2002 |
| EP | 0851224 | 3/2002 |
| EP | 0759553 | 5/2002 |
| EP | 0856586 | 5/2002 |
| EP | 0817809 | 7/2002 |
| EP | 0872728 | 7/2002 |
| EP | 0795748 | 8/2002 |
| EP | 0685737 | 9/2002 |
| EP | 0958495 | 11/2002 |
| EP | 0937249 | 12/2002 |
| EP | 0880692 | 1/2004 |
| EP | 01374770 | 1/2004 |
| EP | 1404232 | 4/2004 |
| EP | 1404233 | 4/2004 |
| EP | 1246688 | 5/2004 |
| EP | 1502614 | 2/2005 |
| EP | 1643908 | 4/2006 |
| GB | 1558111 | 12/1979 |
| GB | 2168815 | 6/1986 |
| GB | 233936 A | 6/1999 |
| GB | 2335860 A | 10/1999 |
| GB | 2335990 A | 10/1999 |
| JP | HEI 4 194660 | 7/1992 |
| JP | 2000-116768 | 4/2000 |
| ME | WO93/00044 | 6/1992 |
| WO | WO 80/01389 | 7/1980 |
| WO | WO 85/04089 | 9/1985 |
| WO | WO 86/07632 | 12/1985 |
| WO | WO86/05966 | 10/1986 |
| WO | WO 91/09139 | 6/1991 |
| WO | WO92/03099 | 3/1992 |
| WO | WO92/06971 | 4/1992 |
| WO | WO92/07263 | 4/1992 |
| WO | WO92/07468 | 5/1992 |
| WO | WO 93/06979 | 4/1993 |
| WO | WO93/09723 | 5/1993 |
| WO | WO 93/25898 | 12/1993 |
| WO | WO 94/27140 | 11/1994 |
| WO | WO 94/29703 | 12/1994 |
| WO | WO 94/29704 | 12/1994 |
| WO | WO 94/29731 | 12/1994 |
| WO | WO 95/00662 | 1/1995 |
| WO | WO 95/10223 | 4/1995 |
| WO | WO95/12583 | 5/1995 |
| WO | WO 95/22597 | 8/1995 |
| WO | WO96/14799 | 5/1996 |
| WO | WO 96/30431 | 10/1996 |
| WO | WO96/037148 | 11/1996 |
| WO | WO 97/02359 | 1/1997 |
| WO | WO 97/02487 | 1/1997 |
| WO | WO 97/11883 | 4/1997 |
| WO | WO 97/11883 A1 | 4/1997 |
| WO | WO 97/18464 | 5/1997 |
| WO | WO97/28741 | 8/1997 |
| WO | WO 97/30344 | 8/1997 |
| WO | WO 97/42882 | 11/1997 |
| WO | WO 97/42888 | 11/1997 |
| WO | WO 97/45720 | 12/1997 |
| WO | WO 98/03431 | 1/1998 |
| WO | WO98/14436 | 4/1998 |
| WO | WO 98/19159 | 5/1998 |
| WO | WO98/19609 | 5/1998 |
| WO | WO 98/20332 | 5/1998 |
| WO | WO 98/20348 | 5/1998 |
| WO | WO98/20867 | 5/1998 |
| WO | WO 98/24366 | 6/1998 |
| WO | WO 98/24373 | 6/1998 |
| WO | WO 98/35225 | 8/1998 |
| WO | WO98/45276 | 10/1998 |
| WO | WO 99/03584 | 1/1999 |
| WO | WO 99/05966 | 2/1999 |
| WO | WO99/07295 | 2/1999 |
| WO | WO 99/07431 A1 | 2/1999 |
| WO | WO 99/13100 | 3/1999 |
| WO | WO 99/17854 | 4/1999 |
| WO | WO 99/18532 | 4/1999 |
| WO | WO 99/19507 | 4/1999 |
| WO | WO 99/19717 | 4/1999 |
| WO | WO 99/27483 | 6/1999 |
| WO | WO 99/27852 | 6/1999 |
| WO | WO 99/62576 | 12/1999 |
| WO | WO 99/64580 | 12/1999 |
| WO | WO 00/06024 | 2/2000 |
| WO | WO 00/09184 | 2/2000 |
| WO | WO 00/11578 | 3/2000 |
| WO | WO 00/15103 | 3/2000 |
| WO | WO 00/17799 | 3/2000 |
| WO | WO 00/17800 | 3/2000 |
| WO | WO 00/18293 | 4/2000 |
| WO | WO 00/19346 | 4/2000 |
| WO | WO 00/20626 | 4/2000 |
| WO | WO00/29577 | 5/2000 |
| WO | WO 00/30186 | 5/2000 |
| WO | WO 00/32097 | 6/2000 |
| WO | WO 00/32098 | 6/2000 |
| WO | WO 00/33236 | 6/2000 |
| WO | WO 00/39914 | 7/2000 |
| WO | WO 00/42422 | 7/2000 |
| WO | WO 00/44084 | 7/2000 |
| WO | WO00/46854 | 8/2000 |

| | | | | | | |
|---|---|---|---|---|---|---|
| WO | WO 00/50771 | 8/2000 | | WO | WO 03/094752 | 11/2003 |
| WO | WO00/55915 | 9/2000 | | WO | WO 03/101297 | 12/2003 |
| WO | WO 00/60340 | 10/2000 | | WO | WO 2004/008130 | 1/2004 |
| WO | WO 00/64022 | 10/2000 | | WO | WO 2004/022133 | 3/2004 |
| WO | WO 00/67245 | 11/2000 | | WO | WO 2004/026130 | 4/2004 |
| WO | WO 00/67268 | 11/2000 | | WO | WO 2004/040285 A2 | 5/2004 |
| WO | WO 00/72452 | 11/2000 | | WO | WO 2004/040287 A1 | 5/2004 |
| WO | WO 01/00090 | 1/2001 | | WO | WO 2004/040948 | 5/2004 |
| WO | WO 01/75433 | 3/2001 | | WO | WO 2004/041082 | 5/2004 |
| WO | WO 01/23885 | 4/2001 | | WO | WO 2004/045375 | 6/2004 |
| WO | WO 01/25775 | 4/2001 | | WO | WO 2004/054455 | 7/2004 |
| WO | WO 01/26813 | 4/2001 | | WO | WO 2004/060174 | 7/2004 |
| WO | WO01/29037 | 4/2001 | | WO | WO 2004/060446 | 7/2004 |
| WO | WO 01/33216 | 5/2001 | | WO | WO 2004/091693 | 10/2004 |
| WO | WO 01/34029 | 5/2001 | | WO | WO 2004/098405 | 11/2004 |
| WO | WO 01/36955 | 5/2001 | | WO | WO 2004/003147 | 12/2004 |
| WO | WO 01/37174 | 5/2001 | | WO | WO 2004/107964 | 12/2004 |
| WO | WO 01/40788 | 7/2001 | | WO | WO 2004/107975 | 12/2004 |
| WO | WO 01/57510 | 8/2001 | | WO | WO 2004/112602 | 12/2004 |
| WO | WO 01/63271 | 8/2001 | | WO | WO 2004/112612 | 12/2004 |
| WO | WO 01/64105 | 9/2001 | | WO | WO 2004/112612 A1 | 12/2004 |
| WO | WO 01/66010 | 9/2001 | | WO | WO 2005/001418 | 1/2005 |
| WO | WO 01/69505 | 9/2001 | | WO | WO 2005/006939 | 1/2005 |
| WO | WO 01/72220 A | 10/2001 | | WO | WO 2005/011774 | 2/2005 |
| WO | WO 01/72225 | 10/2001 | | WO | WO 2005/013824 | 2/2005 |
| WO | WO 01/73124 | 10/2001 | | WO | WO 2005/016125 | 2/2005 |
| WO | WO 01/73395 | 10/2001 | | WO | WO 2005/018425 | 3/2005 |
| WO | WO 01/89691 | 11/2001 | | WO | WO 2005/018430 | 3/2005 |
| WO | WO 01/95806 | 12/2001 | | WO | WO 2005/018454 | 3/2005 |
| WO | WO 02/00101 | 1/2002 | | WO | WO 2005/018709 | 3/2005 |
| WO | WO 02/02796 | 1/2002 | | WO | WO 2005/018710 | 3/2005 |
| WO | WO 02/08750 | 1/2002 | | WO | WO 2005/018711 | 3/2005 |
| WO | WO 02/08753 | 1/2002 | | WO | WO 2005/022143 | 3/2005 |
| WO | WO 02/08950 | 1/2002 | | WO | WO 2005/023088 | 3/2005 |
| WO | WO 02/18940 | 3/2002 | | WO | WO 2005/033659 | 4/2005 |
| WO | WO 02/21317 | 3/2002 | | WO | WO 2005/034720 | 4/2005 |
| WO | WO 02/25551 | 3/2002 | | WO | WO 2005/034721 | 4/2005 |
| WO | WO 02/32559 | 4/2002 | | WO | WO 2005/034741 | 4/2005 |
| WO | WO 02/41227 | 5/2002 | | WO | WO 2005/034778 | 4/2005 |
| WO | WO 02/41779 | 5/2002 | | WO | WO 2005/035017 | 4/2005 |
| WO | WO 02/44948 | 6/2002 | | WO | WO 2005/035018 | 4/2005 |
| WO | WO 02/49507 | 6/2002 | | WO | WO 2005/037095 | 4/2005 |
| WO | WO/249507 | 6/2002 | | WO | WO 2005/046477 | 5/2005 |
| WO | WO/0249507 | 6/2002 | | WO | WO 2005/065399 | 7/2005 |
| WO | WO 02/56769 | 7/2002 | | WO | WO 2005/065414 | 7/2005 |
| WO | WO 02/059734 | 8/2002 | | WO | WO 2005/065415 | 7/2005 |
| WO | WO 02/069791 | 9/2002 | | WO | WO 2005/065545 A2 | 7/2005 |
| WO | WO 02/077638 | 10/2002 | | WO | WO 2005/072604 | 8/2005 |
| WO | WO 02/100251 | 12/2002 | | WO | WO2005/084546 A2 | 9/2005 |
| WO | WO 02/100252 | 12/2002 | | WO | WO 2005/084557 | 9/2005 |
| WO | WO 02/100253 | 12/2002 | | WO | WO 2005/104948 | 11/2005 |
| WO | WO 02/100254 | 12/2002 | | WO | WO 2005/104948 A1 | 11/2005 |
| WO | WO 02/100460 | 12/2002 | | WO | WO 2005/114185 | 12/2005 |
| WO | WO 02/100461 | 12/2002 | | WO | WO 2005/116622 | 12/2005 |
| WO | WO 02/101343 | 12/2002 | | WO | WO 2005/119234 | 12/2005 |
| WO | WO 02/101359 | 12/2002 | | WO | WO 2005/120197 | 12/2005 |
| WO | WO 03/000321 | 1/2003 | | WO | WO 2005/120199 | 12/2005 |
| WO | WO 03/023389 | 3/2003 | | WO | WO 2005/120365 | 12/2005 |
| WO | WO 03/042691 | 5/2003 | | WO | WO 2005/121759 | 12/2005 |
| WO | WO 03/045557 | 6/2003 | | WO | WO 2006/001797 | 1/2006 |
| WO | WO 03/046542 | 6/2003 | | WO | WO 2006/001973 | 1/2006 |
| WO | WO 03/049609 | 6/2003 | | WO | WO 2006/011062 | 2/2006 |
| WO | WO 03/050534 | 6/2003 | | WO | WO 2006/013045 | 2/2006 |
| WO | WO 03/066128 | 8/2003 | | WO | WO 2006/015615 | 2/2006 |
| WO | WO 03/070099 | 8/2003 | | WO | WO 2006/027702 A2 | 3/2006 |
| WO | WO 03/071940 | 9/2003 | | WO | WO 2006/031920 | 3/2006 |
| WO | WO 03/082091 | 10/2003 | | WO | WO 2006/032391 | 3/2006 |
| WO | WO 03/082091 A2 | 10/2003 | | WO | WO 2006/072004 | 7/2006 |
| WO | WO 03/088824 | 10/2003 | | WO | WO 2006/105146 | 10/2006 |
| WO | WO 03/088834 | 10/2003 | | WO | WO 2006/116441 | 11/2006 |
| WO | WO 03/088835 | 10/2003 | | WO | WO 2007/025635 | 3/2007 |
| WO | WO 03/088851 A1 | 10/2003 | | WO | WO 2007/044834 | 4/2007 |
| WO | WO/03088834 | 10/2003 | | WO | WO 2007/054335 | 5/2007 |

| | | |
|---|---|---|
| WO | WO 2007/070719 | 6/2007 |
| WO | WO 2007/084367 | 7/2007 |
| WO | WO 2007/106470 | 9/2007 |
| WO | WO 2007/119900 | 10/2007 |
| WO | WO 2008/112268 | 9/2008 |
| WO | WO 2008/112279 | 9/2008 |

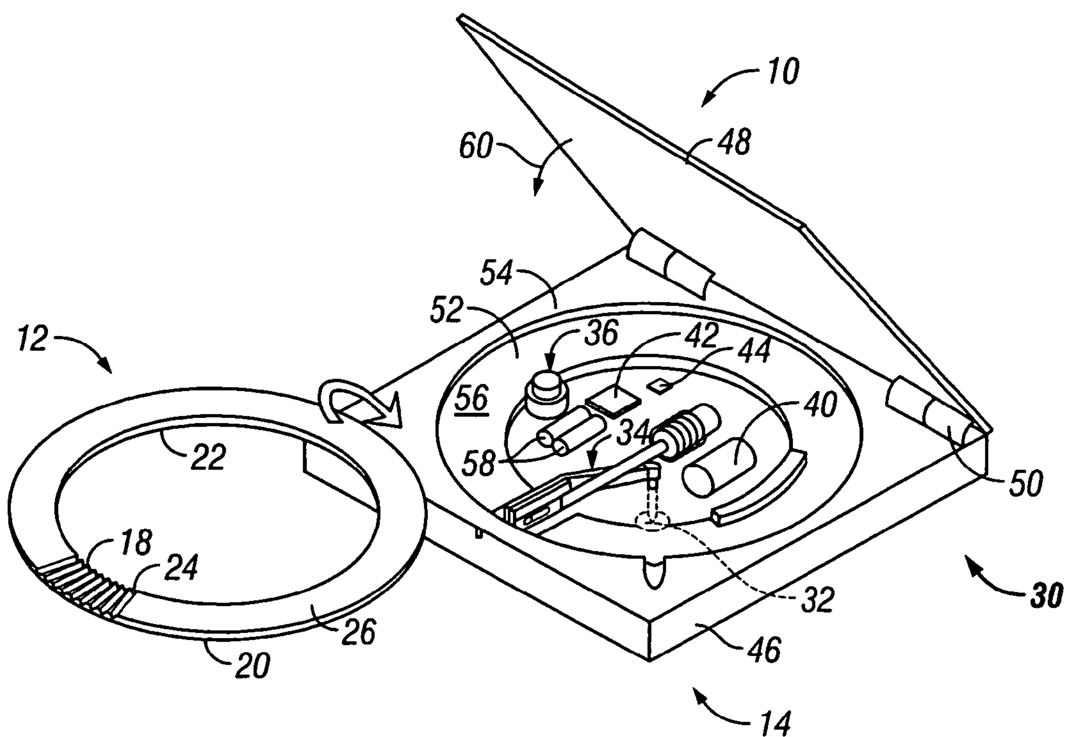
FIG. 1
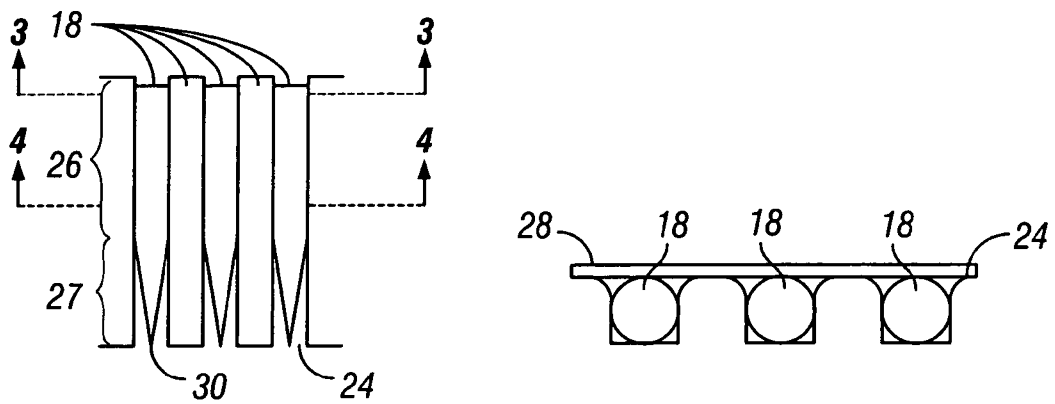
FIG. 2
FIG. 3
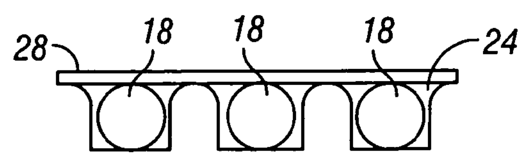
FIG. 4

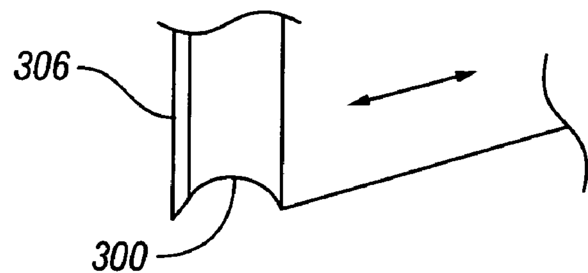
FIG. 27
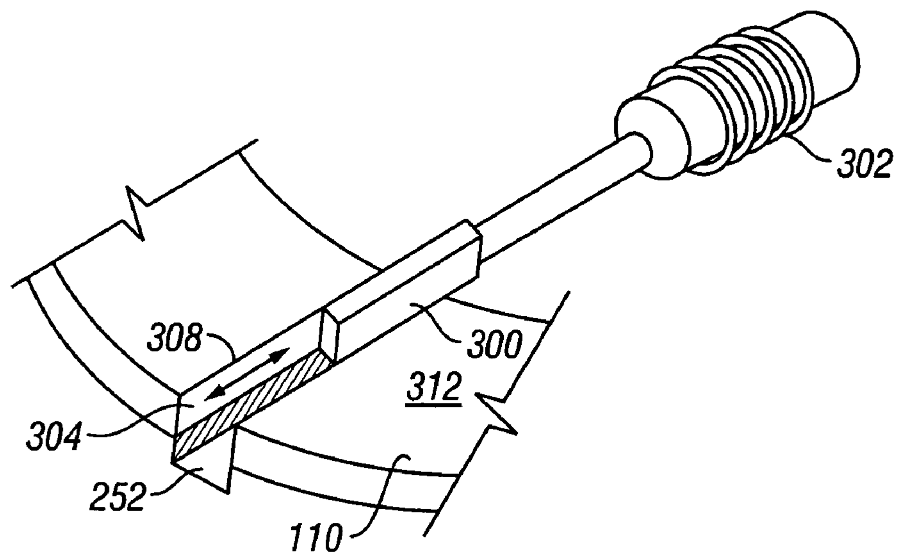
FIG. 28
326
328
316
322
318
320
FIG. 29

METHOD AND APPARATUS FOR BODY FLUID SAMPLING AND ANALYTE SENSING

CROSS-REFERENCE TO RELATED APPLICATIONS

This application is a continuation-in-part of commonly assigned, copending U.S. patent application Ser. No. 10/452,815 filed May 30, 2003. This application is a continuation-in-part of commonly assigned, U.S. patent application Ser. No. 10/323,622 filed on Dec. 18, 2002, now U.S. Pat. No. 7,708,701 which is a continuation-in-part of commonly assigned, U.S. patent application Ser. No. 10/127,395 filed Apr. 19, 2002 now U.S. Pat. No. 7,025,774. This application is also a continuation-in-part of commonly assigned, U.S. patent application Ser. No. 10/237,261 filed Sep. 5, 2002 now U.S. Pat. No. 7,344,507. This application is further a continuation-in-part of commonly assigned, U.S. patent application Ser. No. 10/420,535 filed Apr. 21, 2003 now U.S. Pat. No. 7,258,693. This application is further a continuation-in-part of commonly assigned, U.S. patent application Ser. No. 10/335,142 filed Dec. 31, 2002 now U.S. Pat. No. 7,374,544. This application is further a continuation-in-part of commonly assigned, U.S. patent application Ser. No. 10/423,851 filed Apr. 24, 2003 now U.S. Pat. No. 7,141,058. This application also claims the benefit of priority from commonly assigned, copending U.S. Provisional Patent Application Ser. No. 60/422,988 filed Nov. 1, 2002; commonly assigned, copending U.S. Provisional Patent Application Ser. No. 60/424,429 filed Nov. 6, 2002; and commonly assigned, copending U.S. Provisional Patent Application Ser. No. 60/424,429 filed Nov. 20, 2002. All applications listed above are incorporated herein by reference for all purposes.

BACKGROUND OF THE INVENTION

Lancing devices are known in the medical health-care products industry for piercing the skin to produce blood for analysis. Typically, a drop of blood for this type of analysis is obtained by making a small incision in the fingertip, creating a small wound, which generates a small blood droplet on the surface of the skin.

Early methods of lancing included piercing or slicing the skin with a needle or razor. Current methods utilize lancing devices that contain a multitude of spring, cam and mass actuators to drive the lancet. These include cantilever springs, diaphragms, coil springs, as well as gravity plumbs used to drive the lancet. The device may be held against the skin and mechanically triggered to ballistically launch the lancet. Unfortunately, the pain associated with each lancing event using known technology discourages patients from testing. In addition to vibratory stimulation of the skin as the driver impacts the end of a launcher stop, known spring based devices have the possibility of firing lancets that harmonically oscillate against the patient tissue, causing multiple strikes due to recoil. This recoil and multiple strikes of the lancet is one major impediment to patient compliance with a structured glucose monitoring regime.

Another impediment to patient compliance is the lack of spontaneous blood flow generated by known lancing technology. In addition to the pain as discussed above, a patient may need more than one lancing event to obtain a blood sample since spontaneous blood generation is unreliable using known lancing technology. Thus the pain is multiplied by the number of attempts required by a patient to successfully generate spontaneous blood flow. Different skin thickness may yield different results in terms of pain perception, blood yield and success rate of obtaining blood between different users of the lancing device. Known devices poorly account for these skin thickness variations.

A still further impediment to improved compliance with glucose monitoring are the many steps and inconvenience associated with each lancing event. Many diabetic patients that are insulin dependent may need to self-test for blood glucose levels five to six times daily. The large number of steps required in traditional methods of glucose testing, ranging from lancing, to milking of blood, applying blood to a test strip, and getting the measurements from the test strip, discourages many diabetic patients from testing their blood glucose levels as often as recommended. Older patients and those with deteriorating motor skills encounter difficulty loading lancets into launcher devices, transferring blood onto a test strip, or inserting thin test strips into slots on glucose measurement meters. Additionally, the wound channel left on the patient by known systems may also be of a size that discourages those who are active with their hands or who are worried about healing of those wound channels from testing their glucose levels.

SUMMARY OF THE INVENTION

The present invention provides solutions for at least some of the drawbacks discussed above. Specifically, some embodiments of the present invention provide a multiple lancet solution to measuring analyte levels in the body. The invention may use a high density design. The invention may provide a plurality of analyte detecting members used to sample fluid from tissue. At least some of these and other objectives described herein will be met by embodiments of the present invention.

In one aspect of the present invention, a body fluid sampling system is provided for use on a tissue site. In one embodiment, the system comprises a cartridge; a penetrating member driver; a plurality of penetrating members arranged in a radial configuration on the cartridge wherein sharpened distal tips of the penetrating members point radially outward; wherein an active one of the penetrating members may be operatively coupled to the penetrating member driver, the penetrating member driver moving the active one along a path out of a housing having a penetrating member exit, into the tissue site, stopping in the tissue site, and withdrawing out of the tissue site; and a plurality of analyte detecting members, wherein at least one of the analyte detecting members is positioned to receive fluid from a wound created by the active one of the penetrating members, wherein the detecting members are not pierced by the active one of the penetrating members.

In one embodiment of the present invention, a body fluid sampling system for use on a tissue site is provided. The system comprises a cartridge; a penetrating member driver; a plurality of penetrating members, each having a proximal end, an elongate portion, and a sharpened distal end, the members arranged in a radial configuration on the cartridge wherein sharpened distal tips of the penetrating members point radially outward; wherein an active one of the penetrating members may be operatively coupled to the penetrating member driver, the penetrating member driver moving the active one along a path out of a housing having a penetrating member exit, into the tissue site, stopping in the tissue site, and withdrawing out of the tissue site; and a plurality of analyte detecting members, wherein at least one of the analyte detecting members is positioned to receive fluid from a wound created by the active one of the penetrating members; wherein the unused analyte detecting members are arranged in a stack, the penetrating member driver configured to be controlled to follow a velocity trajectory into the tissue and out of the tissue, wherein the velocity into the tissue is at an average speed greater than an average speed of the penetrating member on the withdrawal.

In another embodiment of the present invention, a body fluid sampling system for use on a tissue site is provided. The system comprises a cartridge; a penetrating member driver; a plurality of penetrating members arranged in a radial configuration on the cartridge wherein sharpened distal tips of the penetrating members point radially outward; wherein an active one of the penetrating members may be operatively coupled to the penetrating member driver, the penetrating member driver moving the active one along a path out of a housing having a penetrating member exit, into the tissue site, stopping in the tissue site, and withdrawing out of the tissue site; and a plurality of analyte detecting members, wherein at least one of the analyte detecting members is positioned to receive fluid from a wound created by the active one of the penetrating members, wherein the detecting members are not pierced by the active one of the penetrating members; a position sensor positioned to provide an indication of a position of the penetrating member during actuation.

In yet another embodiment of the present invention, a body fluid sampling system for use on a tissue site is provided. The system comprises a cartridge; a penetrating member driver; a plurality of penetrating members arranged in a radial configuration on the cartridge wherein sharpened distal tips of the penetrating members point radially outward; wherein an active one of the penetrating members may be operatively coupled to the penetrating member driver, the penetrating member driver moving the active one along a path out of a housing having a penetrating member exit, into the tissue site, stopping in the tissue site, and withdrawing out of the tissue site; and a plurality of analyte detecting members, wherein at least one of the analyte detecting members is positioned to receive fluid from a wound created by the active one of the penetrating members, wherein the detecting members are not pierced by the active one of the penetrating members; a coupler on the penetrating member driver configured to engage at least a portion of the elongate portion of the penetrating member and drive the member along a path into a tissue site and withdrawn from a tissue site.

In a still further another embodiment of the present invention, a body fluid sampling system for use on a tissue site is provided. The system comprises a cartridge; a penetrating member driver; a plurality of penetrating members arranged in a radial configuration on the cartridge wherein sharpened distal tips of the penetrating members point radially outward; wherein an active one of the penetrating members may be operatively coupled to the penetrating member driver, the penetrating member driver moving the active one along a path out of a housing having a penetrating member exit, into the tissue site, stopping in the tissue site, and withdrawing out of the tissue site; and a plurality of analyte detecting members, wherein at least one of the analyte detecting members is positioned to receive fluid from a wound created by the active one of the penetrating members, wherein the detecting members are not pierced by the active one of the penetrating members; a sterility enclosure covering at least a tip of the penetrating member, the sterility enclosure removed from the penetrating member prior to actuation of the member and positioned so that the penetrating member will not contact the enclosure during actuation.

In another embodiment of the present invention, a body fluid sampling system for use on a tissue site is provided. The system comprises a cartridge; a penetrating member driver; a plurality of penetrating members arranged in a radial configuration on the cartridge wherein sharpened distal tips of the penetrating members point radially outward; wherein an active one of the penetrating members may be operatively coupled to the penetrating member driver, the penetrating member driver moving the active one along a path out of a housing having a penetrating member exit, into the tissue site, stopping in the tissue site, and withdrawing out of the tissue site; and a plurality of analyte detecting members, wherein at least one of the analyte detecting members is positioned to receive fluid from a wound created by the active one of the penetrating members, wherein the detecting members are not pierced by the active one of the penetrating members; a user interface for transmitting at least one input between a user.

A further understanding of the nature and advantages of the invention will become apparent by reference to the remaining portions of the specification and drawings.

BRIEF DESCRIPTION OF THE DRAWINGS

FIG. 1 is a perspective view illustrating a system, according to an embodiment for use in piercing skin to obtain a blood sample;

FIG. 2 is a plan view of a portion of a replaceable penetrating member cartridge forming part of the system;

FIG. 3 is a cross-sectional end view on 3-3 in FIG. 2;

FIG. 4 is a cross-sectional end view on 4-4 in FIG. 2;

FIGS. 27 and 28 illustrate an embodiment of a drive member coupled to a driver wherein the drive member includes a cutting member having a sharpened edge which is configured to cut through a sterility barrier of a penetrating member slot during a lancing cycle in order for the drive member to make contact with the penetrating member.

FIGS. 29 and 30 illustrate an embodiment of a penetrating member slot in longitudinal section having a ramped portion disposed at a distal end of the penetrating member slot and a drive member with a cutting edge at a distal end thereof for cutting through a sterility barrier during a lancing cycle.

DESCRIPTION OF THE SPECIFIC EMBODIMENTS

Figure 5:
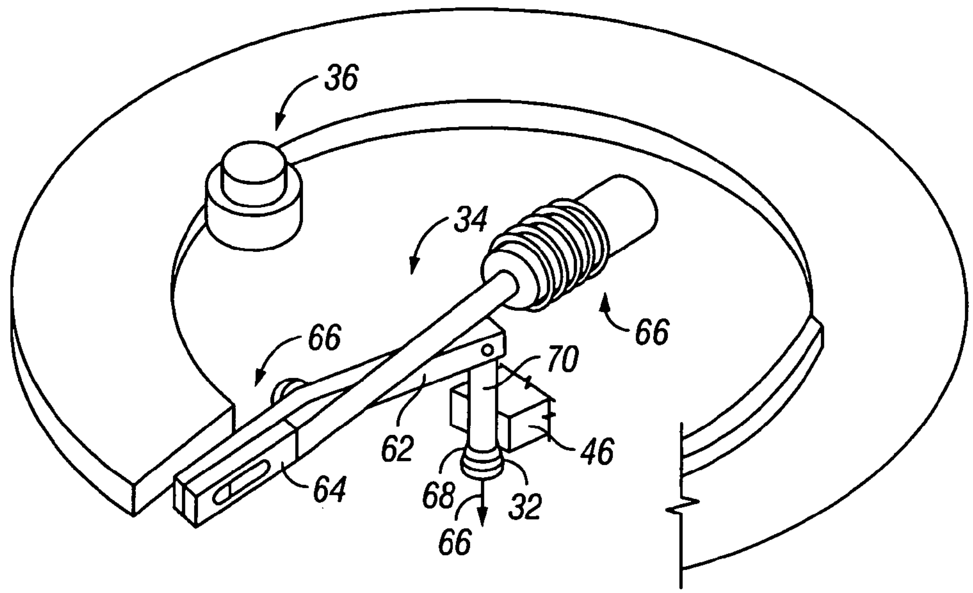
FIG. 5 is a perspective view of an apparatus forming part of the system and used for manipulating components of the cartridge, illustrating pivoting of a penetrating member accelerator in a downward direction.

The present invention provides a multiple analyte detecting member solution for body fluid sampling. Specifically, some embodiments of the present invention provides a multiple analyte detecting member and multiple lancet solution to measuring analyte levels in the body. The invention may use a high density design. It may use lancets of smaller size, such as but not limited to diameter or length, than known lancets. The device may be used for multiple lancing events without having to remove a disposable from the device. The invention may provide improved sensing capabilities. At least some of these and other objectives described herein will be met by embodiments of the present invention.

It is to be understood that both the foregoing general description and the following detailed description are exemplary and explanatory only and are not restrictive of the invention, as claimed. It must be noted that, as used in the specification and the appended claims, the singular forms "a", "an" and "the" include plural referents unless the context clearly dictates otherwise. Thus, for example, reference to "a material" may include mixtures of materials, reference to "a chamber" may include multiple chambers, and the like. References cited herein are hereby incorporated by reference in their entirety, except to the extent that they conflict with teachings explicitly set forth in this specification.

In this specification and in the claims which follow, reference will be made to number of terms which shall be defined to have the following meanings:

"Optional" or "optionally" means that the subsequently described circumstance may or may not occur, so that the description includes instances where the circumstance occurs and instances where it does not. For example, if a device optionally contains a feature for analyzing a blood sample, this means that the analysis feature may or may not be present, and, thus, the description includes structures wherein a device possesses the analysis feature and structures wherein the analysis feature is not present.

"Analyte detecting member" refers to any use, singly or in combination, of chemical test reagents and methods, electrical test circuits and methods, physical test components and methods, optical test components and methods, and biological test reagents and methods to yield information about a blood sample. Such methods are well known in the art and may be based on teachings of, e.g. Tietz Textbook of Clinical Chemistry, 3d Ed., Sec. V, pp. 776-78 (Burtis & Ashwood, Eds., W.B. Saunders Company Philadelphia, 1999); U.S. Pat. No. 5,997,817 to Chrismore et al. (Dec. 7, 1999); U.S. Pat. No. 5,059,394 to Phillips et al. (Oct. 22, 1991); U.S. Pat. No. 5,001,054 to Wagner et al. (Mar. 19, 1991); and U.S. Pat. No. 4,392,933 to Nakamura et al. (Jul. 12, 1983), the teachings of which are hereby incorporated by reference, as well as others. Analyte detecting member may include tests in the sample test chamber that test electrochemical properties of the blood, or they may include optical means for sensing optical properties of the blood (e.g. oxygen saturation level), or they may include biochemical reagents (e.g. antibodies) to sense properties (e.g. presence of antigens) of the blood. The analyte detecting member may comprise biosensing or reagent material that will react with an analyte in blood (e.g. glucose) or other body fluid so that an appropriate signal correlating with the presence of the analyte is generated and can be read by the reader apparatus. By way of example and not limitation, analyte detecting member may be "associated with", "mounted within", or "coupled to" a chamber or other structure when the analyte detecting member participates in the function of providing an appropriate signal about the blood sample to the reader device. Analyte detecting member may also include nanowire analyte detecting members as described herein. Analyte detecting member may use any, singly or in combination, potentiometric, coulometric, or other method useful for detection of analyte levels.

FIGS. 1-11 of the accompanying drawings illustrates one embodiment of a system 10 for piercing tissue to obtain a blood sample. The system 10 may include a replaceable cartridge 12 and an apparatus 14 for removably receiving the cartridge 12 and for manipulating components of the cartridge 12.

Referring jointly to FIGS. 1 and 2, the cartridge 12 may include a plurality of penetrating members 18. The cartridge 12 may be in the form of a circular disc and has an outer circular surface 20 and an opening forming an inner circular surface 22. A plurality of grooves 24 are formed in a planar surface 26 of the cartridge 12. Each groove 24 is elongated and extends radially out from a center point of the cartridge 12. Each groove 24 is formed through the outer circular surface 20. Although not shown, it should be understood that the grooves 24 are formed over the entire circumference of the planar surface 26. As shown in FIGS. 3 and 4, each groove 24 is relatively narrow closer to the center point of the cartridge 12 and slightly wider further from the center point. These grooves 24 may be molded into the cartridge 12, machined into the cartridge, forged, pressed, or formed using other methods useful in the manufacture of medical devices.

In the present embodiment, each penetrating member 18 has an elongated body 26 and a sharpened distal end 27 having a sharp tip 30. The penetrating member 18 may have a circular cross-section with a diameter in this embodiment of about 0.315 mm. All outer surfaces of the penetrating member 18 may have the same coefficient of friction. The penetrating member may be, but is not necessarily, a bare lancet. The lancet is "bare", in the sense that no raised formations or molded parts are formed thereon that are complementarily engageable with another structure. Traditional lancets include large plastic molded parts that are used to facilitate engagement. Unfortunately, such attachments add size and cost. In the most basic sense, a bare lancet or bare penetrating member is an elongate wire having sharpened end. If it is of sufficiently small diameter, the tip may be penetrating without having to be sharpened. A bare lancet may be bent and still be considered a bare lancet. The bare lancet in one embodiment may be made of one material.

In the present embodiment, each penetrating member 18 is located in a respective one of the grooves 24. The penetrating members 18 have their sharpened distal ends 27 pointed radially out from the center point of the cartridge 12. A proximal end of each penetrating member 15 may engage in an interference fit with opposing sides of a respective groove 24 as shown in FIG. 3. Other embodiments of the cartridge 12 may not use such an interference fit. As a nonlimiting example, they may use a fracturable adhesive to releasably secure the penetrating member 18 to the cartridge 12. As shown in FIG. 4, more distal portions of the penetrating member 18 are not engaged with the opposing sides of the groove 24 due to the larger spacing between the sides.

The cartridge 12 may further include a sterilization barrier 28 attached to the upper surface 26. The sterilization barrier 28 is located over the penetrating members 18 and serves to insulate the penetrating members 18 from external contaminants. The sterilization barrier 28 is made of a material that can easily be broken when an edge of a device applies a force thereto. The sterilization barrier 28 alone or in combination with other barriers may be used to create a sterile environment about at least the tip of the penetrating member prior to lancing or actuation. The sterilization barrier 28 may be made of a variety of materials such as but not limited to metallic foil, aluminum foil, paper, polymeric material, or laminates combining any of the above. Other details of the sterilization barrier are detailed herein.

In the present embodiment, the apparatus 14 may include a housing 30, an initiator button 32, a penetrating member movement subassembly 34, a cartridge advance subassembly 36, batteries 38, a capacitor 40, a microprocessor controller 42, and switches 44. The housing 30 may have a lower portion 46 and a lid 48. The lid 48 is secured to the lower portion 46 with a hinge 50. The lower portion 46 may have a recess 52. A circular opening 54 in the lower portion 46 defines an outer boundary of the recess 52 and a level platform 56 of the lower portion 46 defines a base of the recess 52.

In use, the lid 48 of the present embodiment is pivoted into a position as shown in FIG. 1. The cartridge 12 is flipped over and positioned in the recess 52. The planar surface 26 rests against the level platform 56 and the circular opening 54 contacts the outer circular surface 20 to prevent movement of the cartridge 12 in a plane thereof. The lid 48 is then pivoted in a direction 60 and closes the cartridge 12.

Referring to the embodiment shown in FIG. 5, the penetrating member movement subassembly 34 includes a lever 62, a penetrating member accelerator 64, a linear actuator 66, and a spring 68. Other suitable actuators including but not limited to rotary actuators are described in commonly assigned, copending U.S. patent application Ser. No. 10/127,395 filed Apr. 19, 2002. The lever 62 may be pivotably secured to the lower portion 46. The button 32 is located in an accessible position external of the lower portion 46 and is connected by a shaft 70 through the lower portion 46 to one end of the lever 62. The penetrating member accelerator 64 is mounted to an opposing end of the lever 62. A user depresses the button 32 in an upward direction 66 so that the shaft 70 pivots the end of the lever 62 to which it is connected in an upward direction. The opposing end of the lever pivots in a downward direction 66. The spring 46 is positioned between the button 32 and the base 40 and compresses when the button 32 is depressed to create a force that tends to move the button 32 down and pivot the penetrating member accelerator upward in a direction opposite to the direction 64.

Figure 6A:
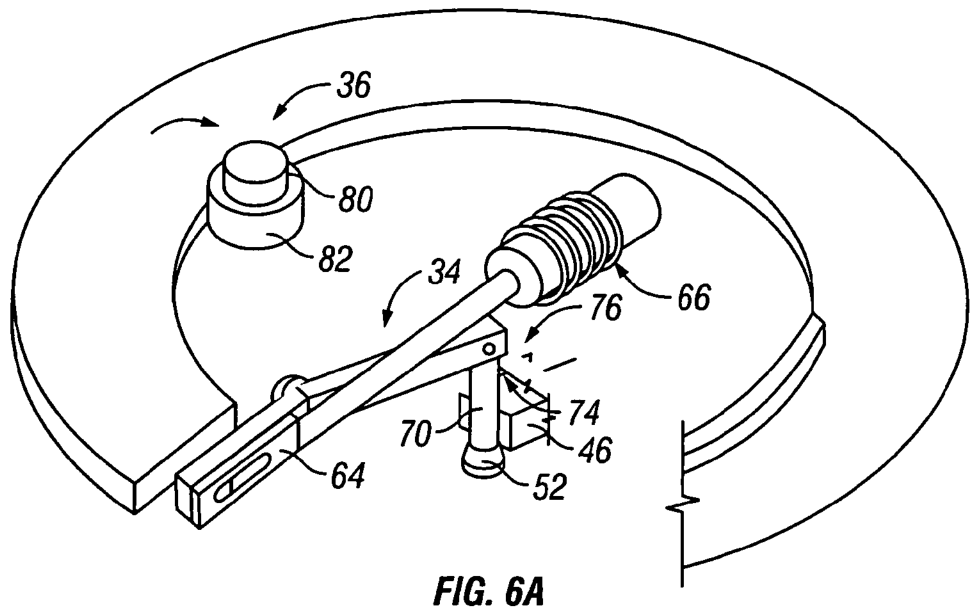
FIG. 6A is a view similar to FIG. 5, illustrating how the cartridge is rotated or advanced.
Figure 6B:
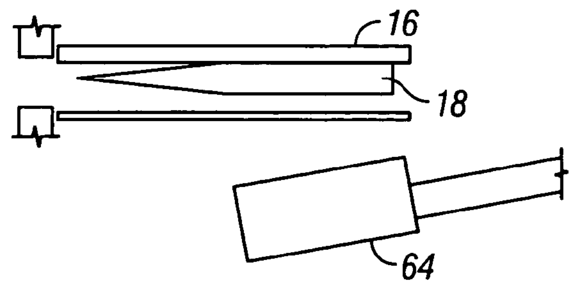
FIG. 6B is a cross-sectional side view illustrating how the penetrating member accelerator allows for the cartridge to be advanced.

Referring to FIGS. 6A and 6B in this particular embodiment, the movement of the button into the position shown in FIG. 5 also causes contact between a terminal 74 on the shaft 20 with a terminal 70 secured to the lower portion 46. Contact between the terminals 74 and 76 indicates that the button 32 has been fully depressed. With the button 32 depressed, the cartridge 12 can be rotated without interference by the penetrating member actuator 64. To this effect, the cartridge advancer subsystem 36 includes a pinion gear 80 and a stepper motor 82. The stepper motor 82 is secured to the lower portion 46. The pinion gear 80 is secured to the stepper motor 82 and is rotated by the stepper motor 82. Teeth on the pinion gear 80 engage with teeth on the inner circular surface 22 of the cartridge 12. Rotation of the pinion gear 80 causes rotation of the cartridge 12 about the center point thereof. Each time that the terminals 74 and 76 make contact, the stepper motor 82 is operated to rotate the cartridge 12 through a discrete angle equal to an angular spacing from a centerline of one of the penetrating members 18 to a centerline of an adjacent penetrating member. A select penetrating member 18 is so moved over the penetrating member accelerator 64, as shown in FIG. 6B. Subsequent depressions of the button 32 will cause rotation of subsequent adjacent penetrating members 18 into a position over the penetrating member accelerator 64.

Figure 7A:
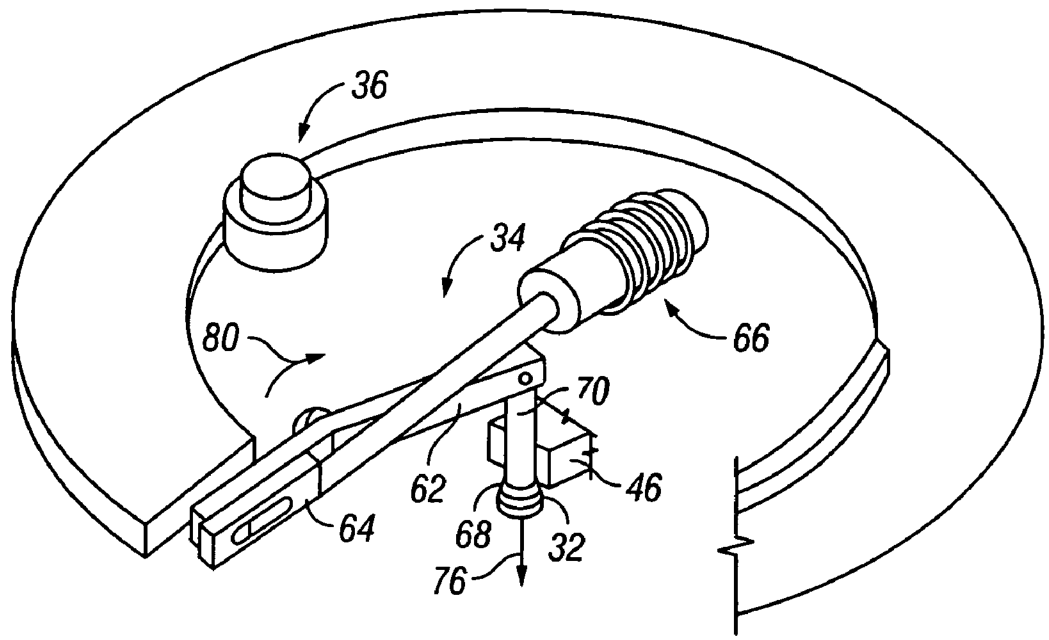
FIGS. 7A and 7B are views similar to FIGS. 6A and 6B, respectively, illustrating pivoting of the penetrating member accelerator in an opposite direction to engage with a select one of the penetrating members in the cartridge.
Figure 7B:
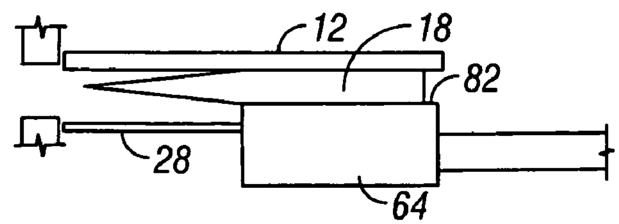

The user then releases pressure from the button, as shown in FIG. 7A. The force created by the spring 68 or other resilient member moves the button 32 in a downward direction 76. The shaft 70 is pivotably secured to the lever 62 so that the shaft 70 moves the end of the lever 62 to which it is connected down. The opposite end of the lever 62 pivots the penetrating member accelerator 64 upward in a direction 80. As shown in FIG. 7B, an edge 82 of the penetrating member accelerator 64 breaks through a portion of the sterilization barrier 28 and comes in to physical contact with a lower side surface of the penetrating member 18.

Figure 8A:
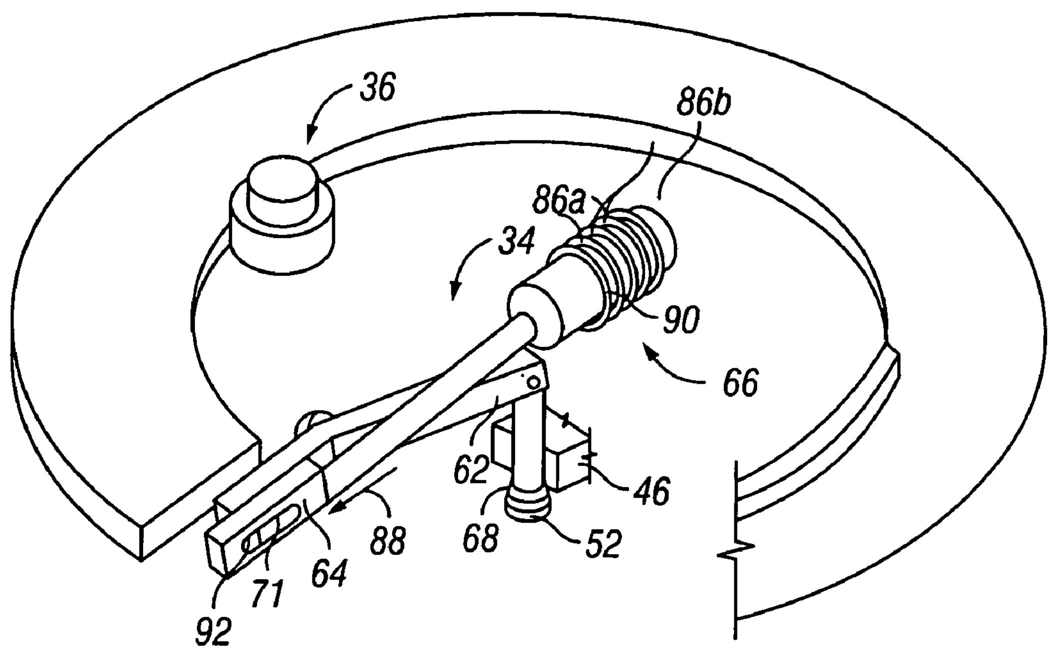
FIGS. 8A and 8B are views similar to FIGS. 7A and 7B, respectively, illustrating how the penetrating member accelerator moves the selected penetrating member to pierce skin.
Figure 8B:
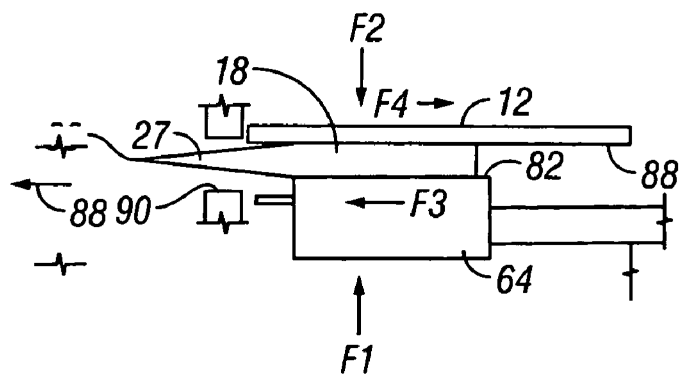

Referring to FIG. 8A, the linear actuator 66 includes separate advancing coils 86A and retracting coils 86B, and a magnetizable slug 90 within the coils 86A and 86B. The coils 86A and 86B are secured to the lower portion of 46, and the slug 90 can move within the coils 86A and 88B. Once the penetrating member accelerator 64 is located in the position shown in FIGS. 7A and 7B, electric current is provided to the advancing coils 86 only. The current in the advancing coils 86 creates a force in a direction 88 on the slug 90 according to conventional principles relating to electromagnetics.

A bearing 91 is secured to the lever and the penetrating member accelerator 64 has a slot 92 over the bearing 91. The slot 92 allows for the movement of the penetrating member accelerator 64 in the direction 88 relative to the lever 62, so that the force created on the slug moves the penetrating member accelerator 64 in the direction 88.

The spring 68 is not entirely relaxed, so that the spring 68, through the lever 62, biases the penetrating member accelerator 64 against the lower side surface of the penetrating member 18 with a force F1. The penetrating member 18 rests against a base 88 of the cartridge 12. An equal and opposing force F2 is created by the base 88 on an upper side surface of the penetrating member 18.

The edge 82 of the penetrating member accelerator 64 has a much higher coefficient of friction than the base 88 of the cartridge 12. The higher coefficient of friction of the edge contributes to a relatively high friction force F3 on the lower side surface of the penetrating member 18. The relatively low coefficient of friction of the base 88 creates a relatively small friction force F4 on the upper side surface of the penetrating member 18. A difference between the force F3 and F4 is a resultant force that accelerates the penetrating member in the direction 88 relative to the cartridge 12. The penetrating member is moved out of the interference fit illustrated in FIG. 3. The bare penetrating member 18 is moved without the need for any engagement formations on the penetrating member. Current devices, in contrast, often make use a plastic body molded onto each penetrating member to aid in manipulating the penetrating members. Movement of the penetrating member 18 moves the sharpened end thereof through an opening 90 in a side of the lower portion 46. The sharp end 30 of the penetrating member 18 is thereby moved from a retracted and safe position within the lower portion 46 into a position wherein it extends out of the opening 90. Accelerated, high-speed movement of the penetrating member is used so that the sharp tip 30 penetrates skin of a person. A blood sample can then be taken from the person, typically for diabetic analysis.

Figure 9A:
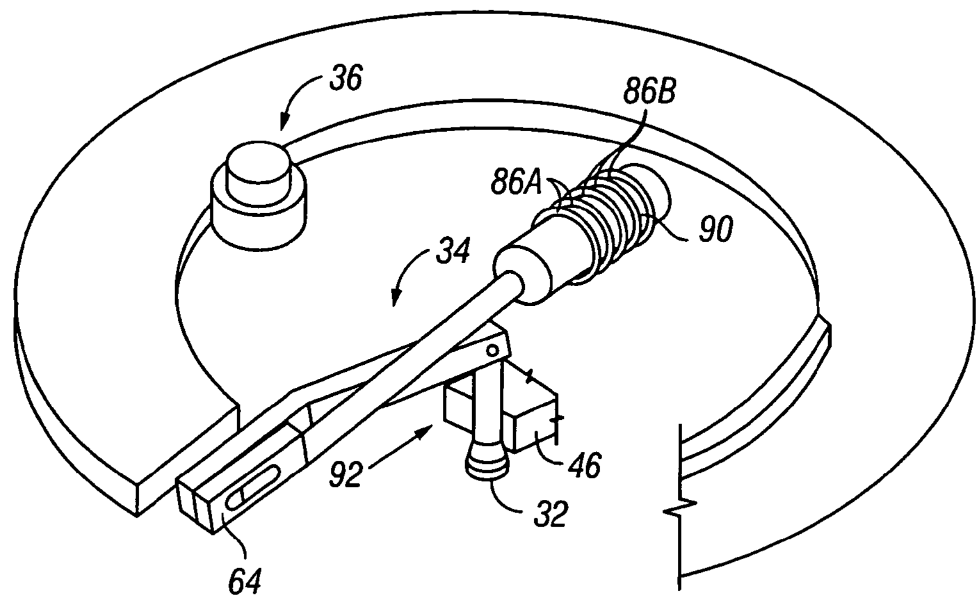
FIGS. 9A and 9B are views similar to FIGS. 8A and 8B, respectively, illustrating how the penetrating member accelerator returns the penetrating member to its original position.
Figure 9B:
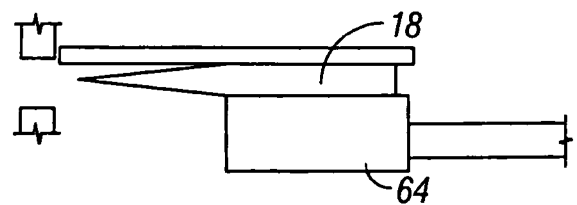

Reference is now made to FIGS. 9A and 9B. After the penetrating member is accelerated (for example, but not limitation, less than 0.25 seconds thereafter), the current to the accelerating coils 86A is turned off and the current is provided to the retracting coils 86B. The slug 90 moves in an opposite direction 92 together with the penetrating member accelerator 64. The penetrating member accelerator 64 then returns the used penetrating member into its original position, i.e., the same as shown in FIG. 7B.

Subsequent depression of the button as shown in FIG. 5 will then cause one repetition of the process described, but with an adjacent sterile penetrating member. Subsequent sterile penetrating members can so be used until all the penetrating members have been used, i.e., after one complete revolution of the cartridge 12. In this embodiment, a second revolution of the cartridge 12 is disallowed to prevent the use of penetrating members that have been used in a previous revolution and have become contaminated. The only way in which the user can continue to use the apparatus 14 is by opening ‘the lid 48 as shown in FIG. 1, removing the used cartridge 12, and replacing the used cartridge with another cartridge. A detector (not shown) detects whenever a cartridge is removed and replaced with another cartridge. Such a detector may be but is not limited to an optical sensor, an electrical contact sensor, a bar code reader, or the like.

Figure 10:
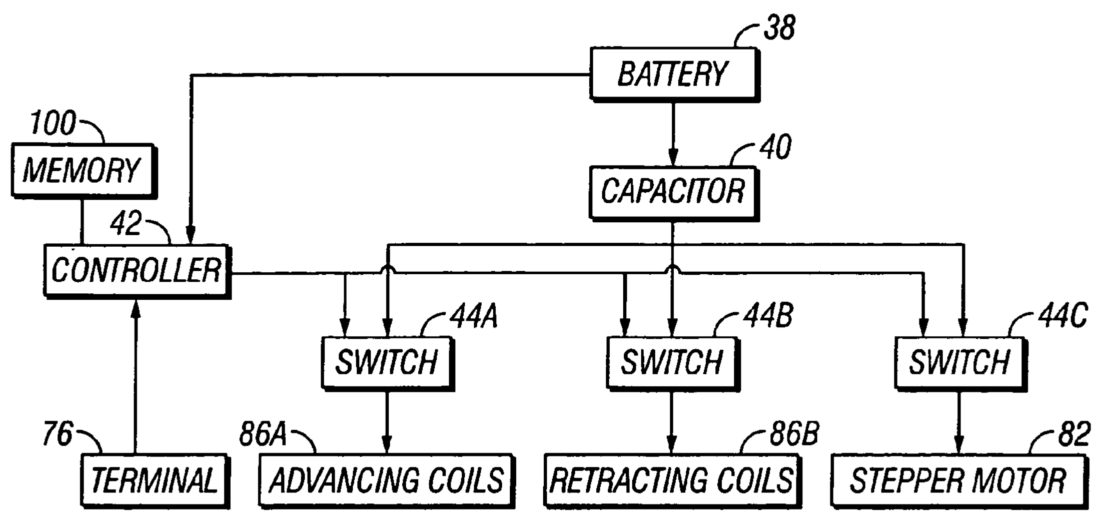
FIG. 10 is a block diagram illustrating functional components of the apparatus.

FIG. 10 illustrates the manner in which the electrical components may be functionally interconnected for the present embodiment. The battery 38 provides power to the capacitor 40 and the controller 42. The terminal 76 is connected to the controller 42 so that the controller recognizes when the button 32 is depressed. The capacitor to provide power (electric potential and current) individually through the switches (such as field-effect transistors) to the advancing coils 86A, retracting coils 86B and the stepper motor 82. The switches 44A, B, and C are all under the control of the controller 42. A memory 100 is connected to the controller. A set of instructions is stored in the memory 100 and is readable by the controller 42. Further functioning of the controller 42 in combination with the terminal 76 and the switches 44A, B, and C should be evident from the foregoing description.

Figure 11:
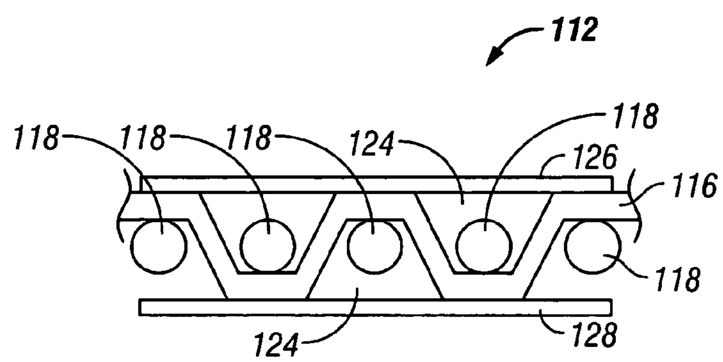
FIG. 11 is an end view illustrating a cartridge according to an optional embodiment that that allows for better adhesion of sterilization barriers.

FIG. 11 illustrates a configuration for another embodiment of a cartridge having penetrating members. The cartridge 112 has a corrugated configuration and a plurality of penetrating members 118 in grooves 124 formed in opposing sides of the cartridge 112. Sterilization barriers 126 and 128 are attached over the penetrating members 118 at the top and the penetrating members 118 at the bottom, respectively. Such an arrangement provides large surfaces for attachment of the sterilization barriers 126 and 128. All the penetrating members 118 on the one side are used first, whereafter the cartridge 112 is turned over and the penetrating members 118 on the other side are used. Additional aspects of such a cartridge are also discussed in FIGS. 42-44.

Figure 12:
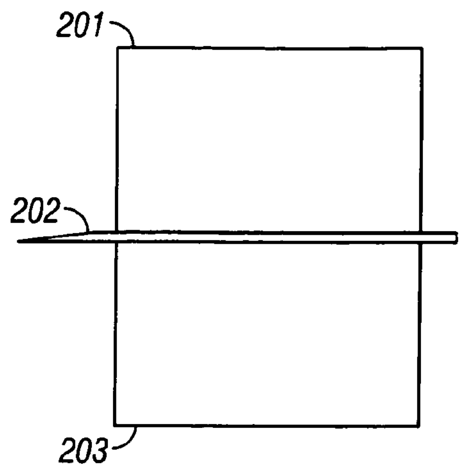
FIG. 12 is a cross-sectional view of an embodiment having features of the invention.
Figure 13:
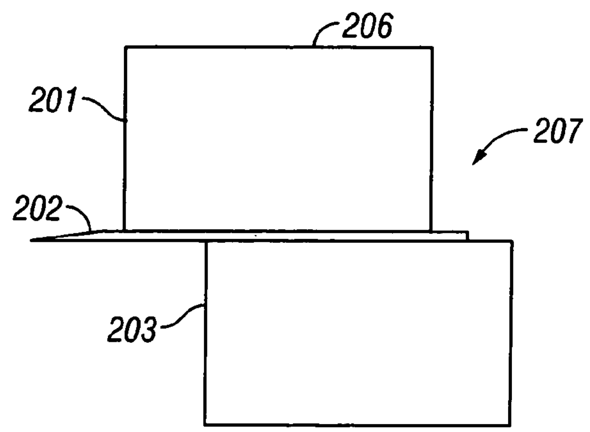
FIG. 13 is a cross-sectional view of an embodiment having features of the invention in operation.

Referring now to FIGS. 12-13, a friction based method of coupling with and driving bare lancets or bare penetrating members will be described in further detail. Any embodiment of the present invention disclosed herein may be adapted to use these methods. As seen in FIG. 12, surface 201 is physically in contact with penetrating member 202. Surface 203 is also physically in contact with penetrating member 202. In the present embodiment of the invention, surface 201 is stainless steel, penetrating member 202 is stainless steel, and surface 203 is polytetrafluoroethylene-coated stainless steel.

FIG. 13 illustrates one embodiment of the friction based coupling in use. Normal force 206 may be applied vertically to surface 201, pressing it against penetrating member 202. Penetrating member 202 is thereby pressed against surface 203. Normal force 206 is transmitted through surface 201 and penetrating member 202 to also act between penetrating member 202 and surface 203. Surface 203 is held rigid or stationary with respect to a target of the lancet. Using the classical static friction model, the maximum frictional force between surface 201 and penetrating member 202 is equal to the friction coefficient between surface 201 and penetrating member 202 multiplied by the normal force between surface 201 and penetrating member 202. In this embodiment, the maximum frictional force between surface 203 and penetrating member 202 is equal to the coefficient of friction between the surface 203 and the penetrating member 202 multiplied by the normal force between the surface 203 and the penetrating member 202. Because friction coefficient between surface 203 and penetrating member 202 is less than friction coefficient between surface 201 and penetrating member 202, the interface between surface 201 and penetrating member 202 can develop a higher maximum static friction force than can the interface between surface 203 and penetrating member 202.

Driving force as indicated by arrow 207 is applied to surface 201 perpendicular to normal force 206. The sum of the forces acting horizontally on surface 201 is the sum of driving force 207 and the friction force developed at the interface of surface 201 and penetrating member 202, which acts in opposition to driving force 207. Since the coefficient of friction between surface 203 and penetrating member 202 is less than the coefficient of friction between surface 201 and penetrating member 202, penetrating member 202 and surface 201 will remain stationary with respect to each other and can be considered to behave as one piece when driving force 207 just exceeds the maximum frictional force that can be supported by the interface between surface 203 and penetrating member 202. Surface 201 and penetrating member 202 can be considered one piece because the coefficient of friction between surface 201 and penetrating member 202 is high enough to prevent relative motion between the two.

In one embodiment, the coefficient of friction between surface 201 and penetrating member 202 is approximately 0.8 corresponding to the coefficient of friction between two surfaces of stainless steel, while the coefficient of friction between surface 203 and penetrating member 202 is approximately 0.04, corresponding to the coefficient of friction between a surface of stainless steel and one of polytetrafluoroethylene. Normal force 206 has a value of 202 Newtons. Using these values, the maximum frictional force that the interface between surface 201 and penetrating member 202 can support is 1.6 Newtons, while the maximum frictional force that the interface between surface 203 and penetrating member 202 can support is 0.08 Newtons. If driving force 207 exceeds 0.08 Newtons, surface 201 and penetrating member 202 will begin to accelerate together with respect to surface 203. Likewise, if driving force 207 exceeds 1.6 Newtons and penetrating member 202 encounters a rigid barrier, surface 201 would move relative to penetrating member 202.

Another condition, for example, for surface 201 to move relative to penetrating member 202 would be in the case of extreme acceleration. In an embodiment, penetrating member 202 has a mass of 8.24×10−6 kg. An acceleration of 194,174 m/s2 of penetrating member 202 would therefore be required to exceed the frictional force between penetrating member 202 and surface 201, corresponding to approximately 19,800 g's. Without being bound to any particular embodiment or theory of operation, other methods of applying friction base coupling may also be used. For example, the penetrating member 202 may be engaged by a coupler using a interference fit to create the frictional engagement with the member.

Figure 14:
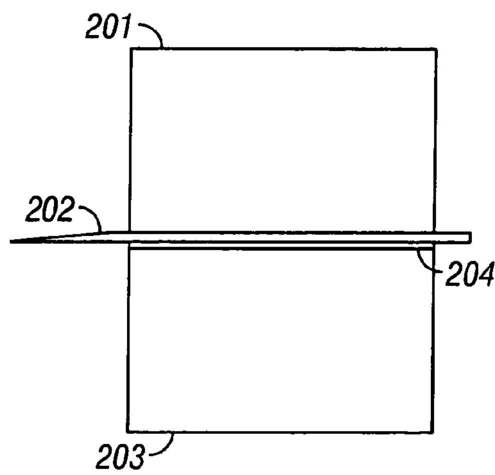
FIG. 14 is a cross-sectional view illustrating a low-friction coating applied to one penetrating member contact surface.
Figure 15:
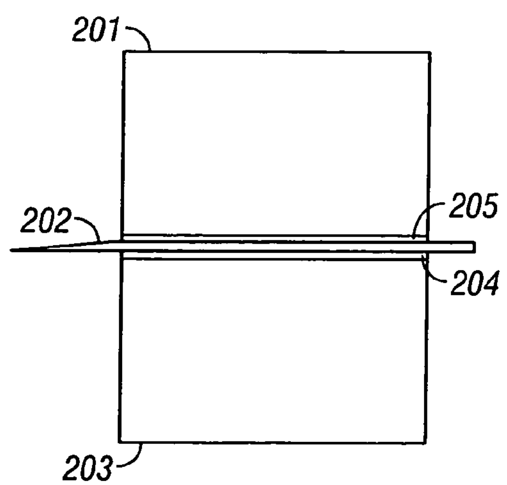
FIG. 15 is a cross-sectional view illustrating a coating applied to one penetrating member contact surface which increases friction and improves the microscopic contact area between the penetrating member and the penetrating member contact surface.

FIG. 14 illustrates a polytetrafluoroethylene coating on stainless steel surface 203 in detail. It should be understood that the surface 203 may be coated with other materials such as but not limited to Telfon®, silicon, polymer or glass. The coating may cover all of the penetrating member, only the proximal portions, only the distal portions, only the tip, only some other portion, or some combination of some or all of the above. FIG. 15 illustrates a doping of lead applied to surface 201, which conforms to penetrating member 202 microscopically when pressed against it. Both of these embodiments and other coated embodiments of a penetrating member may be used with the actuation methods described herein.

The shapes and configurations of surface 201 and surface 102 could be some form other than shown in FIGS. 12-15. For example, surface 201 could be the surface of a wheel, which when rotated causes penetrating member 202 to advance or retract relative to surface 203. Surface 201 could be coated with another conformable material besides lead, such as a plastic. It could also be coated with particles, such as diamond dust, or given a surface texture to enhance the friction coefficient of surface 201 with penetrating member 202. Surface 202 could be made of or coated with diamond, fluorinated ethylene propylene, perfluoroalkoxy, a copolymer of ethylene and tetrafluoroethylene, a copolymer of ethylene and chlorotrifluoroethylene, or any other material with a coefficient of friction with penetrating member 202 lower than that of the material used for surface 201.

Figure 16:
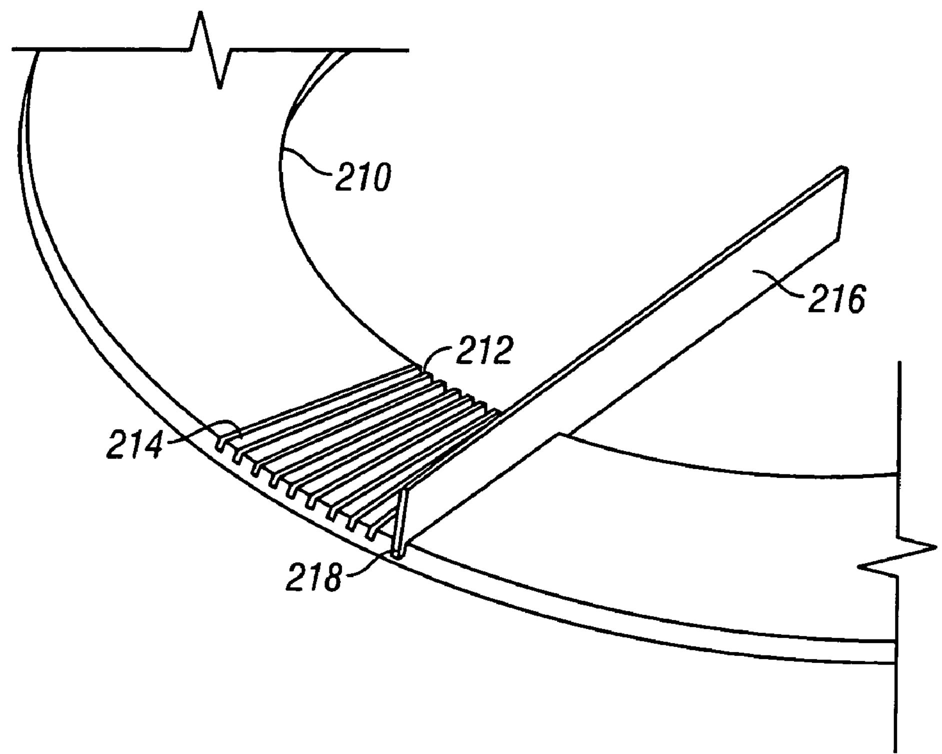
FIG. 16 illustrates a portion of a penetrating member cartridge having an annular configuration with a plurality of radially oriented penetrating member slots and a distal edge of a drive member disposed in one of the penetrating member slots.

Referring to FIG. 16, a portion of a base plate 210 of an embodiment of a penetrating member cartridge is shown with a plurality of penetrating member slots 212 disposed in a radial direction cut into a top surface 214 of the base plate. A drive member 216 is shown with a distal edge 218 disposed within one of the penetrating member slots 212 of the base plate 210. The distal edge 218 of the drive member 216 is configured to slide within the penetrating member slots 212 with a minimum of friction but with a close fit to minimize lateral movement during a lancing cycle.

Figure 17:
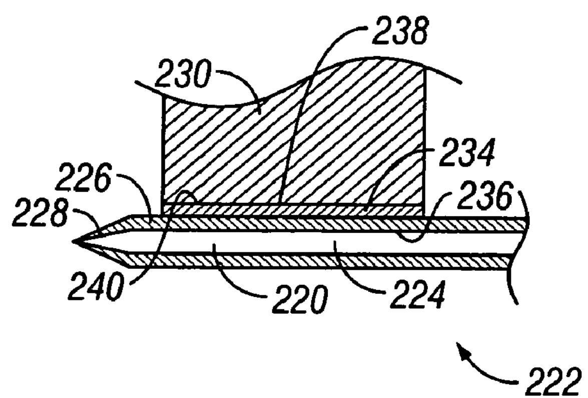
FIG. 17 is an elevational view in partial longitudinal section of a coated penetrating member in contact with a coated penetrating member contact surface.

FIG. 17 shows a distal portion 220 of a coated penetrating member 222 in partial longitudinal section. The coated penetrating member 222 has a core portion 224, a coating 226 and a tapered distal end portion 228. A portion of a coated drive member 230 is shown having a coating 234 with penetrating member contact surface 236. The penetrating member contact surface 236 forms an interface 238 with an outer surface 240 of the coated penetrating member 222. The interface 238 has a characteristic friction coefficient that will depend in part on the choice of materials for the penetrating member coating 226 and the drive member coating 234. If silver is used as the penetrating member and drive member coating 226 and 236, this yields a friction coefficient of about 1.3 to about 1.5. Other materials can be used for coatings 226 and 236 to achieve the desired friction coefficient. For example, gold, platinum, stainless steel and other materials may be used for coatings 226 and 236. It may be desirable to use combinations of different materials for coatings 226 and 236. For example, an embodiment may include silver for a penetrating member coating 226 and gold for a drive member coating. Some embodiments of the interface 238 can have friction coefficients of about 1.15 to about 5.0, specifically, about 1.3 to about 2.0.

Embodiments of the penetrating member 222 can have an outer transverse dimension or diameter of about 200 to about 400 microns, specifically, about 275 to about 325 microns. Embodiments of penetrating member 222 can have a length of about 10 to about 30 millimeters, specifically, about 15 to about 25 millimeters. Penetrating member 222 can be made from any suitable high strength alloy such as stainless steel or the like.

Figure 18:
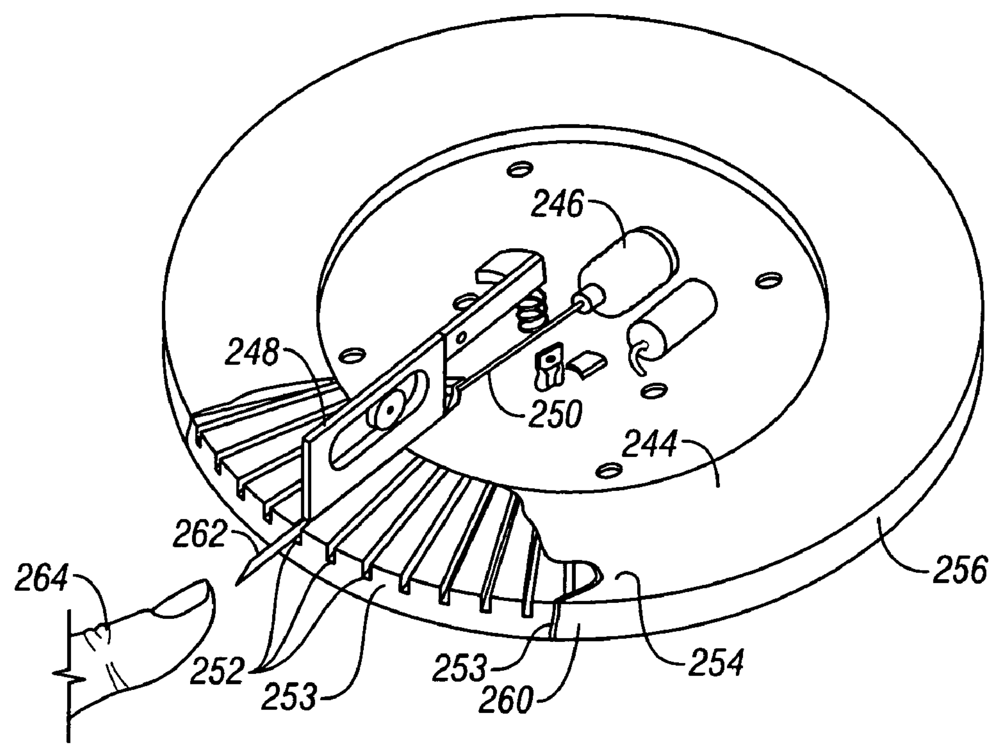
FIG. 18 illustrates an embodiment of a lancing device having features of the invention.

FIG. 18 is a perspective view of a lancing device 242 having features of the invention. A penetrating member cartridge 244 is disposed about a driver 246 that is coupled to a drive member 248 by a coupler rod 250. The penetrating member cartridge 244 has a plurality of penetrating member slots 252 disposed in a radial configuration in a top surface 254 a base plate 256 of the penetrating member cartridge 244. The distal ends 253 of the penetrating member slots 252 are disposed at an outer surface 260 of the base plate 256. A fracturable sterility barrier 258, shown partially cut away, is disposed on the top surface 254 of base plate 256 over the plurality of penetrating member slots 252. The sterility barrier 258 is also disposed over the outer surface 260 of the base plate 256 in order to seal the penetrating member slots from contamination prior to a lancing cycle. A distal portion of a penetrating member 262 is shown extending radially from the penetrating member cartridge 244 in the direction of a patient's finger 264.

Figure 19:
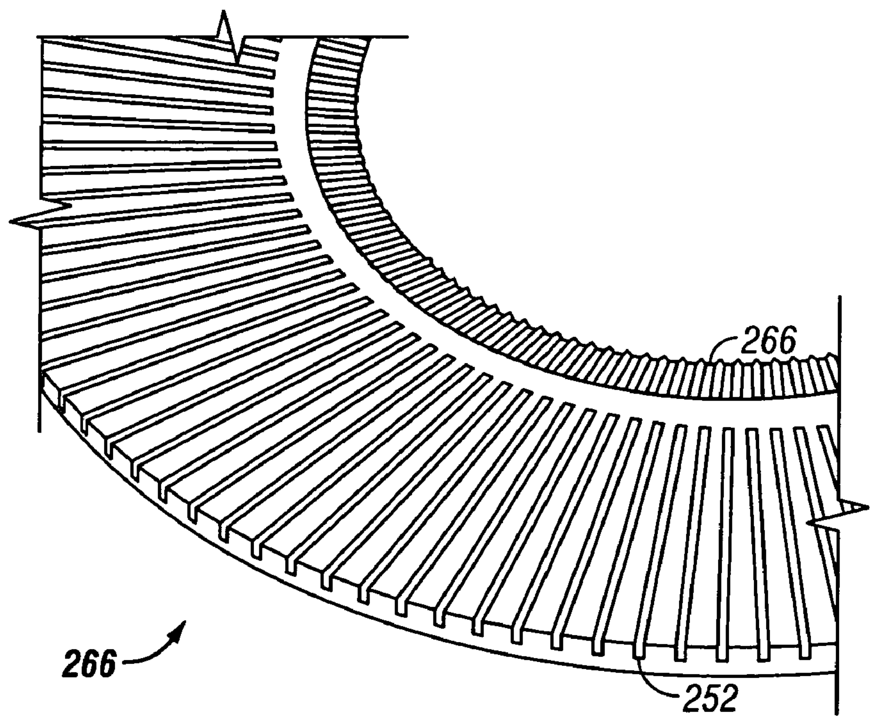
FIG. 19 is a perspective view of a portion of a penetrating member cartridge base plate having a plurality of penetrating member slots and drive member guide slots disposed radially inward of and aligned with the penetrating member slots.

FIG. 19 illustrates a portion of the base plate 256 used with the lancing device 242 in more detail and without sterility barrier 258 in place (for ease of illustration). The base plate 256 includes a plurality of penetrating member slots 252 which are in radial alignment with corresponding drive member slots 266. The drive member slots 266 have an optional tapered input configuration that may facilitate alignment of the drive member 248 during downward movement into the drive member slot 266 and penetrating member slot 252. Penetrating member slots 252 are sized and configured to accept a penetrating member 262 disposed therein and allow axial movement of the penetrating member 262 within the penetrating member slots 252 without substantial lateral movement.

Referring again to FIG. 18, in use, the present embodiment of penetrating member cartridge 242 is placed in an operational configuration with the driver 246. A lancing cycle is initiated and the drive member 248 is brought down through the sterility barrier 258 and into a penetrating member slot 252. A penetrating member contact surface of the drive member then makes contact with an outside surface of the penetrating member 262 and is driven distally toward the patient's finger 264 as described above with regard to the embodiment discussed in FIG. 20. The friction coefficient between the penetrating member contact surface of the drive member 248 and the penetrating member 262 is greater than the friction coefficient between the penetrating member 262 and an interior surface of the penetrating member slots 252. As such, the drive member 248 is able to drive the penetrating member 262 distally through the sterility barrier 258 and into the patient's finger 264 without any relative movement or substantial relative movement between the drive member 248 and the penetrating member 262.

Figure 20:
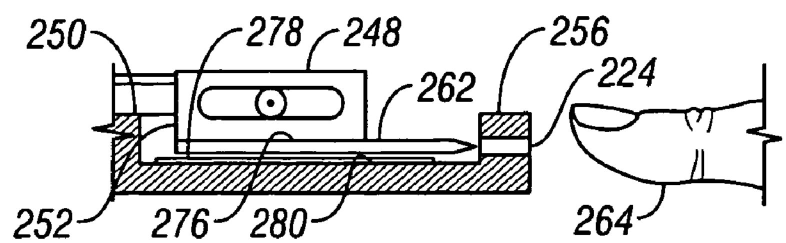
FIGS. 20-22 illustrate a penetrating member cartridge in section, a drive member, a penetrating member and the tip of a patient's finger during three sequential phases of a lancing cycle.
Figure 21:
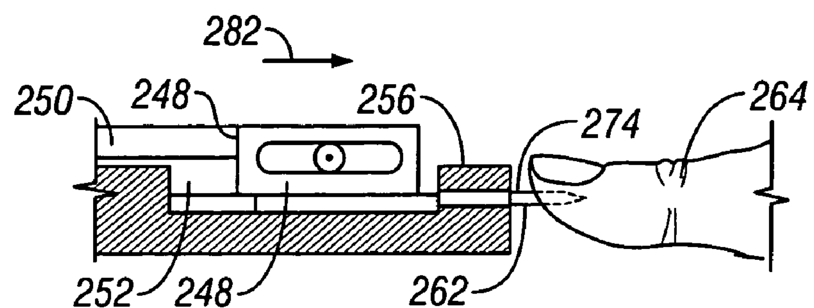
Figure 22:
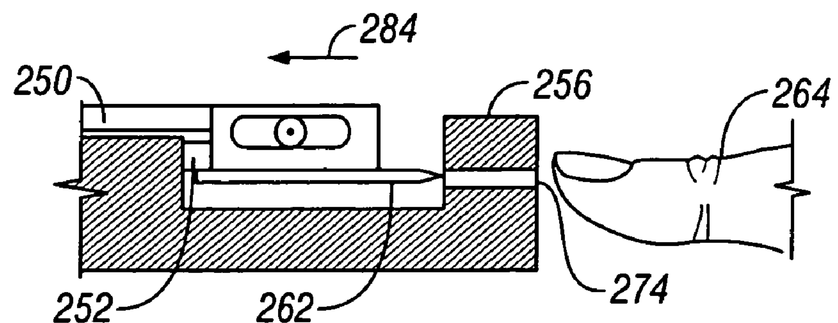
Figure 23:
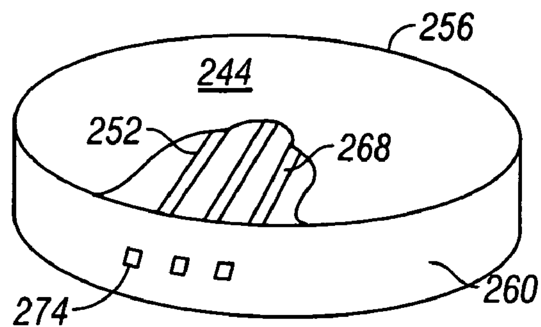
FIG. 23 illustrates an embodiment of a penetrating member cartridge having features of the invention.
Figure 24:
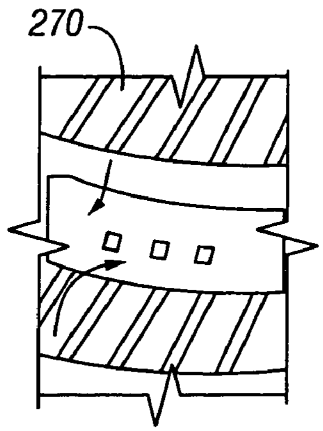
FIG. 24 is an exploded view of a portion of the penetrating member cartridge of FIG. 12.

Referring to FIGS. 20-22, a lancing cycle sequence is shown for a lancing device 242 with another embodiment of a penetrating member cartridge 244 as shown in FIGS. 23 and 24. The base plate 256 of the penetrating member cartridge 242 shown in FIGS. 23 and 24 has a plurality of penetrating member slots 252 with top openings 268 that do not extend radially to the outer surface 260 of the base plate 256. In this way, the penetrating member slots 252 can be sealed with a first sterility barrier 270 disposed on the top surface 254 of the base plate 256 and a second sterility barrier 272 disposed on the outer surface 260 of the base plate 256. Penetrating member outlet ports 274 are disposed at the distal ends of the penetrating member slots 252.

Referring again to FIG. 20, the penetrating member 262 is shown in the proximally retracted starting position within the penetrating member slot 252. The outer surface of the penetrating member 276 is in contact with the penetrating member contact surface 278 of the drive member 248. The friction coefficient between the penetrating member contact surface 278 of the drive member 248 and the outer surface 276 of the penetrating member 262 is greater than the friction coefficient between the penetrating member 262 and an interior surface 280 of the penetrating member slots 252. A distal drive force as indicated by arrow 282 in FIG. 10 is then applied via the drive coupler 250 to the drive member 248 and the penetrating member is driven out of the penetrating member outlet port 274 and into the patient's finger 264. A proximal retraction force, as indicated by arrow 284 in FIG. 22, is then applied to the drive member 248 and the penetrating member 262 is withdrawn from the patient's finger 264 and back into the penetrating member slot 252.

Figure 25:
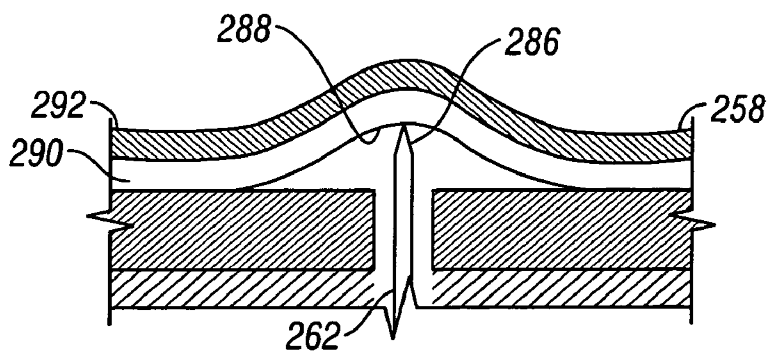
FIGS. 25 and 26 illustrate a multiple layer sterility barrier disposed over a penetrating member slot being penetrated by the distal end of a penetrating member during a lancing cycle.
Figure 26:
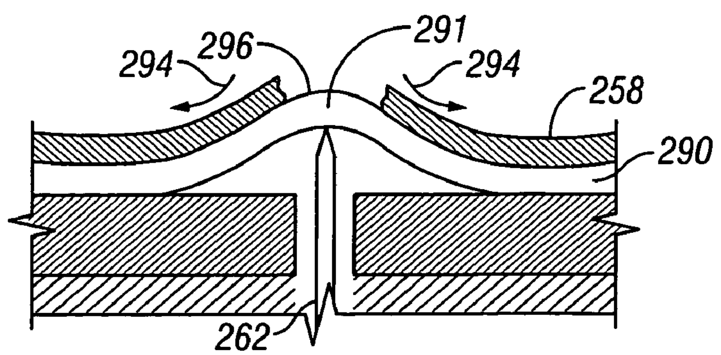

FIGS. 25 and 26 illustrate an embodiment of a multiple layer sterility barrier 258 in the process of being penetrated by a penetrating member 62. It should be understood that this barrier 258 may be adapted for use with any embodiment of the present invention. The sterility barrier 258 shown in FIGS. 25 and 26 is a two layer sterility barrier 258 that facilitates maintaining sterility of the penetrating member 262 as it passes through and exits the sterility barrier 258. In FIG. 25, the distal end 286 of the penetrating member 262 is applying an axial force in a distal direction against an inside surface 288 of a first layer 290 of the sterility barrier 258, so as to deform the first layer 290 of the sterility barrier 258. The deformation 291 of the first layer 290 in turn applies a distorting force to the second layer 292 of the sterility barrier 258. The second layer of the sterility barrier is configured to have a lower tensile strength that the first layer 290. As such, the second layer 292 fails prior to the first layer 290 due to the strain imposed on the first layer 290 by the distal end 286 of the penetrating member 262, as shown in FIG. 26. After the second layer 292 fails, it then retracts from the deformed portion 291 of the first layer 290 as shown by arrows 294 in FIG. 26. As long as the inside surface 288 and outside surface 296 of the first layer 290 are sterile prior to failure of the second layer 292, the penetrating member 262 will remain sterile as it passes through the first layer 290 once the first layer eventually fails. Such a multiple layer sterility barrier 258 can be used for any of the embodiments discussed herein. The multiple layer sterility barrier 258 can also include three or more layers.

Referring to FIGS. 27 and 28, an embodiment of a drive member 300 coupled to a driver 302 wherein the drive member 300 includes a cutting member 304 having a sharpened edge 306 which is configured to cut through a sterility barrier 258 of a penetrating member slot 252 during a lancing cycle in order for the drive member 300 to make contact with a penetrating member. An optional lock pin 308 on the cutting member 304 can be configured to engage the top surface 310 of the base plate in order to prevent distal movement of the cutting member 304 with the drive member 300 during a lancing cycle.

Figure 30:
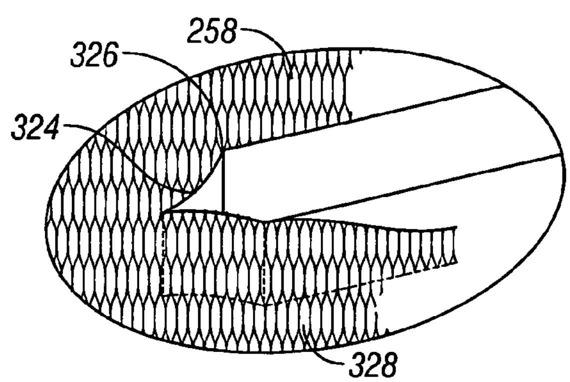

FIGS. 29 and 30 illustrate an embodiment of a penetrating member slot 316 in longitudinal section having a ramped portion 318 disposed at a distal end 320 of the penetrating member slot. A drive member 322 is shown partially disposed within the penetrating member slot 316. The drive member 322 has a cutting edge 324 at a distal end 326 thereof for cutting through a sterility barrier 328 during a lancing cycle. FIG. 30 illustrates the cutting edge 324 cutting through the sterility barrier 328 during a lancing cycle with the cut sterility barrier 328 peeling away from the cutting edge 324.

Figure 31:
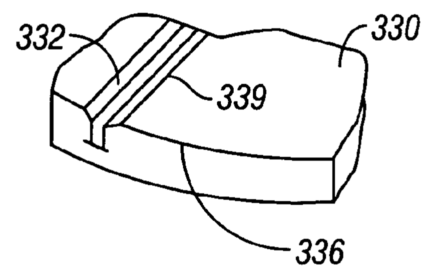
FIGS. 31-34 illustrate drive member slots in a penetrating member cartridge wherein at least a portion of the drive member slots have a tapered opening which is larger in transverse dimension at the top of the drive member slot than at the bottom of the drive member slot.
Figure 32:
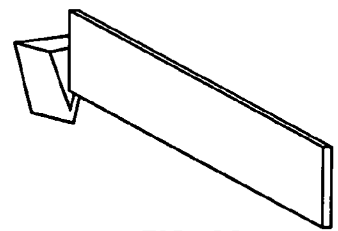
Figure 33:
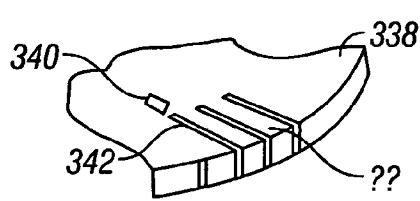
Figure 34:
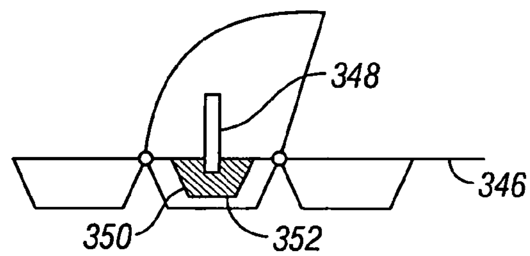

FIGS. 31-34 illustrate drive member slots in a base plate 330 of a penetrating member cartridge wherein at least a portion of the drive member slots have a tapered opening which is larger in transverse dimension at a top surface of the base plate than at the bottom of the drive member slot. FIG. 31 illustrates a base plate 330 with a penetrating member slot 332 that is tapered at the input 334 at the top surface 336 of the base plate 330 along the entire length of the penetrating member slot 332. In such a configuration, the penetrating member slot and drive member slot (not shown) would be in communication and continuous along the entire length of the slot 332. As an optional alternative, a base plate 338 as shown in FIGS. 32 and 33 can have a drive member slot 340 that is axially separated from the corresponding penetrating member slot 342. With this configuration, the drive member slot 340 can have a tapered configuration and the penetrating member slot 342 can have a straight walled configuration. In addition, this configuration can be used for corrugated embodiments of base plates 346 as shown in FIG. 34. In FIG. 34, a drive member 348 is disposed within a drive member slot 350. A penetrating member contact surface 352 is disposed on the drive member 348. The contact surface 352 has a tapered configuration that will facilitate lateral alignment of the drive member 348 with the drive member slot 350.

Figure 35:
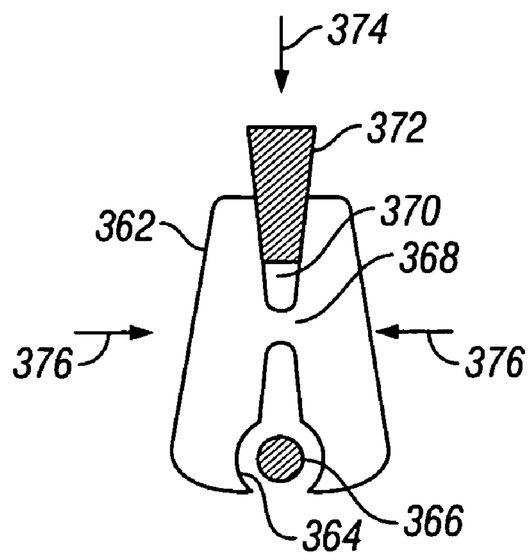
FIGS. 35-37 illustrate an embodiment of a penetrating member cartridge and penetrating member drive member wherein the penetrating member drive member has a contoured jaws configured to grip a penetrating member shaft.
Figure 36:
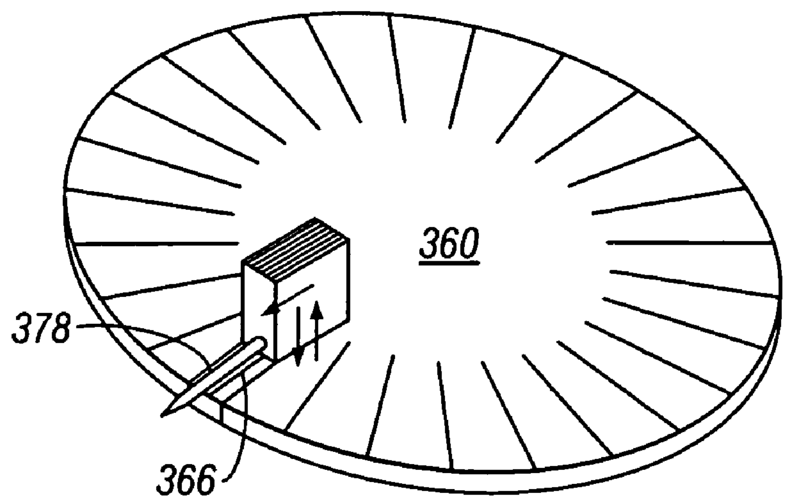
Figure 37:
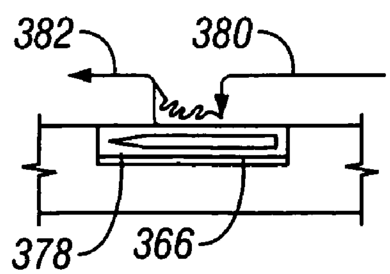

FIGS. 35-37 illustrate an embodiment of a penetrating member cartridge 360 and drive member 362 wherein the drive member 362 has contoured jaws 364 configured to grip a penetrating member shaft 366. In FIG. 35, the drive member 362 and penetrating member shaft 366 are shown in transverse cross section with the contoured jaws 364 disposed about the penetrating member shaft 366. A pivot point 368 is disposed between the contoured jaws 364 and a tapered compression slot 370 in the drive member 362. A compression wedge 372 is shown disposed within the tapered compression slot 370. Insertion of the compression wedge 372 into the compression slot 370 as indicated by arrow 374, forces the contoured jaws 364 to close about and grip the penetrating member shaft 366 as indicated by arrows 376.

FIG. 36 shows the drive member 362 in position about a penetrating member shaft 366 in a penetrating member slot 378 in the penetrating member cartridge 360. The drive member can be actuated by the methods discussed above with regard to other drive member and driver embodiments. FIG. 37 is an elevational view in longitudinal section of the penetrating member shaft 166 disposed within the penetrating member slot 378. The arrows 380 and 382 indicate in a general way, the path followed by the drive member 362 during a lancing cycle. During a lancing cycle, the drive member comes down into the penetrating member slot 378 as indicated by arrow 380 through an optional sterility barrier (not shown). The contoured jaws of the drive member then clamp about the penetrating member shaft 366 and move forward in a distal direction so as to drive the penetrating member into the skin of a patient as indicated by arrow 382.

Figure 38:
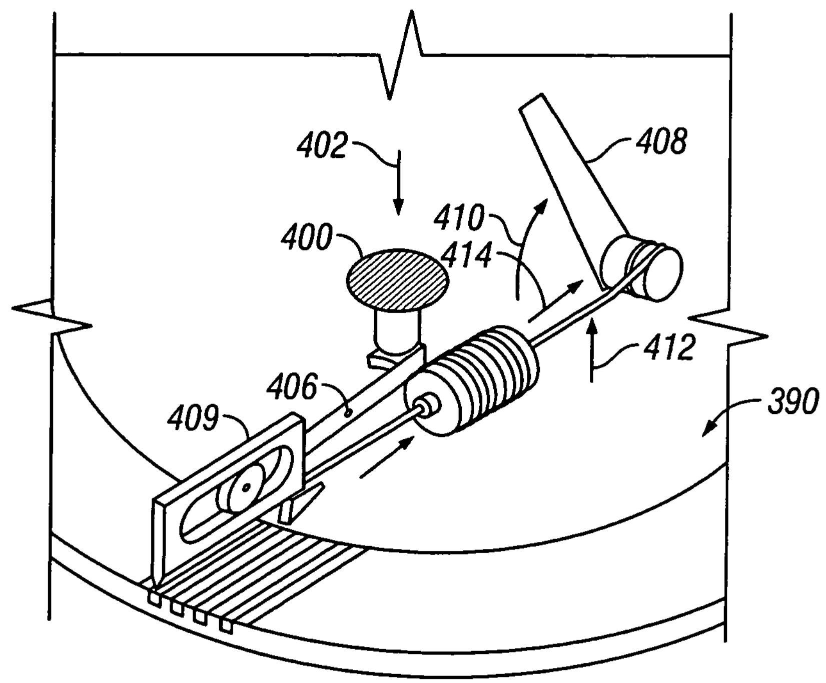
FIGS. 38 and 39 show a portion of a lancing device having a lid that can be opened to expose a penetrating member cartridge cavity for removal of a used penetrating member cartridge and insertion of a new penetrating member cartridge.
Figure 39:
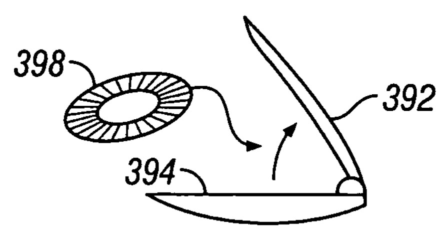

FIGS. 38 and 39 show a portion of a lancing device 390 having a lid 392 that can be opened to expose a penetrating member cartridge cavity 394 for removal of a used penetrating member cartridge 396 and insertion of a new penetrating member cartridge 398. Depression of button 400 in the direction indicated by arrow 402 raises the drive member 404 from the surface of the penetrating member cartridge 396 by virtue of lever action about pivot point 406. Raising the lid 392 actuates the lever arm 408 in the direction indicated by arrow 410 which in turn applies a tensile force to cable 412 in the direction indicated by arrow 414. This action pulls the drive member back away from the penetrating member cartridge 396 so that the penetrating member cartridge 396 can be removed from the lancing device 390. A new penetrating member cartridge 398 can then be inserted into the lancing device 390 and the steps above reversed in order to position the drive member 404 above the penetrating member cartridge 398 in an operational position.

Figure 40:
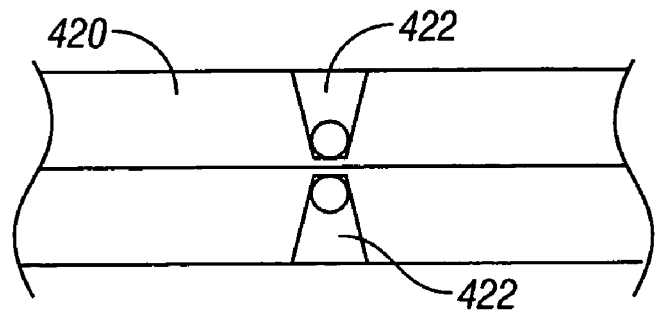
FIGS. 40 and 41 illustrate a penetrating member cartridge that has penetrating member slots on both sides.
Figure 41:
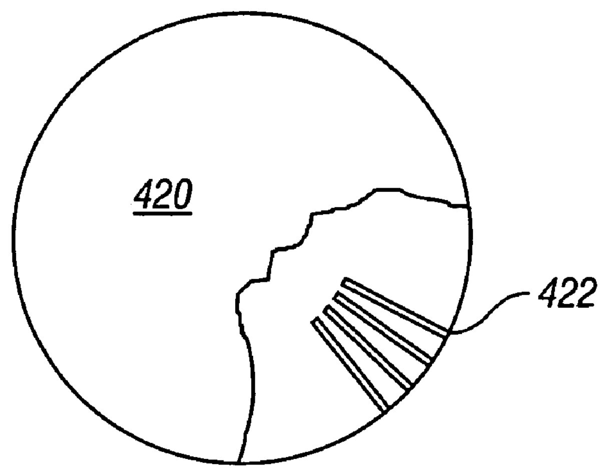

FIGS. 40 and 41 illustrate a penetrating member cartridge 420 that has penetrating member slots 422 on a top side 424 and a bottom side 426 of the penetrating member cartridge 420. This allows for a penetrating member cartridge 420 of a diameter D to store for use twice the number of penetrating members as a one sided penetrating member cartridge of the same diameter D.

Figure 42:
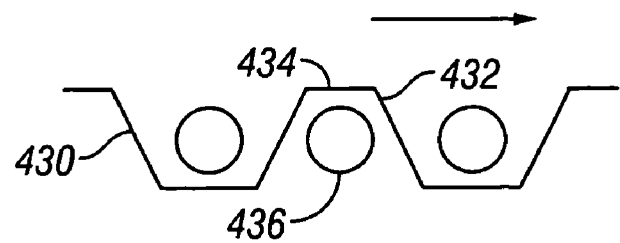
FIGS. 42-44 illustrate end and perspective views of a penetrating member cartridge having a plurality of penetrating member slots formed from a corrugated surface of the penetrating member cartridge.
Figure 43:
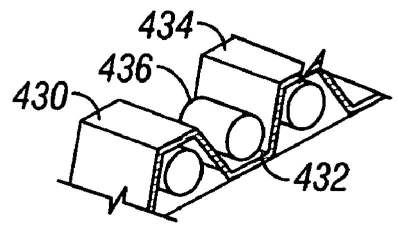
Figure 44:
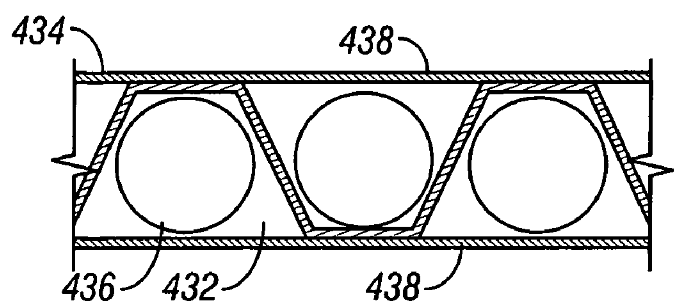

FIGS. 42-44 illustrate end and perspective views of a penetrating member cartridge 430 having a plurality of penetrating member slots 432 formed from a corrugated surface 434 of the penetrating member cartridge 430. Penetrating members 436 are disposed on both sides of the penetrating member cartridge 430. A sterility barrier 438 is shown disposed over the penetrating member slots 432 in FIG. 44.

Figure 45:
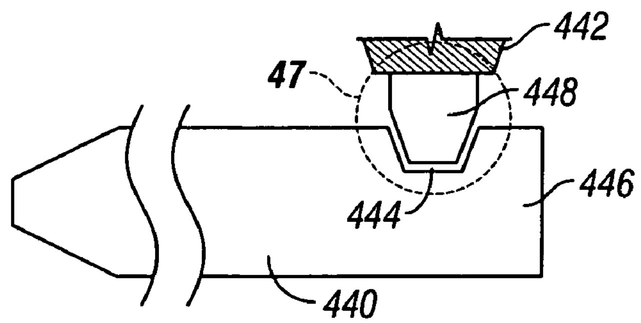
FIGS. 45-48 illustrate embodiments of a penetrating member and drive member wherein the penetrating member has a slotted shaft and the drive member has a protuberance configured to mate with the slot in the penetrating member shaft.
Figure 46:
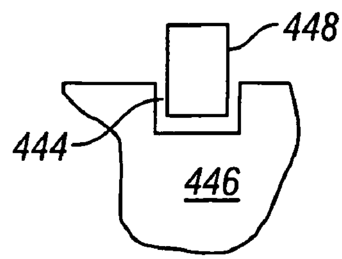
Figure 47:
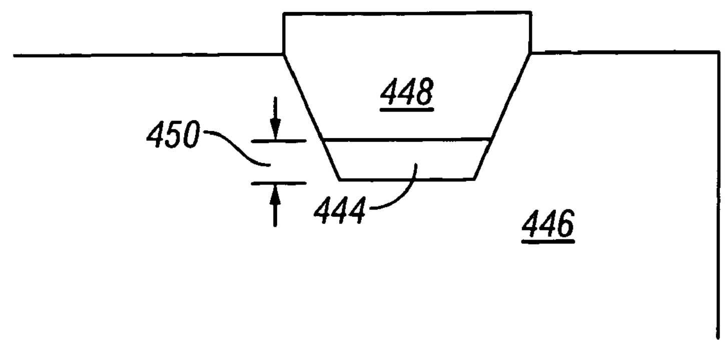

FIGS. 45-48 illustrate embodiments of a penetrating member 440 and drive member 442 wherein the penetrating member 440 has a transverse slot 444 in the penetrating member shaft 446 and the drive member 442 has a protuberance 448 configured to mate with the transverse slot 444 in the penetrating member shaft 446. FIG. 45 shows a protuberance 448 having a tapered configuration that matches a tapered configuration of the transverse slot 444 in the penetrating member shaft 446. FIG. 46 illustrates an optional alternative embodiment wherein the protuberance 448 has straight walled sides that are configured to match the straight walled sides of the transverse slot 444 shown in FIG. 46. FIG. 47 shows a tapered protuberance 448 that is configured to leave an end gap 450 between an end of the protuberance 448 and a bottom of the transverse slot in the penetrating member shaft 446.

Figure 48:
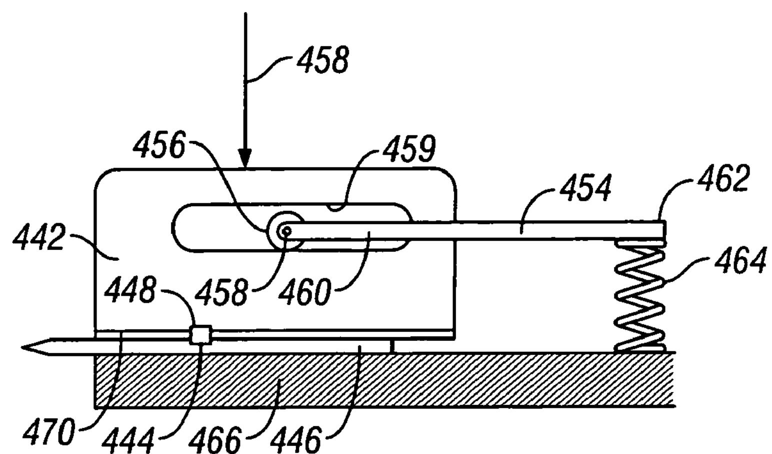

FIG. 48 illustrates a mechanism 452 to lock the drive member 442 to the penetrating member shaft 446 that has a lever arm 454 with an optional bearing 456 on the first end 458 thereof disposed within a guide slot 459 of the drive member 442. The lever arm 454 has a pivot point 460 disposed between the first end 458 of the lever arm 454 and the second end 462 of the lever arm 454. A biasing force is disposed on the second end 462 of the lever arm 454 by a spring member 464 that is disposed between the second end 462 of the lever arm 454 and a base plate 466. The biasing force in the direction indicated by arrow 468 forces the penetrating member contact surface 470 of the drive member 442 against the outside surface of the penetrating member 446 and, in addition, forces the protuberance 448 of the drive member 442 into the transverse slot 444 of the penetrating member shaft 446.

Figure 49:
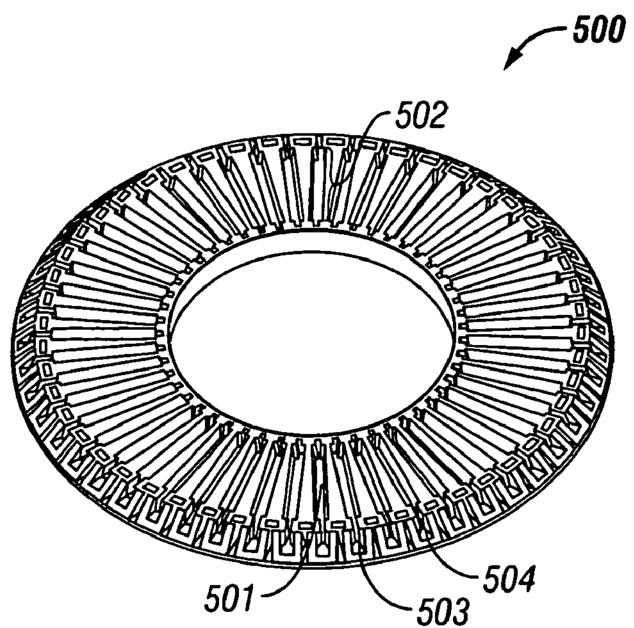
FIG. 49 is a perspective view of a cartridge according to the present invention.

Referring now to FIG. 49, another embodiment of a replaceable cartridge 500 suitable for housing a plurality of individually moveable penetrating members (not shown) will be described in further detail. Although cartridge 500 is shown with a chamfered outer periphery, it should also be understood that less chamfered and unchamfered embodiments of the cartridge 500 may also be adapted for use with any embodiment of the present invention disclosed herein. The penetrating members slidably coupled to the cartridge may be a bare lancet or bare elongate member without outer molded part or body pieces as seen in conventional lancet. The bare design reduces cost and simplifies manufacturing of penetrating members for use with the present invention. The penetrating members may be retractable and held within the cartridge so that they are not able to be used again. The cartridge is replaceable with a new cartridge once all the piercing members have been used. The lancets or penetrating members may be fully contained in the used cartridge so at to minimize the chance of patient contact with such waste.

Figure 50:
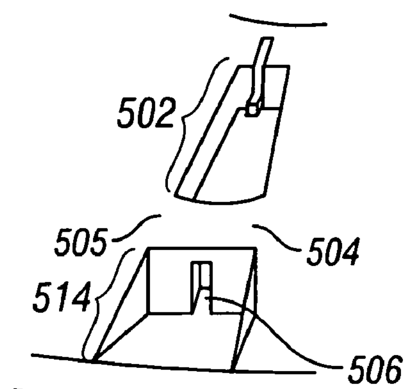
FIGS. 50 and 51 show close-ups of outer peripheries various cartridges.
Figure 51:
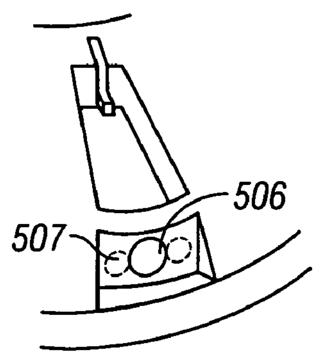

As can be seen in FIG. 49, the cartridge 500 may include a plurality of cavities 501 for housing a penetrating member. In this embodiment, the cavity 501 may have a longitudinal opening 502 associated with the cavity. The cavity 501 may also have a lateral opening 503 allowing the penetrating member to exit radially outward from the cartridge. As seen in FIG. 49, the outer radial portion of the cavity may be narrowed. The upper portion of this narrowed area may also be sealed or swaged to close the top portion 505 and define an enclosed opening 506 as shown in FIG. 50. Optionally, the narrowed area 504 may retain an open top configuration, though in some embodiments, the foil over the gap is unbroken, preventing the penetrating member from lifting up or extending upward out of the cartridge. The narrowed portion 504 may act as a bearing and/or guide for the penetrating member. FIG. 51 shows that the opening 506 may have a variety of shapes such as but not limited to, circular, rectangular, triangular, hexagonal, square, or combinations of any or all of the previous shapes. Openings 507 (shown in phantom) for other microfluidics, capillary tubes, or the like may also be incorporated in the immediate vicinity of the opening 506. In some optional embodiments, such openings 507 may be configured to surround the opening 506 in a concentric or other manner.

Figure 52:
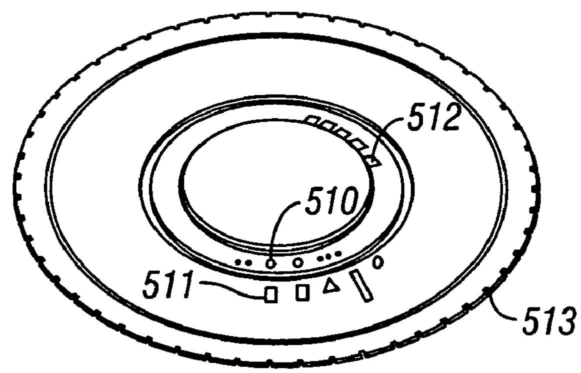
FIG. 52 is a perspective view of an underside of a cartridge.

Referring now to FIG. 52, the underside of a cartridge 500 will be described in further detail. This figures shows many features on one cartridge 500. It should be understood that a cartridge may include some, none, or all of these features, but they are shown in FIG. 52 for ease of illustration. The underside may include indentations or holes 510 close to the inner periphery for purpose of properly positioning the cartridge to engage a penetrating member gripper and/or to allow an advancing device (shown in FIGS. 56B and 56C) to rotate the cartridge 500. Indentations or holes 511 may be formed along various, locations on the underside of cartridge 500 and may assume various shapes such as but not limited to, circular, rectangular, triangular, hexagonal, square, or combinations of any or all of the previous shapes. Notches 512 may also be formed along the inner surface of the cartridge 500 to assist in alignment and/or rotation of the cartridge. It should be understood of course that some of these features may also be placed on the topside of the cartridge in areas not occupied by cavities 501 that house the penetrating members. Notches 513 may also be incorporated along the outer periphery of the cartridge. These notches 513 may be used to gather excess material from the sterility barrier 28 (not shown) that may be used to cover the angled portion 514 of the cartridge. In the present embodiment, the cartridge has a flat top surface and an angled surface around the outside. Welding a foil type sterility barrier over that angled surface, the foil folds because of the change in the surfaces which is now at 45 degrees. This creates excess material. The grooves or notches 513 are there as a location for that excess material. Placing the foil down into those grooves 513 which may tightly stretch the material across the 45 degree angled surface. Although in this embodiment the surface is shown to be at 45 degrees, it should be understood that other angles may also be used. For example, the surface may be at any angle between about 3 degrees to 90 degrees, relative to horizontal. The surface may be squared off. The surface may be unchamfered. The surface may also be a curved surface or it may be combinations of a variety of angled surfaces, curved and straights surfaces, or any combination of some or all of the above.

Referring now to FIGS. 53-54, the sequence in which the cartridge 500 is indexed and penetrating members are actuated will now be described. It should be understood that some steps described herein may be combined or taken out of order without departing from the spirit of the invention. These sequence of steps provides vertical and horizontal movement used with the present embodiment to load a penetrating member onto the driver.

As previously discussed, each cavity on the cartridge may be individually sealed with a foil cover or other sterile enclosure material to maintain sterility until or just before the time of use. In the present embodiment, penetrating members are released from their sterile environments just prior to actuation and are loaded onto a launcher mechanism for use. Releasing the penetrating member from the sterile environment prior to launch allows the penetrating member in the present embodiment to be actuated without having to pierce any sterile enclosure material which may dull the tip of the penetrating member or place contaminants on the member as it travels towards a target tissue. A variety of methods may be used accomplish this goal.

Figure 53A:
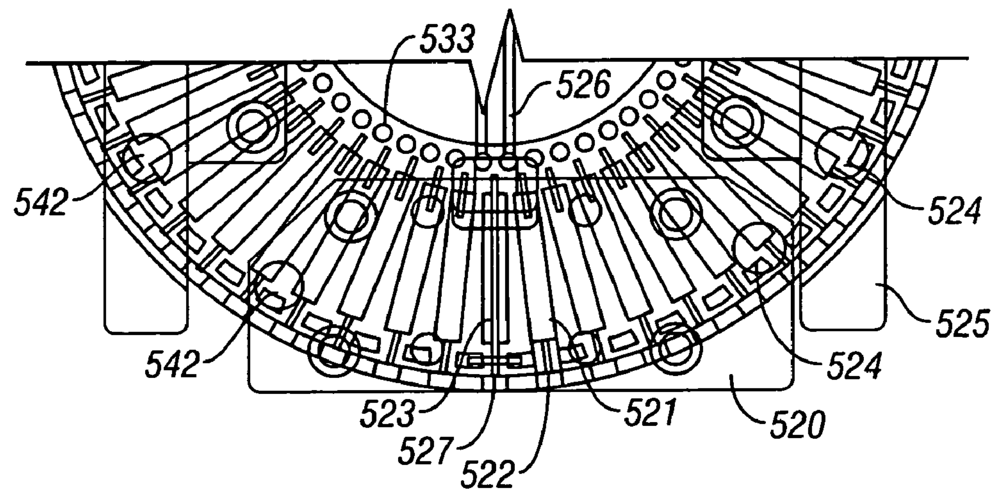
FIG. 53A shows a top down view of a cartridge and the punch and pusher devices.
Figure 53B:
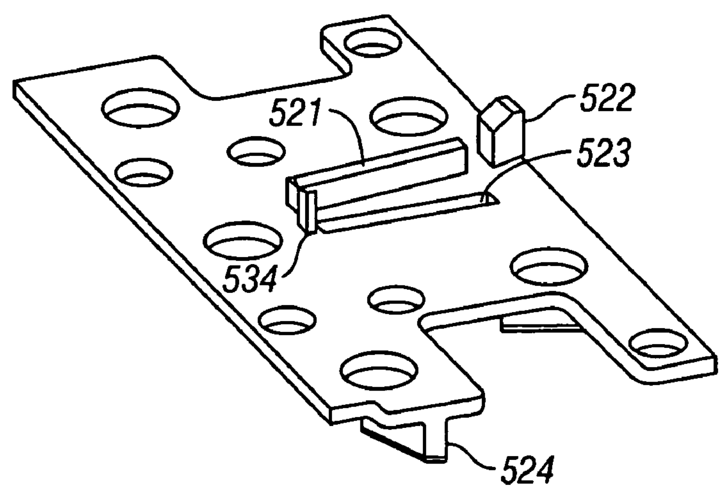
FIG. 53B is a perspective view of one embodiment of a punch plate.
Figure 54A:
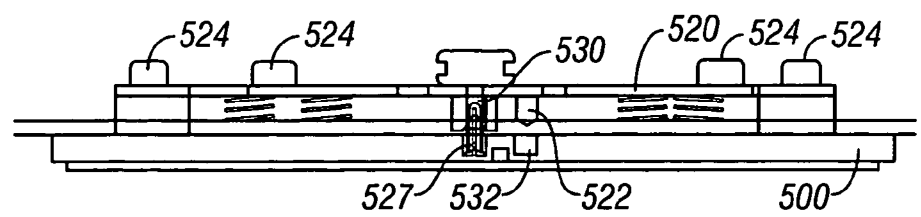
FIGS. 54A-54G show a sequence of motion for the punch plate, the cartridge, and the cartridge pusher.

FIG. 53A shows one embodiment of penetrating member release device, which in this embodiment is a punch plate 520 that is shown in a see-through depiction for ease of illustration. The punch plate 520 may include a first portion 521 for piercing sterile material covering the longitudinal opening 502 and a second portion 522 for piercing material covering the lateral opening 503. A slot 523 allows the penetrating member gripper to pass through the punch plate 520 and engage a penetrating member housed in the cartridge 500. The second portion 522 of the punch plate down to engage sterility barrier angled at about a 45 degree slope. Of course, the slope of the barrier may be varied. The punch portion 522 first contacts the rear of the front pocket sterility barrier and as it goes down, the cracks runs down each side and the barrier is pressed down to the bottom of the front cavity. The rear edge of the barrier first contacted by the punch portion 522 is broken off and the barrier is pressed down, substantially cleared out of the way. These features may be more clearly seen in FIG. 53B. The punch portion 521 may include a blade portion down the centerline. As the punch comes down, that blade may be aligned with the center of the cavity, cutting the sterility barrier into two pieces. The wider part of the punch 521 then pushes down on the barrier so the they align parallel to the sides of the cavity. This creates a complete and clear path for the gripper throughout the longitudinal opening of the cavity. Additionally, as seen in FIGS. 53B and 54A, a plurality of protrusion 524 are positioned to engage a cam (FIG. 55A) which sequences the punching and other vertical movement of punch plate 520 and cartridge pusher 525. The drive shaft 526 from a force generator (not shown) which is used to actuate the penetrating member 527.

Referring now to FIGS. 54A-F, the release and loading of the penetrating members are achieved in the following sequence. FIG. 54A shows the release and loading mechanism in rest state with a dirty bare penetrating member 527 held in a penetrating member gripper 530. This is the condition of the device between lancing events. When the time comes for the patient to initiate another lancing event, the used penetrating member is cleared and a new penetrating member is loaded, just prior to the actual lancing event. The patient begins the loading of a new penetrating member by operating a setting lever to initiate the process. The setting lever may operate mechanically to rotate a cam (see FIG. 55A) that moves the punch plate 520 and cartridge pusher 525. In other embodiments, a stepper motor or other mover such as but not limited to, a pneumatic actuator, hydraulic actuator, or the like are used to drive the loading sequence.

Figure 54B:
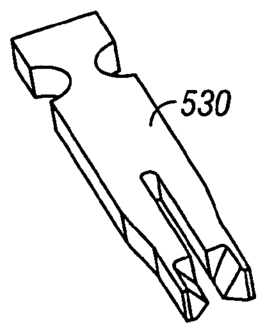

FIG. 54B shows one embodiment of penetrating member gripper 530 in more detail. The penetrating member gripper 30 may be in the form of a tuning fork with sharp edges along the inside of the legs contacting the penetrating member. In some embodiments, the penetrating member may be notched, recessed, or otherwise shaped to receive the penetrating member gripper. As the gripper 530 is pushed down on the penetrating member, the legs are spread open elastically to create a frictional grip with the penetrating member such as but not limited to bare elongate wires without attachments molded or otherwise attached thereon. In some embodiments, the penetrating member is made of a homogenous material without any additional attachments that are molded, adhered, glued or otherwise added onto the penetrating member.

In some embodiments, the gripper 530 may cut into the sides of the penetrating member. The penetrating member in one embodiment may be about 300 microns wide. The grooves that form in the side of the penetrating member by the knife edges are on the order of about 5-10 microns deep and are quite small. In this particular embodiment, the knife edges allow the apparatus to use a small insertion force to get the gripper onto the penetrating member, compared to the force to remove the penetrating member from the gripper the longitudinal axis of an elongate penetrating member. Thus, the risk of a penetrating member being detached during actuation are reduced. The gripper 530 may be made of a variety of materials such as, but not limited to high strength carbon steel that is heat treated to increased hardness, ceramic, substrates with diamond coating, composite reinforced plastic, elastomer, polymer, and sintered metals. Additionally, the steel may be surface treated. The gripper 130 may have high gripping force with low friction drag on solenoid or other driver.

Figure 54C:
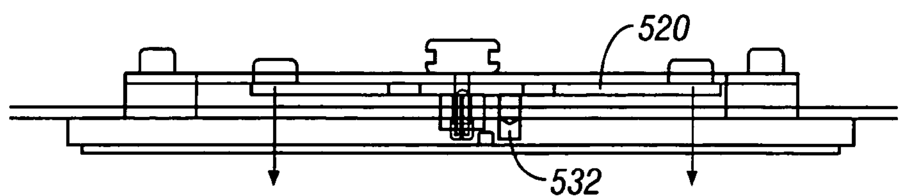

As seen in FIG. 54C, the sequence begins with punch plate 520 being pushed down. This results in the opening of the next sterile cavity 532. In some embodiment, this movement of punch plate 520 may also result in the crimping of the dirty penetrating member to prevent it from being used again. This crimping may result from a protrusion on the punch plate bending the penetrating member or pushing the penetrating member into a groove in the cartridge that hold the penetrating member in place through an interference fit. As seen in FIGS. 53B and 54C, the punch plate 520 has a protrusion or punch shaped to penetrate a longitudinal opening 502 and a lateral opening 503 on the cartridge. The first portion 521 of the punch that opens cavity 532 is shaped to first pierce the sterility barrier and then push, compresses, or otherwise moves sterile enclosure material towards the sides of the longitudinal opening 502. The second portion 522 of the punch pushes down the sterility barrier at lateral opening or penetrating member exit 503 such that the penetrating member does not pierce any materials when it is actuated toward a tissue site.

Figure 54D:
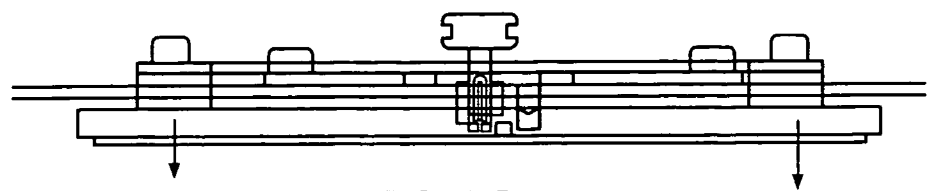

Referring now to FIG. 54D, the cartridge pusher 525 is engaged by the cam 550 (not shown) and begins to push down on the cartridge 500. The punch plate 520 may also travel downward with the cartridge 500 until it is pushed down to it maximum downward position, while the penetrating member gripper 530 remains vertically stationary. This joint downward motion away from the penetrating member gripper 530 will remove the penetrating member from the gripper. The punch plate 520 essentially pushes against the penetrating member with protrusion 534 (FIG. 55A), holding the penetrating member with the cartridge, while the cartridge 500 and the punch plate 520 is lowered away from the penetrating member, gripper 530 which in this embodiment remains vertically stationary. This causes the stripping of the used penetrating member from the gripper 530 (FIG. 45D) as the cartridge moves relative to the gripper.

Figure 54E:
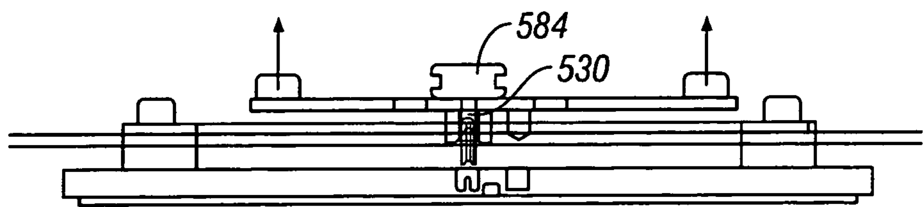
Figure 54F:
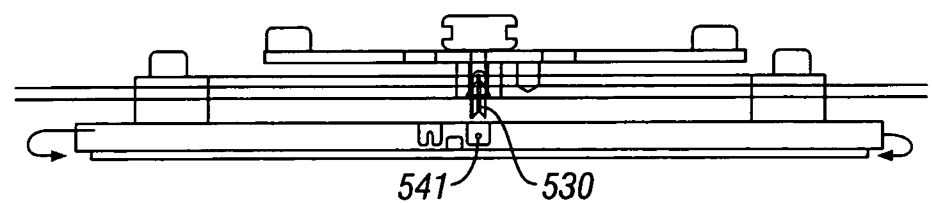

At this point as seen in FIG. 54E, the punch plate 520 retracts upward and the cartridge 500 is pushed fully down, clear of the gripper 530. Now cleared of obstructions and in a rotatable position, the cartridge 500 increments one pocket or cavity in the direction that brings the newly released, sterile penetrating member in cavity 532 into alignment with the penetrating member gripper 530, as see in FIG. 54F. The rotation of the cartridge occurs due to fingers engaging the holes or indentations 533 on the cartridge, as seen in FIG. 54A. In some embodiments, these indentations 533 do not pass completely through cartridge 500. In other embodiments, these indentations are holes passing completely through. The cartridge has a plurality of little indentations 533 on the top surface near the center of the cartridge, along the inside diameter. In the one embodiment, the sterility barrier is cut short so as not to cover these plurality of indentations 533. It should be understood of course that these holes may be located on bottom, side or other accessible surface. These indentations 533 have two purposes. The apparatus may have one or a plurality of locator pins, static pins, or other keying feature that does not move. In this embodiment, the cartridge will only set down into positions where the gripper 530 is gripping the penetrating member. To index the cassette, the cartridge is lifted off those pins or other keyed feature, rotated around, and dropped onto those pins for the next position. The rotating device is through the use of two fingers: one is a static pawl and the other one is a sliding finger. They engage with the holes 533. The fingers are driven by a slider that may be automatically actuated or actuated by the user. This maybe occur mechanically or through electric or other powered devices. Halfway through the stroke, a finger may engage and rotate around the cartridge. A more complete description can be found with text associated with FIGS. 56B-56C.

Figure 54G:
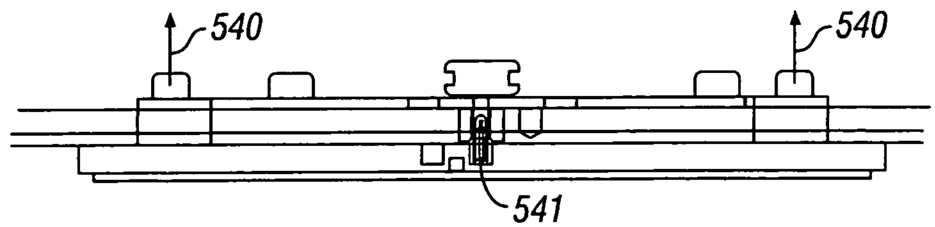

Referring now to FIG. 54G, with the sterile penetrating member in alignment, the cartridge 500 is released as indicated by arrows 540 and brought back into contact with the penetrating member gripper 530. The new penetrating member 541 is inserted into the gripper 530, and the apparatus is ready to fire once again. After launch and in between lancing events for the present embodiment, the bare lancet or penetrating member 541 is held in place by gripper 530, preventing the penetrating member from accidentally protruding or sliding out of the cartridge 500.

Figure 55A:
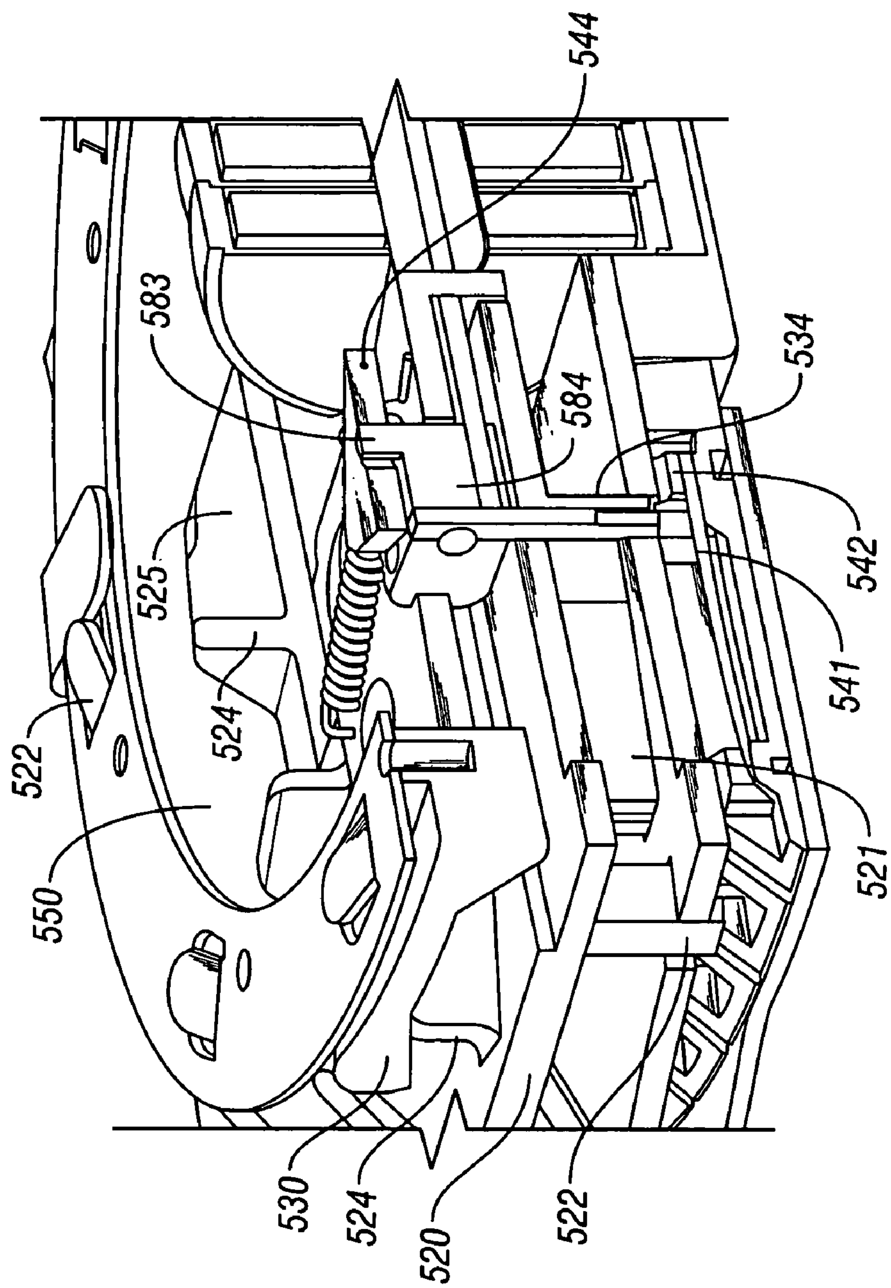
FIGS. 55A-55B show cross-sections of the system according to the present invention.
Figure 55B:
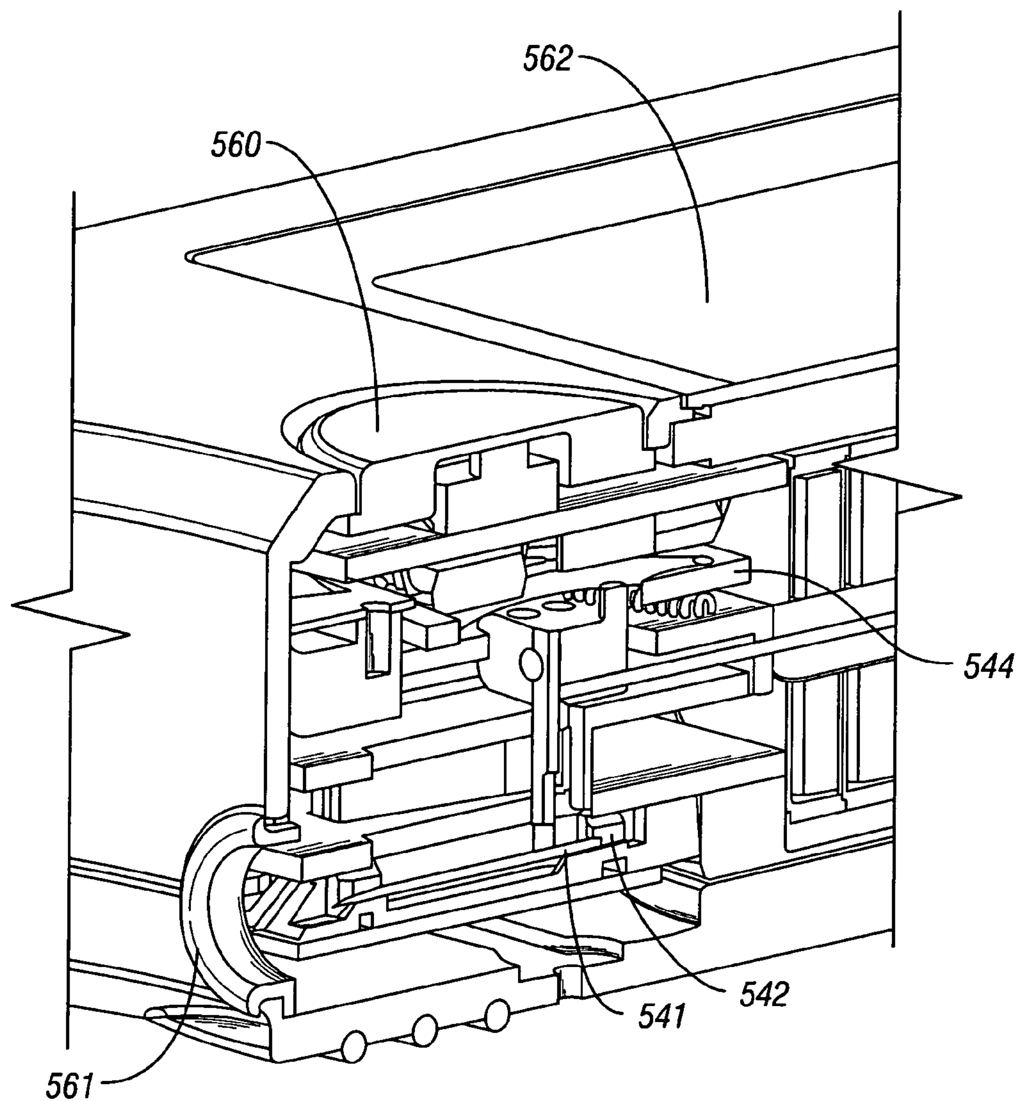

It should be understood of course, that variations can be added to the above embodiment without departing from the spirit of the invention. For example, the penetrating member 541 may be placed in a parked position in the cartridge 500 prior to launch. As seen in FIG. 55A, the penetrating member is held by a narrowed portion 542 of the cartridge, creating an interference fit which pinches the proximal end of the penetrating member. Friction from the molding or cartridge holds the penetrating member during-rest, preventing the penetrating member from sliding back and forth. Of course, other methods of holding the penetrating member may also be used. As seen in FIG. 55B prior to launch, the penetrating member gripper 530 may pull the penetrating member 541 out of the portion 542. The penetrating member 541 may remain in this portion until actuated by the solenoid or other force generator coupled to the penetrating member gripper. A cam surface 544 may be used to pull the penetrating member out of the portion 542. This mechanical cam surface may be coupled to the mechanical slider driven by the patient, which may be considered a separate force generator. Thus, energy from the patient extracts the penetrating member and this reduces the drain on the device's battery if the solenoid or electric driver were to pull out the penetrating member. The penetrating member may be moved forward a small distance (on the order of about 1 mm or less) from its parked position to pull the penetrating member from the rest position gripper. After penetrating tissue, the penetrating member may be returned to the cartridge and eventually placed into the parked position. This may also occur, though not necessarily, through force provided by the patient. In one embodiment, the placing of the lancet into the parked position does not occur until the process for loading a new penetrating member is initiated by the patient. In other embodiments, the pulling out of the parked position occurs in the same motion as the penetrating member actuation. The return into the parked position may also be considered a continuous motion.

FIG. 55A also shows one embodiment of the cam and other surfaces used to coordinate the motion of the punch plate 520. For example, cam 550 in this embodiment is circular and engages the protrusions 524 on the punch plate 520 and the hold the penetrating member in the cartridge 500 while the penetrating member gripper 530 pulls away from the member, relatively speaking. A ratchet surface 552 that rotates with the cam 550 may be used to prevent the cam from rotating backwards. The raising and lower of cartridge 500 and punch plate 50 used to load/unload penetrating members may be mechanically actuated by a variety of cam surfaces, springs, or the like as may be determined by one skilled in the art. Some embodiments may also use electrical or magnetic device to perform the loading, unloading, and release of bare penetrating members. Although the punch plate 520 is shown to be punching downward to displace, remove, or move the foil or other sterile environment enclosure, it should be understood that other methods such as stripping, pulling, tearing, or some combination of one or more of these methods may be used to remove the foil or sterile enclosure. For example, in other embodiments, the punch plate 520 may be located on an underside of the cartridge and punch upward. In other embodiments, the cartridge may remain vertically stationary while other parts such as the penetrating member gripper and punch plate move to load a sterile penetrating member on to the penetrating member gripper.

FIG. 55B also shows other features that may be included in the present apparatus. A fire button 560 may be included for the user to actuate the penetrating member. A front end interface 561 may be included to allow a patient to seat their finger or other target tissue for lancing. The interface 561 may be removable to be cleaned or replaced. A visual display 562 may be included to show device status, lancing performance, error reports, or the like to the patient.

Figure 56A:
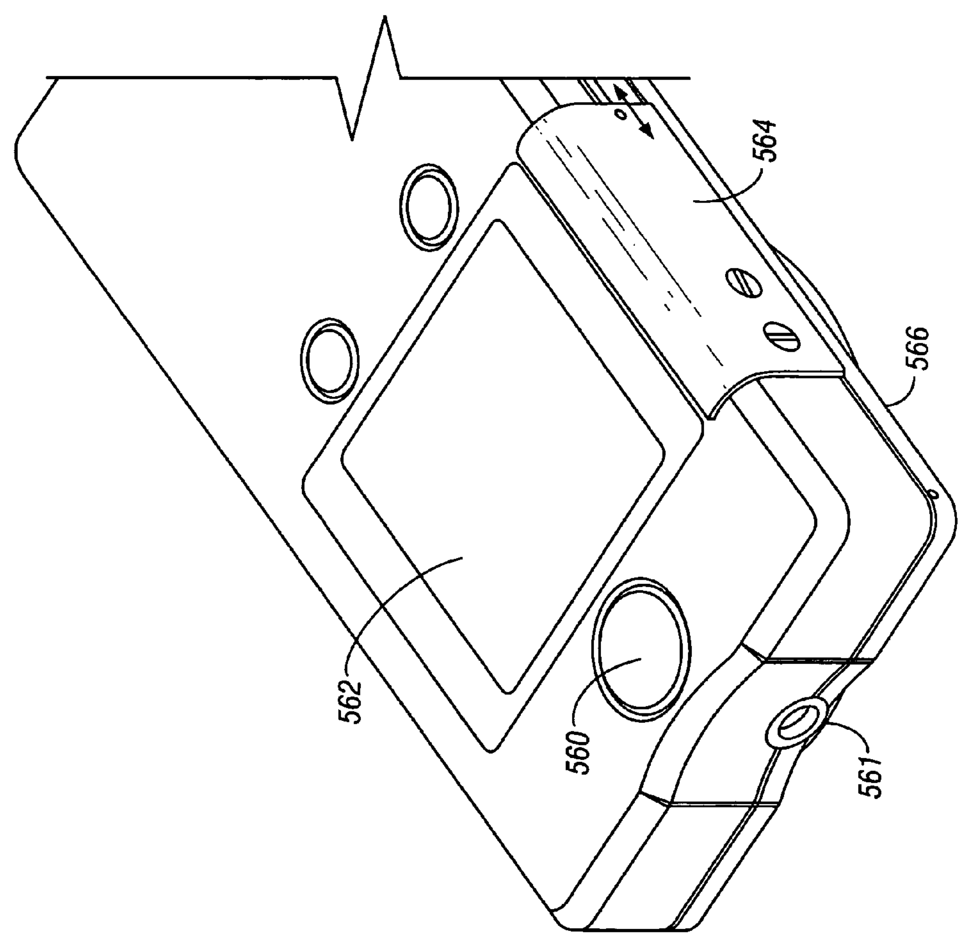
FIG. 56A shows a perspective view of the system according to the present invention.

Referring now to FIG. 56A, a mechanical slider 564 used by the patient to load new penetrating member may also be incorporated on the housing. The slider 564 may also be coupled to activate an LCD or visual display on the lancing apparatus. In addition to providing a source of energy to index the cartridge, the slider 564 may also switch the electronics to start the display. The user may use the display to select the depth of lancing or other feature. The display may go back to sleep again until it is activated again by motion of the slider 564. The underside the housing 566 may also be hinged or otherwise removable to allow the insertion of cartridge 500 into the device. The cartridge 500 may be inserted using technology current used for insertion of a compact disc or other disc into a compact disc player. In one embodiment, there may be a tray which is deployed outward to receive or to remove a cartridge. The tray may be withdrawn into the apparatus where it may be elevated, lowered, or otherwise transported into position for use with the penetrating member driver. In other embodiments, the apparatus may have a slot into which the cartridge is partially inserted at which point a mechanical apparatus will assist in completing insertion of the cartridge and load the cartridge into proper position inside the apparatus. Such device is akin to the type of compact disc player found on automobiles. The insertions/ejection and loading apparatus of these compact disc players uses gears, pulleys, cables, trays, and/or other parts that may be adapted for use with the present invention.

Figure 56B:
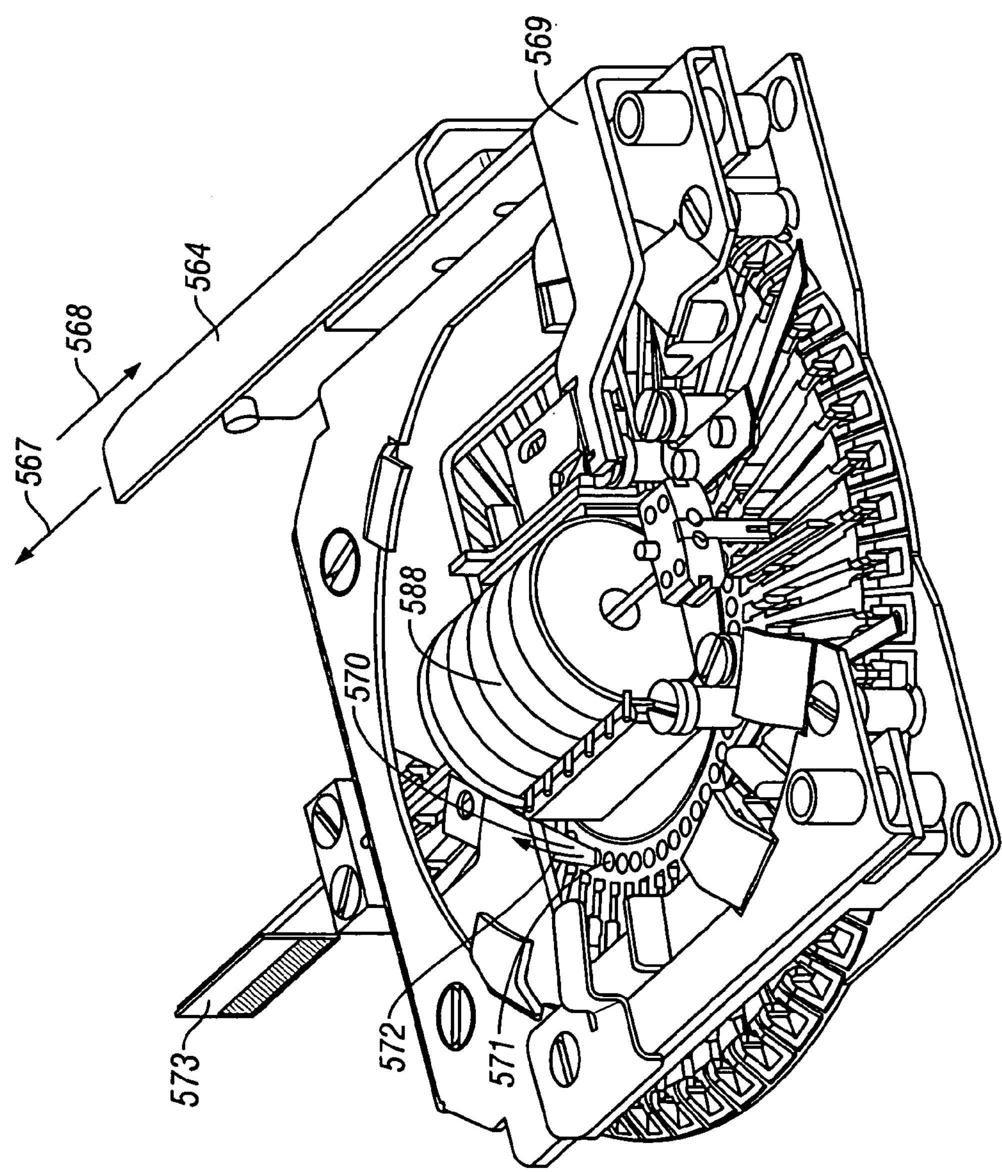
FIGS. 56B-56D are cut-away views showing mechanisms within the present invention.
Figure 66:
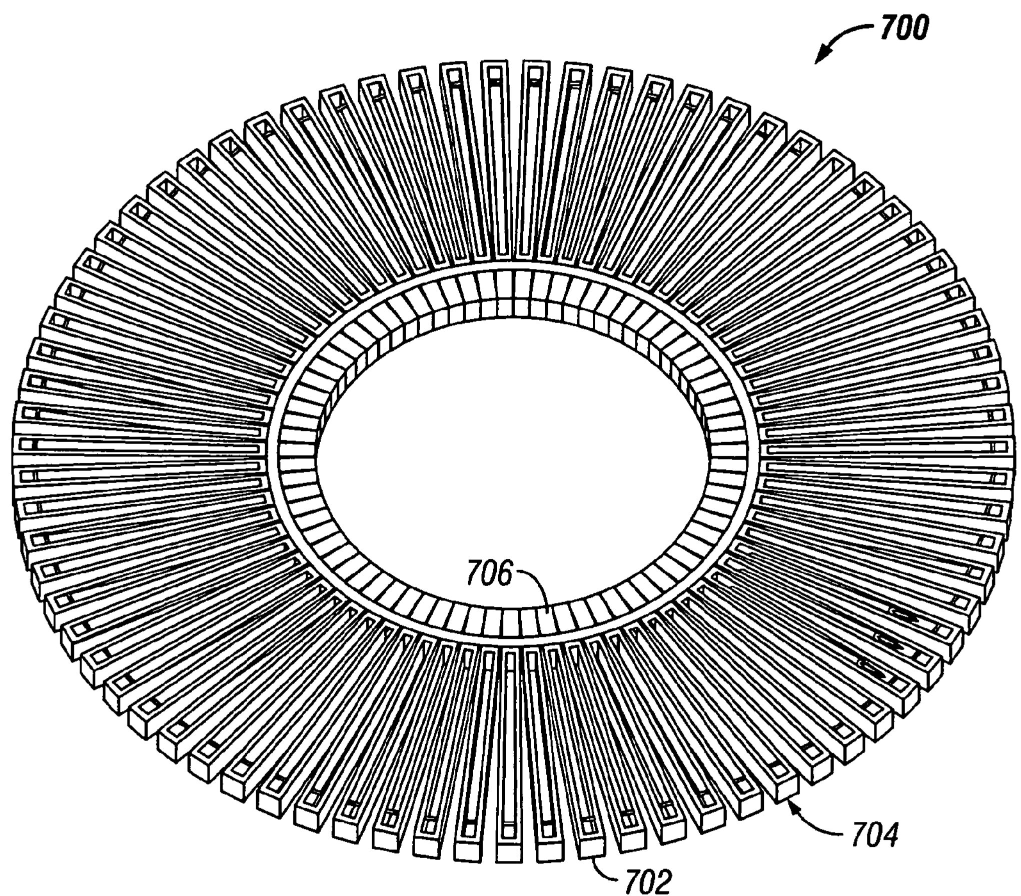
FIGS. 66-68 shows a still further embodiment of a cartridge according to the present invention.

Referring now to FIG. 56B, a more detailed view of one embodiment of the slider 564 is provided. In this embodiment, the slider 564 will move initially as indicated by arrow 567. To complete, the cycle, the patient will return the slider to its home position or original starting position as indicated by arrow 568. The slider 564 has an arm 569 which moves with the slider to rotate the cam 550 and engage portions 522. The motion of the slider 564 is also mechanically coupled to a finger 570 which engage the indentations 571 on cartridge 500. The finger 570 is synchronized to rotate the cartridge 500 by pulling as indicated by arrow 572 in the same plane as the cartridge. It should be understood that in some embodiments, the finger 570 pushes instead of pulls to rotate the cartridge in the correct direction. The finger 570 may also be adapted to engage ratchet surfaces 706 as seen in FIG. 66 to rotate a cartridge. The finger 570 may also incorporate vertical motion to coordinate with the rising and lowering of the cartridge 500. The motion of finger 570 may also be powered by electric actuators such as a stepper motor or other device useful for achieving motion. FIG. 56B also shows a portion of the encoder 573 used in position sensing.

Figure 56C:
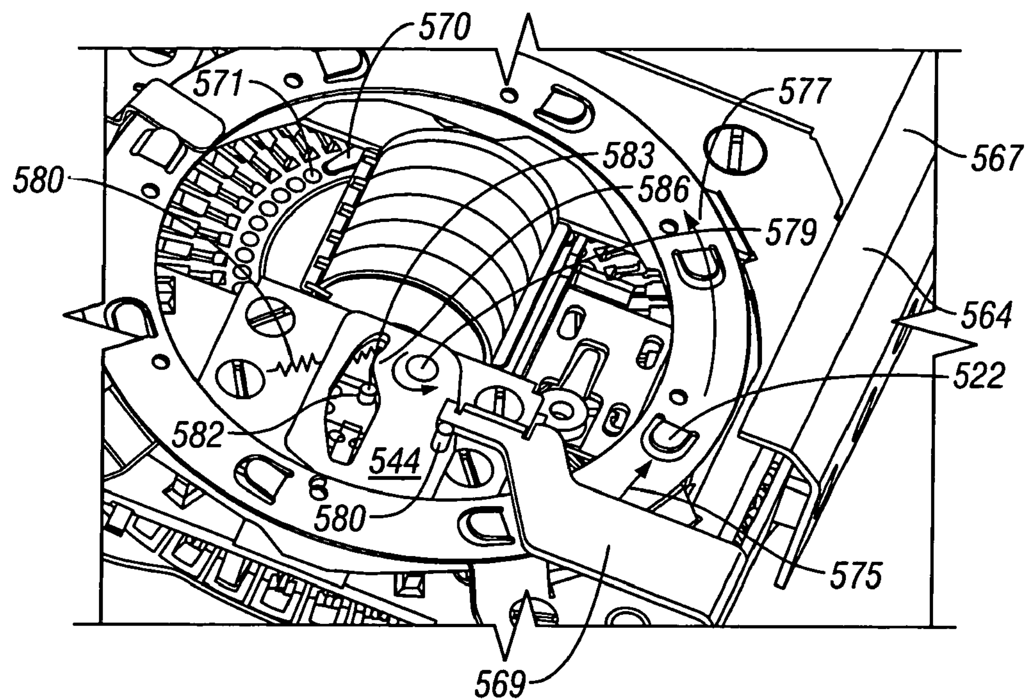

Referring now to FIG. 56C, a still further view of the slider 564 and arm 569 is shown. The arm 569 moves to engage portion 522 as indicated by arrow 575 and this causes the cam 550 to rotate as indicated by arrow 577. In this particular embodiment, the cam 550 rotates about ⅛ of an rotation with each pull of the slider 564. When the slider 564 is return to its home or start position, the arm 569 rides over the portion 522. The movement of the slider also allows the cam surface 544 to rotate about pivot point 579. A resilient member 580 may be coupled to the cam surface 544 to cause it to rotate counterclockwise when the arm 569 moves in the direction of arrow 567. The pin 580 will remain in contact with the arm 569. As the cam surface 544 rotates a first surface 582 will contact the pin 583 on the gripper block 584 and pull the pin 583 back to park a penetrating member into a coupling or narrowed portion 542 of the cartridge 500 as seen in FIG. 55A. As the arm 569 is brought back to the home position, the cam surface 544 rotates back and a second surface 586 that rotates clockwise and pushes the penetrating member forward to be released from the narrowed portion 542 resulting in a position as seen in FIG. 55B. It should be understood that in some embodiments, the release and/or parking of lancet from portion 542 may be powered by the driver 588 without using the mechanical assistance from cam surface 544.

Figure 56D:
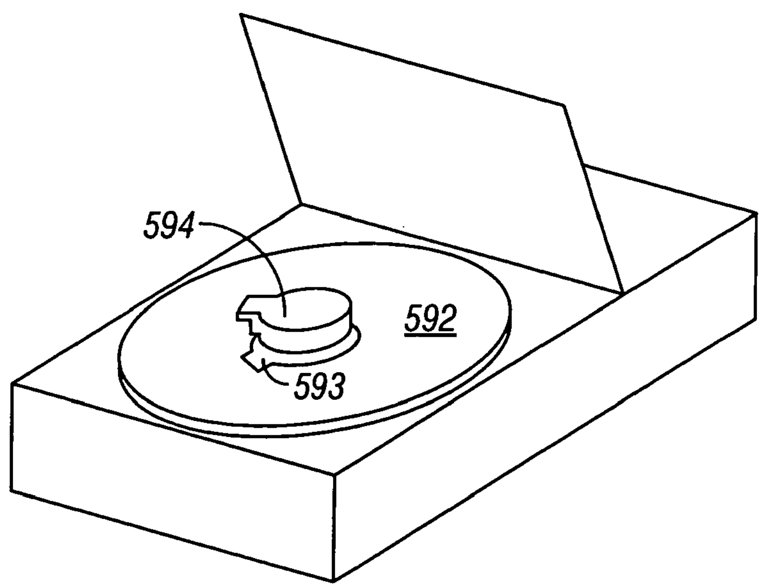

In another embodiment of the cartridge device, a mechanical feature may be included on the cartridge so that there is only one way to load it into the apparatus. For example, in one embodiment holding 50 penetrating members, the cartridge may have 51 pockets or cavities. The $51^{st}$ pocket will go into the firing position when the device is loaded, thus providing a location for the gripper to rest in the cartridge without releasing a penetrating member from a sterile environment. The gripper 530 in that zeroth position is inside the pocket or cavity and that is the reason why one of the pockets may be empty. Of course, some embodiments may have the gripper 530 positioned to grip a penetrating member as the cartridge 500 is loaded into the device, with the patient lancing themselves soon afterwards so that the penetrating member is not contaminated due to prolonged exposure outside the sterile enclosure. That zeroth position may be the start and finish position. The cartridge may also be notched to engaged a protrusion on the apparatus, thus also providing a method for allowing the penetrating member to loaded or unloaded only in one orientation. Essentially, the cartridge 500 may be keyed or slotted in association with the apparatus so that the cartridge 500 can only be inserted or removed at one orientation. For example as seen in FIG. 56D, the cartridge 592 may have a keyed slot 593 that matches the outline of a protrusion 594 such that the cartridge 592 may only be removed upon alignment of the slot 593 and protrusion 594 upon at the start or end positions. It should be understood that other keyed technology may be used and the slot or key may be located on an outer periphery or other location on the cartridge 592 in manner useful for allowing insertion or removal of the cartridge from only one or a select number of orientations.

Figure 57:
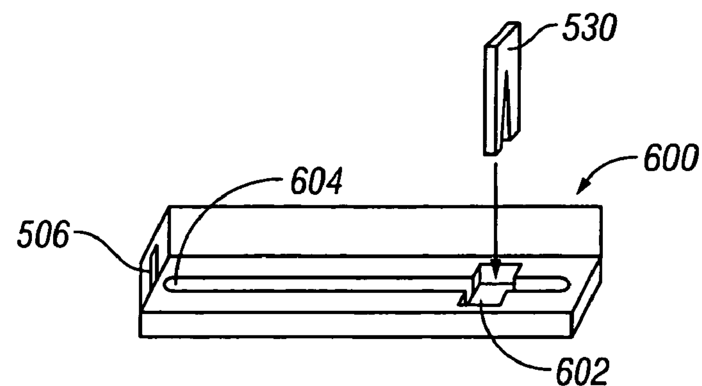
FIGS. 57-65B show optional embodiments according to the present invention.

Referring now to FIG. 57, a cross-section of another embodiment of a cavity 600 housing a penetrating member is shown. The cavity 600 may include a depression 602 for allowing the gripper 530 to penetrate sufficiently deeply into the cavity to frictionally engage the penetrating member 541. The penetrating member may also be housed in a groove 604 that holds the penetrating member in place prior to and after actuation. The penetrating member 541 is lifted upward to clear the groove 604 during actuation and exits through opening 506.

Figure 58:
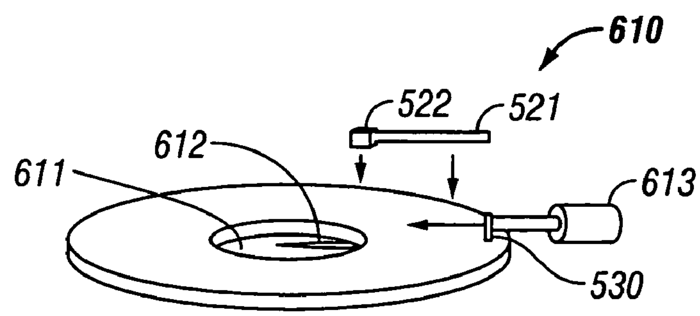

Referring now to FIG. 58, another variation on the system according to the present invention will now be described. FIG. 58 shows a lancing system 610 wherein the penetrating members have their sharpened tip pointed radially inward. The finger or other tissue of the patient is inserted through the center hole 611 to be pierced by the member 612. The penetrating member gripper 530 coupled to drive force generator 613 operate in substantially the same manner as described in FIGS. 54A-G. The punch portions 521 and 522 operate in substantially the same manner to release the penetrating members from the sterile enclosures. The punch portion 522 may be placed on the inner periphery of the device, where the penetrating member exit is now located, so that sterile enclosure material is cleared out of the path of the penetrating member exit.

Figure 59:
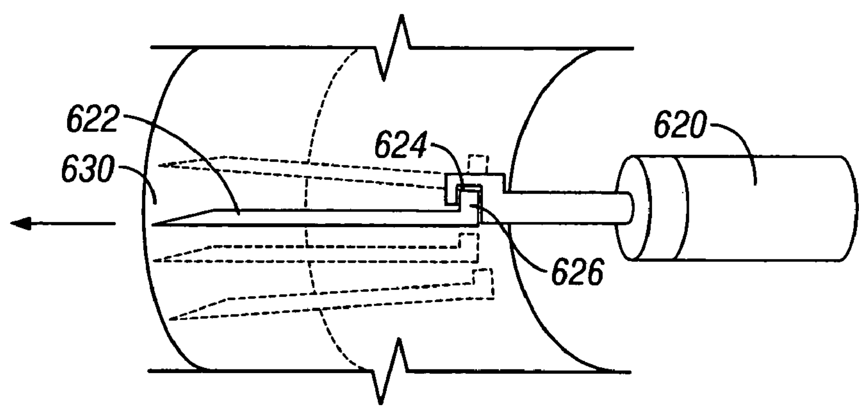

Referring now to FIG. 59, a still further variation on the lancing system according to the present invention will now be described. In the embodiments shown in FIGS. 53-54, the penetrating member gripper 530 approaches the penetrating member from above and at least a portion of the drive system is located in a different plane from that of the cartridge 500. FIG. 59 shows an embodiment where the penetrating member driver 620 is in substantially the same plane as the penetrating member 622. The coupler 624 engages a bent or L shaped portion 626 of the member 622. The cartridge 628 can rotate to engage a new penetrating member with the coupler 624 without having to move the cartridge or coupler vertically. The next penetrating member rotates into position in the slot provided by the coupler 624. A narrowed portion of the cartridge acts as a penetrating member guide 630 near the distal end of the penetrating member to align the penetrating member as it exits the cartridge.

Figure 60A:
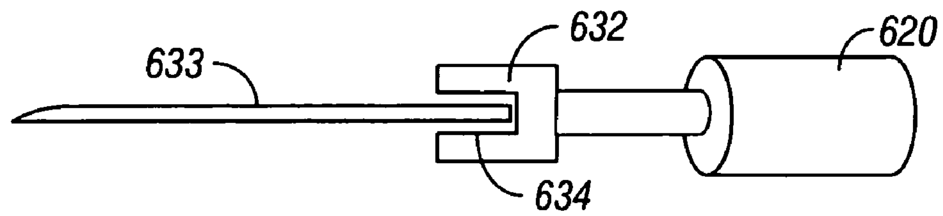
Figure 60B:
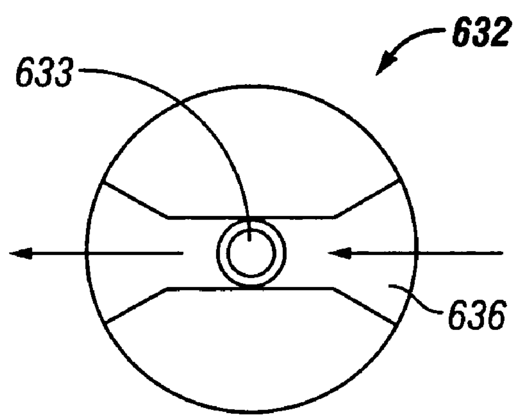
Figure 60C:
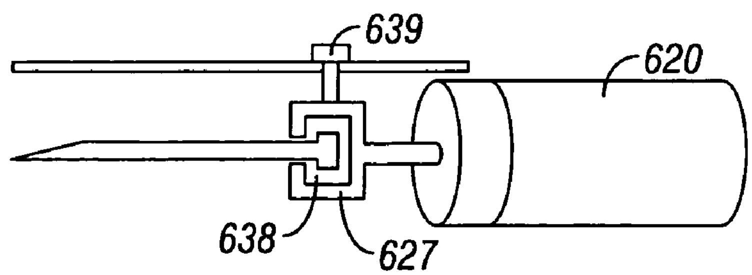

The coupler 624 may come in a variety of configurations. For example, FIG. 60A shows a coupler 632 which can engage a penetrating member 633 that does not have a bent or L-shaped portion. A radial cartridge carrying such a penetrating member 633 may rotate to slide penetrating member into the groove 634 of the coupler 632. FIG. 60B is a front view showing that the coupler 632 may include a tapered portion 636 to guide the penetrating member 633 into the slot 634. FIG. 60C shows an embodiment of the driver 620 using a coupler 637 having a slot 638 for receiving a T-shaped penetrating member. The coupler 637 may further include a protrusion 639 that may be guided in an overhead slot to maintain alignment of the drive shaft during actuation.

Figure 61:
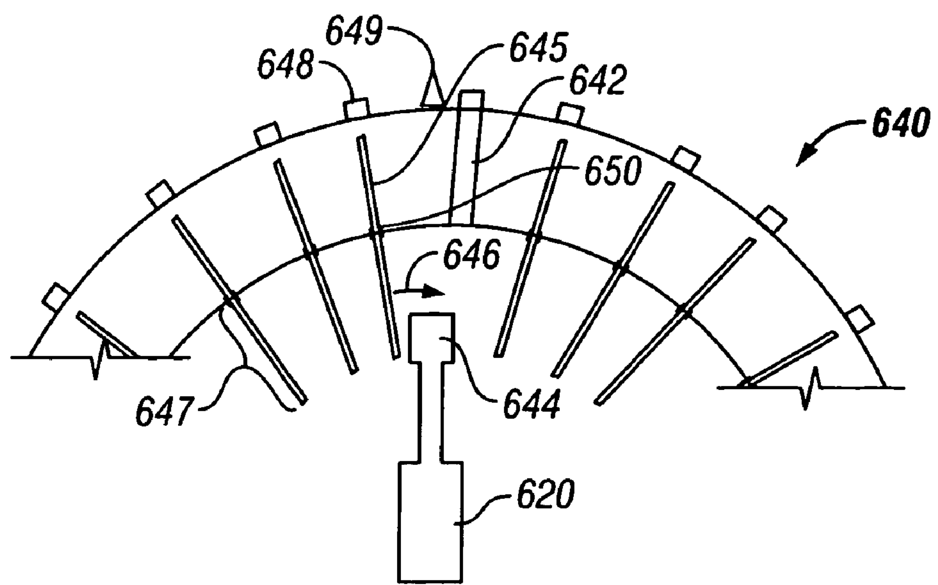

Referring now to FIG. 61, a cartridge 640 for use with an in-plane driver 620 is shown. The cartridge 640 includes an empty slot 642 that allows the cartridge to be placed in position with the driver 620. In this embodiment, the empty slot 642 allows the coupler 644 to be positioned to engage an unused penetrating member 645 that may be rotated into position as shown by arrow 646. As seen in FIG. 61, the cartridge 640 may also be designed so that only the portion of the penetrating member that needs to remain sterile (i.e. the portions that may actually be penetrating into tissue) are enclosed. As seen in FIG. 61, a proximal portion 647 of the penetrating member is exposed. This exposed proximal portion may be about 70% of the penetrating member. In other embodiments it may be between about 69% to about 5% of the penetrating member. The cartridge 640 may further include, but not necessarily, sealing protrusions 648. These protrusions 648 are releasably coupled to the cartridge 640 and are removed from the cartridge 640 by remover 649 as the cartridge rotates to place penetrating member 645 into the position of the active penetrating member. The sterile environment is broken prior to actuation of the member 645 and the member does not penetrate sterile enclosure material that may dull the tip of the penetrating member during actuation. A fracturable seal material 650 may be applied to the member to seal against an inner peripheral portion of the cartridge.

Figure 62:
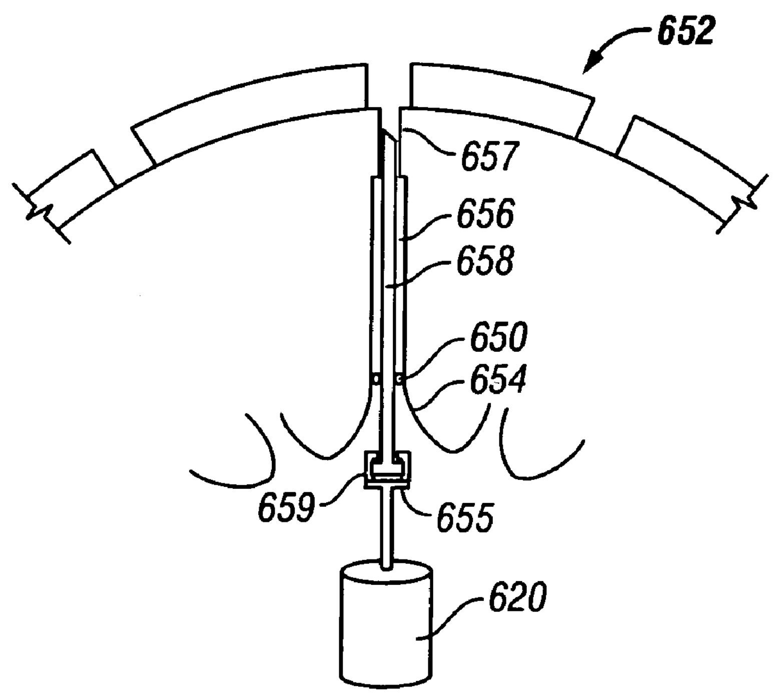

Referring now to FIG. 62, a still further embodiment of a cartridge for use with the present invention will be described. This cartridge 652 includes a tapered portion 654 for allowing the coupler 655 to enter the cavity 656. A narrowed portion 657 guides the penetrating member 658. The coupler 655 may have, but does not necessarily have, movable jaws 659 that engage to grip the penetrating member 658. Allowing the coupler to enter the cavity 656 allows the alignment of the penetrating member to be better maintained during actuation. This tapered portion 654 may be adapted for use with any embodiment of the cartridge disclosed herein.

Figure 63:
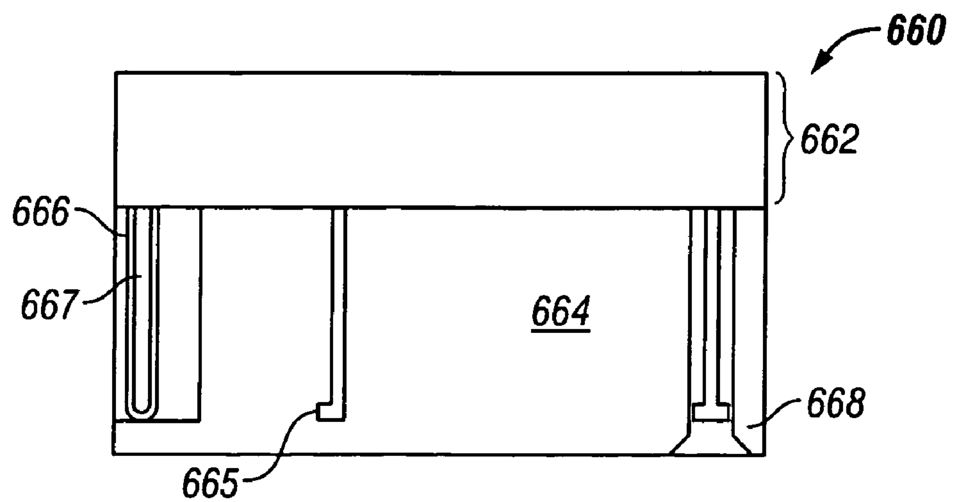

Referring now to FIG. 63, a linear cartridge 660 for use with the present invention will be described. Although the present invention has been shown in use with radial cartridges, the lancing system may be adapted for use with cartridges of other shapes. FIGS. 79-83 show other cartridges of varying shapes adaptable for use with the present invention. FIG. 63 illustrates a cartridge 660 with only a portion 662 providing sterile protection for the penetrating members. The cartridge 660, however, provides a base 664 on which a penetrating member 665 can rest. This provides a level of protection of the penetrating member during handling. The base 664 may also be shaped to provide slots 666 in which a penetrating member 667 may be held. The slot 666 may also be adapted to have a tapered portion 668. These configurations may be adapted for use with any of the embodiments disclosed herein, such as the cartridge 652.

Figure 64A:
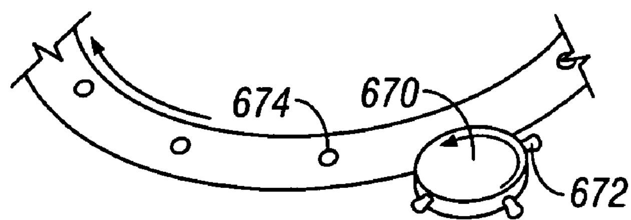
Figure 64B:
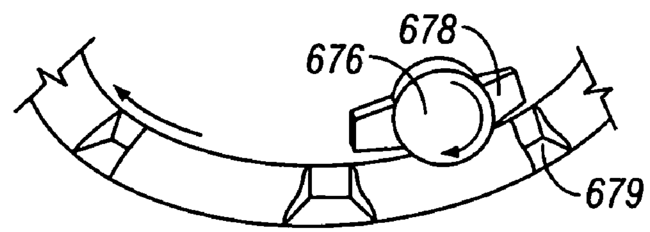
Figure 64C:
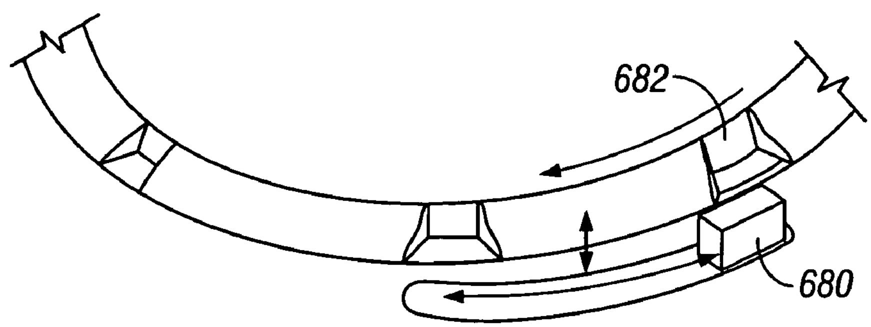

Referring now to FIGS. 64A-64C, a variety of different devices are shown for releasing the sterility seal covering a lateral opening 503 on the cartridge 500. FIG. 64A shows a rotating punch device 670 that has protrusions 672 that punch out the sterility barrier creating openings 674 from which a penetrating member can exit without touching the sterility barrier material. FIG. 64B shows a vertically rotating device 676 with shaped protrusions 678 that punch down the sterility barrier 679 as it is rotated to be in the active, firing position. FIG. 64C shows a punch 680 which is positioned to punch out barrier 682 when the cartridge is lowered onto the punch. The cartridge is rotated and the punch 680 rotates with the cartridge. After the cartridge is rotated to the proper position and lifted up, the punch 680 is spring loaded or otherwise configured to return to the position to engage the sterility barrier covering the next unused penetrating member.

Figure 65A:
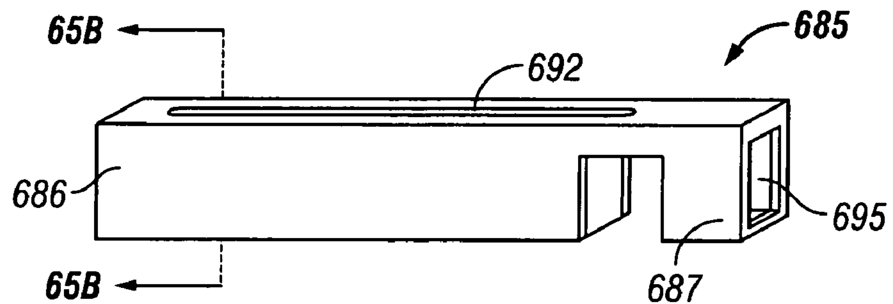
Figure 65B:
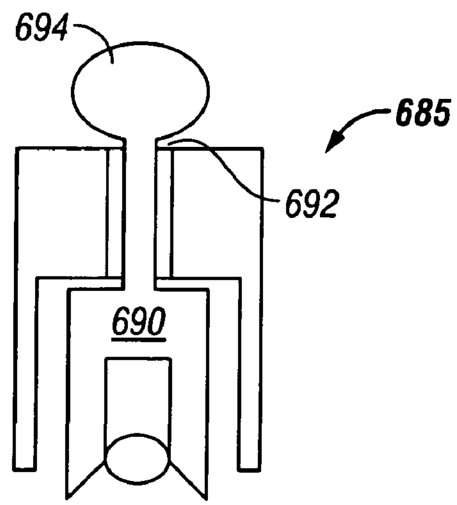

Referring now to FIGS. 65A-65B, another type of punch mechanism for use with a punch plate 520 will now be described. The device shown in FIGS. 53-54 shows a mechanism that first punches and then rotates or indexes the released penetrating member into position. In this present embodiment, the cartridge is rotated first and then the gripper and punch may move down simultaneously. FIG. 65A shows a punch 685 having a first portion 686 and a second portion 687. As seen in cross-sectional view of FIG. 65B, the penetrating member gripper 690 is located inside the punch 685. Thus the penetrating of the sterility barrier is integrated into the step of engaging the penetrating member with the gripper 690. The punch 685 may include a slot 692 allowing a portion 694 of the gripper 690 to extend upward. A lateral opening 695 is provided from which a penetrating member may exit. In some embodiments, the punch portion 687 is not included with punch 686, instead relying on some other mechanism such as those shown in FIGS. 64A-64C to press down on barrier material covering a lateral opening 503.

Figure 67:
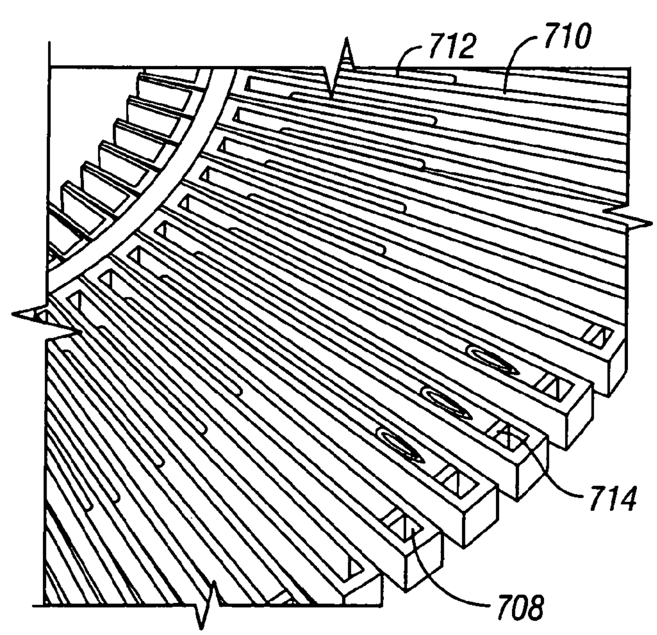
Figure 68:
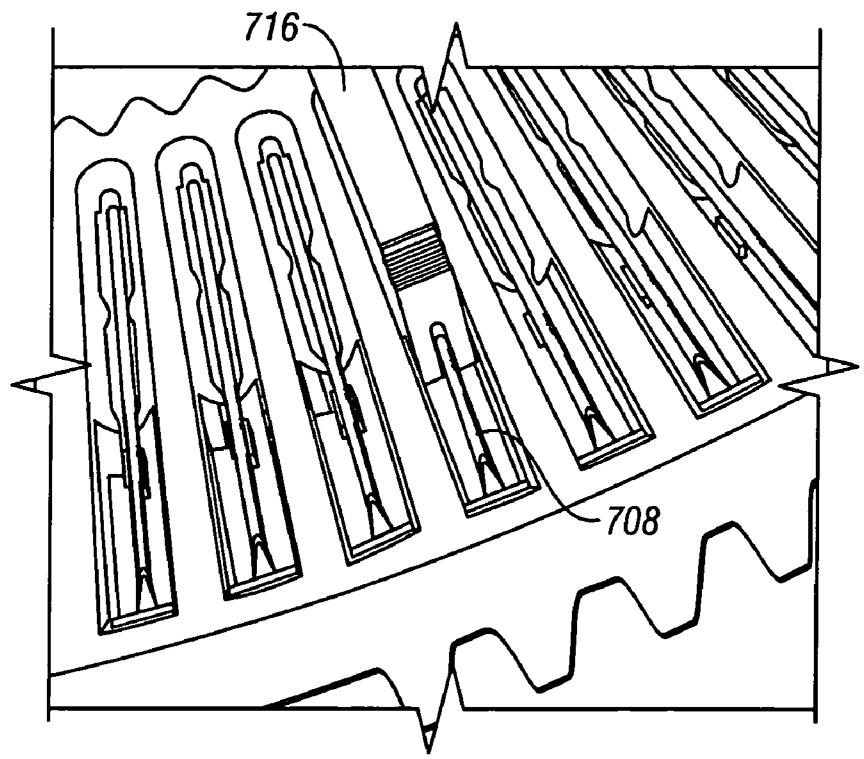

Referring now to FIG. 66, a still further embodiment of a cartridge according to the present invention will be described. FIG. 66 shows a cartridge 700 with a plurality of cavities 702 and individual deflectable portions or fingers 704. The ends of the protective cavities 702 may be divided into individual fingers (such as one for each cavity) on the outer periphery of the disc. Each finger 704 may be individually sealed with a foil cover (not shown for ease of illustration) to maintain sterility until the time of use. Along the inner periphery of the cartridge 700 are raised step portions 706 to create a ratchet type mechanism. As seen in FIG. 67, a penetrating member 708 may be housed in each cavity. The penetrating member may rest on a raised portion 710. A narrowed portion 712 pinches the proximal portions of the penetration member 708. Each cavity may include a wall portion 714 into which the penetrating member 708 may be driven after the penetrating member has been used. FIG. 68 shows the penetrating member gripper 716 lowered to engage a penetrating member 708. For ease of illustration, a sterility barrier covering each of the cavities is not shown.

Figure 69A:
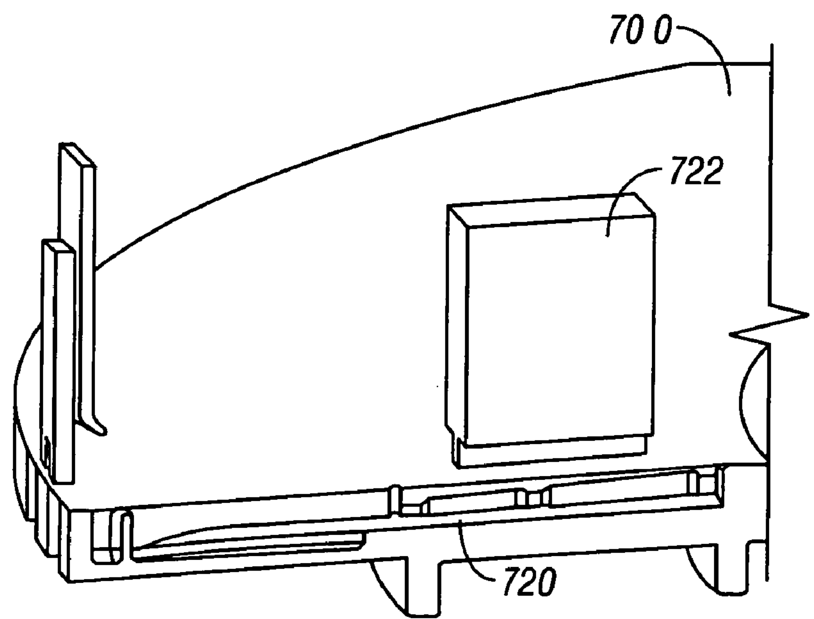
FIGS. 69A-69L show the sequence of motions associated with an optional embodiment of a cartridge according to the present invention.

Referring now to FIGS. 69A-69L, the sequence of steps for actuating a penetrating member in a cartridge 700 will be described. It should be understood that in other embodiments, steps may be combined or reduced without departing from the sprit of the present invention. The last penetrating member to be used may be left in a retracted position, captured by a gripper 716. The end of the protective cavity 704 may be deflected downward by the previous actuation. The user may operate a mechanism such as but not limited to a thumbwheel, lever, crank, slider, etc. . . . that advances a new penetrating member 720 into launch position as seen in FIG. 69A. The mechanism lifts a bar that allows the protective cavity to return to its original position in the plane of the disc.

Figure 69B:
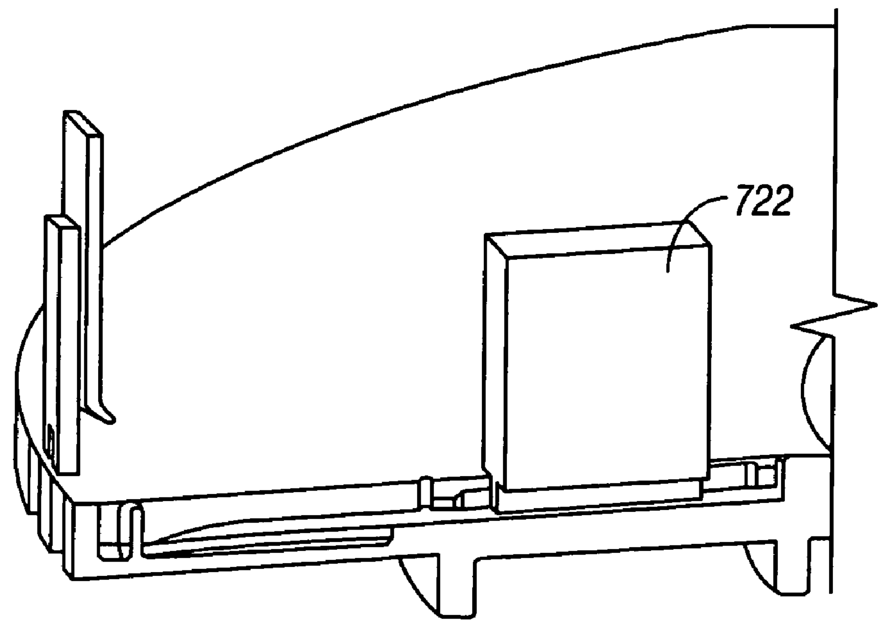

In this embodiment as shown in FIG. 69B, the penetrating member guide 722 presses through foil in rear of pocket to "home" penetrating member and control vertical clearance. For ease of illustration, actuation devices for moving the penetrating member guide 722 and other mechanisms are not shown. They may be springs, cams, or other devices that can lower and move the components shown in these figures. In some embodiments, the cartridge 700 may be raised or lowered to engage the penetrating member guide 722 and other devices.

Figure 69C:
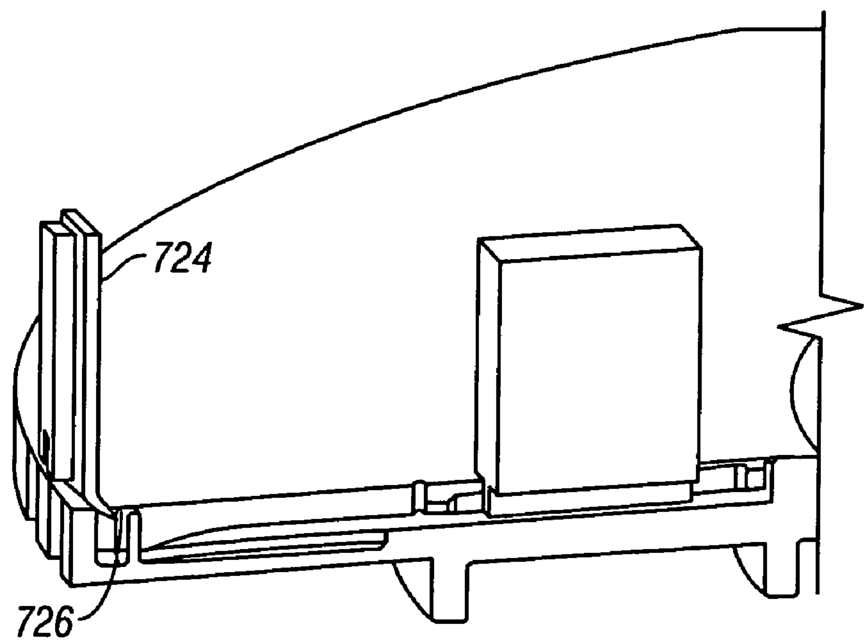

As seen in FIG. 69C, the plough or sterile enclosure release device 724 is lowered to engage the cartridge 700. In some embodiments, the disc or cartridge 700 may raised part way upward until a plough or plow blade 724 pierces the sterility barrier 726 which may be a foil covering.

Figure 69D:
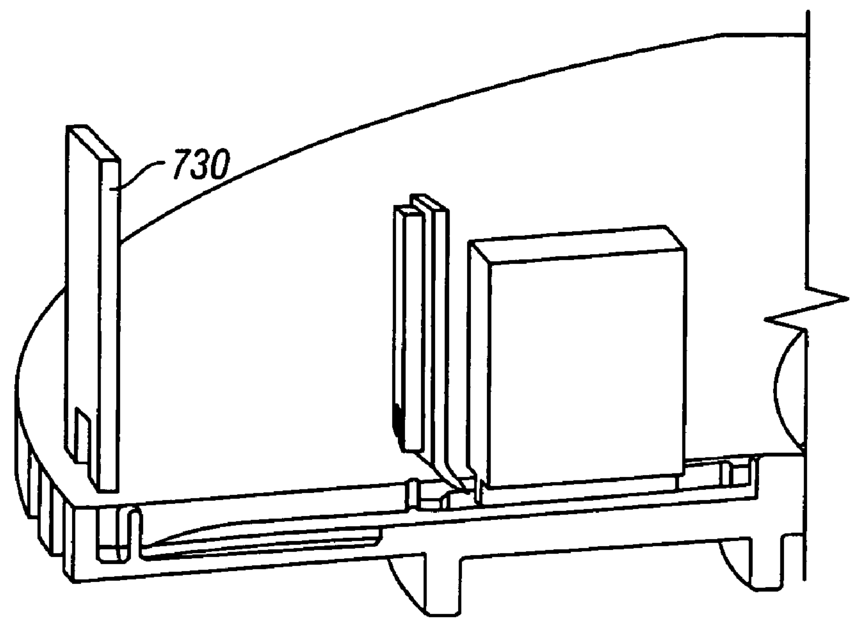

Referring now to FIG. 69D, the plough 724 clears foil from front of pocket and leaves it attached to cartridge 700. The plough 724 is driven radially inward, cutting open the sterility barrier and rolling the scrap into a coil ahead of the plough. Foil naturally curls over and forms tight coil when plough lead angle is around 55 degs to horizontal. If angle of the plough may be between about 60-40 degs, preferably closer to 55 degs. In some embodiments, the foil may be removed in such a manner that the penetrating member does not need to pierce any sterile enclosure materials during launch.

Figure 69E:
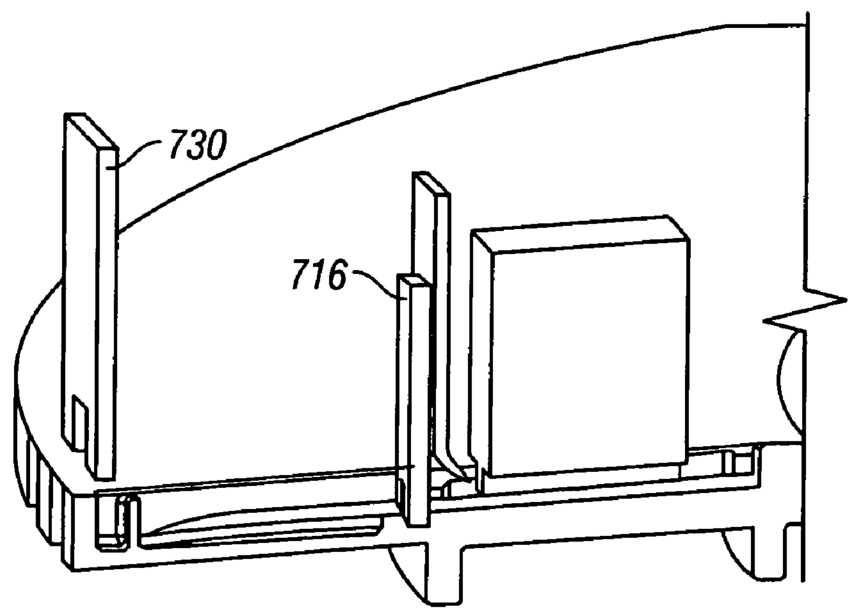

Referring now to FIG. 69E, the gripper 716 may be lowered to engage the bare penetrating member or piercing member 720. Optionally, the disc or cartridge 8000 may be raised until the penetrating member 720 is pressed firmly into the gripper 716. Although not shown in the present figure, the penetrating member driver or actuator of the present embodiment may remain in the same horizontal plane as the penetrating member.

Figure 69F:
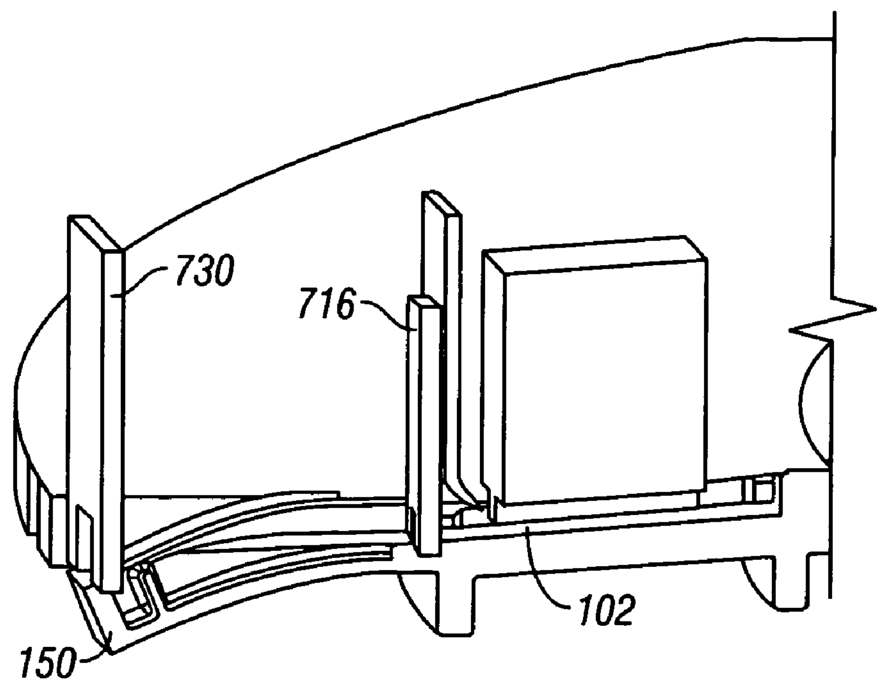

As seen in FIG. 69F, a bar 730 may be pressed downward on the outer end 732 of the protective cavity to deflect it so it is clear of the path of the penetrating member. In the present embodiment, the bar 730 is shaped to allow the bare penetrating member 720 to pass through. It should be understood that other shapes and orientations of the bar (such as contacting only one side or part of end 732) may be used to engage the end 732.

Figure 69G:
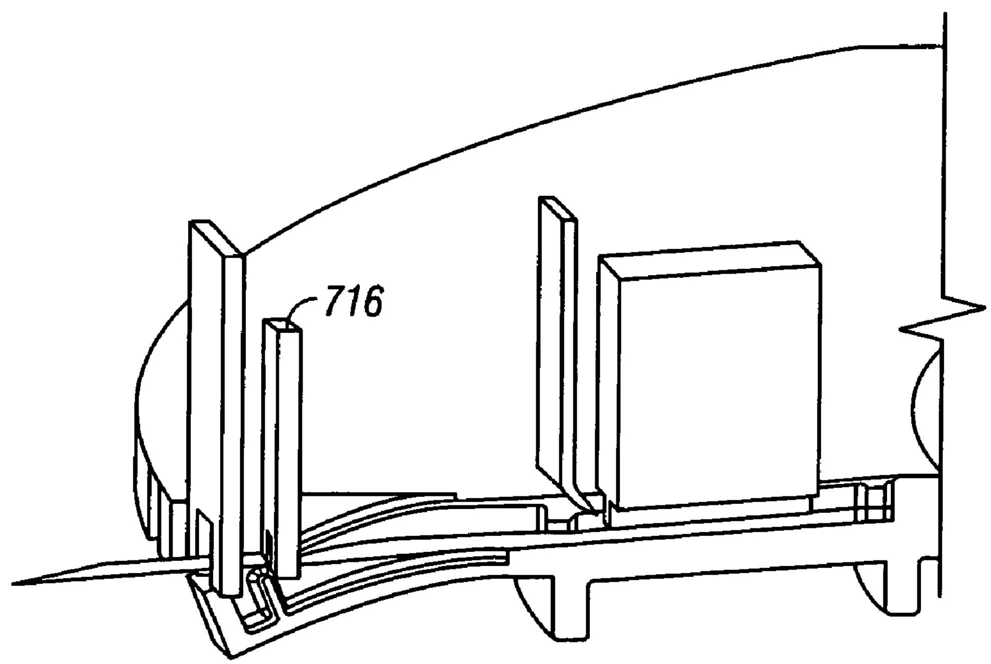

Referring now to FIG. 69G, an electrical solenoid or other electronic or feed-back controllable drive may actuate the gripper 716 radially outward, carrying the bare penetrating member 720 with it. The bare penetrating member projects from the protective case and into the skin of a finger or other tissue site that has been placed over the aperature of the actuator assembly. Suitable penetrating member drivers are described in commonly assigned, copending U.S. patent application Ser. No. 10/127,395 filed Apr. 19, 2002.

Figure 69H:
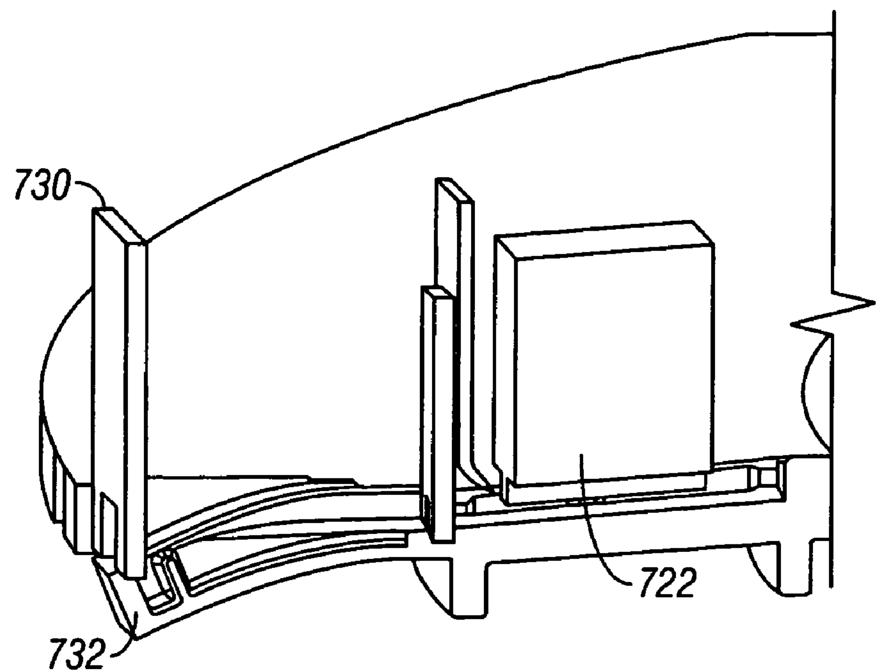

Referring now to FIG. 69H, the solenoid or other suitable penetrating member driver retracts the bare penetrating member 720 into a retracted position where it parks until the beginning of the next lancing cycle.

Figure 69I:
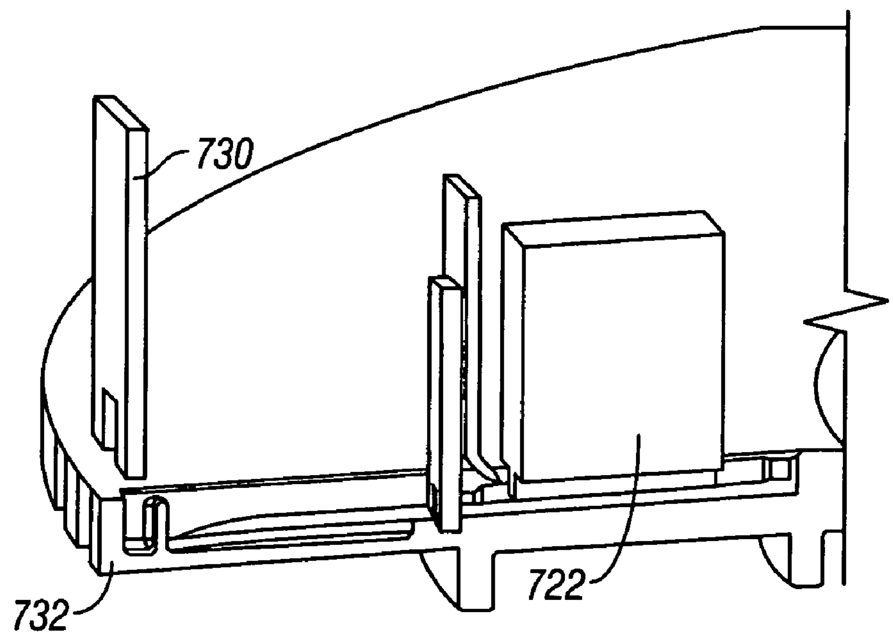

Referring now to FIG. 69I, bar 730 may be released so that the end 150 returns to an in-plane configuration with the cartridge 800.

Figure 69J:
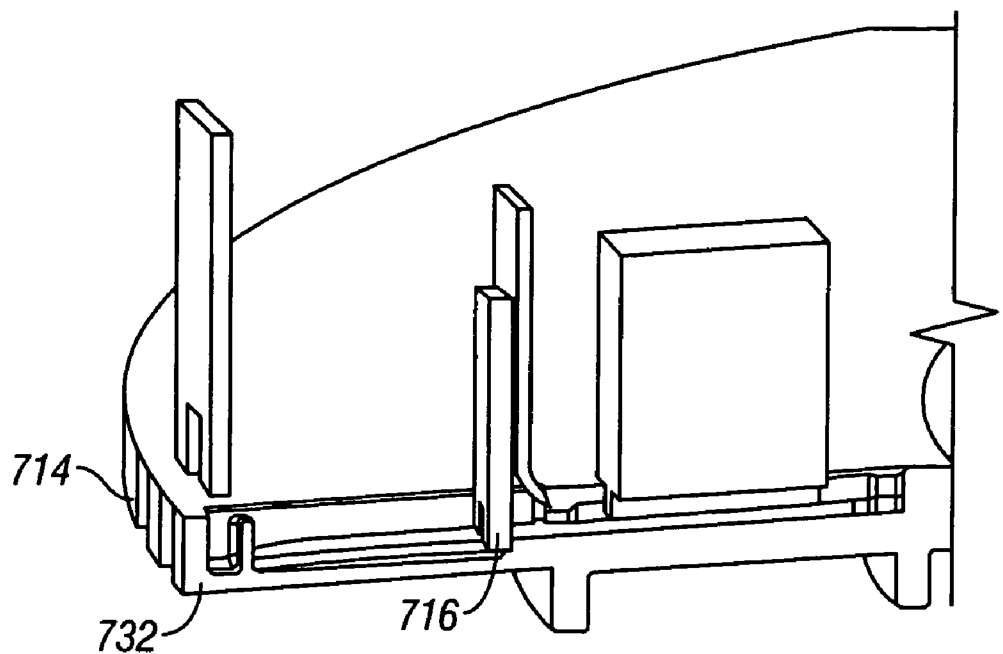

As seen in FIG. 69J, the gripper 716 may drive a used bare penetrating member radially outward until the sharpened tip is embedded into a plastic wall 714 at or near the outward end 732 of the cavity thus immobilizing the contaminated penetrating member.

Figure 69K:
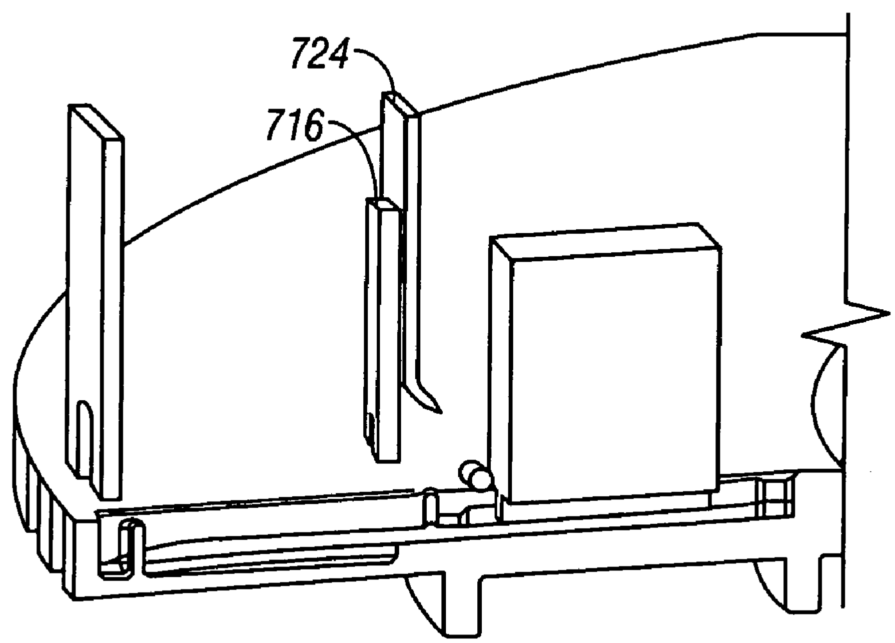
Figure 69L:
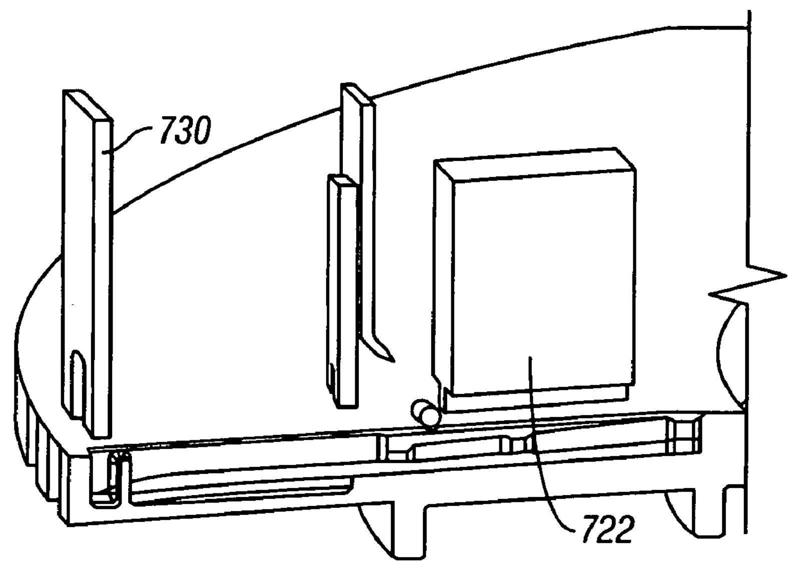

As seen in FIGS. 69K and 69L, the plough 724, the gripper 716, and penetrating member guide 722 may all be disengaged from the bare penetrating member 720. Optionally, it should be understood that the advance mechanism may lower the cartridge 700 from the gripper 716. The used penetrating member, restrained by the tip embedded in plastic, and by the cover foil at the opposite end, is stripped from the gripper. The disc or cartridge 700 may be rotated until a new, sealed; sterile penetrating member is in position under the launch mechanism.

Figure 70:
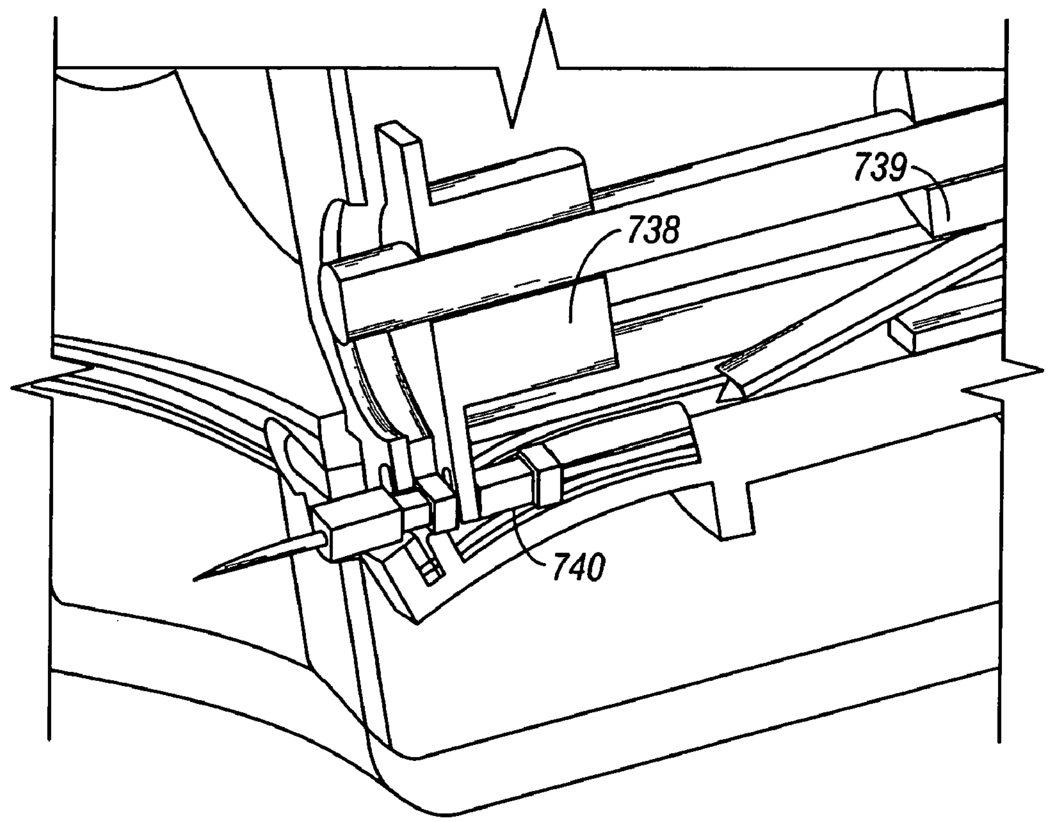
FIGS. 70-72 show views of a sample modules used with still further embodiments of a cartridge according to the present invention.
Figure 71:
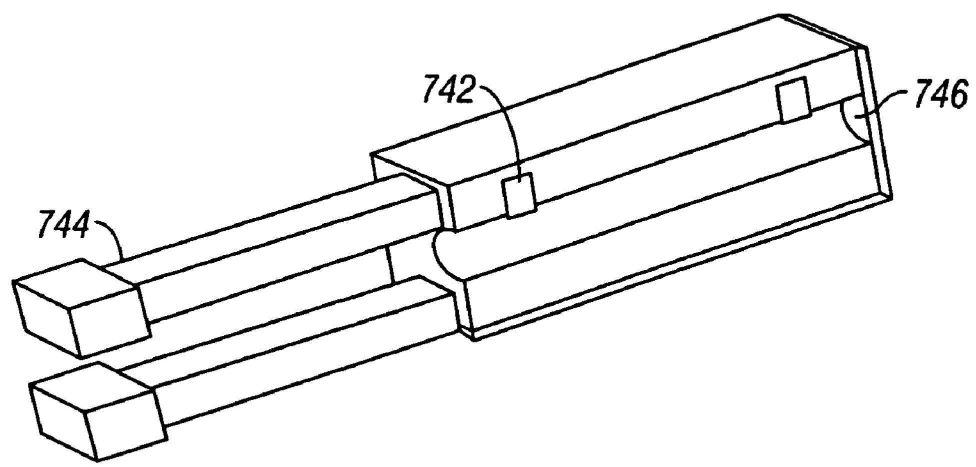

Referring now to FIGS. 70 and 71, one object for some embodiments of the invention is to include blood sampling and sensing on this penetrating member actuation device. In the present embodiment, the drive mechanism (gripper 738 and solenoid drive coil 739) may be used to drive a penetrating member into the skin and couple this lancing event to acquire the blood sample as it forms at the surface of the finger. In a first embodiment shown in FIG. 70, microfluidic module 740 bearing the analyte detecting member chemistry and detection device 742 (FIG. 71) is couple on to the shaft of the penetrating member 720. The drive cycle described above may also actuate the module 740 so that it rests at the surface of the finger to acquire blood once the penetrating member retracts from the wound. The module 740 is allowed to remain on the surface of the finger or other tissue site until the gripper 738 has reached the back end 744 of the microfluidics module 740, at which point the module is also retracted into the casing. The amount of time the module 740 remains on the finger, in this embodiment, may be varied based on the distance the end 744 is located and the amount of time it takes the gripper to engage it on the withdrawal stroke. The blood filled module 740, filled while the module remains on pierced tissue site, may then undergo analyte detection by means such as optical or electrochemical sensing.

The blood may be filled in the lumen that the penetrating member was in or the module may have separately defined sample chambers to the side of the penetrating member lumen. The analyte detecting member may also be placed right at the immediate vicinity or slightly setback from the module opening receiving blood so that low blood volumes will still reach the analyte detecting member. In some embodiments, the analyte sensing device and a visual display or other interface may be on board the apparatus and thus provide a readout of analyte levels without need to plug apparatus or a test strip into a separate reader device. As seen in FIG. 71, the cover 746 may also be clear to allow for light to pass through for optical sensing. The analyte detecting member may be used with low volumes such as less than about 1 microliter of sample, preferably less than about 0.6 microliter, more preferably less than about 0.3 microliter, and most preferably less than about 0.1 microliter of sample.

Figure 72:
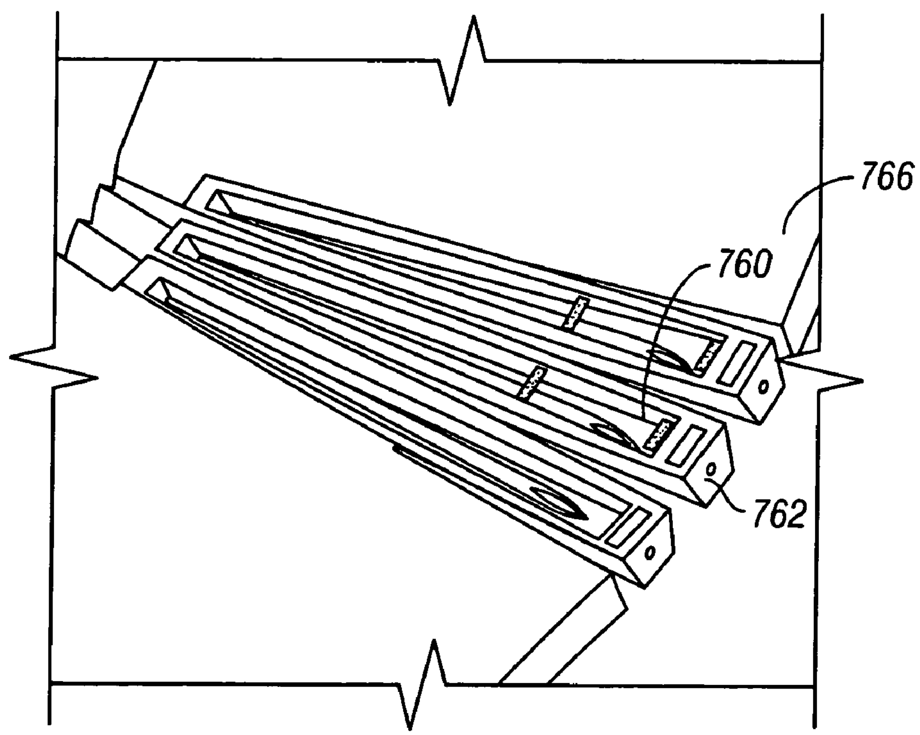

In another embodiment as seen in FIG. 72, sensing elements 760 may be directly printed or formed on the top of bottom of the penetrating member cartridge 700, depending on orientation. The bare penetrating member 720 is then actuated through a hole 762 in the plastic facing, withdrawn into the radial cavity followed by the blood sample. Electrochemical or optical detection for analyte sensing may then be carried out (FIG. 72). Again the cavity 766 may have a clear portion to allow light to pass for optical sensing. In one embodiment, a multiplicity of miniaturized analyte detecting member fields may be placed on the floor of the radial cavity as shown in FIG. 72 or on the microfluidic module shown in FIG. 71 to allow many tests on a single analyte form a single drop of blood to improve accuracy and precision of measurement. Although not limited in this manner, additional analyte detecting member fields or regions may also be included for calibration or other purposes.

Figure 73:
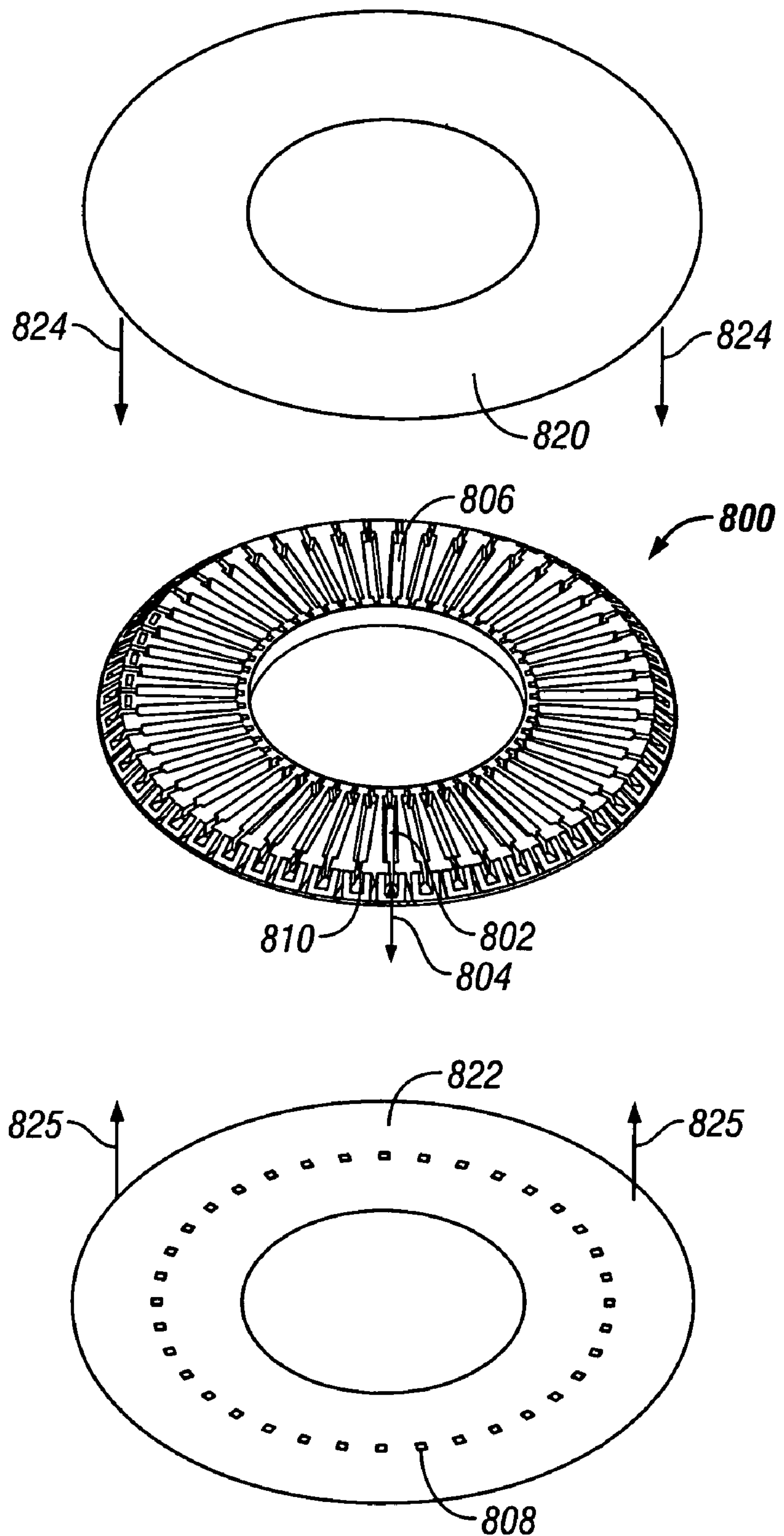
FIG. 73 shows a cartridge with a sterility barrier and an analyte detecting member layer.

Referring now to FIG. 73, a still further embodiment of a cartridge according to the present invention will be described. FIG. 73 shows one embodiment of a cartridge 800 which may be removably inserted into an apparatus for driving penetrating members to pierce skin or tissue. The cartridge 800 has a plurality of penetrating members 802 that may be individually or otherwise selectively actuated so that the penetrating members 802 may extend outward from the cartridge, as indicated by arrow 804, to penetrate tissue. In the present embodiment, the cartridge 800 may be based on a flat disc with a number of penetrating members such as, but in no way limited to, (25, 50, 75, 100, . . . ) arranged radially on the disc or cartridge 800. It should be understood that although the cartridge 800 is shown as a disc or a disc-shaped housing, other shapes or configurations of the cartridge may also work without departing from the spirit of the present invention of placing a plurality of penetrating members to be engaged, singly or in some combination, by a penetrating member driver.

Figure 75:
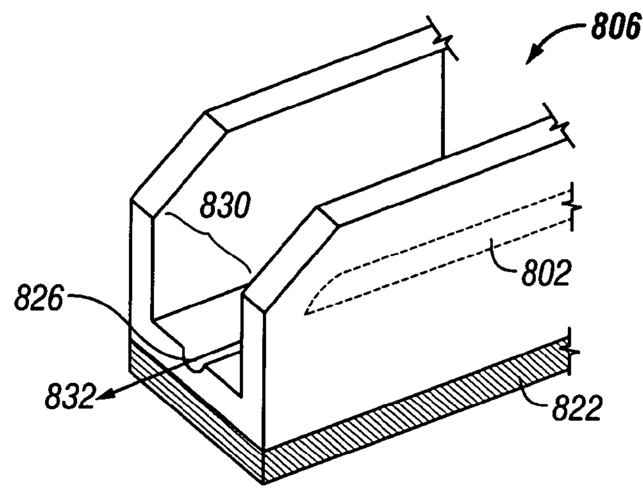

Each penetrating member 802 may be contained in a cavity 806 in the cartridge 800 with the penetrating member's sharpened end facing radially outward and may be in the same plane as that of the cartridge. The cavity 806 may be molded, pressed, forged, or otherwise formed in the cartridge. Although not limited in this manner, the ends of the cavities 806 may be divided into individual fingers (such as one for each cavity) on the outer periphery of the disc. The particular shape of each cavity 806 may be designed to suit the size or shape of the penetrating member therein or the amount of space desired for placement of the analyte detecting members 808. For example and not limitation, the cavity 806 may have a V-shaped cross-section, a U-shaped cross-section, C-shaped cross-section, a multi-level cross section or the other cross-sections. The opening 810 through which a penetrating member 802 may exit to penetrate tissue may also have a variety of shapes, such as but not limited to, a circular opening, a square or rectangular opening, a U-shaped opening, a narrow opening that only allows the penetrating member to pass, an opening with more clearance on the sides, a slit, a configuration as shown in FIG. 75, or the other shapes.

In this embodiment, after actuation, the penetrating member 802 is returned into the cartridge and may be held within the cartridge 800 in a manner so that it is not able to be used again. By way of example and not limitation, a used penetrating member may be returned into the cartridge and held by the launcher in position until the next lancing event. At the time of the next lancing, the launcher may disengage the used penetrating member with the cartridge 800 turned or indexed to the next clean penetrating member such that the cavity holding the used penetrating member is position so that it is not accessible to the user (i.e. turn away from a penetrating member exit opening). In some embodiments, the tip of a used penetrating member may be driven into a protective stop that hold the penetrating member in place after use. The cartridge 800 is replaceable with a new cartridge 800 once all the penetrating members have been used or at such other time or condition as deemed desirable by the user.

Referring still to the embodiment in FIG. 73, the cartridge 800 may provide sterile environments for penetrating members via seals, foils, covers, polymeric, or similar materials used to seal the cavities and provide enclosed areas for the penetrating members to rest in. In the present embodiment, a foil or seal layer 820 is applied to one surface of the cartridge 800. The seal layer 820 may be made of a variety of materials such as a metallic foil or other seal materials and may be of a tensile strength and other quality that may provide a sealed, sterile environment until the seal layer 820 is penetrate by a suitable or penetrating device providing a preselected or selected amount of force to open the sealed, sterile environment. Each cavity 806 may be individually sealed with a layer 820 in a manner such that the opening of one cavity does not interfere with the sterility in an adjacent or other cavity in the cartridge 800. As seen in the embodiment of FIG. 73, the seal layer 820 may be a planar material that is adhered to a top surface of the cartridge 800.

Depending on the orientation of the cartridge 800 in the penetrating member driver apparatus, the seal layer 820 may be on the top surface, side surface, bottom surface, or other positioned surface. For ease of illustration and discussion of the embodiment of FIG. 73, the layer 820 is placed on a top surface of the cartridge 800. The cavities 806 holding the penetrating members 802 are sealed on by the foil layer 820 and thus create the sterile environments for the penetrating members. The foil layer 820 may seal a plurality of cavities 806 or only a select number of cavities as desired.

Figure 76:
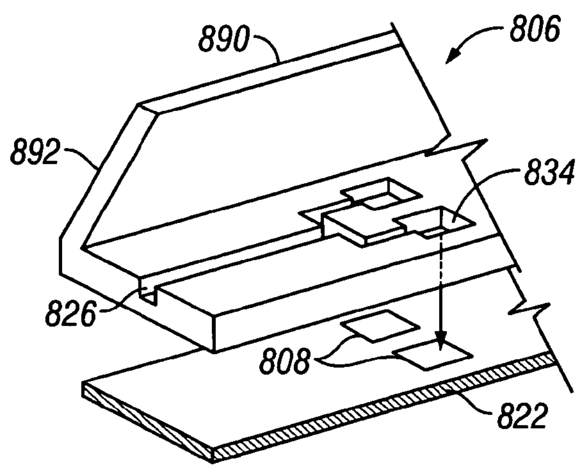

In a still further feature of FIG. 73, the cartridge 800 may optionally include a plurality of analyte detecting members 808 on a substrate 822 which may be attached to a bottom surface of the cartridge 800. The substrate may be made of a material such as, but not limited to, a polymer, a foil, or other material suitable for attaching to a cartridge and holding the analyte detecting members 808. As seen in FIG. 73, the substrate 822 may hold a plurality of analyte detecting members, such as but not limited to, about 10-50, 50-100, or other combinations of analyte detecting members. This facilitates the assembly and integration of analyte detecting members 808 with cartridge 800. These analyte detecting members 808 may enable an integrated body fluid sampling system where the penetrating members 802 create a wound tract in a target tissue, which expresses body fluid that flows into the cartridge for analyte detection by at least one of the analyte detecting members 808. The substrate 822 may contain any number of analyte detecting members 808 suitable for detecting analytes in cartridge having a plurality of cavities 806. In one embodiment, many analyte detecting members 808 may be printed onto a single substrate 822 which is then adhered to the cartridge to facilitate manufacturing and simplify assembly. The analyte detecting members 808 may be electrochemical in nature. The analyte detecting members 808 may further contain enzymes, dyes, or other detectors which react when exposed to the desired analyte. Additionally, the analyte detecting members 808 may comprise of clear optical windows that allow light to pass into the body fluid for analyte analysis. The number, location, and type of analyte detecting member 808 may be varied as desired, based in part on the design of the cartridge, number of analytes to be measured, the need for analyte detecting member calibration, and the sensitivity of the analyte detecting members. If the cartridge 800 uses an analyte detecting member arrangement where the analyte detecting members are on a substrate attached to the bottom of the cartridge, there may be through holes (as shown in FIG. 76), wicking elements, capillary tube or other devices on the cartridge 800 to allow body fluid to flow from the cartridge to the analyte detecting members 808 for analysis. In other configurations, the analyte detecting members 808 may be printed, formed, or otherwise located directly in the cavities housing the penetrating members 802 or areas on the cartridge surface that receive blood after lancing.

The use of the seal layer 820 and substrate or analyte detecting member layer 822 may facilitate the manufacture of these cartridges 10. For example, a single seal layer 820 may be adhered, attached, or otherwise coupled to the cartridge 800 as indicated by arrows 824 to seal many of the cavities 806 at one time. A sheet 822 of analyte detecting members may also be adhered, attached, or otherwise coupled to the cartridge 800 as indicated by arrows 825 to provide many analyte detecting members on the cartridge at one time. During manufacturing of one embodiment of the present invention, the cartridge 800 may be loaded with penetrating members 802, sealed with layer 820 and a temporary layer (not shown) on the bottom where substrate 822 would later go, to provide a sealed environment for the penetrating members. This assembly with the temporary bottom layer is then taken to be sterilized. After sterilization, the assembly is taken to a clean room (or it may already be in a clear room or equivalent environment) where the temporary bottom layer is removed and the substrate 822 with analyte detecting members is coupled to the cartridge as shown in FIG. 73. This process allows for the sterile assembly of the cartridge with the penetrating members 802 using processes and/or temperatures that may degrade the accuracy or functionality of the analyte detecting members on substrate 822. As a nonlimiting example, the entire cartridge 800 may then be placed in a further sealed container such as a pouch, bag, plastic molded container, etc. . . . to facilitate contact, improve ruggedness, and/or allow for easier handling.

In some embodiments, more than one seal layer 820 may be used to seal the cavities 806. As examples of some embodiments, multiple layers may be placed over each cavity 806, half or some selected portion of the cavities may be sealed with one layer with the other half or selected portion of the cavities sealed with another sheet or layer, different shaped cavities may use different seal layer, or the like. The seal layer 820 may have different physical properties, such as those covering the penetrating members 802 near the end of the cartridge may have a different-color such as red to indicate to the user (if visually inspectable) that the user is down to say 10, 5, or other number of penetrating members before the cartridge should be changed out.

Figure 74:
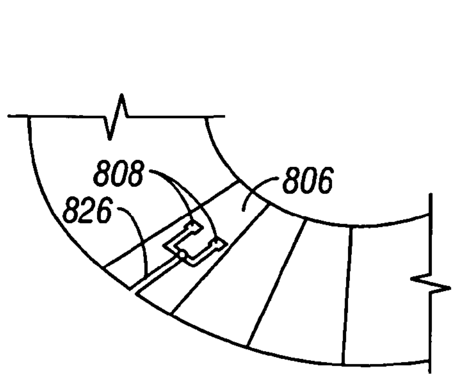
FIGS. 74-78 show still further embodiments of analyte detecting members coupled to a cartridge.

Referring now to FIGS. 74 and 75, one embodiment of the microfluidics used with the analyte detecting members 808 in cartridge 800 will now be described. For ease of illustration, the shape of cavity 806 has been simplified into a simple wedge shape. It should be understood that more sophisticated configurations such as that shown in FIG. 73 may be used. FIG. 74 shows a channel 826 that assists in drawing body fluid towards the analyte detecting members 808. In the present embodiment, two analyte detecting members 808 are shown in the cavity 806. This is purely for illustrative purposes as the cavity 806 may have one analyte detecting member or any other number of analyte detecting members as desired. Body fluid entering cavity 806, while filling part of the cavity, will also be drawn by capillary action through the groove 826 towards the analyte detecting members 808. The analyte detecting members 808 may all perform the same analysis, they may each perform different types of analysis, or there may be some combination of the two (some sensors perform same analysis while others perform other analysis).

FIG. 75 shows a perspective view of a cutout of the cavity 806. The penetrating member 802 (shown in phantom) is housed in the cavity 806 and may extend outward through a penetrating member exit opening 830 as indicated by arrow 832. The position of the tip of penetrating member 802 may vary, such as being near the penetrating member exit port or spaced apart from the exit. The location of the tip relative to the analyte detecting member 808 may also be varied, such as being spaced apart or away from the analyte detecting member or collocated or in the immediate vicinity of the analyte detecting member. Fluid may then enter the cavity 806 and directed by channel 826. The channel 826 as shown in FIG. 75 is a groove that is open on top. The channel 826 may be entirely a groove with an open top or it may have a portion that is has a sealed top forming a lumen, or still further, the groove may be closed except for an opening near the penetrating member exit opening 830. It should be understood that capillary action can be achieved using a groove having one surface uncovered. In some embodiments, the analyte detecting member 808 is positioned close to the penetrating member exit opening 830 so that the analyte detecting member 808 may not need a capillary groove or channel to draw body fluid, such as in FIG. 78.

As seen in FIGS. 75 and 76, the cavity 806 may include the substrate 822 coupled to its bottom surface containing the analyte detecting members 808. With the analyte detecting members 808 located on the underside of the cartridge 800 as seen in the embodiment of FIG. 76, the cartridge 800 may include at least one through hole 834 to provide a passage for body fluid to pass from the cavity 806 to the analyte detecting member 808. The size, location, shape, and other features of the through hole 834 may be varied based on the cavity 806 and number of analyte detecting members 808 to be provided. In other embodiments, wicking elements or the like may be used to draw body fluid from the groove 826 to down to the analyte detecting member 808 via the through hole or holes 834.

Figure 77:
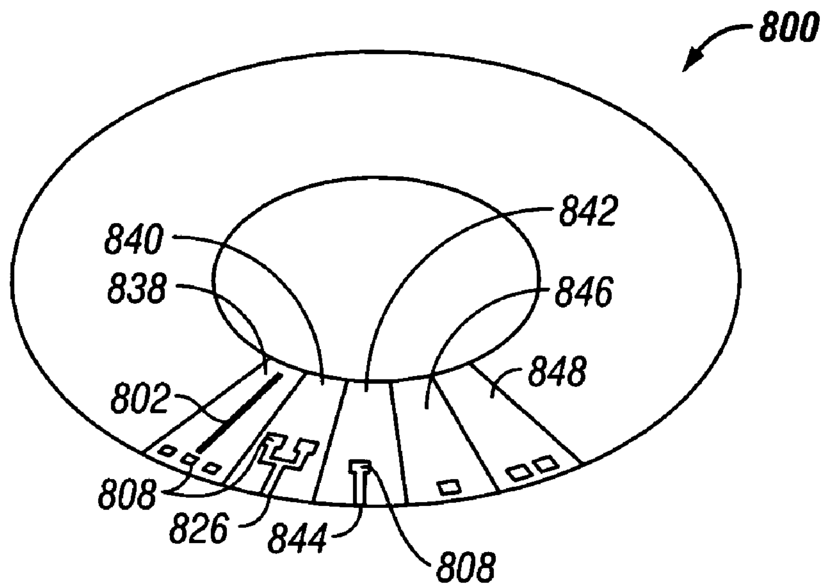

Referring now to FIG. 77, a variety of groove and analyte detecting member configurations are shown on a single cartridge. These configurations are shown only for illustrative purposes and a single cartridge may not incorporate each of these configurations. Some embodiments may use any of the detecting members, singly or in combination. It should be understood, however, that analyte detecting member configuration could be customized for each cavity, such as but not limited to, using a different number and location of analyte detecting members depending lancing variables associated with that cavity, such as but not limited to, the time of day of the lancing event, the type of analyte to be measured, the test site to be lanced, stratum corneum hydration, or other lancing parameter. As a nonlimiting example, the detecting members may be moved closer towards the outer edge of the disc, more on the side walls, any combination, or the like.

FIG. 77 shows a penetrating member 802 in a cavity 838 with three analyte detecting members 808 in the cavity. For ease of illustration, the penetrating member 802 is omitted from the remaining cavities so that the analyte detecting member configurations can be more easily seen. Cavity 840 has a channel 826 with two analyte detecting members 808. Cavity 842 has a channel 844 coupled to a single analyte detecting member 808. Cavities 846 and 848 have one and two analyte detecting members 808, respectively. The analyte detecting members 808 in those cavities may be located directly at the penetrating member exit from the cartridge or substantially at the penetrating member exit. Other analyte detecting member configurations are also possible, such as but not limited to, placing one or more analyte detecting members on a side wall of the cavity, placing the analyte detecting members in particular arrays (for example, a linear array, triangular array, square array, etc. . . . ) on the side wall or bottom surface, using mixed types of analyte detecting members (for example, electrochemical and optical, or some other combination), or mixed positioning of analyte detecting members (for example, at least one analyte detecting member on the substrate below the cartridge and at least one analyte detecting member in the cavity).

Figure 78:
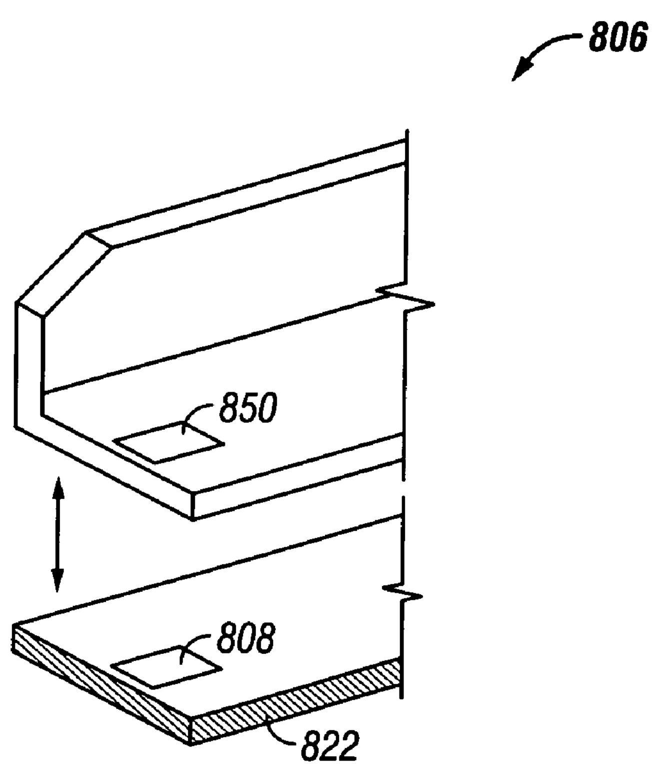

FIG. 78 shows an embodiment of cartridge 800 where the analyte detecting member 850 is located near the distal end of cavity 806. The analyte detecting member 850 may be formed, deposited, or otherwise attached there to the cartridge 800. In another embodiment, the analyte detecting member 850 may be a well or indentation having a bottom with sufficient transparency to allow an optical analyte detecting member to detect analytes in fluid deposited in the well or indentation. The well or indentation may also include some analyte reagent that reacts (fluoresces, changes colors, or presents other detectable qualities) when body fluid is placed in the well. In a still further embodiment, analyte detecting member 850 may be replaced with a through hole that allow fluid to pass there through. An analyte detecting member 808 on a substrate 822 may be attached to the underside of the cartridge 800, accessing fluid passing from the cavity 806 down to the analyte detecting member 808.

As mentioned above, the analyte detecting members 808 may also be placed right at the immediate vicinity or slightly setback from the module opening receiving blood so that low blood volumes will still reach the analyte detecting member. The analyte detecting members 808 may be used with low volumes such as less than about 1 microliter of sample, preferably less than about 0.6 microliter, more preferably less than about 0.3 microliter, and most preferably less than about 0.1 microliter of sample. Analyte detecting members 808 may also be directly printed or formed on the bottom of the penetrating member cartridge 800. In one embodiment, a multiplicity of miniaturized analyte detecting member fields may be placed on the floor of the radial cavity or on the microfluidic module to allow many tests on a single analyte form a single drop of blood to improve accuracy and precision of measurement. Although not limited in this manner, additional analyte detecting member fields or regions may also be included for calibration or other purposes.

Figure 79:
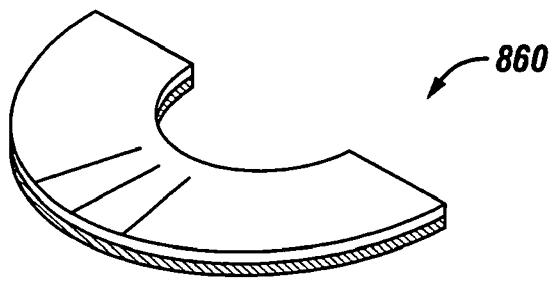
FIGS. 79-84 show optional configurations for a cartridge for use with the present invention.
Figure 80:
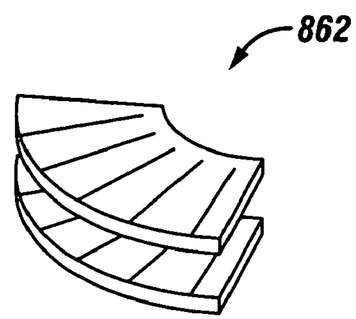
Figure 81:
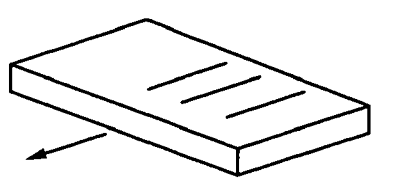
Figure 82:
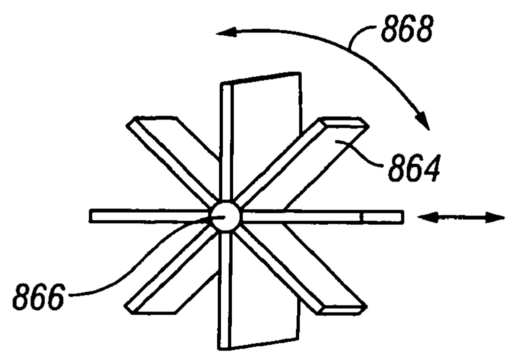
Figure 83:
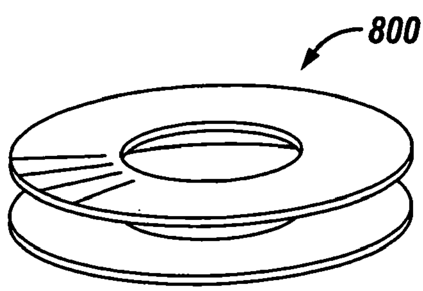
Figure 84:
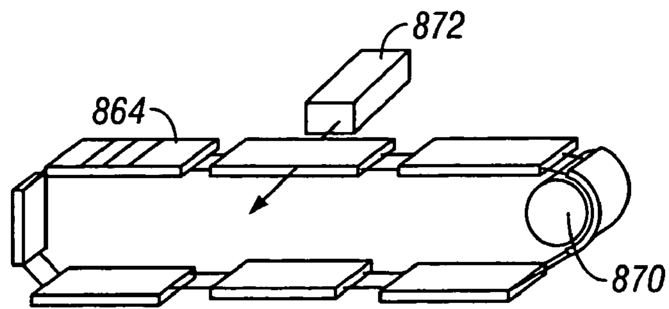

Referring now to FIGS. 79-84, further embodiments of the cartridge 800 will now be described. FIG. 79 shows a cartridge 860 having a half-circular shape. FIG. 80 shows a cartridge 862 in the shape of a partial curve. FIG. 80 also shows that the cartridges 862 may be stacked in various configurations such as vertically, horizontally, or in other orientations. FIG. 81 shows a cartridge 864 having a substantially straight, linear configuration. FIG. 82 shows a plurality of cartridges 864 arranged to extend radially outward from a center 866. Each cartridge may be on a slide (not shown for simplicity) that allows the cartridge 864 to slide radially outward to be aligned with a penetrating member launcher. After use, the cartridge 864 is slide back towards the center 866 and the entire assembly is rotated as indicated by arrow 868 to bring a new cartridge 864 into position for use with a penetrating member driver. FIG. 83 shows a still further embodiment where a plurality of cartridges 800 may be stacked for use with a penetrating member driver (see FIG. 85). The driver may be moved to align itself with each cartridge 800 or the cartridges may be moved to alight themselves with the driver. FIG. 84 shows a still further embodiment where a plurality of cartridge 864 are coupled together with a flexible support to define an array. A roller 870 may be used to move the cartridges 864 into position to be actuated by the penetrating member driver 872.

Figure 85:
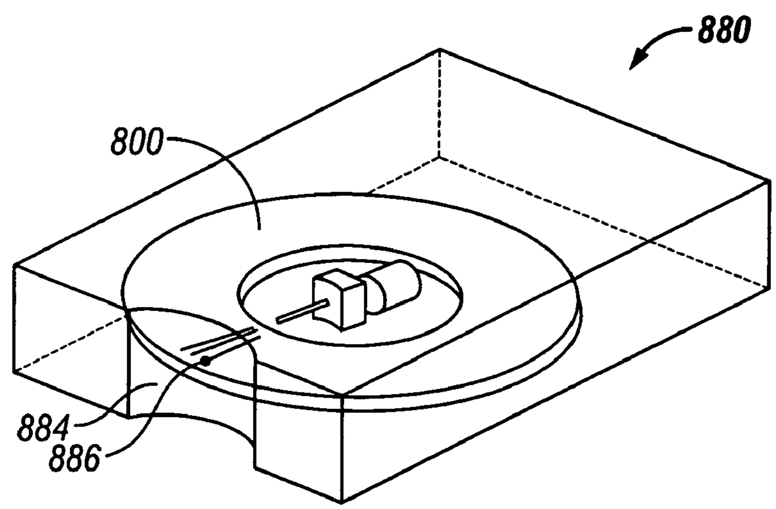
FIG. 85 shows a see-through view of one embodiment of a system according to the present invention.

Referring now to FIG. 85, one embodiment of an apparatus 880 using a radial cartridge 800 with a penetrating member driver 882 is shown. A contoured surface 884 is located near a penetrating member exit port 886, allowing for a patient to place their finger in position for lancing. Although not shown, the apparatus 880 may include a human readable or other type of visual display to relay status to the user. The display may also show measured analyte levels or other measurement or feedback to the user without the need to plug apparatus 880 or a separate test strip into a separate analyte reader device. The apparatus 880 may include a processor or other logic for actuating the penetrating member or for measuring the analyte levels. The cartridge 800 may be loaded into the apparatus 880 by opening a top housing of the apparatus which may be hinged or removably coupled to a bottom housing. The cartridge 800 may also drawn into the apparatus 880 using a loading mechanism similar in spirit to that found on a compact disc player or the like. In such an embodiment, the apparatus may have a slot (similar to a CD player in an automobile) that allows for the insertion of the cartridge 800 into the apparatus 880 which is then automatically loaded into position or otherwise seated in the apparatus for operation therein. The loading mechanism may be mechanically powered or electrically powered. In some embodiments, the loading mechanism may use a loading tray in addition to the slot. The slot may be placed higher on the housing so that the cartridge 800 will have enough clearance to be loaded into the device and then dropped down over the penetrating member driver 882. The cartridge 800 may have an indicator mark or indexing device that allows the cartridge to be properly aligned by the loading mechanism or an aligning mechanism once the cartridge 800 is placed into the apparatus 880. The cartridge 800 may rest on a radial platform that rotates about the penetrating member driver 882, thus providing a method for advancing the cartridge to bring unused penetrating members to engagement with the penetrating member driver. The cartridge 800 on its underside or other surface, may shaped or contoured such as with notches, grooves, tractor holes, optical markers, or the like to facilitate handling and/or indexing of the cartridge. These shapes or surfaces may also be varied so as to indicate that the cartridge is almost out of unused penetrating members, that there are only five penetrating members left, or some other cartridge status indicator as desired.

A suitable method and apparatus for loading penetrating members has been described previously in commonly assigned, copending U.S. patent applications 60/393,706 filed Jul. 1, 2002 and 60/393,707 filed Jul. 1, 2002, and are included here by reference for all purposes. Suitable devices for engaging the penetrating members and for removing protective materials associated with the penetrating member cavity are described in commonly assigned, copending U.S. patent applications 60/422,988 filed Nov. 1, 2002 and 60/424,429 filed Nov. 6, 2002, and are included here by reference for all purposes. For example in the embodiment of FIG. 78, the foil or seal layer 820 may cover the cavity by extending across the cavity along a top surface 890 and down along the angled surface 892 to provide a sealed, sterile environment for the penetrating member and analyte detecting members therein. A piercing element described in U.S. patent application 60/424,429 filed Nov. 6, 2002 has a piercing element and then a shaped portion behind the element which pushes the foil to the sides of the cavity or other position so that the penetrating member 802 may be actuated and body fluid may flow into the cavity.

Figure 86:
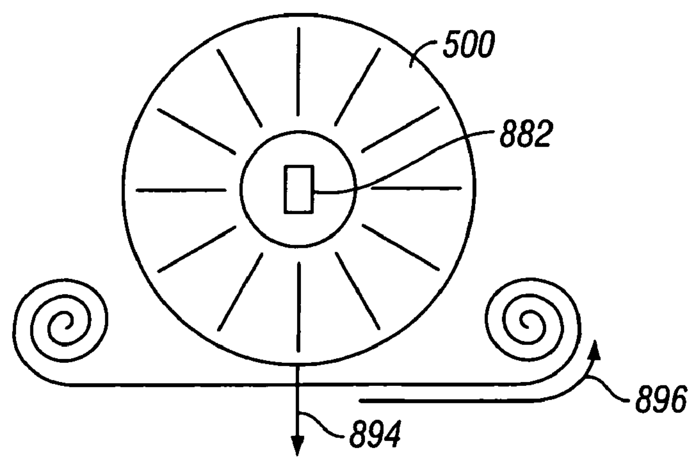
FIG. 86 is a schematic of an optional embodiment of a system according to the present invention.

Referring now to FIG. 86, a still further embodiment of a lancing system according to the present invention will be described. A radial cartridge 500 may be incorporated for use with a penetrating member driver 882. A penetrating member may be driven outward as indicated by arrow 894. A plurality of analyte detecting members are presented on a roll 895 that is laid out near a penetrating member exit. The roll 895 may be advanced as indicated by arrow 896 so that used analyte detecting members are moved away from the active site. The roll 895 may also be replaced by a disc holding a plurality of analyte detecting members, wherein the analyte detecting member disc (not shown) is oriented in a plane substantially orthogonal to the plane of cartridge 500. The analyte detecting member disc may also be at other angles not parallel to the plane of cartridge 500 so as to be able to rotate and present new, unused analyte detecting member in sequence with new unused penetrating members of cartridge 500.

Figure 87A:
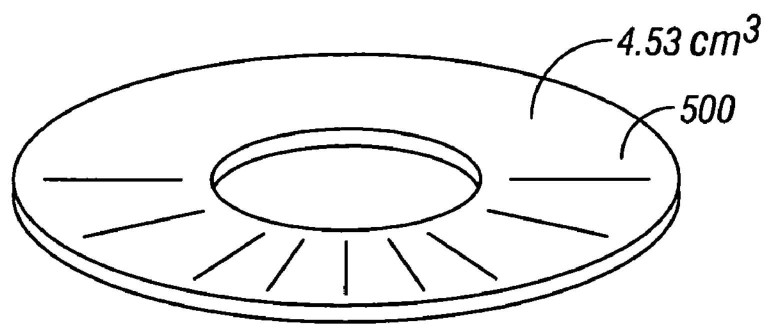
FIGS. 87A-87B show still further embodiments of cartridges according to the present invention.

Referring now to FIG. 87A, the cartridge 500 provides a high density packaging system for a lancing system. This form factor allows a patient to load a large number penetrating members through a single cartridge while maintaining a substantially handheld device. Of course such a cartridge 500 may also be used in non-handheld devices. The present cartridge 500 provide a high test density per volume of the disposable. For embodiments of a cartridge that includes analyte detecting members in addition to penetrating members such as cartridge 800, the density may also be measured in terms of density of analyte detecting members and penetrating members in a disposable. In other embodiments, the density may also be expressed in terms of analyte detecting members per disposable. For example, by taking the physical volume of one embodiment or the total envelope, this number can be divided by the number of penetrating members or number of tests. This result is the volume per penetrating member or per test in a cassetted fashion. For example, in one embodiment of the present invention, the total volume of the cartridge 500 is determined to be 4.53 cubic centimeters. In this one embodiment, the cartridge 500 holds 50 penetrating members. Dividing the volume by 50, the volume per test is arrived at 0.090 cubic centimeters. Conventional test devices such as drum is in the range of 0.720 or 0.670 cubic centimeters and that is simply the volume to hold a plurality of test strips. This does not include penetrating members as does the present embodiment 800. Thus, the present embodiment is at a substantially higher density. Even a slightly lower density device having penetrating members and analyte detecting members in the 0.500 cubic centimeter range would be a vast improvement over known devices since the numbers listed above for known devices does not include penetrating members, only packaging per test strip.

Each penetrating member (or penetrating member and analyte detecting member, as the case may be) may have a packing density, or occupied volume, in cartridge 500. In various embodiments, the packing density or occupied volume of each penetrating member in cartridge 500 may be no more than about 0.66 cm3, 0.05 cm3, 0.4 cm3, 0.3 cm3, 0.2 cm3, 0.1 cm3, 0.075 cm3, 0.05 cm3, 0.025 cm3, 0.01 cm3, 0.090 cm3, 0.080 cm3, and the like. These numbers applicable to volumes for penetrating members alone, or for combined penetrating members and analyte detecting members. In other words, the volume required for each penetrating member does not exceed 0.66 cm3/penetrating member, 0.05 cm3/penetrating member, 0.4 cm3/penetrating member, 0.3 cm3/penetrating member, 0.2 cm3/penetrating member, 0.1 cm3/penetrating member, 0.075 cm3/penetrating member, 0.05 cm3/penetrating member, 0.025 cm3/penetrating member, 0.01 cm3/penetrating member, 0.090 cm3/penetrating member and the like. So, if the total package volume of the cartridge is defined as X and the cartridge includes Y number of penetrating members, penetrating members and test area, or other unit 395, the volume for each unit does not exceed 0.66 cm3, 0.05 cm3, 0.4 cm3, 0.3 cm3, 0.2 cm3, 0.1 cm3, 0.075 cm3, 0.05 cm3, 0.025 cm3, 0.01 cm3, 0.090 cm3, 0.080 cm3, and the like.

Figure 87B:
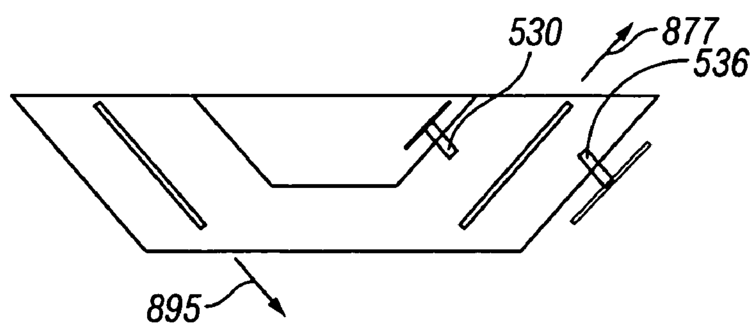

Referring now to FIG. 87B, a still further embodiment of a cartridge according to the present invention will now be described. FIG. 87B shows a cross-section of a conical shaped cartridge with the penetrating member being oriented in one embodiment to move radially outward as indicated by arrow 897. In another embodiment, the penetrating member may be oriented to move radially inward as indicated by arrow 895. The gripper may be positioned to engage the penetrating member from an inner surface or an outer surface of the cartridge.

Figure 88:
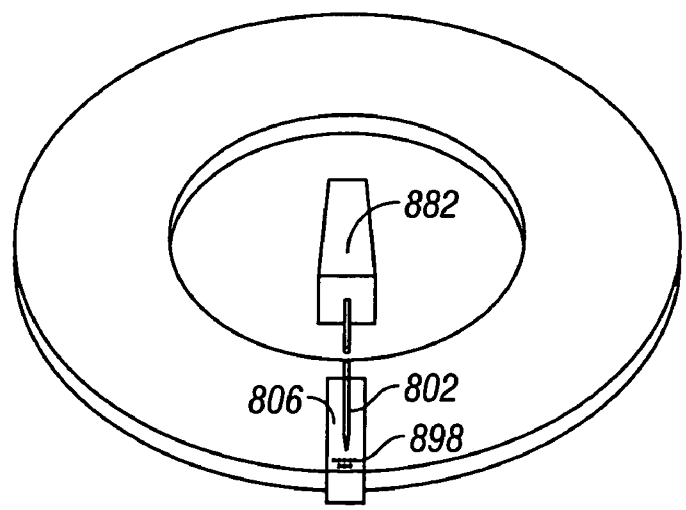
FIG. 88 shows a cartridge having an array of analyte detecting members.

Referring now to FIG. 88, nanowires may also be used to create low volume analyte detecting members used with the cartridge 800. Further details of a nanowire device is described in commonly assigned, copending U.S. Provisional Patent Application Ser. No. 60/433,286 filed Dec. 13, 2002, fully incorporated herein by reference for all purposes. These nanowire analyte detecting members 898 may be incorporated into the cavity 806 housing the penetrating member 802. They may be placed on the floor or bottom surface of the cavity 806, on the wall, on the top surface, or any combinations of some or all of these possibilities. The analyte detecting members 898 may be designed to have different sensitivity ranges so as to enhance the overall sensitivity of an array of such analyte detecting members. Methods to achieve this may include, but are not limited to, using nanowires of varying sizes, varying the number of nanowires, or varying the amount of glucose oxidase or other glucose detection material on the nanowires. These nanowire analyte detecting members may be designed to use low volumes of body fluid for each sample, due to their size. In some embodiments, each of the analyte detecting members are accurate using volumes of body fluid sample less than about 500 nanoliters. In some embodiments, each of the analyte detecting members are accurate using volumes of body fluid sample less than about 300 nanoliters. In still other embodiments, each analyte detecting member is accurate with less than about 50 nanoliters, less than about 30 nanoliters, less than about 10 nanoliters, less than about 5 nanoliters, and less than about 1 nanoliters of body fluid sample. In some embodiments, the combined array of analyte detecting members uses less than 300 nanoliters of body fluid to arrive at an analyte measurement.

Figure 89:
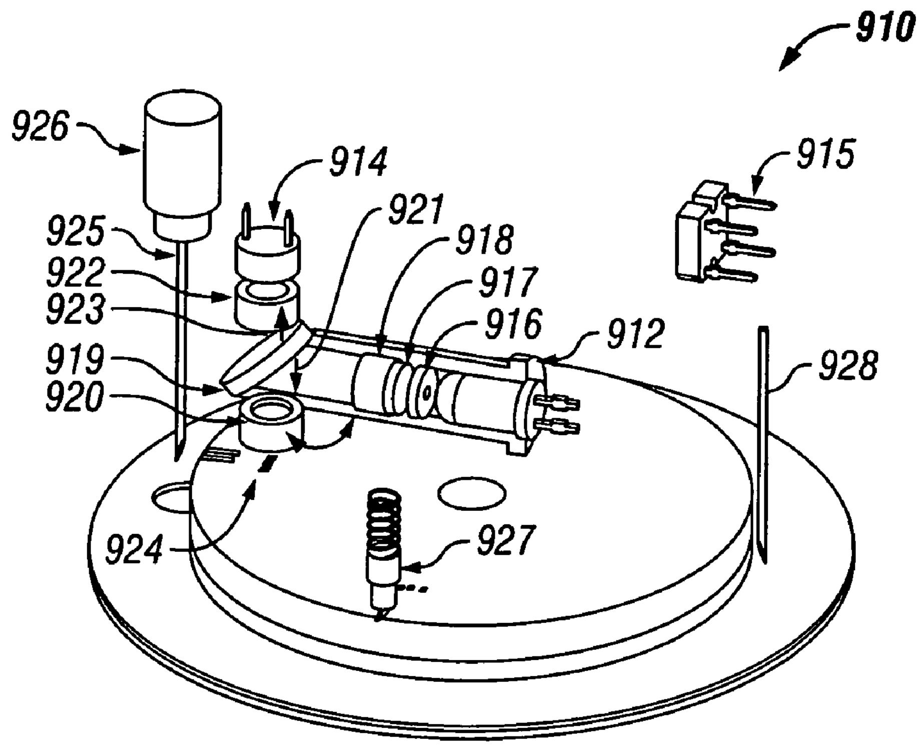
FIGS. 89-90 show embodiments of illumination systems for use with the present invention.

Referring now to FIG. 89, a still further embodiment of the present invention will be described. FIG. 89 shows one embodiment of an optical illumination system 910 for use with optical analyte detecting members (FIG. 91) that may be in contact with a body fluid sample. The overall system may include a plurality of analyte detecting members which provide some optical indicator, a light source 912 for providing light to shine on the analyte detecting members, at least one light detector 914, and a processor (not shown). The analyte detecting member or analyte detecting members are exposed to a sample of the fluid of unknown composition. A plurality of analyte detecting members may be arranged into an array of analyte detecting members exposed to one fluid sample, each group targeting a specific analyte and may contain an analyte-specific chemical that interacts more specifically with one analyte than with some other analytes to be analyzed. Each analyte detecting member may also have different sensitivity ranges so as to maximize overall sensitivity of an array of such analyte detecting members. The light source 912 shines light on at least one analyte detecting member to cause light interaction. The differences, in the analyte detecting members may lead to differences in the light interaction. The light detector detects the light interaction by the analyte detecting members. The processor analyzes the light interaction by the analyte detecting members to take into account interference in light interaction among the analytes, thereby determining the concentration of the desired analyte in the fluid.

Figure 91:
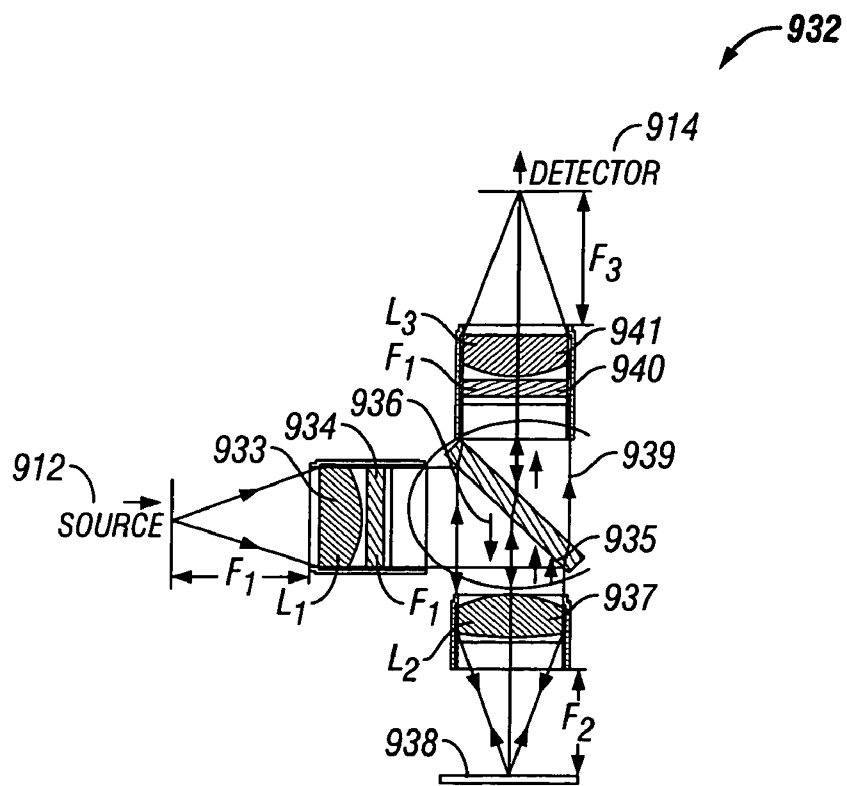
FIGS. 91-96 show further embodiments using optical methods for analyte detection.

Referring still to the embodiment of FIG. 89, the light source 912 may be but is not limited to an LED. An alternative LED 915 may also be used with the present invention. Light, illumination, or excitation energy from LED 912 travels along a path through a pinhole 916, a filter 917, and a lens 918. The light then comes into contact with a beamsplitter 919 such as a dichroic mirror or other device useful for beamsplitting. The light is then directed towards lens 920 as indicated by arrow 921. The lens 920 focuses light onto the analyte detecting member (FIG. 91). This excitation energy may cause a detectable optical indicator from the analyte detecting member. By way of example and not limitation, fluorescence energy may be reflected bay up the lens 920. This energy passes through the beamsplitter 919 and to lens 922 which is then received by detector 914 as indicated by arrow 923. The detector 914 measures the energy and this information is passed on to the processor (not shown) to determine analyte levels. The illumination system 910 may also include cells 924 on the disc surface. In this specific embodiment, a penetrating member 925 drive by a force generator 926 such as but not limited to a solenoid may be used to obtain the fluid sample. A detent 927 may also be included with the device along with other bare lancets or penetrating members 928.

Figure 90:
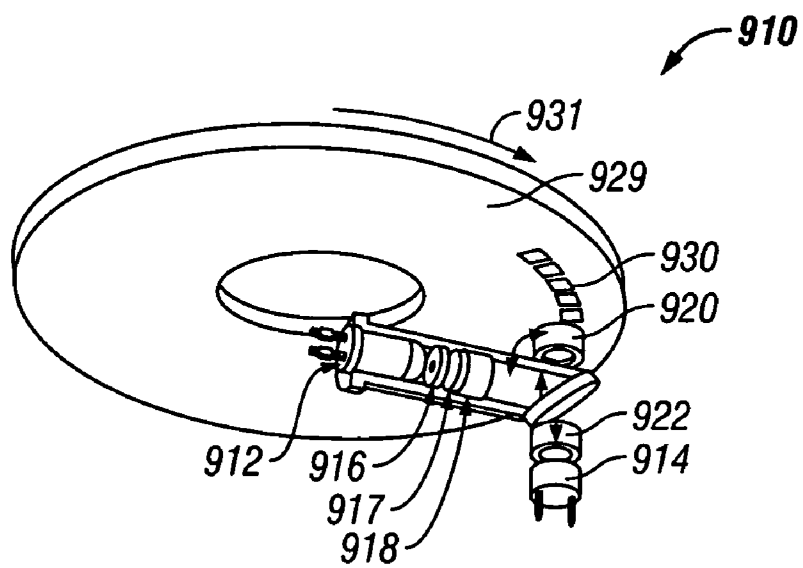

Referring now to FIG. 90, another embodiment of the illumination system 910 is shown for use with a cartridge 929. Cartridge 929 is similar to cartridge 800. Cartridge 929 is a single cartridge having a plurality of penetrating members and a plurality of optical analyte detecting members (not shown). The cartridge 929 further includes a plurality of optically transparent portions 930 which may be but is not limited to windows or the like for the light from LED 912 to shine into a cavity of the cartridge 929. In one embodiment, each cavity of the cartridge 929 may include at least one transparent portion 930. This allows the light to generate energy that may be read by analyte detecting member 914. The cartridge 929 may be used a driver 882 to actuate penetrating members and the cartridge 929 may rotate as indicated by arrow 931.

Referring now to FIG. 91, a cross-section of a similar embodiment of the illumination system is shown. This system 932 has source 912 with a lens 933 having an excitation filter 934. This excitation filter 934, in one embodiment, only allows excitation energy to pass. This filter 934 allows the excitation energy to pass to dichroic mirror 935, but does not let it return to source 912. Excitation energy is reflected down as indicated by arrow 936. Lens 937 focuses the energy to optical analyte detecting member 938. Fluorescence energy 939 passes through the dichroic mirror 935 and towards a fluorescent filter 940. In one embodiment, the fluorescent filter 940 only allows fluorescent energy to pass through to lens 941. Thus, the detector 914 only receives fluorescent energy from the analyte detecting member 938. It should be understood of course, that the filter may be changed to allow the type of energy being generated by analyte detecting member 938 to pass. In some embodiments, no filter may be used. The dichroic mirror 935 may be a Bk7 substrate, 63×40×8 mm. The filters may also be a Bk7 substrate about 40 mm in diameter and about 6 mm thick. The lens 933, 937, and 941 may be achormat:bfl=53.6, working aperture 38 mm.

Figure 92:
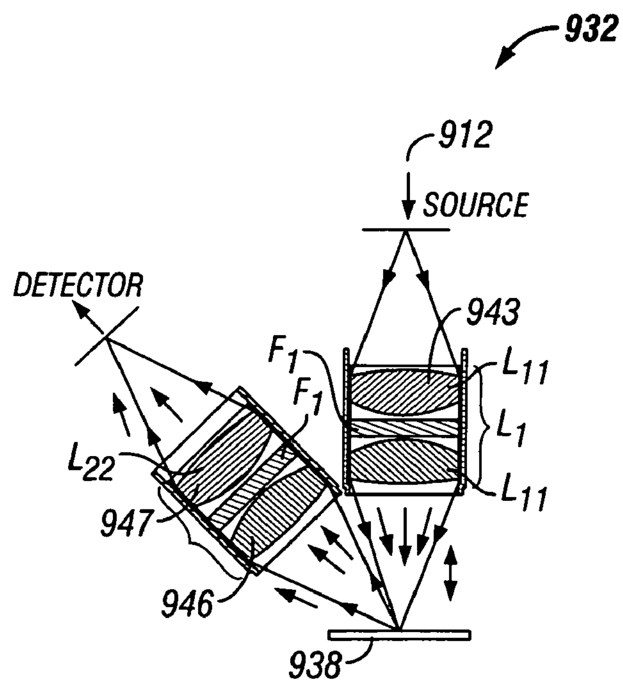

Referring now to FIG. 92, a still further embodiment of an illumination system 942 will be described. This system does not use a beamsplitter or dichroic mirror. Instead, both the source or LED 912 and detector 914 have direct line of sight to the optical analyte detecting member 938. In this embodiment, multiple elements are combined into a single housing. For example, lens 943, lens 944, and filter 945 are combined while lens 946, lens 947, and filter 948 are also combined.

Figure 93:
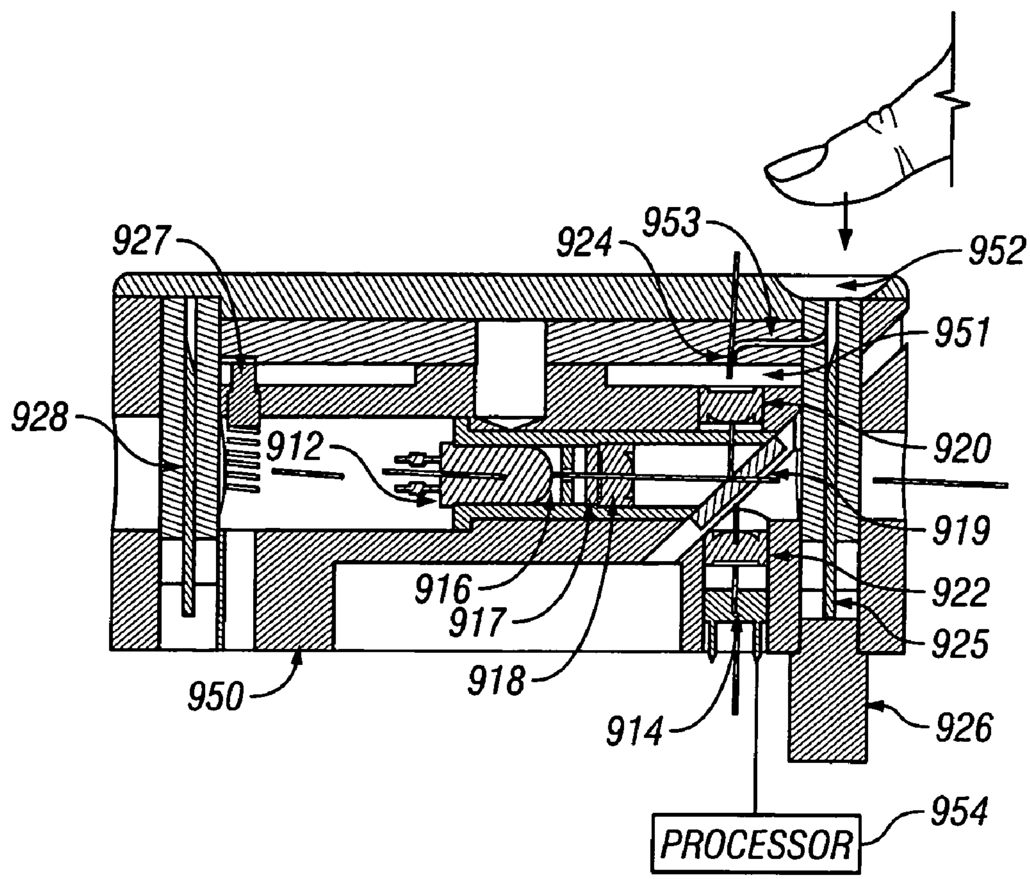

Referring now to FIG. 93, a cross-section of a system similar to that of FIG. 89 is shown in a housing 950. LED 912 sends light to mirror 919 to a light path 951 to cells 924 on a surface of the disc. A finger access 952 allows a sample to be obtained and flow along a fluid pathway 953 to be analyzed. A processor 954 may be coupled to detector 914 to analyze the results.

Figure 94:
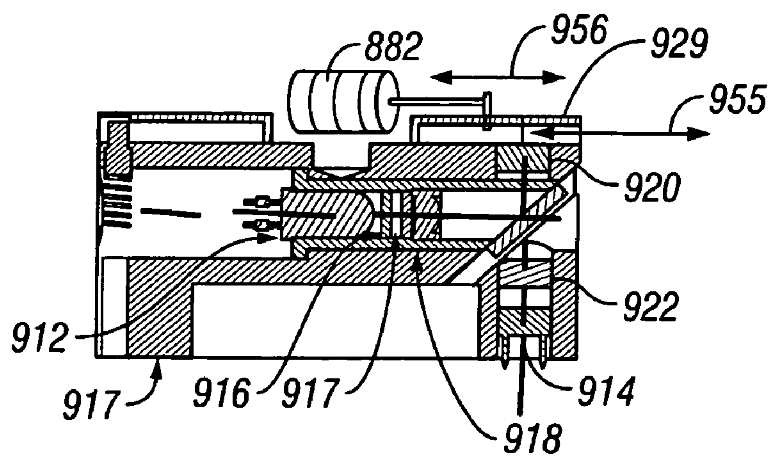
Figure 95:
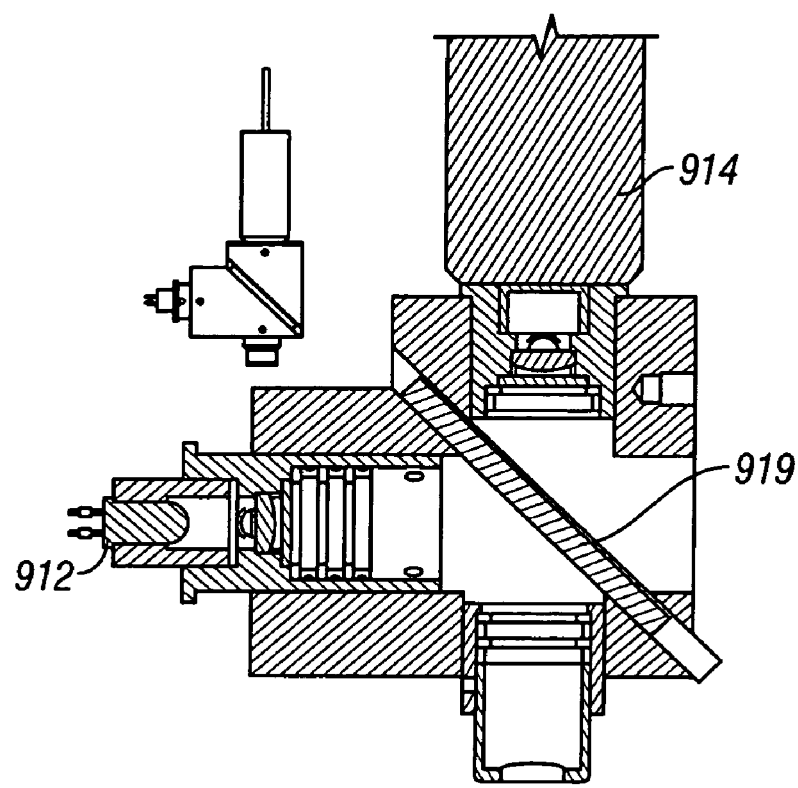
Figure 96:
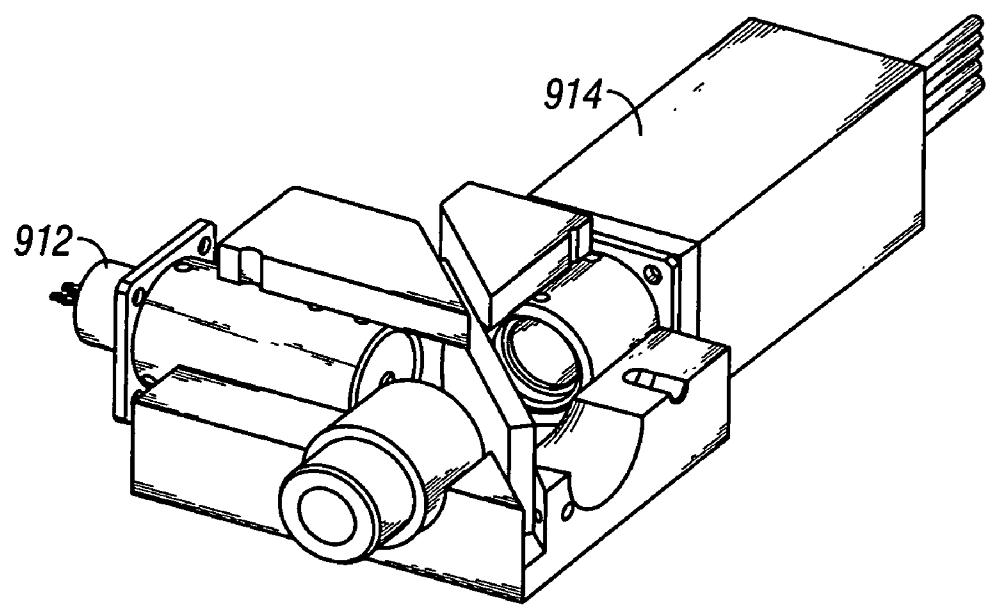

Referring now to FIG. 94, a cross-section of a system similar to that of FIG. 90 will be further described. This shows a cartridge 929 used with a driver 882. This allows for a radial design where the penetrating members extend radially outward as indicated by arrow 955. The driver 882 may have a coupler portion that reciprocates as indicated by arrow 956. FIGS. 95 and 96 provide further views of a system similar to that of FIG. 89. The embodiment of FIGS. 95 and 96 may include additional lenses or filters as may be useful to refine energy detection.

Figure 97:
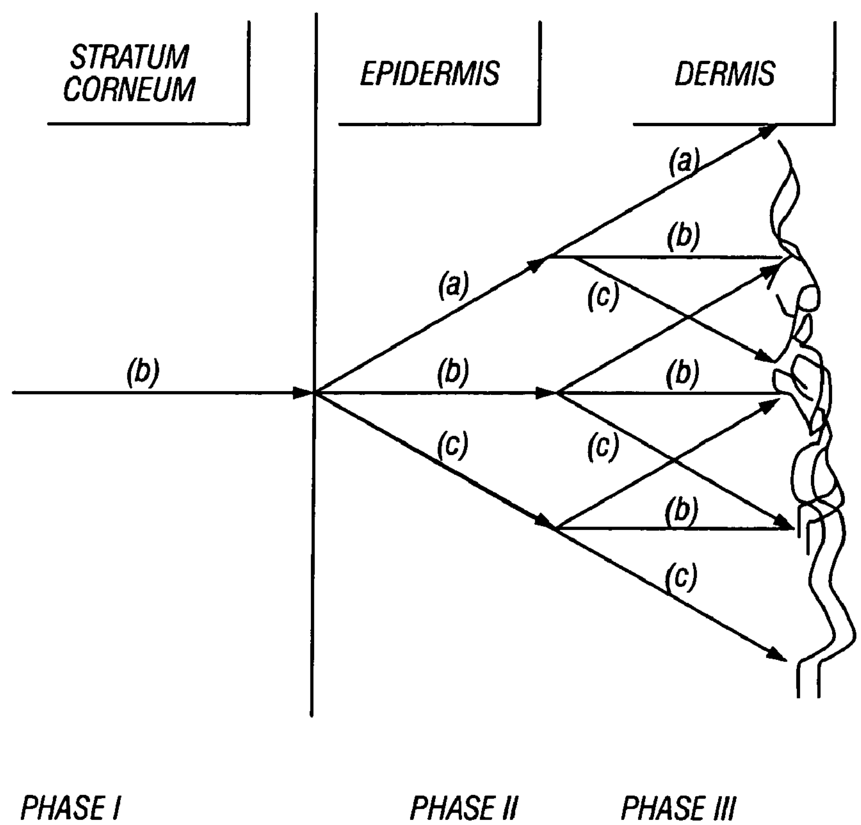
FIG. 97 shows a chart of varying penetrating member velocity in different parts of the tissue.

Referring now to FIG. 97, the area of interest is the velocity profile 1000 while the lancet is cutting through the skin layers in the finger until it reaches a predetermined depth. More specifically, variation of lancet velocity through different phases of the inbound trajectory is shown in FIG. 97. In this embodiment, Phase I corresponds to the stratum corneum, phase II to the epidermis and phase III to the dermis. At each phase (and during the phase), the options are to maintain current velocity, increase current velocity or decrease current velocity. Based on the thickness of the stratum corneum, velocity could be monitored and changed in this embodiment at 9 points in the stratum corneum, 6 points in the epidermis, and 29 points in the dermis using the four edge detection algorithm and the 360 strips per inch encoder strip. It should be noted that although the embodiment of the driver discussed herein produces the previously discussed number of monitoring points for a given displacement, other driver and position sensor embodiments may be used that would give higher or lower resolution.

For the purposes of the present discussion for this nonlimiting example, the skin is viewed as having three distinct regions or tissue layers: the stratum corneum SC (Phase I), the epidermis E (Phase II) and the dermis D (Phase III). In one embodiment, the lancet or penetrating member 10 is accelerated to a first desired velocity. This velocity may be predetermined or it may be calculated by the processor during actuation. The processor is also used to control the lancet velocity in tissue. At this velocity, the lancet 10 will impact the skin and initiate cutting through the stratum corneum. The stratum corneum is hard, hence in this embodiment, maximum velocity of the penetrating member 10 may be employed to efficiently cut through this layer, and this velocity may be maintained constant until the lancet passes through the layer. Power will likely need to be applied to the lancet drive 12 while the lancet is cutting through the stratum corneum in order to maintain the first velocity. Average stratum corneum thickness is about 225 μm. Using a four-edge detection algorithm for the position sensor 14 of this embodiment, the opportunity to verify and feed back velocity information can be carried out at 225/17 or roughly 13 points. In another embodiment accelerating through the stratum corneum following impact may improve cutting efficiency. Acceleration may be possible if the lancet has not reached its target or desired velocity before impact. FIG. 4 shows the result of increasing ((a) arrows, maintaining ((b) arrows) or reducing ((c) arrows) velocity on the lancet trajectory for each of the tissue layers.

On reaching the epidermis E (Phase II), an embodiment of a method may decrease the velocity ((c) arrows) from the first velocity so that tissue compression is reduced in this second tissue layer. Thus the lancet 10, in this nonlimiting example, may have a second desired velocity that is less than the first velocity. The reduced speed in the second tissue layer may reduce the pain experienced by the mechano receptor nerve cells in the dermal layer (third tissue layer). In the absence of tissue compression effects on the dermal layer, however, lancet velocity may be kept constant for efficient cutting (i.e. second velocity may be maintained the same as the first velocity). In another embodiment, velocity may be increased in the second tissue layer from the first velocity.

In Phase III, the lancet or penetrating member 10 may reach the blood vessels and cut them to yield blood. The innervation of this third tissue layer and hence pain perception during lancing could be easily affected by the velocity profile chosen. In one embodiment, a third desired velocity may be chosen. The velocity may be chosen to minimize nerve stimulation while maintaining cutting efficiency. One embodiment would involve reducing velocity from the second velocity to minimize pain, and may increase it just before the blood vessels to be cut. The number of velocity measurement steps possible for the position sensor described above in the dermis is approximately 58. The user would determine the best velocity/cutting profile by usage. The profile with the least amount of pain on lancing, yielding a successful blood sample would be programmable into the device.

Currently users optimize depth settings on mechanical launchers by testing various settings and through usage, settle on a desired setting based on lancing comfort. Embodiments of the device and methods discussed herein provide a variety of velocity profiles (FIG. 97), which can be optimized by the user for controlled lancing, and may include: controlling the cutting speed of a lancet with the lancet within the skin; adjusting the velocity profile of the lancet while the lancet is in the skin based upon the composition of the skin layers; lancing according to precise regional velocity profiles based on variation in cell type from the surface of the skin down through the epidermis and dermis; lancing at a desired velocity through any tissue layer and varying the velocity for each layer. This may include maximum velocity through the stratum corneum, mediation of velocity through epidermis to minimize shock waves to pain sensors in dermis, and mediation of velocity through dermis for efficient cutting of blood vessels without stimulating pain receptors. Additional details may be found in commonly assigned, co-pending U.S. patent application Ser. No. 10/420,535 filed Apr. 21, 2003, included herein by reference.

Figure 98:
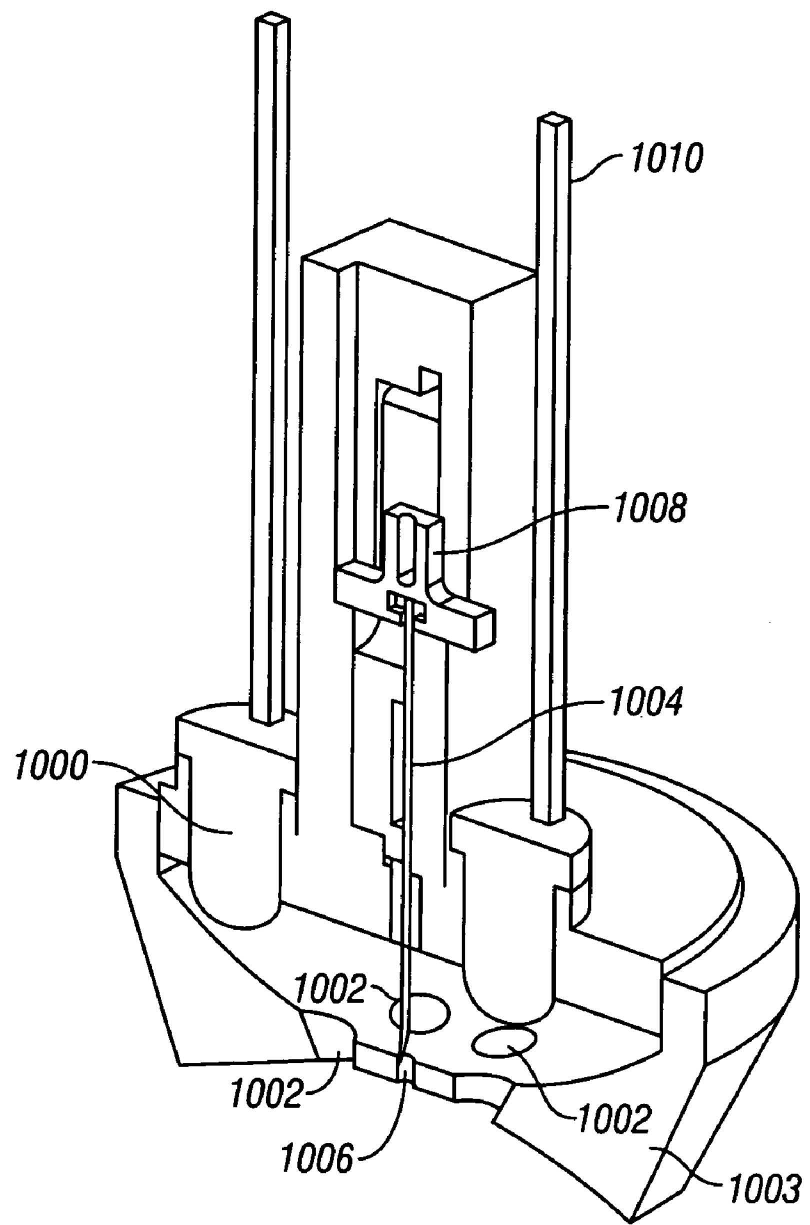
FIGS. 98 and 99 show schematic views of penetrating member drivers according to the present invention.

Referring now to FIG. 98, a still further embodiment of an actuator according to the present invention will now be described. The present invention relates to an actuator 1010 that will launch a lancet or penetrating member 1020 into skin or an anatomical feature in a controlled manner so as to produce a small drop of blood or body fluid while minimizing patient discomfort. As a nonlimiting example, energy stored in a compressed spring, gas, or other actuation technique is released to actuate a lancet 1020. Through the use of processor 1012, the motion of the lancet or penetrating member 1020 is controlled by an iron-loaded fluid 1022 that changes viscosity in response to an imposed magnetic field. A motor or other device (not shown) may be used to control the retraction rate of the lancet 1020 from the skin or other targeted anatomical feature. It should be understood, of course, that other magnetically controllable fluid as known to those skilled in the art may also be used.

FIG. 98 documents the concept of using a magnetic fluid to control the action of a mechanical spring. In the embodiment of FIG. 98, energy is stored in the compressed spring and released at the time of actuation. As previously discussed, other actuators besides the compressed spring may also be used without departing from the spirit of the present invention. The motion of the lancet is controlled by means of an electromagnet that is arranged to produce a magnetic field in a fluid consisting of fine iron particles suspended in oil, silicone fluid, or other medium. When a magnetic field is imposed on the fluid, the iron particles align with the field, and resist motion. Fluid firmness increases with field strength. A suitable fluid can be purchased as MRF-132AD Rheonetic Fluid from Lord Corporation (888) 811-5673.

Figure 99:
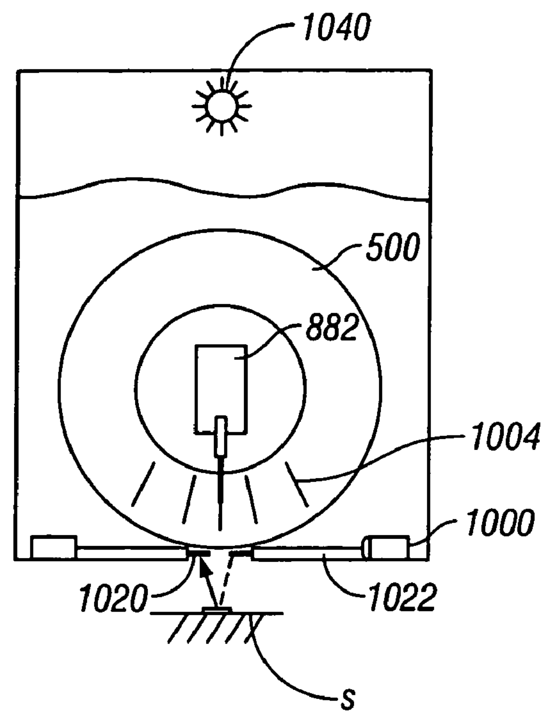

FIG. 99 provide details about launching and resetting the actuator for the present embodiment. A firing catch 1030 is shown to hold the spring 1010 in a cocked position prior to firing. An optically reflective member such as a flag 1032 is shown attached to the lancet coupler 1034 to provide position feedback through an optical position transducer. In some embodiments, the flag 1032 may be attached to a drive shaft (not shown). This feedback allows a processor 1012 to modulate the current to the electromagnetic coil or other magnetic field generator as known to one skilled in the art, to control the actuation profile of the lancet. A disc 1036 is shown attached to the penetrating member coupler 1034 and the disc is submerged in the rheonetic fluid. Suitable seals may be used to contain the fluid while allowing the shaft 1038 to pass through the dashpot chamber. In some embodiments, the disc 1036 is mounted about shaft 1040 and the entire dashpot chamber is also mounted about a portion of the shaft 1040. A motor 1042, or other retraction device is shown to move the dashpot and carry the drive shaft back to the cocked position. The motor then resets the dashpot to the desired stop position, and the actuation cycle is ready to repeat.

One advantage of this design is that each actuator can be matched to a portion of the actuation cycle. Rapid energy release is provided by the spring 1010 to bring the lancet or penetrating member 1020 up to speed. In one embodiment, excess energy stored in the spring allows the actuator 1010 to maintain the desired lancet speed regardless of skin or tissue consistency. The rheonetic fluid 1022 in the dashpot, controlled by the electromagnet, dissipates the excess energy from the spring 1010. A DC reset motor 1042 can be driven at variable speeds by controlling the motor drive current. By this means, the retraction speed of the lancet can be controlled.

Another advantage of this present embodiment is that power consumption is reduced through the use of a small DC motor instead of a solenoid. The motor draws energy from a battery at a much lower rate and over a longer time, resulting in more efficient battery use.

In another aspect, the present embodiment provides a device for storing and rapidly releasing energy. The device controls the release of stored energy to control motion, controls the release of energy to provide a low impact stop, controls the storage of energy to control retraction motion, and stores energy for rapid release at the start of the next cycle.

Figure 100:
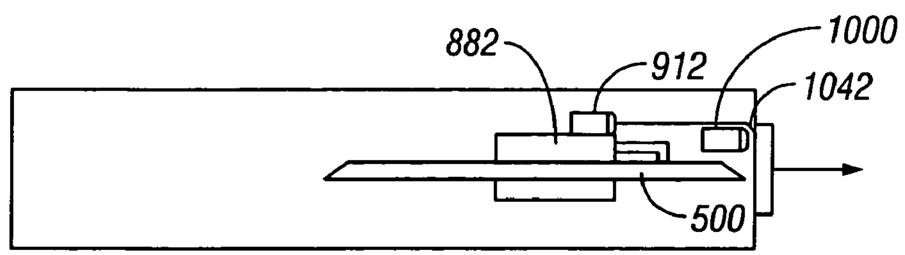
FIG. 100 shows a penetrating member driver according to the present invention for use with a cartridge containing a plurality of penetrating members.

FIG. 100 shows that embodiments of the lancet actuators of FIGS. 98 and 99 may be configured for use with a radial cartridge 1050 having a plurality of penetrating members 1020. Accordingly, these launchers may be coupled with single use or multiple use lancing devices. As a nonlimiting example, these devices may be used with a cartridge 500.

Figure 101:
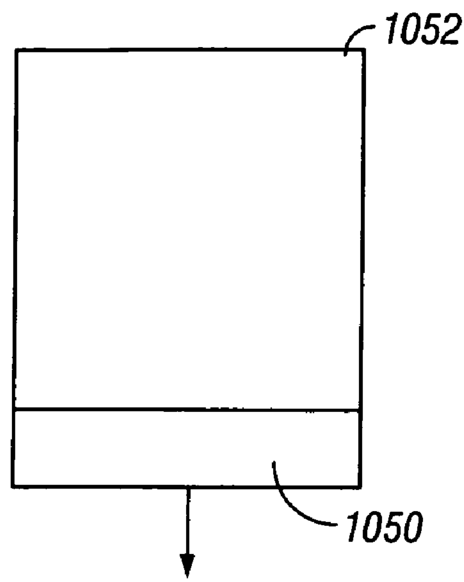
FIGS. 101 and 102 show a penetrating member driver using a magnetically controllable fluid device.

FIG. 101 shows a more detailed view of one embodiment of an electromagnetic field generator 1052 coupled to a power source 1054 controlled by a processor 1012.

Figure 102:
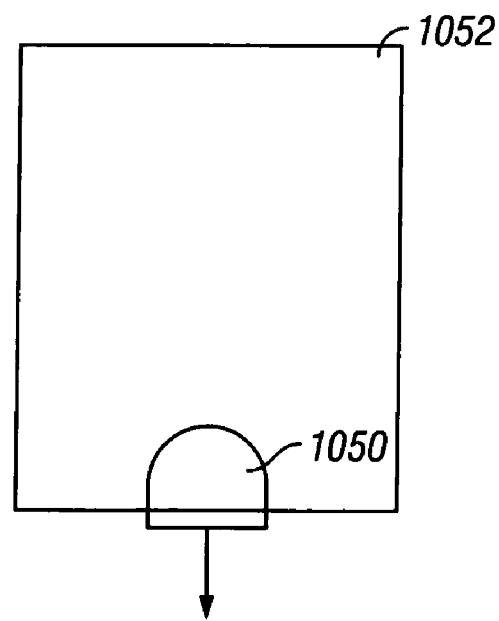
Figure 103:
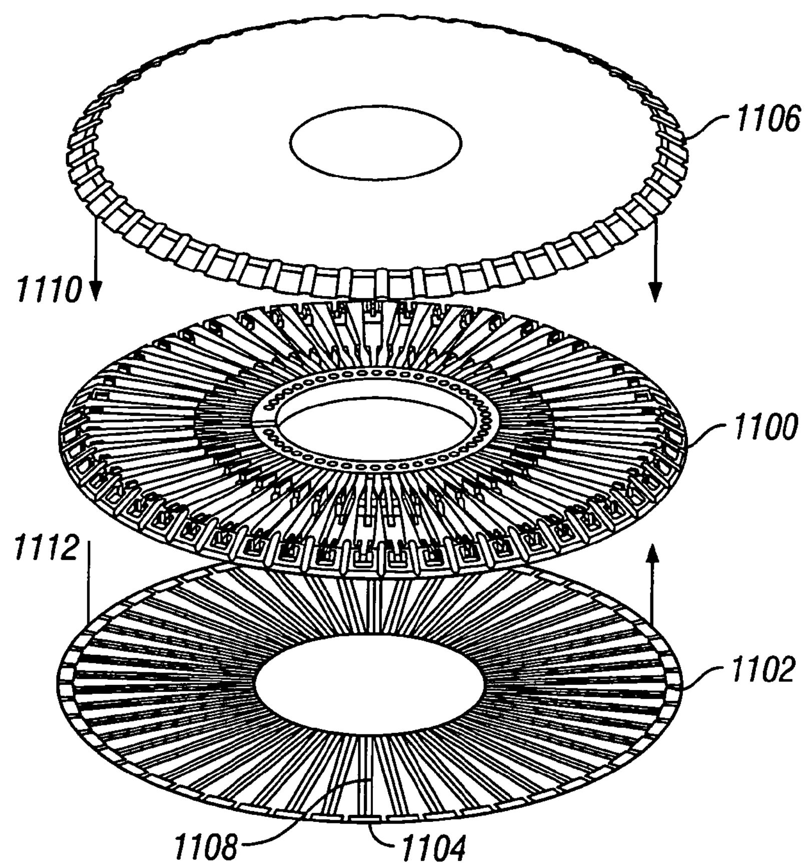
FIGS. 103-104 show embodiments of an improved penetrating member.

FIG. 102 shows a still further embodiment similar to that shown in FIG. 99. This embodiment includes an actuator 1010 (shown in this nonlimiting example to be a spring), a disc 1036 coaxially mounted about a shaft 1040 in a ferrofluid 1022, and a flag 1032 for monitoring lancet or penetrating member position. The launch device of FIG. 102 may also be adapted for use with a radial cartridge (shown in phantom) having a plurality of penetrating members 1020 which may be coupled to the coupler 1034.

Referring still to FIG. 102, energy is stored in the compressed spring used as actuator 1010 and is released at the time of actuation. In this embodiment, the motion of the penetrating member 1020 is controlled by an electromagnet 1052 that is arranged to produce a magnetic field in a fluid consisting of fine iron particles or other material suspended in but not limited to oil, silicone fluid, or other medium. When a magnetic field is imposed on the fluid, the iron particles align with the field, and resist motion. Fluid firmness increases with field strength. Such fluid can be purchased as MRF-132AD Rheonetic Fluid from Lord Corporation (888) 811-5673. A flag is shown attached to the drive shaft to provide position feedback through an optical position transducer. This feedback allows a processor to modulate the current to the electromagnetic coil to control the actuation profile of the lancet. A disc is shown attached to the drive shaft and submerged in the rheonetic fluid. Suitable seals are required to contain the fluid while allowing the shaft to pass through the dashpot chamber. A motor, or other driving device is shown to move the dashpot and carry the drive shaft back to the cocked position. The motor then resets the dashpot to the desired stop position, and the actuation cycle is ready to repeat. The advantage of this design is that each actuator may be matched to a portion of the actuation cycle. Rapid energy release is provided by the spring to bring the lancet up to speed. Excess energy stored in the spring allows the actuator to maintain the desired lancet speed regardless of skin consistency. The rheonetic fluid in the dashpot, controlled by the electromagnet, dissipates the excess energy from the spring. Of course, other dashpots or dampers as disclosed herein or as known to one of skill in the art may also be used. In one embodiment, a DC reset motor can be driven at variable speeds by controlling the motor drive current. By this motor, the retraction speed of the penetrating member 1020 can be controlled. A second advantage of this invention is that power consumption is reduced through the use of a small DC motor instead of a solenoid. The motor draws energy from a battery at a much lower rate and over a longer time, resulting in more efficient battery use. This hybrid device could also be configured to yield a "smart braking" pattern so that residual pain is minimized.

Referring now to FIGS. 103A to 103E, a still further embodiment of a lancing apparatus relates to the spring actuation of a lancet to pierce the skin of a finger to produce a drop of blood for analysis. Blood yield may be increased by causing the lancet to dwell at the end of its stroke, and then retract at a slower rate.

As seen in FIG. 103A, one embodiment of a simple lancet launcher 1060 comprises a compressed spring 1062 driving a moving mass 1064 that is attached to a lancet or penetrating member 1020 that pierces the skin or a targeted anatomical feature. When released (as seen in FIG. 103B), the spring 1062 accelerates the mass 1064 to a maximum speed at, or near, the point of contact between the lancet and skin. As the penetrating member 1020 pierces the skin or anatomical feature, the drive spring 1062 is extended and begins to slow the penetrating member 1020 (FIG. 103C). The lancet penetration depth is set approximately by providing an adjustable mechanical stop 1066 for the moving mass. As soon as the mass and lancet are stopped (FIG. 103D), the actuation spring 1062, which is extended by the momentum of the mass, begins to withdraw the lancet.

In some embodiments, electronic actuation methods can delay the start of the retraction, providing a dwell of the penetrating member 1020 in the skin or tissue to allow some visco-elastic setting of the skin and promoting blood yield. Electronic actuators can also withdraw the lancet slowly to allow the blood to fill the wound channel, also promoting blood yield.

One economical solution to the lancet dwell requirement is to detach the drive spring 1062 from the actuator housing, preventing extension of the spring. As illustrated in FIG. 103A, the drive spring 1062 accelerates the mass 1064 and lancet 1020 to speed, then travels with the mass as the lancet enters the skin. At impact of the mass 1064 with the travel stop 1066, the spring 1062 continues to move until it is brought to a stop in a partially compressed state (FIG. 103D). The drive spring 1062 then rebounds and carries the mass 1064 and lancet 1020 with it (FIG. 103E). By adjusting the weight and spring constant of the drive spring, the length of dwell produced by the drive spring rebound can be varied. Some control over the retraction speed can be had through adjusting the weight and damping of the drive spring.

Figure 104:
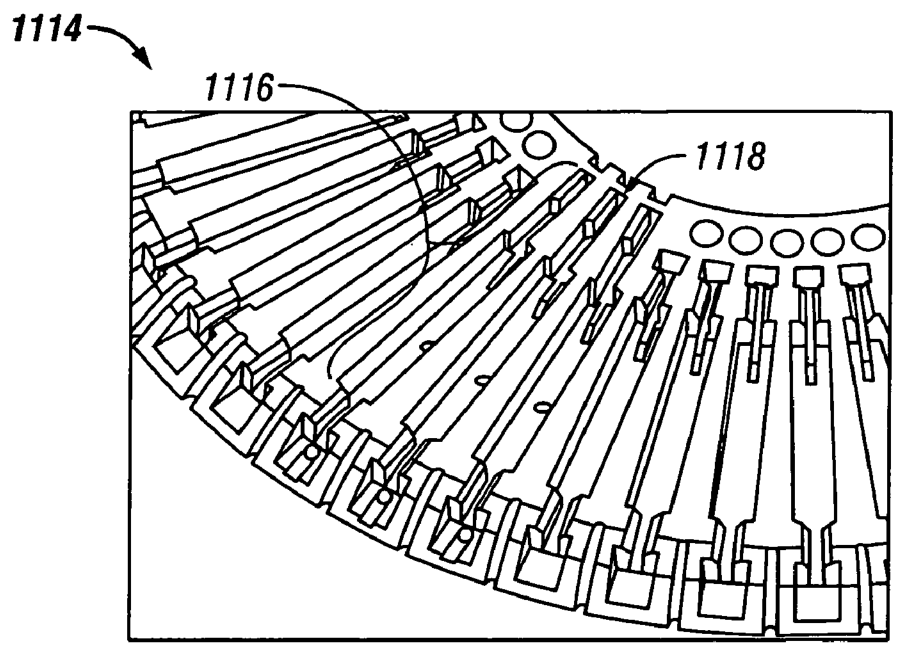

In a still further embodiment, adding a second, lower spring-constant, return spring 1070 can provide further control over the retraction speed. This return spring or return springs 1070 also insures that the penetrating member 1020 retracts into the actuator housing instead of relying on the kinetic energy of the rebounding drive spring 1070. As seen in FIGS. 104A-104C, a variety of return devices may be used. In FIG. 104A, the rebounding drive spring 1070 comprises an elastomeric element. In FIG. 104B, two rebounding springs 1072 and 1074 are used. As seen in FIG. 104C, a single spring 1076 may be coaxially mounted about the penetrating member 1020. In one regard, the embodiments shown in FIGS. 103-104 allow some control over the dwell and retraction speed of the lancet without resorting to expensive electronics. As a nonlimiting example, these embodiments of FIGS. 103-104 may provide a dwell time for a lancet while piercing skin, a slower retraction rate during lancet withdrawal, and positive retraction of the lancet. The mechanism may be purely mechanical and less costly that electronic solutions.

Figure 105:
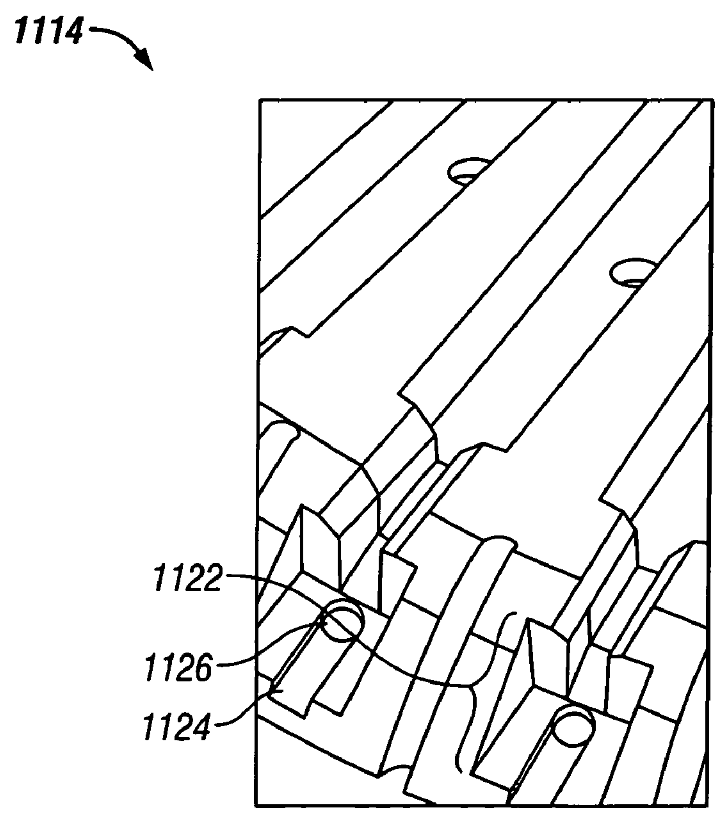
FIGS. 105-109 shows a penetrating member driver using a spring and a non-spring based retractor device.

Referring now to FIG. 105, a still further embodiment of an actuator according to the present invention will now be described. The embodiment in FIG. 105 includes an inbound drive device 1080 and an outbound retraction device 1082. As seen in the FIG. 105, the inbound drive device 1080 is in its forward position. The inbound drive device 1080 includes a plunger 1084 mounted with a spring 1086. Pulling back on the plunger 1084 pulls back on the gripper block 1088 and compresses the spring 1086. In this embodiment, a piston 1090 that slides into the damper 1092 also moves with the plunger 1084. As the plunger 1084 is pulled back, it will come to a position (not shown) where the latch 1094 engages the gripper block 1088 and holds the plunger 1084 in a launch position. A button or other linking device may be coupled to the latch 1094 to allow a user to launch the penetrating member 1020.

Moving the latch 1094 will release the gripper block 1088, release the energy in the compressed spring 1086, and drive the penetrating member 1020 towards the tissue or anatomical feature. It should be noted that in this embodiment, the open end 1096 of the damper 1092 is cone or funnel shaped. So initially, as the piston 1090 flies into the damper 1092, it is flying there through air. As the piston 1090 is advanced, it runs into a narrowed portion of the damper 1092 that provides a close fit with the piston 1090. In some embodiments, there may be an interference fit between the piston 1090 and the narrowed portion of the damper 1092. In other embodiments, elastomeric material, other damping material, damping structure, or any combination of any of these elements may be used to provide a desired deceleration velocity profile. In this nonlimiting example, the damper 1092 provides variable damping as it allows the gripper block 1088 to be accelerated to its terminal velocity, driving the penetrating member 1020 at this high velocity, before encountering the damper 1092. As the piston travels further into the damper, the damping factor may increase and provide further deceleration to the gripper block 1088, thus also decelerating the penetrating member 1020. In one embodiment, the gripper block 1088 slows to near a complete stop prior to encountering the hard stop 1098 on the carrier 1100. In some embodiments, the hard stop 1098 may be covered with an elastomeric material, other damping material, damping structure, or any combination of any of these elements to provide a controlled stop of the gripper block.

Referring still to the embodiment of FIG. 105, the outbound retraction device 1082 may use a motor 1102, or motor/gear box combination, to turn a screw 1104 and retract carrier 1100 housing the inbound drive device 1080. A switch 1106 positioned at the stop or some other sensor device may be used to indicate when the inbound stroke is completed. In other embodiments, the motor 1102 or motor/gear box combination may be activated prior to the gripper block 1088 impacting the stop or prior to the gripper block 1088 coming to a complete stop. In such an embodiment, a sensor (not shown) may be positioned at a location prior to the gripper block 1088 reaching the stop 1098 and activate the motor 1102. This may provide a further method for decelerating or braking the gripper block 1088. In some embodiments, retraction by the outbound device 1082 may be delayed for a selectable amount of time such as, but not limited to, 1-200 ms to allow the penetrating member to come to rest in the tissue. In some further embodiments, retraction by the outbound device 1082 may be initiated for a selectable distance such as, but not limited to, about 20-50 microns based on how far the screw 1104 pulls back on carrier 1126, and then stopped. It should be understood of course, that other distances such as about 50-75 microns, 75-100 microns, 100-125 microns may also be selected. This may be also used to minimize oscillation of the penetrating member 1020 against the tissue by withdrawing the penetrating member a small amount while the penetrating member 1020 is coming to rest against the stop 1096. After the penetrating member 1020 has come to a stop, it may be held for a selectable amount of time, such as but not limited to 1-200 ms and then withdrawn, or in some embodiments, it may be withdrawn without a delay period. All of the above elements may be coupled to a chassis 1108.

The depth of penetration by the penetrating member 1020 may also be determined by using the screw 1104 to control the position of the carrier 1126. This controls depth since the protrusion distance by the penetrating member 1020 from the carrier 1126 is substantially constant. Thus by varying the position of the carrier 1126 in this embodiment, the penetration depth of the member 1020 relative to the front end 1127 is selectable. The position of the carrier 1126 may be selectable before each lancing event. The position of carrier 1126 may be determined by the user. The position of carrier 1126 may also be determined by a processor (not shown) which may track the penetration depth of previous lancing events and match it with some other variable such as but not limited to pain feedback number from the user, spontaneous blood generation, user hydration, or any other variable as described in commonly assigned, copending U.S. patent application Ser. No. 10/335,215 filed Dec. 31, 2002. The screw 1104 may be controlled to provide varied depth control with resolution such as, but not limited to, about 1-5 microns, about 5-20 microns, other distance per adjustment. In some embodiments, this motor may be a stepper motor. In other embodiments, it may be an actuator such as but not limited to a pneumatic actuator, electric motor, or device with a position sensor to provide feedback as to carrier position.

Figure 106:
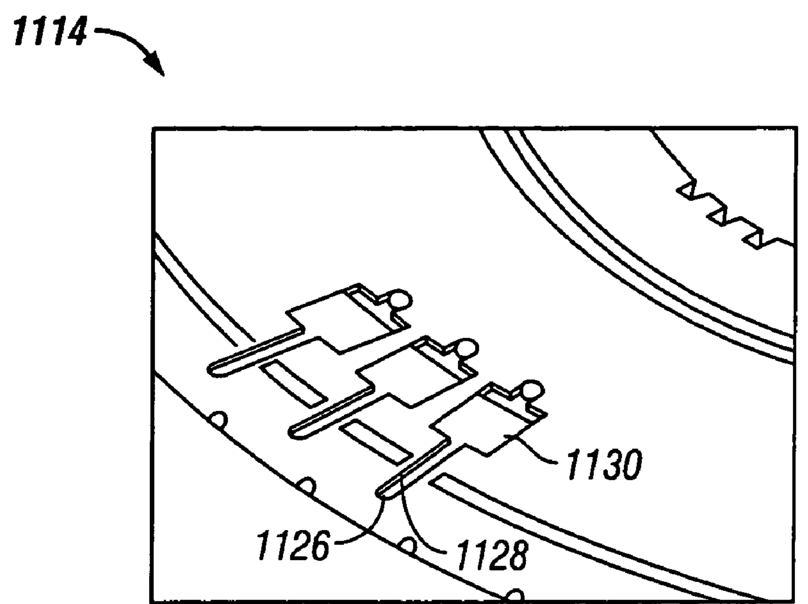

Referring now to FIGS. 106 to 109 show a still further embodiment of a device having an inbound drive device 1110 and an outbound retraction device 1112. Referring now the configuration shown in FIG. 106, the inbound drive device 1110 may include a spring 1086 coupled to a gripper block 1088. A plunger 1114 is provided for use with a damper 1116 mounted concentrically about the shaft of the plunger. A latch 1094 with a flag portion 1118 is used to hold the gripper block 1088 in a launch position with the spring 1086 compressed. As seen in FIG. 106, the penetrating member 1020 may be guided by a front bearing 1120 and a rear bearing 1122. It should be understood, that some embodiments may use one bearing, while other embodiments, may use two or more bearings. The type of clearance and support provided by the bearing may also be selectable. As a nonlimiting example, the bearings 1120 and 1122 may be structures with openings therethrough and have side-to-side clearance from about 20-40 microns and a vertical clearance from about 40-60 microns. Other embodiments may have greater clearances such as, but not limited to, about 60-100 microns, about 100-300 microns, or the like.

Figure 107:
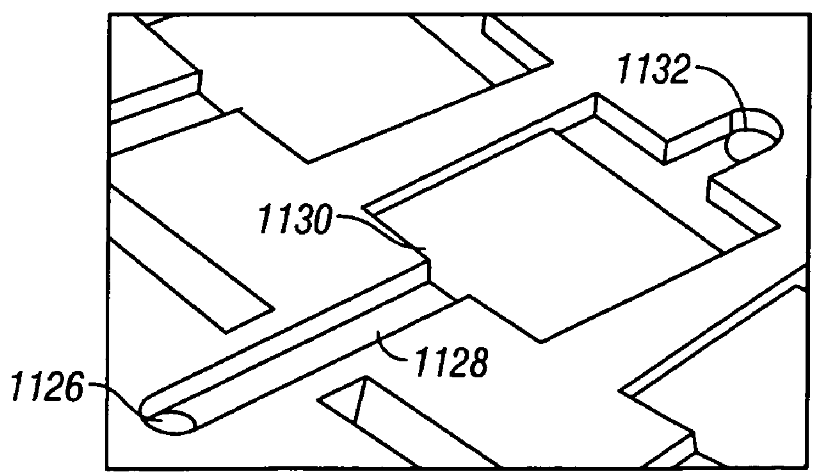

Referring now to FIG. 107, the device is now shown in a fired configuration with the penetrating member 1020 positioned fully forward; As seen, the gripper block 1088 or penetrating member coupler is now resting against the stop 1126. Prior to the gripper block 1088 coming to a rest, the damper 1116 (shown more clearly in FIG. 110) will engage the plunger 1114 to slow the gripper block 1088 prior to the block coming to rest.

Figure 108:
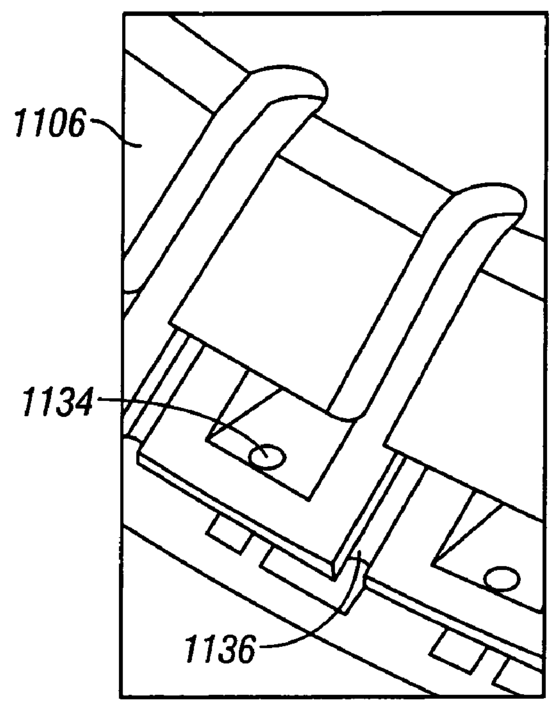

Referring now to FIG. 108, the device is now shown with the plunger 1116 and gripper block 1088 in a fired configuration. However, the entire carrier 1130 having the gripper block 1088 and plunger 1116 is retracted in the direction indicated by arrow 1132. As the carrier 1130 is drawn into the position shown in FIG. 108, the reset latch 1134 coupled to the chassis 1136 will lock into position against the gripper block 1088. With the reset latch 1134 in this position, the spring 1086 can be compressed and the gripper block 1088 moved back into its launch position by moving the carrier 1126 forward as shown in FIG. 109.

Figure 109:
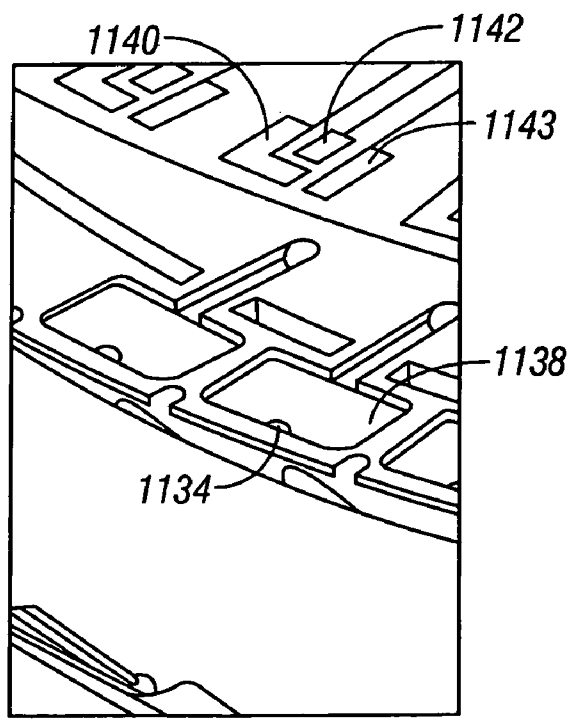

Referring now to FIG. 109, carrier 1130 is advanced as indicated by arrow 140. As the carrier 1130 is advanced by the screw 1194, the latch 1094 will ride over the gripper block 1088 and then drop into place as shown in FIG. 109. The position in FIG. 109 shows the latch 1094 locked against the gripper block 1088. A flag 1142 or cam surface offset to the side of the latch 1094 will engage a flag 1144 or cam surface on the reset latch 1134. This moves the reset latch 1134 downward, releasing the latch from its locked position against the gripper block 1088. Eventually, the reset latch 1134 will ride underneath the gripper block 1088 until the reset latch 1134 comes to rest in a position as shown in FIG. 106. In other embodiments, the reset latch 1124 may be coupled to a disposable such as a cartridge containing a plurality of penetrating members. In other embodiments, the reset latch 1134 may be attached to the same frame of reference as that of the motor 1102. It may be part of the launcher and not the disposable. As a nonlimiting example, a cantilever beam may run from the chassis portion under the motor 1102 to hold the reset latch 1134 in position, as part of the launcher and not the disposable.

Figure 110:
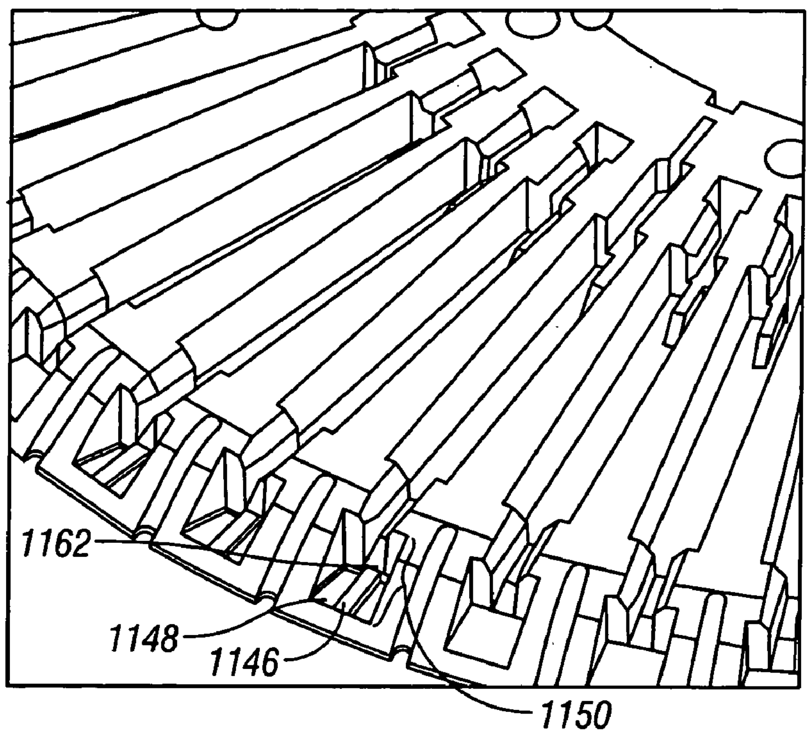
FIG. 110 shows an embodiment of a damper according to the present invention.

FIG. 110 shows an enlarged view of one embodiment of the damper 1116. The damper 1116 may have a surface 1150 that is funnel shaped and a second surface 1152 configured to engage the widened portion 1154 of the plunger 1114. It should be understood that the shape of the surface 1152 may be varied to create the desired velocity deceleration profile. As a nonlimiting example, the surface 1152 may define an interference fit with the plunger 1114. In another embodiment, the damper 1116 is made of an elastomeric material and may function to provide more resistance against motion in one direction than another. This may be due in part to the elastomeric quality of the material which forms about the penetrating member during withdrawal from the damper 1116 to hold the penetrating member in. In some embodiments, the damper 1116 is cylindrical about plunger 1114. In other embodiments, the damper 1116 may simply be two opposing surfaces 1152 and 1153, without fully surround the shaft, that provides frictional resistance to the travel of the plunger 1114.

Figure 111:
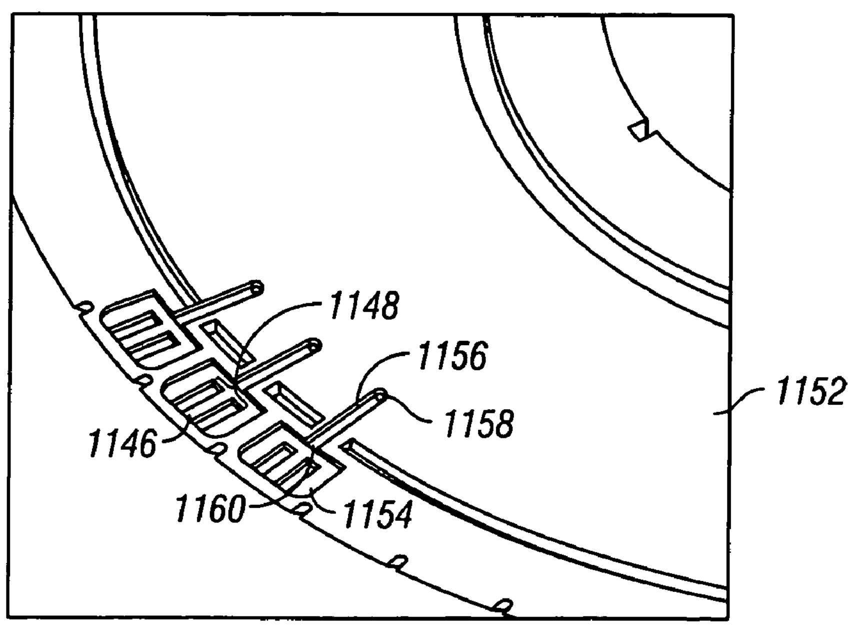
FIGS. 111-116 shows a cartridge and a penetrating member driver according to the present invention.

Referring now to FIG. 111, a cross sectional view is shown of a spring-based penetrating member driver according to the present invention. In the embodiment of FIG. 111, a gripper block 1160 is used to engage a penetrating member 1020. The gripper block 1160 is coupled to a shaft 1162 that has an enlarged end portion 1164. A drive spring 1166 is provided about the shaft 1162 and compresses between the gripper block 1160 and the protrusion 1168. In one embodiment, a second spring 1170 may also be provided and coupled to the shaft 1162 and the protrusion 1168. In such an embodiment, the second spring 1170 may be configured as a return spring to urge the penetrating member 1020 back into the cartridge after the member has penetrated tissue. In some embodiments, a soft stop 1172 may also be used to assist the return of the penetrating member 1020 into the cartridge 1173. A plunger 1174 may be pulled back in the direction indicated by arrow 1176 to place the gripper block 1160 and the penetrating member 1020 in a launch configuration. Release of trigger 1178 will cause the penetrating member 1020 to launch.

Figure 112:
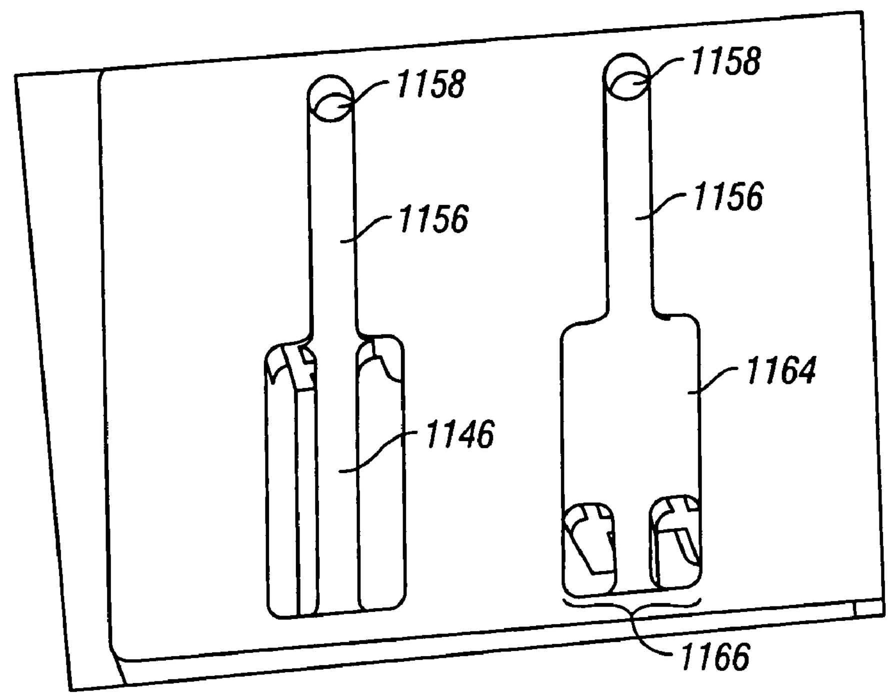

Referring now to FIG. 112, it shown that in one embodiment where the gripper block extends into the cartridge 1173, the launcher and the cartridge 1173 maybe vertically separated as indicated by arrow 1180 to allow the cartridge 1173 which may be but is not limited to a disc shape, to rotate to position an unused penetrating member into contact with the gripper block 1160. Vertically separating the parts allows the cartridge 1173 to be rotated without the gripper block 1160 interfering. In other embodiments, the gripper block may be designed so that the penetrating member has a portion that extend upward to engage the gripper block. In still other embodiments, the separation between the cartridge and the launcher may be such that gripper block remains in the cartridge but travels in a radial groove and is lifted enough to allow an unused lancet to be rotated into position. Vertical separation as shown in FIG. 112 may involve the user physically pulling the parts away from each other or using cam surfaces such as those shown in FIG. 55A.

Figure 113:
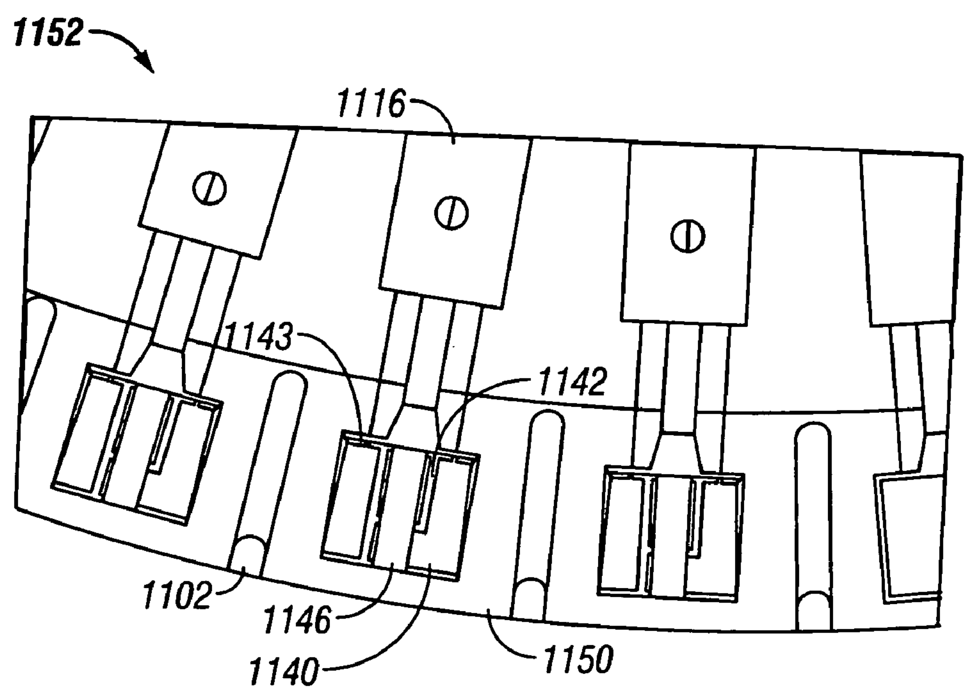
Figure 114:
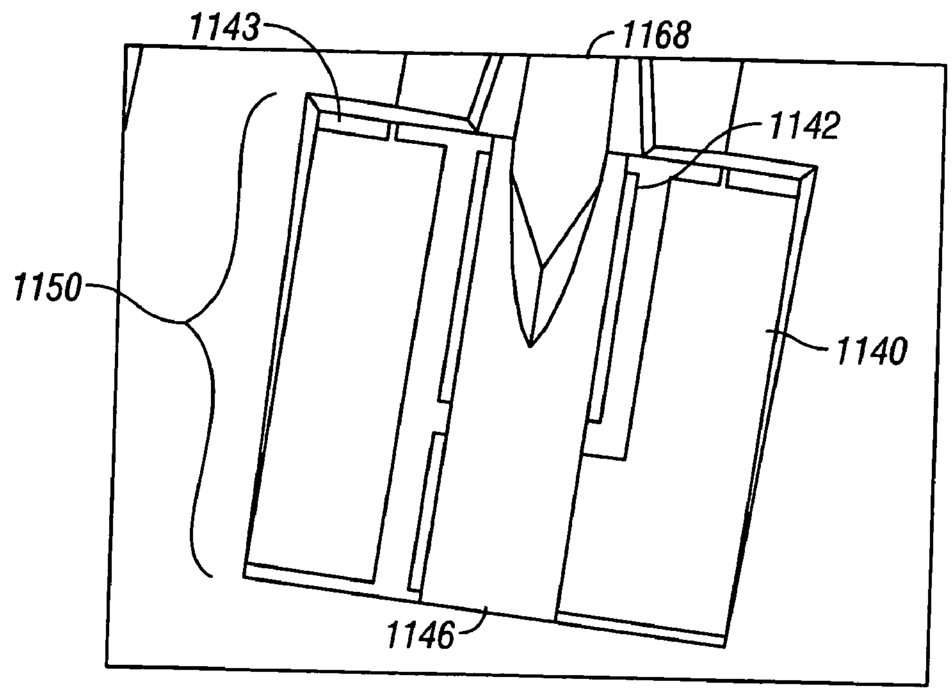

Referring now to FIG. 113, a still further embodiment is shown where a cartridge 1200 is shown in a cylindrical configuration. A penetrating member driver 1202 will be used to engage the penetrating members in the cartridge 1200. As a nonlimiting example, the driver may be an electromechanical device, a mechanical, spring-based device, or other actuator as described herein. Each cartridge 1200 may be rotated clockwise or counterclockwise to position the penetrating members into active alignment with the driver 1202. After each cartridge 1200 is ready to be disposed, it may be moved forward as indicated by arrow 1204 and ejected from the sampling device. Another cartridge 1206 shown in phantom may be move forward by techniques using, but not limited to, a stepper motor, mechanical slider, or gravity to replace the used cartridge 1200. FIG. 114 shows a still further embodiment wherein the penetrating member driver 1202 is positioned to be within the center opening of cartridge 1200 to engage each penetrating member. As a nonlimiting example, the cartridge 1200 may be advanced by a stepper motor (not shown) or a mechanical slider mechanism to position an unused penetrating member into alignment with the driver 1202.

Figure 115:
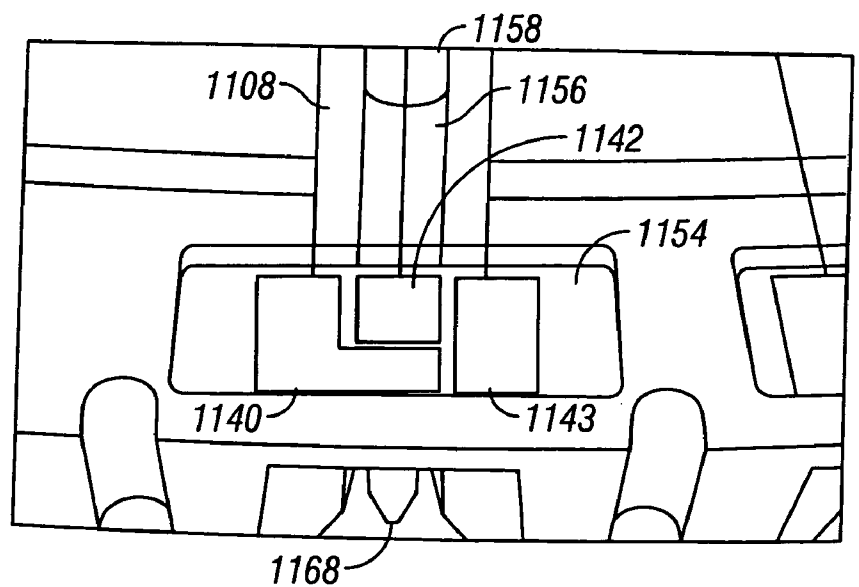
Figure 116:
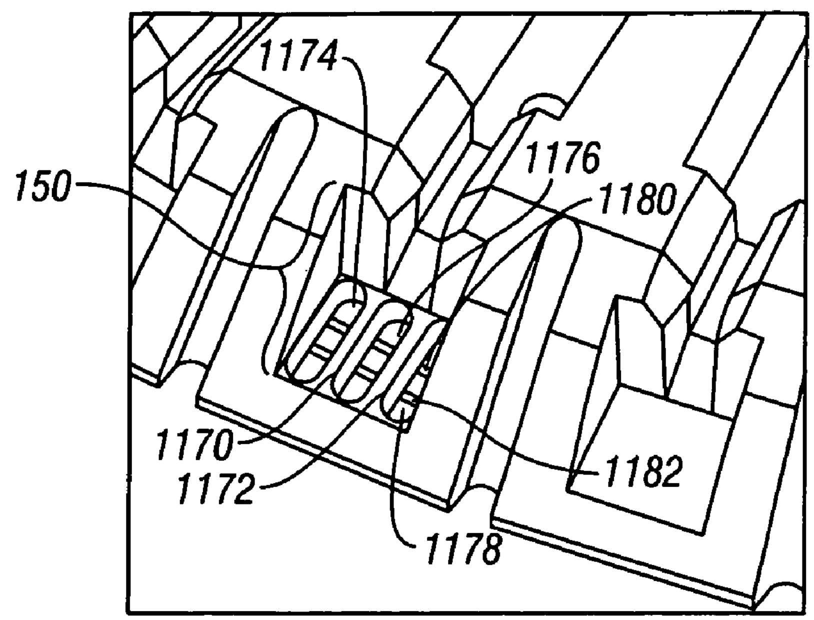

Referring now to FIG. 115, the number of penetrating members remaining in the cartridge 1210 may be determined using a variety of devices. The cartridge 1210 may have markings or notches 1212 detectable by device 1214 which will keep count of the number of penetrating members used. In other embodiments, a processor 1216 will track the number of actuations and use that number to determine the number of penetrating members that remain unused in the cartridge 1210. In such a configuration, the processor 1216 may assume that a new cartridge 1210 will contain X number of penetrating members and each actuation will reduce the number of unused penetrating members. Each time a new cartridge 1210 is loaded, the processor will assume that there are a full X number penetrating members available. The processor 1216 may also be coupled to the device 1214 to determine when the cartridge 1210 is rotated. FIG. 115 also shows in phantom that a display 1218 may also be included to show the number of penetrating members remaining or other applicable variables to spring-based penetrating member driver 1220 as disclosed in commonly assigned, copending U.S. patent application Ser. No. 10/10/335,215 filed Dec. 31, 2002. The device may include a slider for rotating the cartridge 1210 as shown in FIG. 56A and/or buttons to adjust settings on the display. As seen in FIG. 115, a plunger 1222 (shown in phantom) may be extended to protrude outward from a rear portion of the housing. In some embodiment the driver or just the plunger 1222 may extend above a top surface of the housing as seen in FIG. 116.

Figure 117:
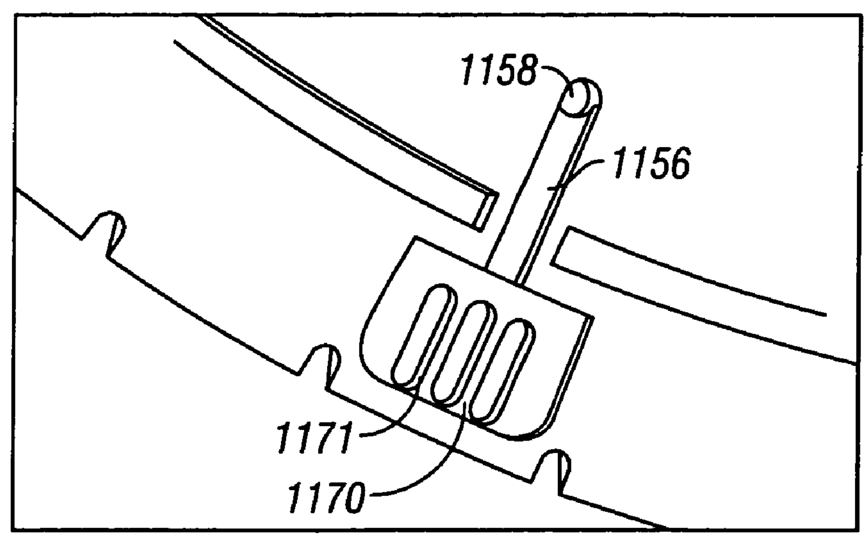
FIGS. 117 and 118 show penetrating member drivers according to the present invention.
Figure 118:
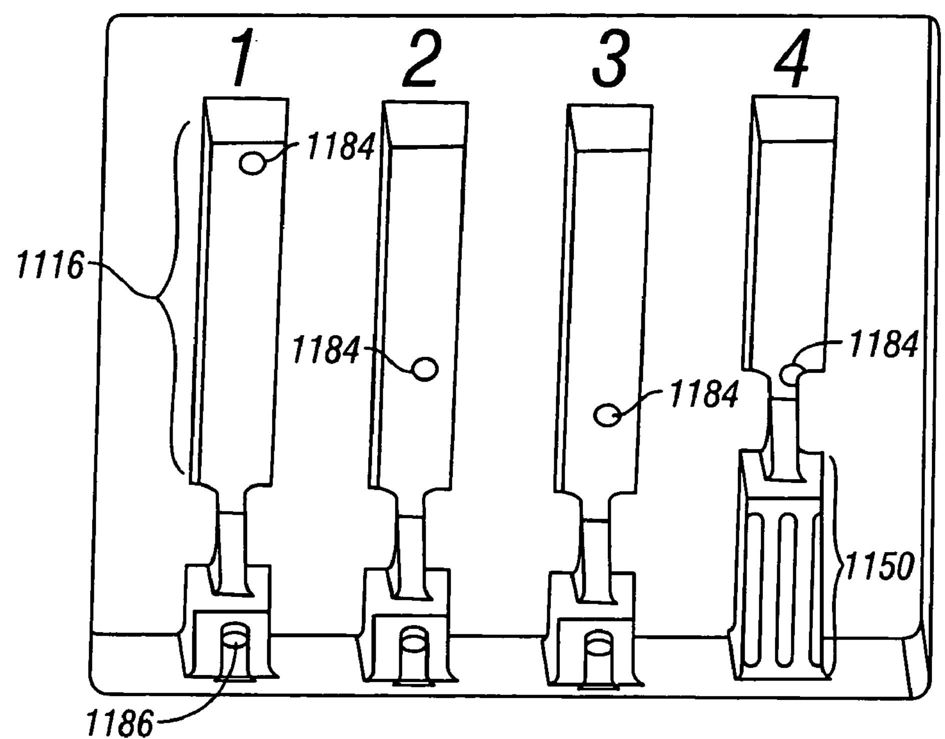

Referring now to FIGS. 117 and 118, still further combinations of mechanical and electrical actuators are shown. In one embodiment, FIG. 117 shows an electric driver 1230 for advancing a gripper block or coupler 1232 in the direction indicated by arrow 1234. A spring 1236 will be extended when the gripper block 1232 is moved. The spring 1236 will provide the retraction force and draw the gripper block 1232 and attached penetrating member back. In this embodiment, the electric driver 1230 will be relaxed or turned off after actuation, thus allowing the spring 1236 to draw the gripper block 1232 back.

FIG. 118 shows another embodiment where, in the launch configuration, the spring 1236 is extended and the electric driver 1240 is in a forward position. From this forward position, the driver 1240 may advance the penetrating member 1020 into targeted tissue. After reaching desired depth, a trigger 1242 will release the driver 1240 and pull the entire driver 1240 and penetrating member 1020 in the direction indicated by arrow 1244. In some embodiments, this withdrawal motion may occur prior to the electric driver finishing its forward stroke.

Figure 119:
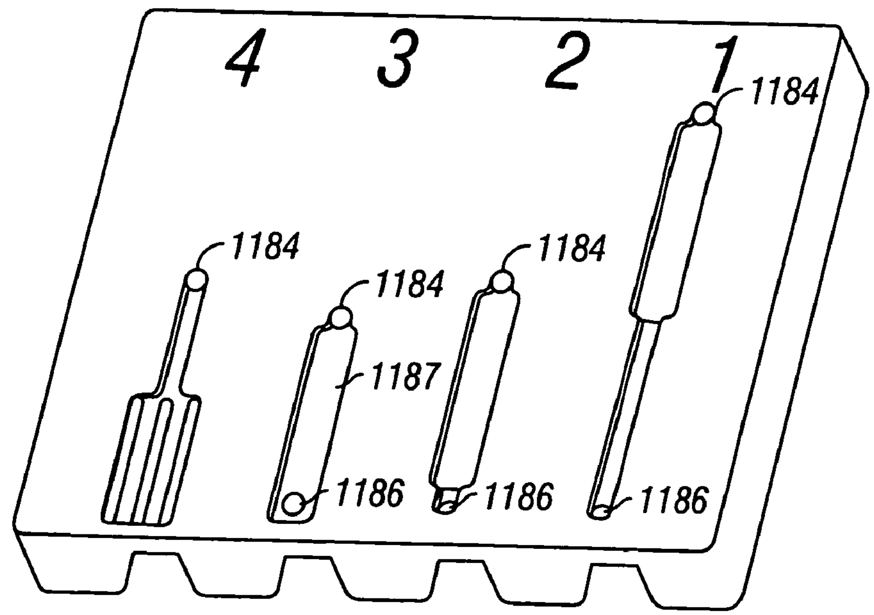
FIGS. 119-120 show a depth setting device according to the present invention.
Figure 120:
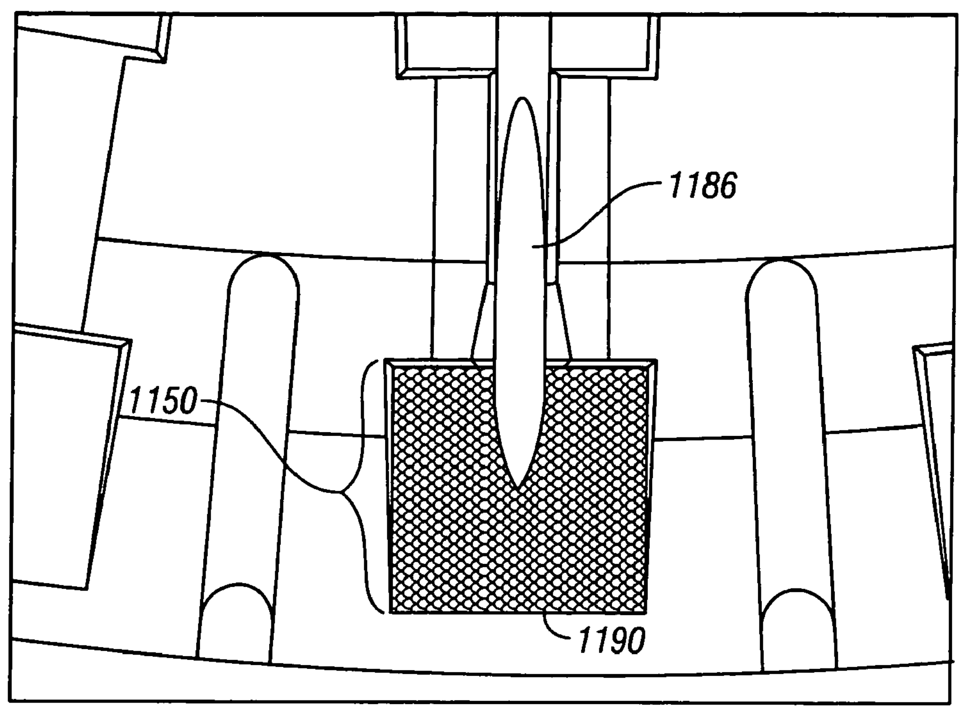

Referring now to FIGS. 119 and 120, further embodiments of the present invention are shown where the depth of penetration into tissue may be set, in part, using a front end apparatus 1250. The front end apparatus 1250 is rotated as indicated by arrow 1252. Rotation in either direction will adjust the vertical separation 1254. This vertical separation 1254 will change how close tissue may be placed against the sampling device. The greater the vertical separation 1254, the less the penetrating member will protrude outward, and the less the penetration depth. FIG. 120 shows an embodiment where the front end apparatus 1250 is recessed. This front end apparatus 1250 may be used with any of the penetrating member drivers described herein.

Figure 121:
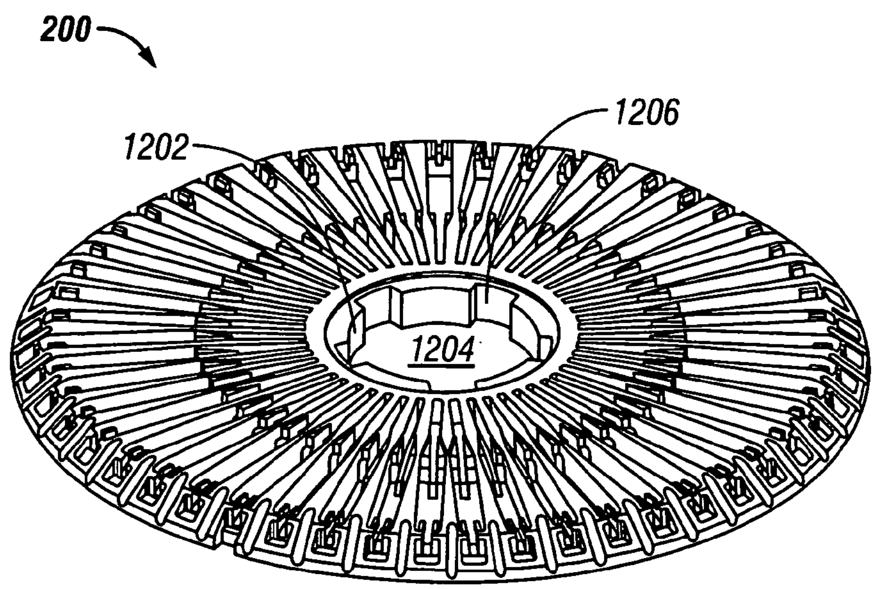
FIG. 121 shows a cam groove according to the present invention.

Referring now to FIG. 121, a still further aspect of a drive mechanism according to the present invention will be described. FIG. 121 shows a cam groove 1260 that is followed by penetrating member driver. As a nonlimiting example, the driver may be a spring based device. The driver has a protrusion or follower that will follow the path provided by the cam groove 1260 to provide a desired velocity profile. One known device which also uses a cam groove is disclosed in U.S. Pat.

No. 5,318,584, fully incorporated herein by reference. The follower 1262 indicated by a circle will follow the groove downward on the inbound stroke portion 1264. After reaching maximum penetration, the follower 1262 will travel along the return portion 1266. This return portion will provide a slower return velocity as the groove 1260 is configured at a shallow slope that requires the follower 1262 to follow a longer path that may bring the follower around the backside of the cylinder as indicated by arrow 1268. This profile can provide a fast-in, slow-out velocity profile desired by some embodiments of the present invention. As a nonlimiting example, the return velocity may be ½, ¼, or any other fraction, percentage or portion of the inbound velocity.

In yet another aspect of the present invention, the current engine functions as a variable reluctance device and may be composed of an electronic drive unit or solenoid, an optical position sensor and a mechanism to couple the whole to the lancet. As a nonlimiting example, the penetrating member actuator may comprise of 2×6800 mF capacitors, a CR 123A 3V lithium primary battery, and a 5-coil solenoid of 30 G wire. In this embodiment, there is one circuit board, which contains a processor (MPS430) for controlling the user interface, and another processor (SX 28) controlling the drive coils. The penetrating member may be driven by a series of solenoid coils (of which currently there are five in this embodiment), which are enclosed in a coil pack and surround the coupler shaft proximally to the penetrating member. A magnetic bead or "slug" may be attached to the coupler shaft and is configured to slide within the axial lumen of the driver coils. The driver coils are made of windings of copper wire, such as but not limited to about 32 gauge. The coils or "solenoids" drive the penetrating member using either magnetic attraction or repulsion of the slug.

Several possibilities exist for modification of the current solenoid drive. The specific advantages to be achieved are a reduction in size, and increase in efficiency, thus reducing power consumption requirements during the lancing process.

In one embodiment of the solenoid according to the present invention, a five-coil configuration was conceived because of a desired stroke distance of 8 mm determined from a displacement range needed to cover the sum of thick stratum corneum (up to 600 mm), tenting of about 1 mm or more and a maximum penetration of up to about 3.5 mm and acceleration distance enough to reach about 10 m/s. Stroke may be specified as the total displacement from one end of travel to the other end, or as a plus/minus (±) displacement from mid-stroke reference. Since these experiments were carried out it has been determined through patient testing in the lab that shallow lancing to about 1 mm may be sufficient to obtain the volumes of blood required to fill a sample chamber of 0.5 μl or less. Stroke distance, in such an embodiment, can therefore be reduced to (maximum tenting+depth+thickest stratum corneum=1 mm+1 mm+0.6 mm) 2.6 mm without consequence. This could reduce the number of coils in the system, reducing the size of the device and therefore lowering cost. It does require a slightly "fatter" set of coils since more turns may be used to maintain the drive power as well as a change in the slug size (longer) to reach the new spacing distance, but overall size should decrease.

In another embodiment of the solenoid, the flat coil embodiment was initially proposed as the first approach for driving the lancet electronically. In one embodiment, it uses a metal flag be attached to the penetrating member shaft to drive the lancet rather than a metal "slug". This is somewhat disadvantageous to using bare penetrating members. The motivation for the flat coil configuration was miniaturization of the driver so as to fit in to a handheld glucose spot-monitoring device. Manufacturing of the coils can be by multi-layer printed circuit board (PCB) so it is straightforward. Such an embodiment is shown in commonly assigned, copending U.S. patent application Ser. No. 10/127,395.

In yet another embodiment of the solenoid, the multi-coil penetrating member driver with programmable excitation of the various energizing coils acting on a movable soft-iron "slug" works by timing the excitation of the various coils to provide motion in the desired direction. In some known configurations, there may be a series of stable "dead points" where the slug remains stationary unless the local coil is de-energized and the next coil is energized. This can create an inefficient "bumpy" force profile. The "rail-gun" approach provides a coil configuration for continuous (as opposed to step-wise) acceleration of the magnetic slug. It creates the required inhomogeneous magnet field to propel the slug and the attached lancet at a progressively increasing speed towards the target. At no point does the magnetic field of the coil oppose the desired motion of the slug. It facilitates the "fast entry—delay—slow retraction" mode of operation for minimum pain and maximum blood recovery. The coil could be wound with an increasing number of turns from the start point to the end point creating the required non-uniform magnetic field profile. A second coil could be wound in the remaining "free" space with increasing turns from the insertion point to the fully retracted point to implement retraction of the lancet, preferably at slow speed, using a weaker current feed. This economizes on electric drive power demand and uses the available space to the best advantage. Any desired time-dependent-profile could be achieved with spatially uniform winding geometry and a programmable time-dependent current feed with current increasing with time for insertion, but decreasing with time for retraction.

The excitation coils may also be divided into a set of adjacent smaller coils fed with increasing currents from start point to end point, either according to position or as an increasing function of time. Continuous acceleration (as opposed to a step-wise drive with separate coils in the prior-art multi-coil device) may favor long slim coil geometry. One practical advantage is simplicity: in the basic embodiment no electronic control circuitry is required, just a simple on-off current switching control. However it allows electronic control to be added to determine penetration depth, using appropriate depth sensing and feedback. A fail-safe feature would be to feed the retraction coil with a weak continuous current to ensure that the lancet is always returned to the start position (full retraction). The soft-iron slug attached to the penetrating member may be replaced by a small permanent magnet attached to the penetrating member. Additional disclosure can be found in commonly assigned copending U.S. patent application Ser. No. 10/127,395, incorporated herein by reference.

In another embodiment, slug shaping is based on the goal of increasing the force or efficiency of the coils by sculpting or changing the profile of the slug. The chisel point slug also fits in this category. The net result may be to reduce the size of the coil driver.

In one other embodiment, having two slugs in the field rather than one might increase the sensitivity to position and would require half of the energy. In addition large variations in force could be avoided making the control system more predictable and stable.

In yet another embodiment using a high voltage drive, this is a size reduction play by substituting the two-capacitor drive with a single smaller capacitor. The rationale for the dual capacitor drive is that the resistance drops for the two capacitors in parallel and the circulating currents in the coils should be reduced. Substitution of a single capacitor will result in an increase in resistance and hence the current requirement goes up and therefore there is a loss of efficiency of charge storage because of the increase in the voltage drop.

Figure 122:
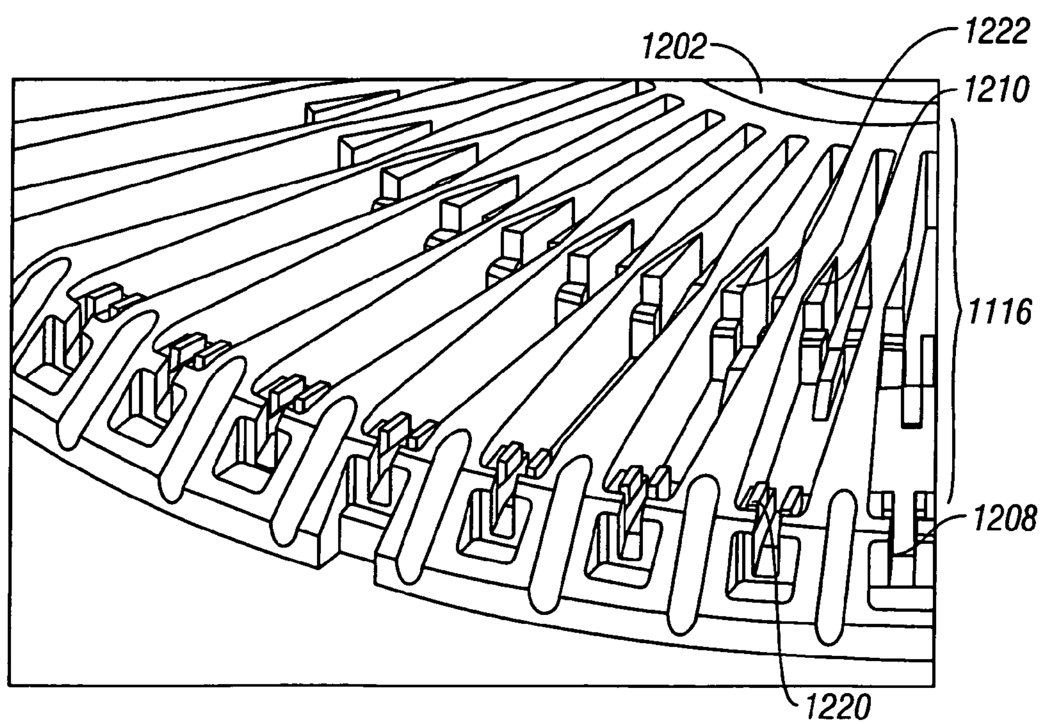
FIGS. 122-124 show various penetrating member devices according to the present invention.

In a further aspect of the present invention, a mechanical inbound/electric withdrawal configuration may be used for penetrating member actuation and withdrawal. FIG. 122 shows such an embodiment. Cheap mechanical actuation such as spring or cam drives 1300 may be supplemented by electronic withdrawal device 1310 for slow out retraction of the penetrating member 1020. All of the embodiments below can be hybridized with a mechanical spring or cam driven inbound actuation. The mechanical inbound drives 1300 may be used with a soft braking mechanism such as but not limited to a soft stop 1312 or any other damping device disclosed herein or known to one of skill in the art. In the embodiment shown in FIG. 122, the withdrawal device 1310 may be used to move the entire carrier 1314 having the mechanical inbound drive 1300. The use of electric withdrawal of a penetrating member 1020 from the anatomical feature at velocity less than that on the inbound may be used to increase the likelihood spontaneous fluid generation from a wound created in the feature. These components may all be contained in a housing 1320 (shown in phantom) that may optionally include an adjustable front end 1322 for adjusting depth of penetrating member penetration.

Figure 123:
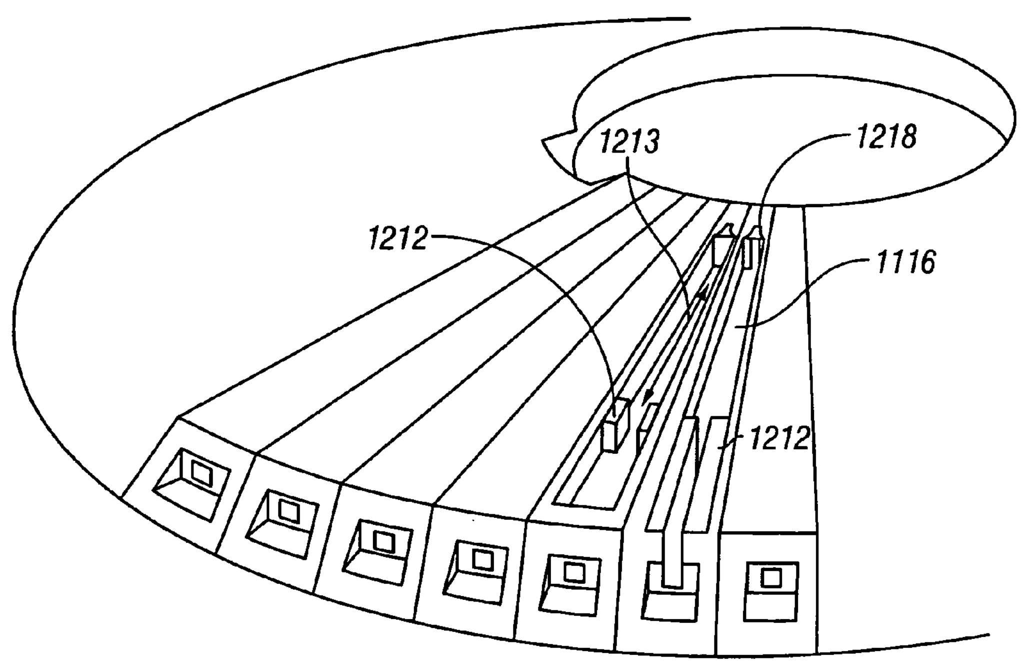

Referring now to FIG. 123, the device 1310 is not coupled to the carrier 1314. It maybe used to withdraw the spring launched penetrating member 1020 as indicated by arrow 1324. This allows the spring device to be pulled back and in some embodiments, reset for the next lancing event. It should be understood that the soft stop 1312 may also be configured to be on both sides of the penetrating member as shown in FIG. 122.

In one embodiment of the present invention, a DC Gear motor may be used as the device 1310. In an embodiment similar that shown in FIG. 102, spring actuation or dashpot can be used for the inbound and the spring stays compressed against the dashpot. The motor 1042 drags the dashpot back and compresses the spring on its way. It can even re-cock the spring. This is a small DC motor with a speed reducing gear head. The DC motor can drive a jackscrew such that the withdrawal can be achieved in small steps as required by switching the motor on and off (see 1042). Position feedback may be used for better control. These motors are cheap and mass manufactured for cameras, toys and therefore this would be a cost reduction play.

In yet another embodiment of the present invention, a stepper motor may also be used as the device 1310. The stepper motor can replace the gear motor and tend to run at a lower speed. It can run open loop so that position feedback would not be required. These motors are precise and would give a more compact package and better control method. In yet another embodiment of the present invention, a inductive motor may be used. This was the very first concept investigated for driving the lancet due to its ability to move penetrating members at high speeds and large throw. Unfortunately it is not very efficient due hysteretic losses, and the control problem is complicated.

In yet another embodiment of the present invention, a nanomuscle may be used as device 1310. Nanomuscle actuators are based on shape memory alloys, that, when heated, their crystalline structures change and this result in mechanical contraction. Current is passed through the alloys to heat them. They claim to be over five times more efficient than a DC micro actuator of the equivalent size, faster and lighter. In one embodiment, they are about the size of a paperclip and are capable of 1,000,000 actuations. There are also supposed to produce rated force over their entire trajectory and allow position, speed and force to be controlled. In one embodiment, the extent of the nanomuscle stroke is about 4.0 mm, which should be enough to cover shallow lancing depth for a range of skin types. For a higher displacement or throw, several nano-muscles could be placed in series, thus raising the cost. Power consumption in the nanomuscle actuator is much less on the retraction phase than the actuation phase, which is why these devices were suggested for lancet withdrawal.

In yet another embodiment of the present invention, a liquid magnetic coil may be used as device 1310. Energy stored in a compressed spring, gas, or other means is released to actuate a penetrating member towards the skin or an anatomical feature. In one nonlimiting example, the velocity trajectory of the penetrating member is controlled by an iron-loaded fluid that changes viscosity in response to an imposed magnetic field. The current can be switched on when a desired slowing in the spring withdrawal (or inbound trajectory—see below for details and drawing) to produce a controlled withdrawal profile. The withdrawal profile could be computer controlled so that switching on the field occurs in a specified pattern to simulate the best profile.

In yet another embodiment of the present invention, a electromechanical hybrid may be used. As a nonlimiting example, cheap electronic drive for inbound (hybrid spring and magnetic fluid), combined with cheap electronic for withdrawal using the same hybrid design may be a way to design a cost effective device with performance requirements to achieve low pain and spontaneity. Alternatively a motor can be used to control the retraction rate of the lancet from the skin if it is more cost effective or performs better on the withdrawal phase. Many miniaturized motors tested have been deficient in either the inbound speed or the throw, so it may be that two different engine types will have to be contemplated to achieve the speed and throw of the current design.

In yet another embodiment of the present invention, a hybrid liquid magnetic coil may be used. A version of the hybrid electromechancial device for both actuation and retraction is shown below. The electromagnetic field generator 1052 is coupled to a power source 1054 controlled by a processor 1012.

Some embodiments of the present invention may also be configured to use a mechanical inbound with slow mechanical withdrawal or outbound device. As a nonlimiting example similar to that used with a cassette player lid, a dashpot device and would be coupled with a spring. This is a WYSIWYG system, so withdrawal will be at a (uncontrolled) uniform rate. No user definable withdrawal profile is the disadvantage of this set up.

In another nonlimiting example, a wax or other material with high thermal coefficient of expansion could be heated. As it expands and displaces a piston, it is coupled to a mechanism to withdraw the lancet. Similar to nanomuscle in actuation by heating.

In a still further nonlimiting example, a piezo electric bending mechanism may be used. There are electromechanical transducers that possess high motion and voltage sensitivity. Generally in motor applications two piezoelectric sheets are bonded together, one layer expands laterally and the other layer contracts when an electric field is applied. The opposing strains result in a deflection, which is proportional to the applied voltage, generating a displacement at low levels of electrical drive.

In a still further nonlimiting example, a traction drive may be used. A spinning rubber tire running at constant speed driven by DC motor drives a flat plate in contact with its outer circumference to withdraw the lancet and compressing the actuation spring. This can be used in the same manner to actuate as well as withdraw the device.

Figure 124:
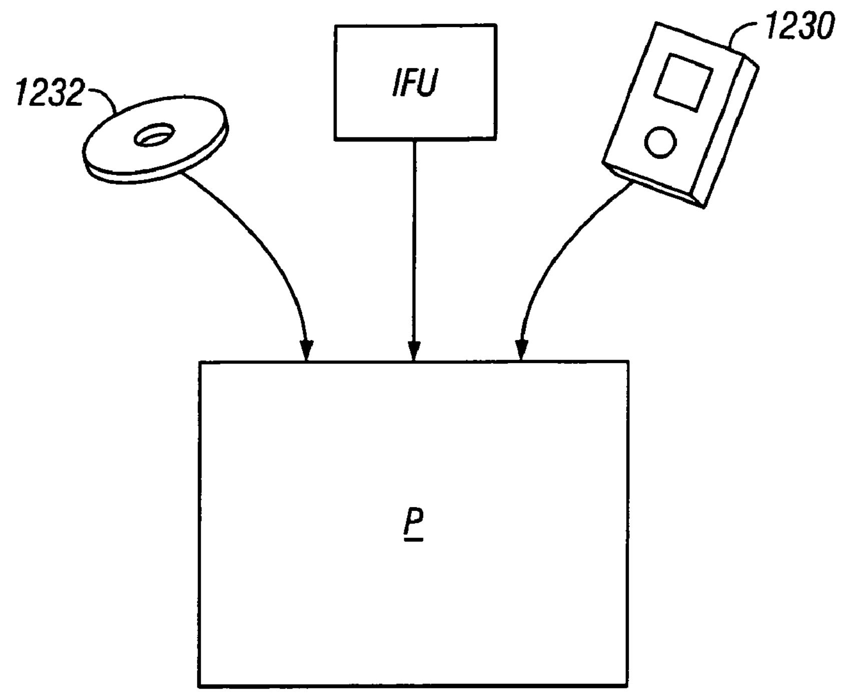

FIG. 124 shows a schematic view of a penetrating member driver 1350 where the drive may be, but is not limited to, a nanomuscle, a liquid magnetic coil actuation, a stepper motor, a micro-clutch device, and an inductive motor. The driver 1350 may be used to provide both inbound and outbound motion for the penetrating member 1020 attached to a coupler 1034.

Figure 125:
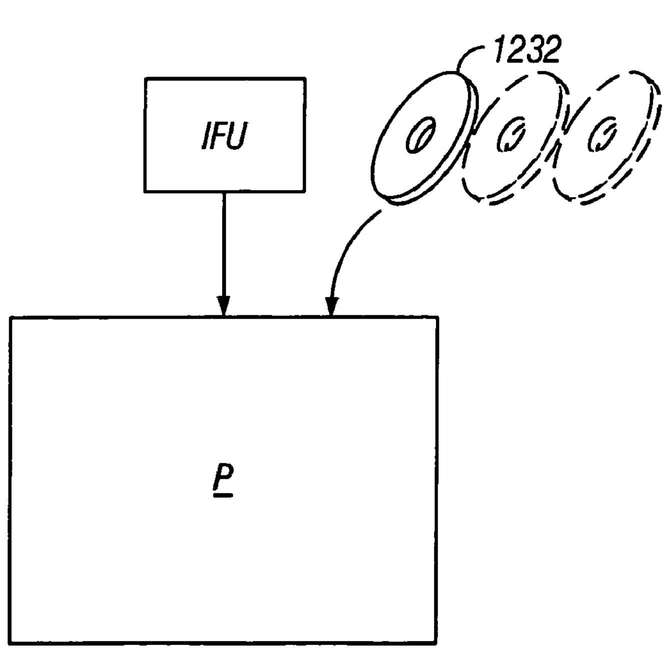
FIGS. 125A-125B show kits according to the present invention.
Figure 126:
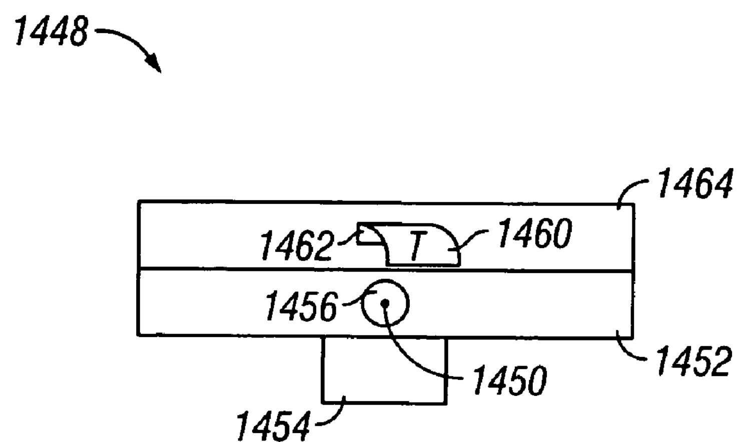
FIGS. 126-129 show embodiments of the present invention according to the present invention using a test strip.

Referring now to FIGS. 125 and 126, embodiments of the present invention may comprise kits containing any of the penetrating member actuators 1430 disclosed herein. The kit may further include instructions for use IFU setting forth any of the methods described above. Optionally, the kit may further comprise a cartridge containing a plurality of penetrating members. The cartridge 1432 may be of any of the embodiments disclosed herein. Usually, the kit components will be packaged together in a pouch P or other conventional medical device packaging, such as a box, tray, tube, or the like. In many embodiments, the cartridge will be disposable. The cartridge 1432 may itself be contained in a separate pouch or container and then inserted into the container P. In some embodiments, the IFU may be printed on the container P. In a nonlimiting example, the container P may only contain an actuator 1430, without the cartridge 1432.

Referring now to FIG. 125, embodiments of the present invention may include kits that only include a cartridge 1432. IFU may also be included. In some embodiments, a plurality of cartridges 1432 (shown in phantom) may be included. Any of the elements in these figures or other elements described in this application may be placed in the container P, singly or in any combination. It should also be understood that the cartridges maybe of any shape as disclosed herein and are not limited to disc shaped embodiments.

Referring now to FIG. 126, a still further embodiment according to the present invention will now be described. FIG. 126 shows an embodiment of a sampling device 1448 having a plurality of penetrating members 1450 housing in a cartridge (not shown) in the housing 1452. The penetrating members 1450 may be operatively coupled to a penetrating member driver 1454 to extend the penetrating member 1450 from a penetrating member exit 1456. In this embodiment, a test strip 1460 may be extended outward from a opening 1462 in a housing 1464. It should be understood that in some embodiments, the housing 1452 and housing 1464 may be integrated together into a single housing. In other embodiments, the housings 1452 and 1464 may be separate devices that are coupled together. They may rotate in the same direction or in some embodiments may rotate in opposite directions. The housing 1464 may have its own slider or actuator for extending the test strip 1460 out from the housing 1464. The test strip may be of a type known to those of skill in the art for measuring analytes in a body fluid. One suitable device suitable for a housing 1464 is described in U.S. Pat. No. 5,854,074 to Charlton et al., fully incorporated herein by references for all purposes. Although not limited to the following, the penetrating member driver 1454 may be a spring based launcher or any of the driver or combination of drivers disclosed herein.

Figure 127:
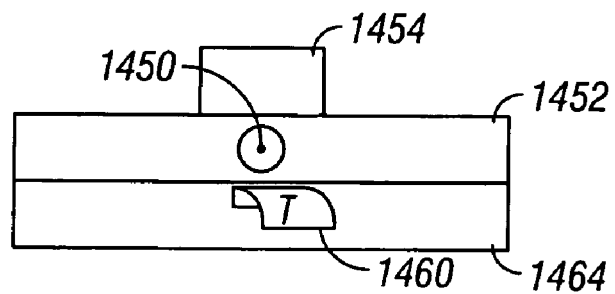
Figure 128:
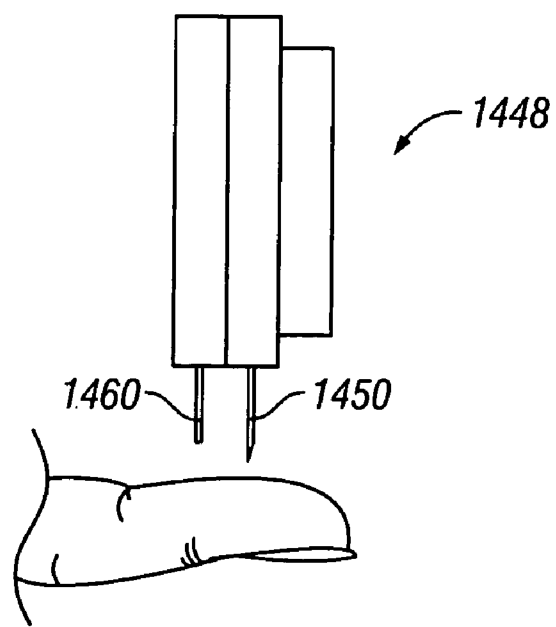
Figure 129:
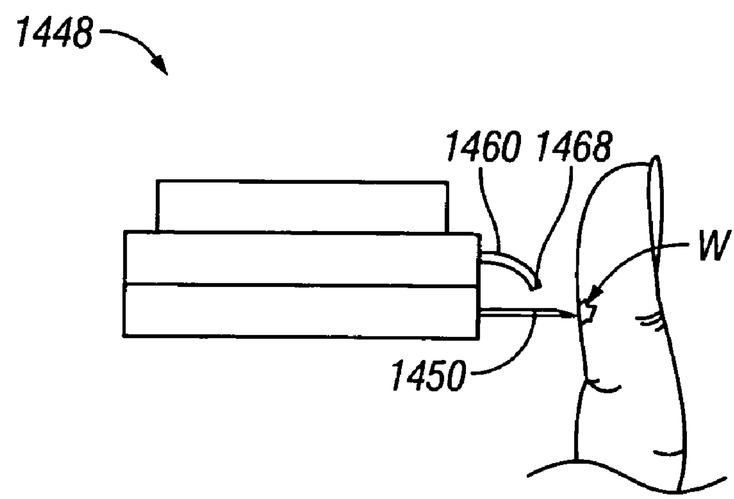

FIG. 127 shows that the device of FIG. 126 may also be configured so that penetrating member 1450 is on top while the test strip 1460 is on the bottom (when held horizontally). FIG. 128 shows that the device 1448 may be used in a vertical orientation. FIG. 129 shows that the device 1448 may also be used in a horizontal orientation. As seen in FIG. 129, the test strip 1460 may be made of flexible material such as a polymer or other material as known to those of skill in the art. This may allow gravity to bend the strip 1460 as shown in FIG. 129 to bring the strip closer to the wound W on the tissue. Although not limited to the following, some embodiments of the test strip 1460 may have a capillary channels, tubes or members to draw fluid into the test strip 1460. Wicking members, wicking materials, or absorbent materials may also be used in other embodiments of the test strip or any of the above may be combined in any order on a test strip. In some embodiments, the test strip 1460 may be oriented to extend outward at a diagonal, relative to the penetrating member, so that the distal end of the strip 1460 will be brought closer to the wound created by the penetrating member.

Figure 130:
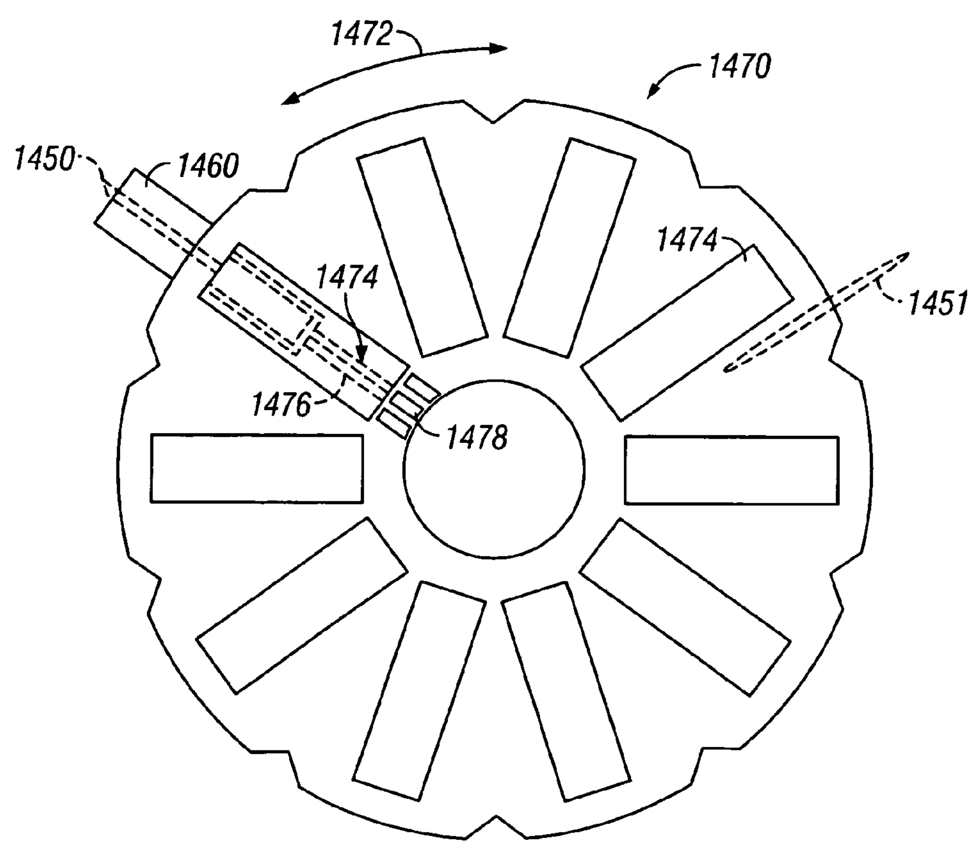
FIG. 130 shows one embodiment of a cartridge according to the present invention.

Referring now to FIG. 130, one embodiment of a cartridge 1470 according to the present invention and suitable for use with device 1448. The cartridge 1470 may be rotated as indicated by arrow 1472. One suitable device suitable for cartridge 1470 is described in U.S. Pat. No. 5,854,074 to Charlton et al., fully incorporated herein by references for all purposes. In one embodiment, the test strip 1460 may be ejected from the sealed container area 1474 to engage fluid from the wound. After use, the test strip 1460 may be removed from the cartridge or it may be reinserted into the cartridge. In some embodiments, the test strip 1460 may be coupled to electrode leads 1476 which extend back to contact pads 1478 that allow an analysis device to receive signal from a test strip. In one embodiment, a penetrating member 1450 (shown in phantom in FIG. 130) may be associated with each test strip 1460. In some embodiments, the penetrating member 1450 may be in the same cartridge 1470 or in a separate cartridge in other embodiments. It should be understood that the cartridge 1470 may be modified to include the features o the device disclosed in U.S. Pat. No. 5,854,074 to Charlton et al. In other embodiments, the penetrating member 1451 may be aligned to one side or the other of container 1474.

Figure 131:
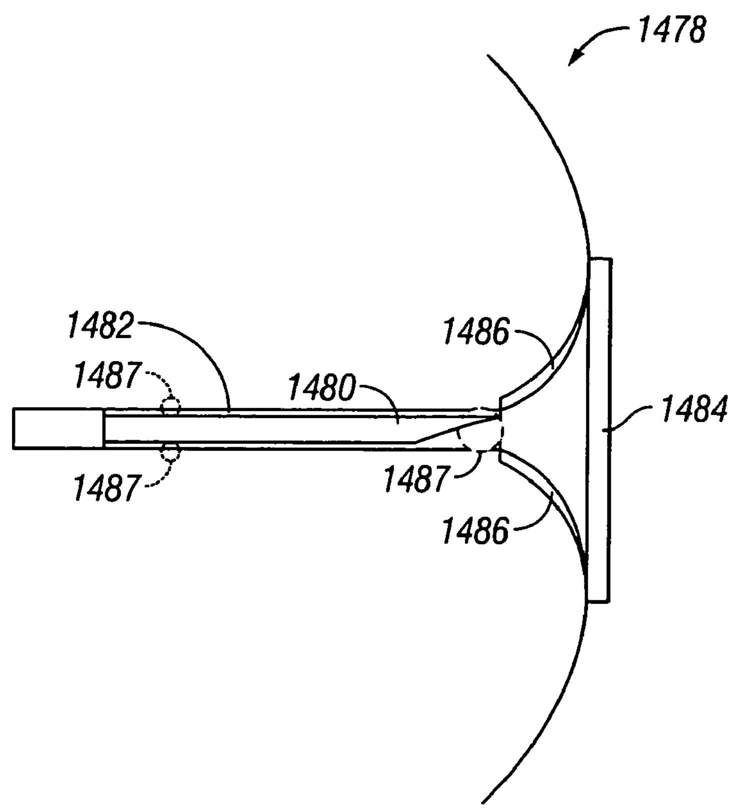
FIGS. 131 and 132 shows a top down view and side view of another embodiment according to the present invention.

Referring now to FIG. 131, a still further embodiment of the present invention will now be described. A penetrating member 1480 is housed in a cavity 1482. A sterility barrier 1484 is used to maintain the penetrating member 1480 and analyte detecting members 1486 in a sterile environment. In some embodiments, these analyte detecting members 1486 may be coupled to electrode leads to bring signals to an analyte measurement device. In still further embodiments, one or more fracturable seals 1487 (shown in phantom) may be included with the device.

Figure 132:
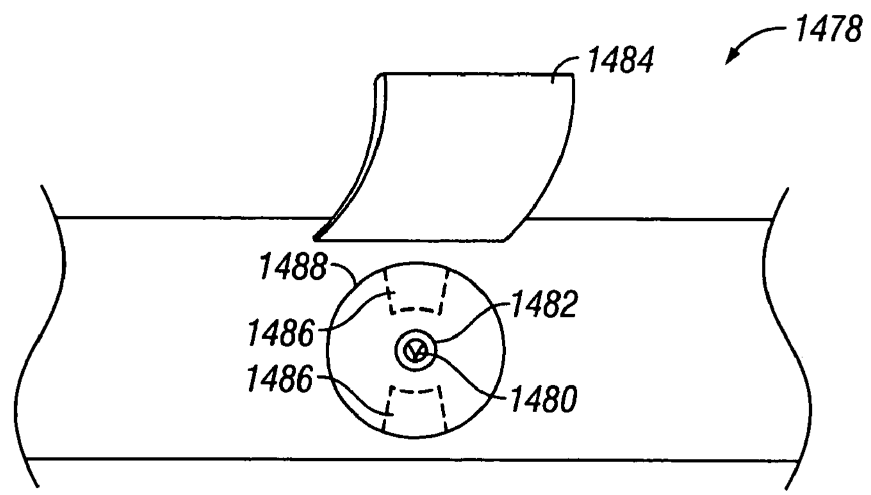

FIG. 132 shows the cartridge 1478 with the sterility barrier pealed back revealing the analyte detecting members 1486 and the penetrating member 1480. It should be understood that some embodiment may use only a single analyte detecting member 1486. Others may use analyte detecting members 1486 that operate in the optical domain. The analyte detecting members 1486 may be individual elements as seen in FIG. 132. In other embodiments, analyte detecting members 1486 maybe circular in shape or other shape to take up the entire area 1488, substantially encircling the penetrating member exit.

Figure 133:
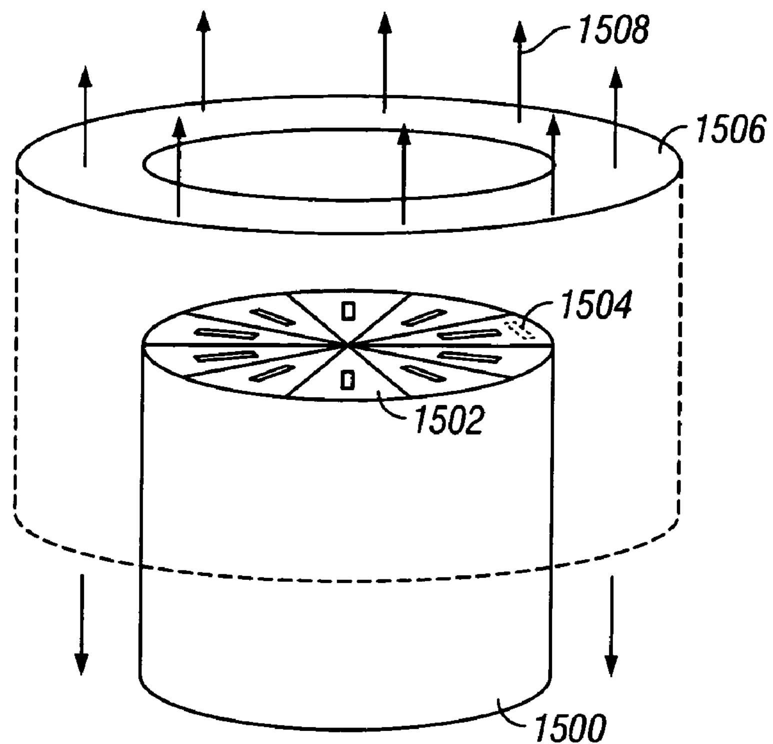
FIGS. 133 and 135 show a still further embodiment of a cartridge according to the present invention.

Referring now to FIG. 133, a still further embodiment of the present invention is shown. The cartridge 1500 includes a plurality of test strips 1502. The test strips 1502 may be oriented as shown or may be configured as indicated by the test strip 1504 (shown in phantom). A second cartridge 1506 containing a plurality of penetrating members may be placed or lowered about the cartridge 1500. In some embodiments, the cartridges 1500 and 1506 may be integrated together. The penetrating members in the cartridge 1506 may extend outward as indicated by arrows 1508. In one embodiment, the penetrating members extend outward when they are in the active position and are operatively coupled to the penetrating member driver. The test strips may extend outward in substantially the same direction as the arrows 1508. A suitable device for cartridge 1500 is shown in U.S. Pat. No. 5,510,266 to Bonner, fully incorporated herein by reference for all purposes.

Figure 134:
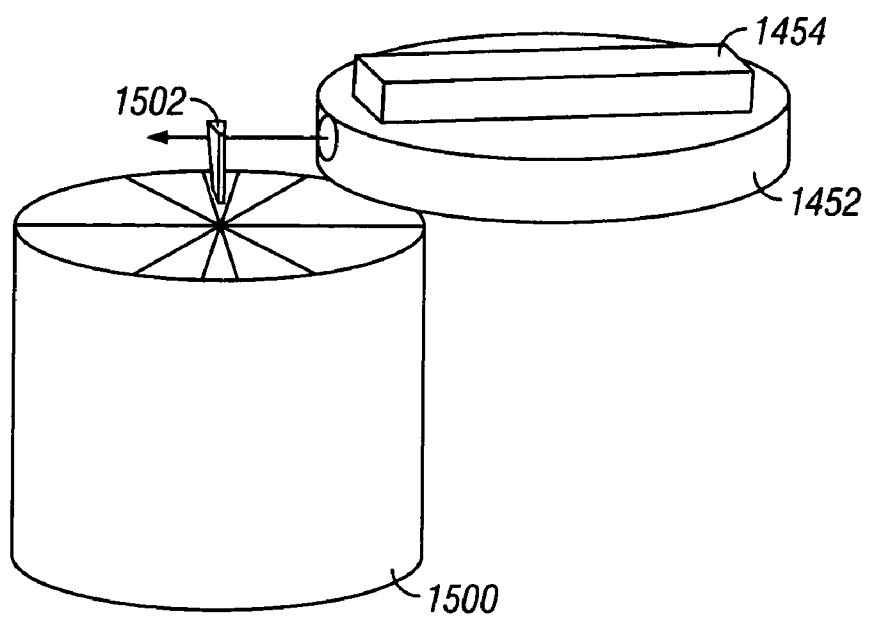

Referring now to FIG. 134, yet another embodiment of the present invention is shown. A cartridge 1500 is shown having a plurality of test strips 1502. In some embodiments, the test strip 1502 is raised so that the strip is brought near but is not pierced by the penetrating member. In other embodiments, the penetrating member 1450 may pierce the test strip 1502. A housing (not shown) may be implemented hold these devices in the orientations shown.

Figure 135:
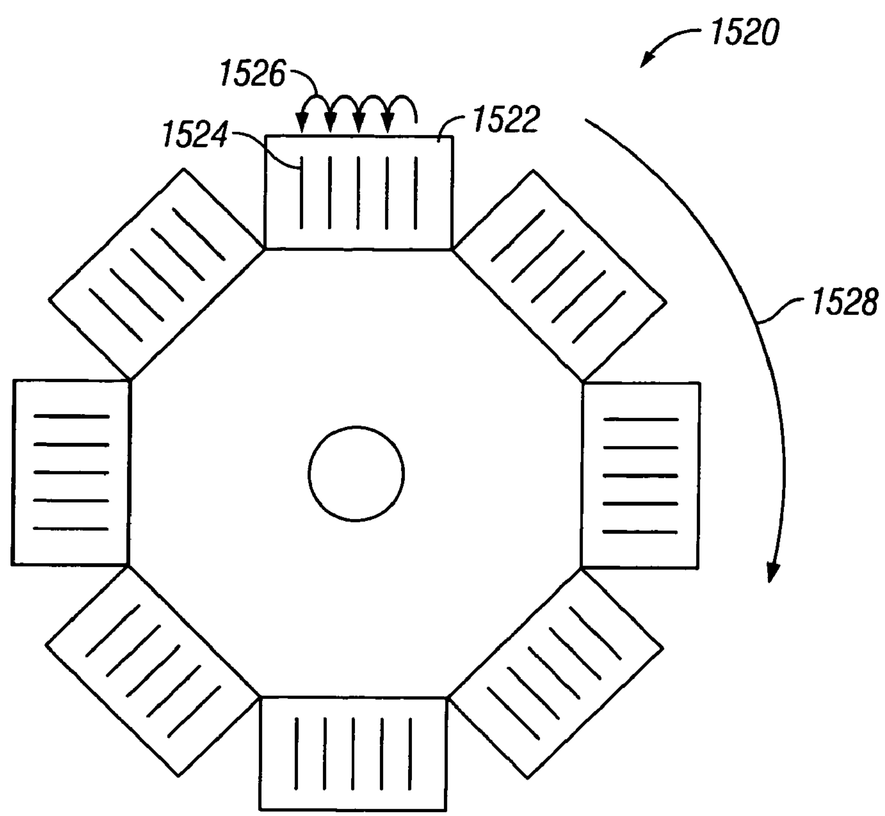

Referring now to FIG. 135, a still further embodiment of a cartridge 1520 according to the present invention is shown. There are portions 1522 where a plurality of penetrating members 1524 are housed. A penetrating member coupler (not shown) may be moved as indicated by arrows 1526. In another embodiment, the entire cartridge is rotated as indicated by arrow 1528. After the cartridge 1520 has made one complete revolution, the penetrating member holder may be moved over one position as indicated by arrow 1526. The entire cartridge 1520 is then rotated again through one revolution, before the penetrating member coupler is shifted one more position as indicated by arrow 1528.

Figure 136:
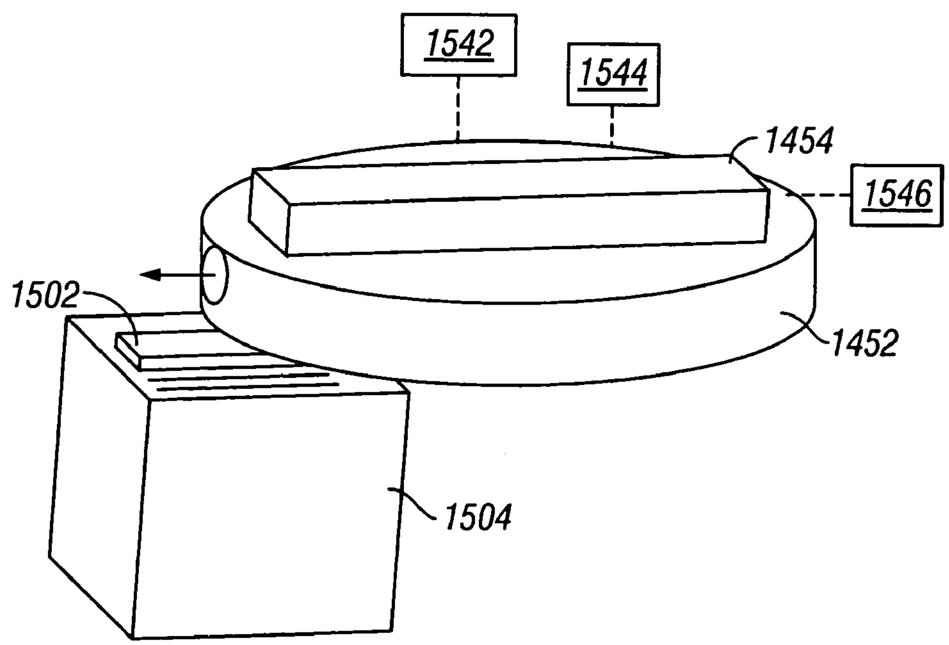
FIG. 136 shows a penetrating member device used with a stack of analyte detecting members.

Referring now to FIG. 136, a still further embodiment is shown where a plurality of analyte detecting members 1502 are shown in a stack configuration. After each detecting member 1502 is used, it may be removed and a new one will be revealed. It may also be pushed up by a biasing member (not shown). The cartridge 1540 may be integrated with the cartridge 1452. It may also be shaped to be similar to the shape of cartridge 1452. Still further, a housing may be used to hold a cartridge 1540 in relation to the cartridge 1452. A user interface 1542 may be coupled to the device. A processor 1544 may be coupled to the device. A position sensor 1546 may be incorporated with the device so that lancing performance and/or tracking of position of the driver (and thus the penetrating member) may be monitored. Any of the embodiments of the present invention may be modified to include these elements.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, with any of the above embodiments; the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). With any of the above embodiments, the penetrating members may be a bare penetrating member during launch. With any of the above embodiments, the penetrating members may be bare penetrating members prior to launch as this may allow for significantly tighter densities of penetrating members. In some embodiments, the penetrating members may be bent, curved, textured, shaped, or otherwise treated at a proximal end or area to facilitate handling by an actuator. The penetrating member may be configured to have a notch or groove to facilitate coupling to a gripper. The notch or groove may be formed along an elongate portion of the penetrating member. With any of the above embodiments, the cavity may be on the bottom or the top of the cartridge, with the gripper on the other side. In some embodiments, analyte detecting members may be printed on the top, bottom, or side of the cavities. The front end of the cartridge maybe in contact with a user during lancing. The same driver may be used for advancing and retraction of the penetrating member. The penetrating member may have a diameters and length suitable for obtaining the blood volumes described herein. The penetrating member driver may also be in substantially the same plane as the cartridge. The driver may use a through hole or other opening to engage a proximal end of a penetrating member to actuate the penetrating member along a path into and out of the tissue.

Any of the features described in this application or any reference disclosed herein may be adapted for use with any embodiment of the present invention. For example, the devices of the present invention may also be combined for use with injection penetrating members or needles as described in commonly assigned, copending U.S. patent application Ser. No. 10/127,395 filed Apr. 19, 2002. An analyte detecting member to detect the presence of foil may also be included in the lancing apparatus. For example, if a cavity has been used before, the foil or sterility barrier will be punched. The analyte detecting member can detect if the cavity is fresh or not based on the status of the barrier. It should be understood that in optional embodiments, the sterility barrier may be designed to pierce a sterility barrier of thickness that does not dull a tip of the penetrating member. The lancing apparatus may also use improved drive mechanisms. For example, a solenoid force generator may be improved to try to increase the amount of force the solenoid can generate for a given current. A solenoid for use with the present invention may have five coils and in the present embodiment the slug is roughly the size of two coils. One change is to increase the thickness of the outer metal shell or windings surround the coils. By increasing the thickness, the flux will also be increased. The slug may be split; two smaller slugs may also be used and offset by ½ of a coil pitch. This allows more slugs to be approaching a coil where it could be accelerated. This creates more events where a slug is approaching a coil, creating a more efficient system.

In another optional alternative embodiment, a gripper in the inner end of the protective cavity may hold the penetrating member during shipment and after use, eliminating the feature of using the foil, protective end, or other part to retain the used penetrating member. Some other advantages of the disclosed embodiments and features of additional embodiments include: same mechanism for transferring the used penetrating members to a storage area; a high number of penetrating members such as 25, 50, 75, 100, 500, or more penetrating members may be put on a disk or cartridge; molded body about a lancet becomes unnecessary; manufacturing of multiple penetrating member devices is simplified through the use of cartridges; handling is possible of bare rods metal wires, without any additional structural features, to actuate them into tissue; maintaining extreme (better than 50 micron—lateral—and better than 20 micron vertical) precision in guiding; and storage system for new and used penetrating members, with individual cavities/slots is provided. The housing of the lancing device may also be sized to be ergonomically pleasing. In one embodiment, the device has a width of about 56 mm, a length of about 105 mm and a thickness of about 15 mm. Additionally, some embodiments of the present invention may be used with non-electrical force generators or drive mechanism. For example, the punch device and methods for releasing the penetrating members from sterile enclosures could be adapted for use with spring based launchers. The gripper using a frictional coupling may also be adapted for use with other drive technologies.

Still further optional features may be included with the present invention. For example, with any of the above embodiments, the location of the penetrating member drive device may be varied, relative to the penetrating members or the cartridge. With any of the above embodiments, the penetrating member tips may be uncovered during actuation (i.e. penetrating members do not pierce the penetrating member enclosure or protective foil during launch). The penetrating members may be a bare penetrating member during launch. In some embodiments, the penetrating member may be a patent needle. The same driver may be used for advancing and retraction of the penetrating member. Different analyte detecting members detecting different ranges of glucose concentration, different analytes, or the like may be combined for use with each penetrating member. Non-potentiometric measurement techniques may also be used for analyte detection. For example, direct electron transfer of glucose oxidase molecules adsorbed onto carbon nanotube powder microelectrode may be used to measure glucose levels. In some embodiments, the analyte detecting members may formed to flush with the cartridge so that a "well" is not formed. In some other embodiments, the analyte detecting members may formed to be substantially flush (within 200 microns or 100 microns) with the cartridge surfaces. In all methods, nanoscopic wire growth can be carried out via chemical vapor deposition (CVD). In all of the embodiments of the invention, preferred nanoscopic wires may be nanotubes. Any method useful for depositing a glucose oxidase or other analyte detection material on a nanowire or nanotube may be used with the present invention. Additionally, for some embodiments, any of the cartridge shown above may be configured without any of the penetrating members, so that the cartridge is simply an analyte detecting device. Still further, the indexing of the cartridge may be such that adjacent cavities may not necessarily be used serially or sequentially. As a nonlimiting example, every second cavity may be used sequentially, which means that the cartridge will go through two rotations before every or substantially all of the cavities are used. As another nonlimiting example, a cavity that is 3 cavities away, 4 cavities away, or N cavities away may be the next one used. This may allow for greater separation between cavities containing penetrating members that were just used and a fresh penetrating member to be used next. It should be understood that the spring-based drivers shown in the present invention (FIGS. 98-112) may be adapted for use with any of the cartridges shown herein such as, but not limited to, those shown in FIGS. 61 and 62. These spring-based drivers may also be paired with gripper blocks that are configured to penetrate into cartridges that fully seal penetrating member therein, in order engage those penetrating members. The start and end positions of the penetrating members may also be the same. The penetrating members may be parked in a holder before actuation, and in some embodiments, into a holder after actuation (as seen in cartridge 500 or any other cartridge herein). Embodiments of the present invention may also include guides which provide lateral constraints and/or vertical constraints about penetrating member. These constraints may be positioned about the shaft portions of the penetrating member.

This application cross-references commonly assigned copending U.S. patent application Ser. No. 10/323,622 filed Dec. 18, 2002; commonly assigned copending U.S. patent application Ser. No. 10/323,623 filed Dec. 18, 2002; and commonly assigned copending U.S. patent application Ser. No. 10/323,624 filed Dec. 18, 2002. This application is also related to commonly assigned copending U.S. patent application Ser. Nos. 10/335,142, 10/335,215, 10/335,258, 10/335,099, 10/335,219, 10/335,052, 10/335,073, 10/335,220, 10/335,252, 10/335,218, 10/335,211, 10/335,257, 10/335,217, 10/335,212, and 10/335,241, 10/335,183, filed Dec. 31, 2002. All applications listed above are fully incorporated herein by reference for all purposes. Expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A body fluid sampling system for use on a tissue site, the system comprising:

a disposable;

a penetrating member driver;

a plurality of penetrating members arranged in a radial configuration in the disposable, wherein sharpened distal tips of the penetrating members point radially outward, and wherein each of the plurality of penetrating members has a packing density of about 0.1 $cm^3$;

wherein an active one of said penetrating members is operatively coupled to said penetrating member driver, said penetrating member driver moving said active one of said penetrating members along a path out of a housing having a penetrating member exit, into said tissue site, stopping in said tissue site, and withdrawing out of said tissue site;

a processor coupled to the penetrating member driver and configured to provide instructions to the penetrating member driver for a fast-into of said active one penetrating members into the tissue site and slow-out velocity out of the tissue site; and a plurality of analyte detecting members positioned in the disposable, wherein at least one of said analyte detecting members is positioned to receive less than about 0.1 μL of body fluid from a wound created by said active one of said penetrating members, and wherein said plurality of analyte detecting members are not pierced by the active one of the penetrating members.

2. A system as in claim 1, further comprising a penetrating member sensor positioned to monitor the active one of said penetrating members coupled to said penetrating member driver, the penetrating member sensor configured to provide information relative to a depth of penetration of the active one of said penetrating members through a skin surface of the tissue site.

3. The system of claim 2, wherein the depth of penetration is about 100 to 2500 microns.

4. The system of claim 2, wherein the depth of penetration is 500 to 750 microns.

5. The system of claim 2, wherein the depth of penetration is no more than about 1000 microns beyond a stratum corneum thickness of the skin surface.

6. The system of claim 2, wherein the depth of penetration is no more than about 500 microns beyond a stratum corneum thickness of the skin surface.

7. The system of claim 1, wherein the penetrating member driver is selected from one of the following: a voice coil, a rotary voice coil, a solenoid, a motor and gear box, a nanomuscle, or a combination of any of the above.

8. The system of claim 1, wherein the processor is utilized to monitor position and speed of the active one of said penetrating members as the active one of said penetrating member moves in a first direction.

9. The system of claim 1, wherein the processor is utilized to monitor position and speed of the active one of said penetrating members as the active one of said penetrating members moves in a first direction toward the tissue site, wherein an application of a launching force to the active one of said penetrating members is controlled based on a position and a speed of the active one of said penetrating members.

10. The system of claim 1, wherein each of the plurality of penetrating members is an elongate member without molded attachments.

11. A body fluid sampling system for use on a tissue site, the system comprising:

a disposable;

a penetrating member driver;

a plurality of penetrating members arranged in a radial configuration in the disposable, wherein sharpened distal tips of the plurality of penetrating members point radially outward, and wherein each of the plurality of penetrating members has an elongate portion and a packing density of about 0.1 $cm^3$;

wherein an active one of said penetrating members is operatively coupled to said penetrating member driver, said penetrating member driver moving said active one of said penetrating members along a path out of a housing having a penetrating member exit, into said tissue site, stopping in said tissue site, and withdrawing out of said tissue site;

a processor coupled to the penetrating member driver and configured to provide feedback and instructions to the penetrating member driver for a fast-into velocity of said active one of said penetrating members into the tissue site, a rest time of the sharpened distal tip of said active one of said penetrating members in the tissue site and a slow-out velocity of said active one of said penetrating members out of the tissue site;

a plurality of analyte detecting members positioned in the disposable, wherein at least one of said analyte detecting members is positioned to receive less than about 0.1 μL of body fluid from a wound created by said active one of said penetrating members, and wherein said plurality of analyte detecting members are not pierced by the active one of the penetrating members; and a coupler on said penetrating member driver configured to engage at least a portion of said elongate portion of said active one of said penetrating members and to drive said active one of said penetrating members along the path into the tissue site and to withdraw it from the tissue site.

* * * * *